(12) United States Patent
Blaney et al.

(10) Patent No.: US 8,637,526 B2
(45) Date of Patent: Jan. 28, 2014

(54) PYRAZOLOPYRIMIDINE JAK INHIBITOR COMPOUNDS AND METHODS

(75) Inventors: Jeffrey Blaney, Piedmont, CA (US); Paul A. Gibbons, San Francisco, CA (US); Emily Hanan, Redwood City, CA (US); Joseph P. Lyssikatos, Piedmont, CA (US); Steven R. Magnuson, Dublin, CA (US); Richard Pastor, San Francisco, CA (US); Thomas E. Rawson, Mountain View, CA (US); Aihe Zhou, San Jose, CA (US); Bing-Yan Zhu, Palo-Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/099,179

(22) Filed: May 2, 2011

(65) Prior Publication Data

US 2012/0022043 A1    Jan. 26, 2012

Related U.S. Application Data

(63) Continuation of application No. PCT/US2009/063014, filed on Nov. 2, 2009.

(60) Provisional application No. 61/110,497, filed on Oct. 31, 2008.

(51) Int. Cl.
*A01N 43/90* (2006.01)
*A61K 31/519* (2006.01)
*C07D 487/00* (2006.01)

(52) U.S. Cl.
USPC ...................................... 514/259.3; 544/281

(58) Field of Classification Search
None
See application file for complete search history.

(56) References Cited

U.S. PATENT DOCUMENTS

| | | | |
|---|---|---|---|
| 4,603,139 A | 7/1986 | King | |
| 4,847,256 A | 7/1989 | Tseng et al. | |
| 5,705,625 A | 1/1998 | Civin et al. | |
| 6,136,595 A | 10/2000 | Ihle et al. | |
| 6,210,654 B1 | 4/2001 | Ihle et al. | |
| 6,235,741 B1 | 5/2001 | Bilodeau et al. | |
| 7,070,972 B1 | 7/2006 | O'Shea et al. | |
| 7,161,003 B1 | 1/2007 | Guzi et al. | |
| 7,306,631 B2 | 12/2007 | Glenn et al. | |
| 2004/0097485 A1 | 5/2004 | Burkitt et al. | |
| 2005/0245546 A1 | 11/2005 | Cristalli | |
| 2005/0288502 A1 | 12/2005 | Andersen et al. | |
| 2006/0089362 A1 | 4/2006 | Seno et al. | |
| 2006/0142612 A1 | 6/2006 | Anthony et al. | |
| 2006/0153852 A1 | 7/2006 | Coleman et al. | |
| 2007/0082902 A1 | 4/2007 | Paruch et al. | |
| 2007/0270408 A1 | 11/2007 | Andersen et al. | |
| 2009/0054410 A1 | 2/2009 | Griffioen et al. | |
| 2009/0163545 A1 | 6/2009 | Goldfarb | |

FOREIGN PATENT DOCUMENTS

| | | |
|---|---|---|
| EP | 1 040 817 A1 | 10/2000 |
| EP | 1 221 444 A1 | 7/2002 |
| WO | 98/14451 A1 | 4/1998 |
| WO | 01/42246 | 6/2001 |
| WO | 2004/037823 A1 | 5/2004 |
| WO | 2004/052315 | 6/2004 |
| WO | 2004/089471 | 10/2004 |
| WO | 2005/002552 A2 | 1/2005 |
| WO | 2005/058837 A1 | 6/2005 |
| WO | 2005/110477 A2 | 11/2005 |
| WO | 2005/110477 A3 | 11/2005 |
| WO | 2007/013673 | 2/2007 |
| WO | 2007/039797 A1 | 4/2007 |
| WO | 2007/048066 A2 | 4/2007 |
| WO | 2007/048066 A3 | 4/2007 |
| WO | 2007/065664 A2 | 6/2007 |
| WO | 2007/065664 A3 | 6/2007 |
| WO | 2007/108750 A1 | 9/2007 |
| WO | 2008/004698 A2 | 1/2008 |
| WO | 2008/004698 A3 | 1/2008 |
| WO | 2008/008539 A2 | 1/2008 |
| WO | 2008/008539 A3 | 1/2008 |
| WO | 2008/052734 A1 | 5/2008 |
| WO | 2008/063671 A2 | 5/2008 |

(Continued)

OTHER PUBLICATIONS

Gausterer, et. al., Anti-Inflammatory & Anti-Allergy Agents in Medicinal Chemistry, 2007, 6, 29-45.*

(Continued)

*Primary Examiner* — Jeffrey Murray
(74) *Attorney, Agent, or Firm* — Tamara Kale; Genentech, Inc.

(57) ABSTRACT

The invention provides JAK kinase inhibitors of Formula Ia, enantiomers, diastereomers or pharmaceutically acceptable salts thereof, wherein $R^1$, $R^2$, $R^7$ and Z are defined herein, a pharmaceutical composition that includes a compound of Formula Ia and a pharmaceutically acceptable carrier, adjuvant or vehicle, and methods of treating or lessening the severity of a disease or condition responsive to the inhibition of a JAK kinase activity in a patient.

Ia

18 Claims, No Drawings

(56) References Cited

FOREIGN PATENT DOCUMENTS

| WO | 2008/063671 A3 | 5/2008 |
|----|----|----|
| WO | 2009/017954 A1 | 2/2009 |
| WO | 2009/047359 A1 | 4/2009 |
| WO | 2009/073153 A2 | 6/2009 |
| WO | 2009/073153 A3 | 6/2009 |
| WO | 2010/019762 A1 | 2/2010 |
| WO | WO2010063487 * | 6/2010 |
| WO | 2010/089292 A1 | 8/2010 |
| WO | 2010/094647 A1 | 8/2010 |
| WO | 2011/006074 A1 | 1/2011 |
| WO | 2011/003065 A2 | 2/2011 |
| WO | 2011/003065 A3 | 2/2011 |
| WO | 2011/048082 A1 | 4/2011 |
| WO | 2011/113802 A2 | 9/2011 |
| WO | 2011/134831 A1 | 11/2011 |

OTHER PUBLICATIONS

Gavrin, et. al., Journal of Organic Chemistry (2007), 72(3), 1043-1046.*
(International Preliminary Report on Patentability for International Patent Application No. PCT/US2009/063014), (May 3, 2011).
Baslund et al., "Targeting interleukin-15 in patients with rheumatoid arthritis: a proof-of-concept study" *Arthritis Rheum* 52(9):2686-92 (Sep. 2005).
Changelian et al., "Prevention of organ allograft rejection by a specific Janus kinase 3 inhibitor" *Science* 302:875-8 (Oct. 2003).
Dameshek, "Editorial: Some Speculations on the Myeloproliferative Syndromes" *Blood* 6(4):372-375 (1951).
Firmbach-Kraft et al., "tyk2, prototype of a novel class of non-receptor tyrosine kinase genes" *Oncogene* 5:1329-36 (1990).
Gavrin et al., "Synthesis of pyrazolo[1,5-alpha]pyrimidinone regioisomers" *J Org Chem.* 72(3):1043-6 (Feb. 2007).
Kisseleva et al., "Signaling through the JAK/STAT pathway, recent advances and future challenges" *Gene* 285:1-24 (Feb. 2002).
Krueger et al., "A human interleukin-12/23 monoclonal antibody for the treatment of psoriasis" *New Engl J Med* 356(6):580-92 (Feb. 2007).
Levy et al., "Stats: transcriptional control and biological impact" *Nat Rev Mol Cell Biol.* 3(9):651-62 (2002).
Mannon et al., "Anti-interleukin-12 antibody for active Chrohn's disease" *New Engl J Med* 351(20):2069-79 (Nov. 2004).
Morgan et al., "A Role for JAK2 Mutations in Myeloproliferative Diseases" *Annu Rev Med* 59:213-222 (2008).
O'Shea et al., "Cytokine Signaling in 2002: New Surprises in the Jak/Stat Pathway" *Cell* 109:S121-S131 (Apr. 2002).
Reich et al., "Ustekinumab" *Nat Rev Drug Discov* 8(5):355-6 (May 2009).
Scheinecker et al., "Tocilizumab" *Nat Rev Drug Discov* 8(4):273-4 (Apr. 2009).
Schindler et al., "JAK-STAT signaling: from interferons to cytokines" *J Biol Chem* 282(28):20059-63 (Jul. 2007).
Watford et al., "Human tyk2 kinase deficiency: another primary immunodeficiency Syndrome" *Immunity* 25:695-7 (Nov. 2006).
Wilks et al., "Two novel protein-tyrosine kinases, each with a second phosphotransferase-related catalytic domain, define a new class of protein kinase" *Mol Cell Biol* 11:2057-2065 (1991).
Wilks, "Two putative protein-tyrosine kinases identified by application of the polymerase chain reaction" *P Natl Acad Sci USA* 86:1603-1607 (1989).
Yang et al., "Use of N-(thiofuran-2) pyrazolo [1, 5-a] pyrimidine-3-methanamide compound for preparing the antineoplastic medicine" (Abstract Patent/Publication: CN101537007A), (Oct. 12, 2011).
(EP Office Action dated Aug. 13, 2013).
(File Registry RN 1252132-61-8 Entered STN: Nov. 9, 2010).
(File Registry RN 1316553-50-0 Entered STN: Aug. 12, 2011).
(File Registry RN 1319894-27-3 Entered STN: Aug. 19, 2011).
(International Preliminary Report on Patentability for International Patent Application No. PCT/US2010/040906), (Jan 4, 2012).
(PCT ISR and the Written Opinion for PCT/EP2011/070313).

(PCT ISR and Written Opinion for PCT/EP2011/053826).
Anderson et al., "Chemistry of the adenosine monophosphate site of rabbit muscle glycogen phosphorylase. I. Hydrophobic nature and affinity labeling of the allosteric site" Biochemistry 12(10):1895-900 (1973).
Barraclough et al., "Inotropic 'A' ring substituted sulmazole and isomazole analogues" J Med Chem. 33(8):2231-9 (1990).
Borrmann et al., "Structure-activity relationships of adenine and deazaadenine derivatives as ligands for adenine receptors, a new purinergic receptor family" J Med Chem. 52:5974-89 (2009).
Cartwright et al., "Imidazopyridine and pyrimidinopyridine systems from perfluorinated pyridine derivatives" Tetrahedron 63(30) (Jun. 13, 2007).
CAS Registry Database, 1089652-06-1.
CAS Registry Database, 1147525-55-0.
CAS Registry Database, 1214490-10-4.
CAS Registry Database, 1223183-38-7.
Database Registry [Online] Chemical Abstracts Service, Columbus, Ohio, US; Jun. 10, 2008, 'Not yet assigned', Database accession No. 1026925-65-4 the whole document.
Database Registry [Online] Chemical Abstracts Service, Columbus, Ohio, US; Aug. 29, 2004, '9H-Purine, 9-(4-cholorphenyl)-8-(2-fluorophenyl)-6-(1 -pyrrolidinyl)-', Database accession No. 734532-63-9 the whole document.
Database Registry [Online] Chemical Abstracts Service, Columbus, Ohio, US; Jun. 8, 2008, 'Not yet assigned', Database accession No. 1026421-43-1 the whole document.
Database Registry [Online] Chemical Abstracts Service, Columbus, Ohio, US; Nov.10, 2004, '3-Azabicyclo[3.1.0]hexan-6-amine, 3-[9-(4-chlorophenyl)-8-(2,3-dichloropheny 1)-9H-purin-6-yl]-N,N-dimethyl-, (1.alpha.-5.alpha.,6.beta.)-', Database accession No. 777853-55-1 the whole document.
Database Registry [Online] Chemical Abstracts Service, Columbus, Ohio, US; Sep. 8, 2004, '3-Azabicyclo[3.1.0]hexan-6-amine, 3-[9-(4-chlorophenyl)-8-(2,3-dichloropheny 1)-9H-purin-6-yl]-N,N-dimethyl-, (1. alpha.-5. alpha., 6. beta.)-, Database accession No. 741249-27-4 the whole document.
Database Registry [Online] Chemical Abstracts Service, Columbus, Ohio, US; Apr. 4, 2003, '9H-Purin-6-amine, 8-(2,4-dichlorophenyl)-', Database accession No. 501657-71-2 the whole document.
Database Registry [Online] Chemical Abstracts Service, Columbus, Ohio, US; Jun. 10, 2008, 'Not yet assigned', Database accession No. 1027012-36-7 the whole document.
Database Registry [Online] Chemical Abstracts Service, Columbus, Ohio, US; Jun. 13, 2008, 'Not yet assigned', Database accession No. 1027914-11-9 the whole document.
Database Registry [Online] Chemical Abstracts Service, Columbus, Ohio, US; Jul. 12, 2818 (2810-87-12), '9H-Purine, 8-(2-chlorophenyl)-6-(4-methyl-l-piperazin yl)-9-[(tetrahydro-2H-piran-4-yl)methyl]-' Database accession No. 1231299-64-1 the whole document.
Database Registry [Online] Chemical Abstracts Service, Columbus, Ohio, US; Sep. 14, 2010, '1H-Imidazo[4,5-c]pyridin-4-amine, 2-(2-clorophenyl)-N43 -methoxy-4 -(3-methyl-1H-1,2,4-triazol-1-yl]phenyl]-1-(methylethyl=-', Database accession No. 1240783-28-1 the whole document.
Geldenhuys et al., "Virtual screening to identify novel antagonists for the G protein-coupled NK3 receptor" J Med Chem. 53:8080-8 (Nov. 2010)
Griffith et al., "Discovery of 1-[9-(4-chlorophenyl)-8-(2-chlorophenyl)-9H-purin-6-yl]-4-ethylaminopiperidine-4-carboxyli c acid amide hydrochloride (CP-945,598), a novel, potent, and selective cannabinoid type 1 receptor antagonist" J Med Chem. 52(2):234-7 (Jan 22, 2009).
Hasnik et al., "Cross-Coupling reactions of Halopurines with Aryl- and alkyltrifluoroborates; The Scope and Limitations in the Synthesis of Modified Purines" Synthesis 9:1309-17 (Mar. 25, 2009).
Iupac Ed—Macnaught Alan D et al. Compendium of Chemical Terminology: Iupac Recommendations; [Iupac Chemical Data Series], [ISBN: 978-0-86542-684-9] "cycloalkyl groups, [retrieved on Apr. 20, 2012; http://goldbook.iupac.org/about.html/]" Oxford [U.A.]:Blackwell Science, Oxford [U.A.].

(56) References Cited

OTHER PUBLICATIONS

Iupac Ed—Macnaught Alan D et al. Compendium of Chemical. Terminology: Iupac Recommendations; [Iupac Chemical Data Series], [ISBN: 978-0-86542-684-9] "alkyl groups, [retrieved on Apr. 20, 2012; http://goldbook.iupac.org/about.html/]" Blackwell Science, Oxford [U.A.].

Jacob, "Resolution of (+/−)-5-Bromonornicitine. Synthesis of (R)- and (S)-Nornicotine of High Enantiomeric Purity" J Org Chem 47:4165-67 (1982).

McCloskey et al., "New insights into the design of inhibitors of human S-adenosylmethionine decarboxylase: studies of adenine C8 substitution in structural analogues of S-adenosylmethionine" J Med Chem. 52(5):1388-407 (2009).

Medebielle et al., "Electrochemically induced SRNI substitution of fluorinated aryl halides Application to the synthesis of fluorinated-aryl heterocycles" Electrochimica Acta 42(13):2049-55 (1997).

Ragan et al., "Development of a practical and Efficient Synthesis of CP-945,598-02,a CBI Antagonist for the Treatment of Obesity" Organic Process Research and Development 13(2):192 (Dec. 22, 2008).

Sahnoun et al., "A site selective C-H arylation of free-(NH2) adenines with aryl chlorides: application to the synthesis of 6,8-disubstituted adenines" Org Biomol Chem. 7(20):4271-8 (Aug. 14, 2009).

Sahnoun et al., "Microwave-assisted Pd(OH)2-catalyzed direct C-H arylation of free-(NH2) adenines with aryl halides" Tetrahedron Letters 49(51):7279-83 (Dec. 15, 2008).

Saltzman et al. et al., "Cloning and characterization of human Jak-2 kinase: high mRNA expression in immune cells and muscle tissue" Biochem Bioph Res Co 246:627-33 (May 1998).

Sasaki et al., "Syntheses of Fused Heterocycles via cycloaddition of Hetaryne Studies on Heteroaromaticity, Part XLVII" Bulletin Of the Chemical Society of Japan 44(3) (Jan. 1, 1971).

Storr et al., "Pd(0)/Cu(I)-mediated direct arylation of 2'-deoxyadenosines: mechanistic role of Cu(I) and reactivity comparisons with related purine nucleosides" J Org Chem 74(16):5810-21 (2009).

Young et al., "Purine derivatives as competitive inhibitors of human erythrocyte membrane phosphatidylinositol 4-kinase" J Med Chem. 33(8):2073-80 (Aug. 1990).

* cited by examiner

US 8,637,526 B2

PYRAZOLOPYRIMIDINE JAK INHIBITOR COMPOUNDS AND METHODS

CROSS REFERENCE TO RELATED APPLICATIONS

This non-provisional application claims the benefit under 35 USC §§120 and 365 of International Application Serial No. PCT/US2009/063014 filed Nov. 2, 2009, and under 35 USC §119(e) of U.S. Provisional Application Ser. No. 61/110,497 filed on Oct. 31, 2008, both of which are incorporated by reference herein in their entirety for all purposes.

FIELD OF THE INVENTION

Pyrazolopyrimidine compounds, inhibitors of JAK kinases, as well as compositions containing these compounds and methods of use including, but not limited to, in vitro, in situ and in vivo diagnosis or treatment of mammalian cells.

BACKGROUND OF INVENTION

Cytokine pathways mediate a broad range of biological functions, including many aspects of inflammation and immunity. Janus kinases (JAK), including JAK1, JAK2, JAK3 and TYK2 are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, *J Biol. Chem.* 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence.

JAK1 was initially identified in a screen for novel kinases (Wilks A. F., 1989, *Proc. Natl. Acad. Sci. U.S.A.* 86:1603-1607). Genetic and biochemical studies have shown that JAK1 is functionally and physically associated with the type I interferon (e.g., IFNalpha), type II interferon (e.g., IFN-gamma), IL-2 and IL-6 cytokine receptor complexes (Kisseleva et al., 2002, gene 285:1-24; Levy et al., 2005, Nat. Rev. Mol. Cell. Biol. 3:651-662; O'Shea et al., 2002, *Cell*, 109 (suppl.): S121-S131). JAK1 knockout mice die perinatally due to defects in LIF receptor signaling (Kisseleva et al., 2002, gene 285:1-24; O'Shea et al., 2002, *Cell*, 109 (suppl.): S121-S131). Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, Nat. Rev. Drug Discov. 8:273-274).

Myeloproliferative disorders (MPD) originate in hematopoietic stem cells and primarily manifest in elevated counts of mostly normal cells of the myeloid lineage. A primary distinction between Philadelphia-chromosome positive (Ph+) and Philadelphia-chromosome negative (Ph−) can be made. Ph+ MPD results in chronic myelogenous leukemia and is driven by a bcr-abl fusion protein that drives hematopoietic cell proliferation. Ph− MPD can be further subclassified into three distinct disorders by related varieties, namely polycythemia vera (PV), essential thrombocythemia (ET) and idiopathic myelofibrosis (IMF). Dameshek, W., *Blood* 6(4): 372-375 (1951). Patients with PV suffer from high counts of red blood cells, whereas patients with ET have high levels of circulating platelets. If left untreated, both diseases can result in life-threatening thrombotic events. Patients with IMF experience fibrosis of the bone marrow with subsequent displacement of hematopoiesis into the spleen and liver. This primarily leads to splenomegaly, which is followed by anemia in later stages of the disease as hematopoiesis becomes nonproductive. These patients have a poor prognosis, although under certain conditions they can be cured by means of an allogeneic bone marrow transplant. There is no known cure for Ph− MPD diseases.

An activating mutation in the tyrosine kinase JAK2 is associated with PV, ET, IMF and other diseases. Virtually all patients with PV and about 50% patients with ET and IMF harbor this mutation. Morgan, K. J. and Gilliland, D. G., *Ann. Rev. Med.* 59:213-222 (2008). The mutation is an exchange from valine to phenylalanine at position 617 in the mature human JAK2 protein (V617F). Additional mutations in JAK2, commonly found in exon 12 and referred to as exon 12 mutations, also have an activating effect and can lead to MPD. Furthermore, a T875N mutation was associated with megakaryoblastic leukemia. Finally, JAK2 fusion proteins have been identified in acute leukemias.

The V617F mutation functions to activate JAK2, which leads to MPD. In non-mutated form, JAK2 is linked to cytokine receptors (i.e. EPO-R, TPO-R and others) and only gets activated if the receptor itself is activated by stimulation with the cognate cytokine ligand. Hematopoiesis as a whole is then regulated through the availability of ligands. For example, the cytokine erythropoietin (EPO) stimulates hematopoietic progenitor cells to give rise to red blood cells. A mutation that uncouples JAK2 activation from EPO, therefore, leads to elevated levels of red blood cells. By analogy, thrombopoietin (TPO) regulates platelet growth by binding to the TPO-R, which in turn also signals through JAK2. Thus, elevated levels of platelets can also result from aberrant JAK2 activation.

Compounds are needed that inhibit JAK2, which would be beneficial to patients with JAK2 driven myeloproliferative disorders, as well as, other diseases that are responsive to the inhibition of JAK2. Such diseases include both diseases in which JAK2 is activated by mutation or amplification, as well as, diseases in which JAK2 activation is a part of the oncogenic cascade. Numerous tumor cell lines and tumor samples have high levels of phospho-STAT3, which is a JAK2 target gene.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, *Cell*, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, *Arthritis &Rheumatism* 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, *Gene* 285:1-24; Watford, W. T. & O'Shea, J. J., 2006, *Immunity* 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and 11-23 cytokines (Ustekinumab) was recently approved by the European Commission for the treatment of moderate-to-severe plaque psoriasis (Krueger et al., 2007, *N. Engl. J. Med.* 356:580-92; Reich et al., 2009, *Nat. Rev. Drug Discov.* 8:355-356). In addition, an antibody targeting the IL-12 and IL-23 pathways underwent clinical trials for treating Crohn's Disease (Mannon et al., 2004, *N. Engl. J. Med.* 351:2069-79).

SUMMARY OF INVENTION

One embodiment includes a compound of Formula I:

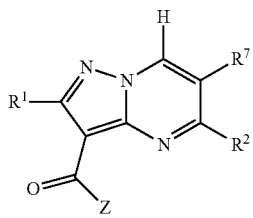

Ia enantiomers, diasteriomers or pharmaceutically acceptable salts thereof, wherein $R^1$, $R^2$, $R^7$ and Z are defined herein.

One embodiment includes a compound of Formula I:

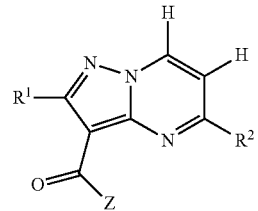

I enantiomers, diasteriomers or pharmaceutically acceptable salts thereof, wherein $R^1$, $R^2$ and Z are defined herein.

Another embodiment includes a pharmaceutical composition that includes a compound of Formula Ia and a pharmaceutically acceptable carrier, adjuvant or vehicle.

Another embodiment includes a pharmaceutical composition that includes a compound of Formula I and a pharmaceutically acceptable carrier, adjuvant or vehicle.

Another embodiment includes a method of treating or lessening the severity of a disease or condition responsive to the inhibition of a JAK kinase activity in a patient, comprising administering to the patient a therapeutically effective amount of a compound of Formula Ia.

Another embodiment includes a method of treating or lessening the severity of a disease or condition responsive to the inhibition of JAK2 kinase activity in a patient. The method includes administering to the patient a therapeutically effective amount of a compound of Formula I.

Another embodiment includes a kit for treating a disease or disorder responsive to the inhibition of a JAK kinase. The kit includes a first pharmaceutical composition comprising a compound of Formula I and instructions for use. In another embodiment, the kit includes a first pharmaceutical composition comprising a compound of Formula Ia and instructions for use.

DETAILED DESCRIPTION OF THE INVENTION

Reference will now be made in detail to certain embodiments, examples of which are illustrated in the accompanying structures and formulas. While the invention will be described in conjunction with the enumerated embodiments, the invention is intended to cover all alternatives, modifications, and equivalents, which may be included within the scope of the present invention as defined by the claims. One skilled in the art will recognize methods and materials similar or equivalent to those described herein, which could be used in the practice of the present invention.

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_4$, or $C_1$-$C_3$. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl.

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—$CH=CH_2$), prop-1-enyl (—$CH=CHCH_3$), prop-2-enyl (—$CH_2CH=CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—$C\equiv CH$), prop-1-ynyl (—$C\equiv CCH_3$), prop-2-ynyl (propargyl, —$CH_2CCH$), but-1-ynyl, but-2-ynyl and but-3-ynyl.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane.

"Aryl" refers to a cyclic aromatic hydrocarbon group optionally substituted independently with one or more substituents described herein. In one example, the aryl group is 6-20 carbon atoms ($C_6$-$C_{20}$). In another example, the aryl group is $C_6$-$C_{10}$. In another example, the aryl group is $C_6$-$C_9$. In another example, the aryl group is a $C_6$ aryl group. Aryl includes bicyclic groups comprising an aromatic ring with a fused non-aromatic or partially saturated ring. Bicyclic aryl groups may be attached via the aromatic, non-aromatic or partially saturated ring, as shown, for example, below:

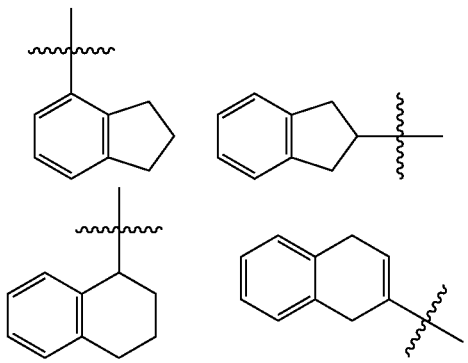

Example aryl groups include, but are not limited to, phenyl, naphthalenyl, anthracenyl, indenyl, indanyl, 1,2-dihydronapthalenyl and 1,2,3,4-tetrahydronaphthyl. In one example, aryl includes phenyl.

"Halo" refers to F, Cl, Br or I.

"Heterocyclyl" refers to a saturated, partially unsaturated (i.e., having one or more double and/or triple bonds within the ring) or aromatic (heteroaryl)cyclic group in which at least one ring atom is a heteroatom independently selected from nitrogen, oxygen, phosphorus and sulfur, the remaining ring atoms being carbon. The heterocyclyl group may be optionally substituted with one or more substituents described below. In one embodiment, heterocyclyl includes monocycles or bicycles having 1 to 9 carbon ring atoms ($C_1$-$C_9$) with the remaining ring atoms being heteroatoms selected from N, O, S and P. In other examples, heterocyclyl includes monocycles or bicycles having $C_1$-$C_5$, $C_3$-$C_5$, $C_3$-$C_9$ or $C_4$-$C_5$, with the remaining ring atoms being heteroatoms selected from N, O, S and P. In another embodiment, heterocyclyl includes monocyclic 3-, 4-, 5-, 6- and 7-membered rings, containing one or more heteroatoms independently selected from N, O and S, with the remaining ring atoms being carbon. In another embodiment, heterocyclyl includes monocyclic 5-, 6- and 7-membered rings, containing one or more heteroatoms independently selected from N, O, S and P. Examples of bicycle systems include, but are not limited to, [3,5], [4,5], [5,5], [3,6], [4,6], [5,6], or [6,6] systems. In another embodiment, heterocyclyl includes bridged ring systems having [2.2.1], [2.2.2], [3.2.2] and [4.1.0] arrangements, and having 1 to 3 heteroatoms selected from N, O, S and P. In another embodiment, heterocyclyl includes spiro groups having 1 to 3 heteroatoms selected from N, O, S and P. The heterocyclyl group may be a carbon-linked group or heteroatom-linked group. "Heterocyclyl" includes a heterocyclyl group fused to a cycloalkyl. "Heterocyclyl" also includes a heterocyclyl group fused to an, aryl or heteroaryl group. Additional example heterocyclyl groups include 2,3-dihydrobenzofuranyl, octahydrobenzofuranyl, 1,3-dihydroisobenzofuran, chromanyl, isochromanyl, thiochromanyl, isothiochromanyl, 2,3-dihydrobenzo[b]thiophene, 2,3-dihydrobenzo[b]thiophene 1,1-dioxide, 1,3-dihydrobenzo[c]thiophene, 1,3-dihydrobenzo[c]thiophene 2,2-dioxide, isoindolinyl, indolinyl and 2,3-dihydro-1H-pyrrolo[2,3-b]pyridine.

Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, morpholinyl, thiomorpholinyl, thioxanyl, piperazinyl, homopiperazinyl, homopiperidinyl, oxepanyl, thiepanyl, oxazepinyl, diazepinyl, thiazepinyl, dihydrothienyl, dihydropyranyl, dihydrofuranyl, tetrahydrofuranyl, tetrahydrothienyl, tetrahydrothienyl 1,1-dioxide, tetrahydrothienyl 1-oxide, tetrahydropyranyl, tetrahydrothiopyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl, dithianyl, dithiolanyl, pyrazolidinylimidazolinyl, imidazolidinyl, 3-azabicyco[3.1.0]hexanyl, 3-azabicyclo[4.1.0]heptanyl and azabicyclo[2.2.2]hexanyl. Examples of a heterocyclyl group wherein a ring atom is substituted with oxo (=O) are pyrimidinonyl and 1,1-dioxo-thiomorpholinyl. The heterocyclyl groups herein are optionally substituted independently with one or more substituents described herein. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

The term "heteroaryl" refers to an aromatic carbocyclic radical in which at least one ring atom is a heteroatom independently selected from nitrogen, oxygen and sulfur, the remaining ring atoms being carbon. Heteroaryl groups may be optionally substituted with one or more substituents described herein. In one example, the heteroaryl group contains 1 to 9 carbon ring atoms ($C_1$-$C_9$). In other examples, the heteroaryl group is $C_1$-$C_5$, $C_3$-$C_5$ or $C_4$-$C_5$. In one embodiment, exemplary heteroaryl groups include monocyclic aromatic 5-, 6- and 7-membered rings containing one or more heteroatoms independently selected from nitrogen, oxygen, and sulfur. In another embodiment, exemplary heteroaryl groups include fused ring systems of up to 9 carbon atoms wherein at least one aromatic ring contains one or more heteroatoms independently selected from nitrogen, oxygen, and sulfur. "Heteroaryl" includes heteroaryl groups fused with an aryl, cycloalkyl or other heterocyclyl group.

Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl and furopyridinyl.

In certain embodiments, the heterocyclyl or heteroaryl group is C-attached. By way of example and not limitation, carbon bonded heterocyclyls include bonding arrangements at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. (2-pyridyl, 3-pyridyl, 4-pyridyl, 5-pyridyl, 6-pyridyl).

In certain embodiments, the heterocyclyl or heteroaryl group is N-attached. By way of example and not limitation, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Treat" and "treatment" includes both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder, (for example, through a genetic mutation) or those in which the condition or disorder is to be prevented.

The phrase "therapeutically effective amount" means an amount of a compound of the present invention that (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In one embodiment, the therapeutic effective amount is an amount sufficient to decrease or alleviate the symptoms of a disorder responsive to the modulation of JAK2 kinase. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). In one embodiment, the therapeutic effective amount is an amount sufficient to decrease or alleviate the symptoms of a disorder responsive to the modulation of JAK1 TYK2 or JAK3 kinase. In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of B-cells.

The term "inhibition" indicates a significant decrease in the baseline activity of a biological activity or process "Inhibition of a JAK kinase activity" refers to a decrease in activity of a JAK1, JAK2, JAK3 or TYK2 kinase as a response to the presence of at least one chemical entity described herein, relative to the activity of the JAK1, JAK2, JAK3 or TYK2 kinase in the absence of the at least one chemical entity. Inhibition of JAK kinase activity also refers to observable inhibition of JAK kinase activity in a biochemical assay for JAK kinase activity, such as the assays described herein.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include Erlotinib (TARCEVA®, Genentech, Inc./OSI Pharm.), Trastuzumab (HERCEPTIN®, Genentech, Inc.); bevacizumab (AVASTIN®, Genentech, Inc.); Rituximab (RITUXAN®, Genentech, Inc./Biogen Idec, Inc.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf and H-Ras; (vii) ribozymes such as VEGF inhibitors (e.g., ANGIOZYME®) and (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents; and (x) pharmaceutically acceptable salts, acids and derivatives of any of the above.

Additional chemotherapeutic agents include therapeutic antibodies such as alemtuzumab (Campath), cetuximab (ERBITUX®, Imclone), panitumumab (VECTIBIX®, Amgen), pertuzumab (OMNITARG®, 2C4, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$λ antibody genetically modified to recognize interleukin-12 p40 protein.

The term "prodrug" as used in this application refers to a precursor or derivative form of a pharmaceutically active substance that is less efficacious to the patient or cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

"Liposome" refers to a vesicle composed of one or more lipids, phospholipids and/or surfactants, which is useful for delivery of a drug (such as a compound of the present invention and, optionally, a chemotherapeutic agent) to a mammal. The components of the liposome can be in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities.

Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of a compound of the present invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

A "solvate" refers to an association or complex of one or more solvent molecules and a compound of the present invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, phthalimido, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include acetyl, trialkylsilyl, dialkylphenylsilyl, benzoyl, benzyl, benzyloxymethyl, methyl, methoxymethyl, triarylmethyl, and tetrahydropyranyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see T. W. Greene and P. Wuts, Protective Groups in Organic Synthesis, Third Ed., John Wiley & Sons, New York, 1999; and P. Kocienski, Protecting Groups, Third Ed., Verlag, 2003.

The term "patient" includes human patients and animal patients. The term "animal" includes companion animals (e.g., dogs, cats and horses), food-source animals, zoo animals, marine animals, birds and other similar animal species.

The phrase "pharmaceutically acceptable" indicates that the substance or composition must be compatible chemically and/or toxicologically, with the other ingredients comprising a formulation, and/or the mammal being treated therewith.

The terms "compound(s) of this invention," and "compound(s) of the present invention", unless otherwise indicated, include compounds of Formula I and Ia, and stereoisomers, tautomers, solvates, metabolites, salts (e.g., pharmaceutically acceptable salts), polymorphs and prodrugs thereof. Unless otherwise stated, structures depicted herein are also meant to include compounds that differ only in the presence of one or more isotopically enriched atoms. For example, compounds of Formulas I and Ia, and formulas 1a-1l, wherein one or more hydrogen atoms are replaced by deuterium or tritium, or one or more carbon atoms are replaced by a $^{13}$C- or $^{14}$C-enriched carbon are within the scope of this invention.

Pyrazolopyrimidine JAK Inhibitor Compounds

In one embodiment, a compound of Formula Ia, and pharmaceutical formulations thereof, are provided that are useful in the treatment of diseases, conditions and/or disorders responsive to the inhibition of JAK kinases.

In one embodiment, a compound of Formula I, and pharmaceutical formulations thereof, are provided that are useful in the treatment of diseases, conditions and/or disorders responsive to the inhibition of JAK kinases.

Another embodiment includes compounds of Formula Ia:

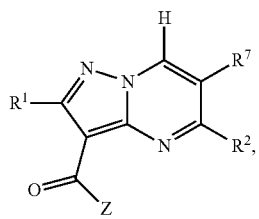

Ia enantiomers, diastereomers or pharmaceutically acceptable salts thereof, wherein:

$R^1$ is H;

$R^2$ is —$OR^4$, —$NR^3R^4$, —$NR^3NR^{12}R^4$, —$NR^3S(O)R^4$ or —$NR^3S(O)_2R^4$;

$R^3$ is H or $C_1$-$C_6$ alkyl, $C_2$-$C_6$ alkenyl, $C_2$-$C_6$ alkynyl, wherein said alkyl, alkenyl and alkynyl are optionally substituted by oxo, F, $OR^a$ or $NR^aR^b$;

$R^4$ is H, $C_1$-$C_6$ alkyl, $C_2$-$C_6$ alkenyl, $C_2$-$C_6$ alkynyl, —($C_0$-$C_5$ alkyl)($C_1$-$C_9$ heterocyclyl), —($C_0$-$C_5$ alkyl)($C_3$-$C_6$ cycloalkyl), —($C_0$-$C_5$ alkyl)($C_1$-$C_9$ heteroaryl), —($C_0$-$C_5$ alkyl)($C_6$-$C_{10}$ aryl), wherein said alkyl, alkenyl and alkynyl are optionally substituted by $R^8$, and said aryl, cycloalkyl, heteroaryl and heterocyclyl are optionally substituted by $R^9$; or $R^3$ and $R^4$ are taken together with the nitrogen to which they are attached to form a $C_1$-$C_9$ heterocyclyl optionally substituted by $R^{13}$;

Z is —$OR^6$ or —$NR^5R^6$;

$R^5$ is H or $C_1$-$C_3$ alkyl;

$R^6$ is H, $C_1$-$C_{10}$ alkyl, $C_2$-$C_{10}$ alkenyl, $C_2$-$C_{10}$ alkynyl, —($C_0$-$C_5$ alkyl)($C_1$-$C_9$ heterocyclyl), —($C_0$-$C_5$ alkyl)($C_3$-$C_8$ cycloalkyl), —($C_0$-$C_5$ alkyl)($C_1$-$C_9$ heteroaryl), —($C_0$-$C_5$ alkyl)($C_6$-$C_9$ aryl), wherein said alkyl, alkenyl and alkynyl are optionally substituted by $R^{10}$, and said aryl, cycloalkyl, heteroaryl and heterocyclyl are optionally substituted by $R^{11}$;

$R^7$ is H, halo, $C_1$-$C_3$ alkyl, $C_2$-$C_3$ alkenyl, $C_2$-$C_3$ alkynyl or —O($C_1$-$C_3$ alkyl);

$R^8$ is independently oxo, F, $OR^a$ or $NR^aR^b$;

$R^9$ is independently oxo, —CN, —$CF_3$, halo, —C(O)$C_1$-$C_6$ alkyl, —C(O)$OR^a$, —C(O)$NR^aR^b$, —($C_0$-$C_5$ alkyl)$NR^aR^b$, —($C_0$-$C_5$ alkyl)$OR^a$, —($C_0$-$C_5$ alkyl)$SR^a$, —O[C($R^a$)$_2$]$_{1-3}$O—, $C_1$-$C_3$ alkyl optionally substituted by oxo or F, —($C_0$-$C_5$ alkyl)$C_1$-$C_9$ heterocyclyl optionally substituted by halo, oxo, $C_1$-$C_3$ alkyl or C(O)$C_1$-$C_3$ alkyl, —($C_0$-$C_5$ alkyl)$C_6$ aryl optionally substituted by halo or $C_1$-$C_3$ alkyl —O($C_1$-$C_3$ alkyl), or —($C_0$-$C_5$ alkyl)$C_1$-$C_9$ heteroaryl optionally substituted by halo or $C_1$-$C_3$ alkyl;

$R^{10}$ is independently oxo, F, $OR^a$ or $NR^aR^b$;

$R^{11}$ is independently oxo, —CN, —$CF_3$, halo, —O[C($R^a$)$_2$]$_{1-3}$O—, —C(O)$C_1$-$C_6$ alkyl, —C(O)$OR^a$, —C(O)$NR^aR^b$, —($C_0$-$C_5$ alkyl)$NR^aR^b$, —($C_0$-$C_5$ alkyl)$OR^a$, $C_1$-$C_6$ alkyl optionally substituted by oxo or F, —($C_0$-$C_5$ alkyl)$C_1$-$C_9$ heterocyclyl optionally substituted by halo, oxo, $C_1$-$C_3$ alkyl or C(O)$C_1$-$C_3$ alkyl, —($C_0$-$C_5$ alkyl)$C_1$-$C_9$ heteroaryl optionally substituted by halo or $C_1$-$C_3$ alkyl, —($C_0$-$C_5$ alkyl) phenyl optionally substituted by $C_1$-$C_3$ alkyl, —$CF_3$, halo, —CN, —$OR^a$ or —$NR^aR^b$, or —($C_0$-$C_5$ alkyl)$C_3$-$C_6$ cycloalkyl optionally substituted by oxo, —$NR^cR^d$, $C_1$-$C_3$ alkyl or F;

$R^{12}$ is H or $C_1$-$C_3$ alkyl;

$R^{13}$ is oxo, halo, $C_1$-$C_3$ alkyl, —C(O)$C_1$-$C_6$ alkyl, —C(O)$OR^a$, $C_6$ aryl, $C_3$-$C_6$ cycloalkyl, $C_1$-$C_5$ heteroaryl or $C_4$-$C_5$ heterocyclyl; wherein said aryl, cycloalkyl, heteroaryl and heterocyclyl are optionally substituted by $C_1$-$C_4$ alkyl, —($C_0$-$C_3$ alkyl)$OR^c$, oxo, halo or $NR^cR^d$;

$R^a$ and $R^b$ are independently H, —$CF_3$, —$CHF_2$, —$CH_2F$, $C_1$-$C_6$ alkyl, $C_6$ aryl, $C_3$-$C_6$ cycloalkyl or $C_4$-$C_5$ heterocyclyl; wherein said alkyl, aryl and cycloalkyl are optionally substituted by $C_1$-$C_4$ alkyl, —($C_0$-$C_3$ alkyl)$OR^c$, oxo, halo, $NR^cR^d$ or $C_4$-$C_5$ heterocyclyl; or $R^a$ and $R^b$ together with the atom to which they are attached form a $C_1$-$C_5$ heterocyclyl optionally substituted by oxo, F, $C_1$-$C_3$ alkyl, —C(O)$C_1$-$C_6$ alkyl or —C(O)$OR^a$; and $R^c$ and $R^d$ are independently H, $C_1$-$C_3$ alkyl, $C_3$-$C_6$ cycloalkyl or phenyl, wherein said alkyl, cycloalkyl and phenyl are optionally substituted by halo, $CH_3$, OH, $NH_2$, C(O)O($C_1$-$C_6$ alkyl) or C(O)NH($C_1$-$C_6$ alkyl).

Another embodiment includes compounds of Formula I:

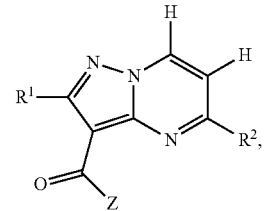

I enantiomers, diastereomers or pharmaceutically acceptable salts thereof, wherein:

$R^1$ is H;

$R^2$ is —$OR^4$ or —$NR^3R^4$;

$R^3$ is H or $C_1$-$C_6$ alkyl, $C_2$-$C_6$ alkenyl, $C_2$-$C_6$ alkynyl, wherein said alkyl, alkenyl and alkynyl are optionally substituted by oxo, F, $OR^a$ or $NR^aR^b$;

$R^4$ is H, $C_1$-$C_6$ alkyl, $C_2$-$C_6$ alkenyl, $C_2$-$C_6$ alkynyl, —($C_0$-$C_5$ alkyl)($C_1$-$C_9$ heterocyclyl), —($C_0$-$C_5$ alkyl)($C_3$-$C_6$ cycloalkyl), —($C_0$-$C_5$ alkyl)($C_1$-$C_9$ heteroaryl), —($C_0$-$C_5$ alkyl)($C_6$-$C_9$ aryl), wherein said alkyl, alkenyl and alkynyl are optionally substituted by oxo, F, $OR^a$ or $NR^aR^b$, and said aryl, cycloalkyl, heteroaryl and heterocyclyl are optionally substituted by oxo, —CN, —CF$_3$, halo, —C(O)C$_1$-C$_6$ alkyl, —C(O)OR$^a$, —C(O)NR$^a$R$^b$, —(C$_0$-C$_5$ alkyl)NR$^a$R$^b$, —(C$_0$-C$_5$ alkyl)OR$^a$, —O[C(R$^a$)$_2$]$_{1-3}$O—, C$_1$-C$_3$ alkyl optionally substituted by oxo or F, —(C$_0$-C$_5$ alkyl)C$_1$-C$_9$ heterocyclyl optionally substituted by halo, oxo, C$_1$-C$_3$ alkyl or C(O)C$_1$-C$_3$ alkyl, or —(C$_0$-C$_5$ alkyl)C$_1$-C$_9$ heteroaryl optionally substituted by halo or C$_1$-C$_3$ alkyl;

R$^3$ and R$^4$ are taken together with the nitrogen to which they are attached to form a C$_1$-C$_5$ heterocyclyl optionally substituted by oxo, F, C$_1$-C$_3$ alkyl, —C(O)C$_1$-C$_6$ alkyl or —C(O)OR$^a$;

R$^3$ and R$^4$ are taken together with the nitrogen to which they are attached to form a C$_1$-C$_5$ heterocyclyl optionally substituted by oxo, F, C$_1$-C$_3$ alkyl, —C(O)C$_1$-C$_6$ alkyl or —C(O)OR$^a$;

Z is —OR$^6$ or —NR$^5$R$^6$;

R$^5$ is H or C$_1$-C$_3$ alkyl;

R$^6$ is H, C$_1$-C$_{10}$ alkyl, C$_2$-C$_{10}$ alkenyl, C$_2$-C$_{10}$ alkynyl, —(C$_0$-C$_5$ alkyl)(C$_1$-C$_9$ heterocyclyl), —(C$_0$-C$_5$ alkyl)(C$_3$-C$_8$ cycloalkyl), —(C$_0$-C$_5$ alkyl)(C$_1$-C$_9$ heteroaryl), —(C$_0$-C$_5$ alkyl)(C$_6$-C$_9$ aryl), wherein said alkyl, alkenyl and alkynyl are optionally substituted by oxo, F, OR$^a$ or NR$^a$R$^b$, and said aryl, cycloalkyl, heteroaryl and heterocyclyl are optionally substituted by oxo, —CN, —CF$_3$, halo, —O[C(R$^a$)$_2$]$_{1-3}$O—, —C(O)C$_1$-C$_6$ alkyl, —C(O)OR$^a$, —C(O)NR$^a$R$^b$, —(C$_0$-C$_5$ alkyl)NR$^a$R$^b$, —(C$_0$-C$_5$ alkyl)OR$^a$, C$_1$-C$_6$ alkyl optionally substituted by oxo or F, —(C$_0$-C$_5$ alkyl)C$_1$-C$_9$ heterocyclyl optionally substituted by halo, oxo, C$_1$-C$_3$ alkyl or C(O)C$_1$-C$_3$ alkyl, —(C$_0$-C$_5$ alkyl)C$_1$-C$_9$ heteroaryl optionally substituted by halo or C$_1$-C$_3$ alkyl, —(C$_0$-C$_5$ alkyl)phenyl optionally substituted by C$_1$-C$_3$ alkyl, —CF$_3$, halo, —CN, —OR$^a$ or —NR$^a$R$^b$, or —(C$_0$-C$_5$ alkyl)C$_3$-C$_6$ cycloalkyl optionally substituted by oxo, —NR$^c$R$^d$, C$_1$-C$_3$ alkyl or F;

R$^a$ and R$^b$ are independently H, —CF$_3$, —CHF$_2$, —CH$_2$F, C$_1$-C$_6$ alkyl, C$_6$ aryl, C$_3$-C$_6$ cycloalkyl or C$_4$-C$_5$ heterocyclyl; wherein said alkyl, aryl and cycloalkyl are optionally substituted by C$_1$-C$_4$ alkyl, (C$_0$-C$_3$ alkyl)OR$^c$, oxo, halo, NR$^c$R$^d$ or C$_4$-C$_5$ heterocyclyl; or R$^a$ and R$^b$ together with the atom to which they are attached form a C$_1$-C$_5$ heterocyclyl optionally substituted by oxo, F, C$_1$-C$_3$ alkyl, —C(O)C$_1$-C$_6$ alkyl or —C(O)OR$^a$; and R$^c$ and R$^d$ are independently H, C$_1$-C$_3$ alkyl, C$_3$-C$_6$ cycloalkyl or phenyl, wherein said alkyl, cycloalkyl and phenyl are optionally substituted by halo, CH$_3$ OH or NH$_2$, C(O) O(C$_1$-C$_6$ alkyl) or C(O)NH(C$_1$-C$_6$ alkyl).

In one embodiment, R$^2$ is —NR$^3$R$^4$, —NR$^3$NR$^{12}$R$^4$, —NR$^3$S(O)R$^4$ or —NR$^3$S(O)$_2$R$^4$. In another embodiment, R$^2$ is —NR$^3$R$^4$, —NR$^3$NR$^{12}$R$^4$ or —NR$^3$S(O)$_2$R$^4$. In another embodiment, R$^2$ is —NR$^3$S(O)$_2$R$^4$. In another embodiment, R$^2$ is —NR$^3$NR$^{12}$R$^4$. In one embodiment, R$^2$ is —NR$^3$R$^4$. In one embodiment, R$^2$ is —NHR$^4$.

In one embodiment of Formula I, R$^2$ is —NR$^3$R$^4$.
In one embodiment of Formula I, R$^2$ is —NHR$^4$.
In one embodiment of Formula I, R$^2$ is —OR$^4$.
In one embodiment of Formula I, R$^2$ is —NR$^3$R$^4$, and R$^3$ is H or C$_1$-C$_4$ alkyl optionally substituted by OH.
In one embodiment of Formula I, R$^4$ is H or C$_1$-C$_4$ alkyl optionally substituted by OH.
In one embodiment of Formula I, R$^4$ is H, methyl, ethyl, i-propyl or —CH$_2$CH$_2$OH.
In one embodiment of Formula I, R$^2$ is —NR$^3$R$^4$, and R$^3$ and R$^4$ are H.

In one embodiment of Formula I, R$^4$ is C$_1$-C$_6$ alkyl, —(C$_0$-C$_3$ alkyl)phenyl, (C$_0$-C$_3$ alkyl)(C$_3$-C$_5$ heterocyclyl), —(C$_0$-C$_3$ alkyl)(C$_6$-C$_7$ cycloalkyl), —(C$_0$-C$_3$ alkyl)(C$_3$-C$_5$ heteroaryl), wherein said alkyl is optionally substituted by oxo, F, OR$^a$ or NR$^a$R$^b$, and said phenyl, cycloalkyl, heteroaryl and heterocyclyl are optionally substituted by C$_1$-C$_3$ alkyl optionally substituted by F, —O[C(R$^a$)$_2$]$_{1-3}$O—, —CF$_3$, —OCF$_3$, —OCHF$_2$, halo, —C(O)C$_1$-C$_6$ alkyl, —C(O)OR$^a$, —C(O)NR$^a$R$^b$, —(C$_0$-C$_5$ alkyl)NR$^a$R$^b$, —(C$_0$-C$_5$ alkyl)OR$^a$, —(C$_0$-C$_3$ alkyl)C$_3$-C$_5$ heterocyclyl optionally substituted by halo, oxo, C$_1$-C$_3$ alkyl or C(O)C$_1$-C$_6$ alkyl, or —(C$_0$-C$_3$ alkyl)C$_3$-C$_5$ heteroaryl optionally substituted by halo or C$_1$-C$_3$ alkyl.

In one embodiment, R$^4$ is C$_1$-C$_6$ alkyl, —(C$_0$-C$_5$ alkyl)(C$_1$-C$_9$ heterocyclyl), —(C$_0$-C$_5$ alkyl)(C$_3$-C$_6$ cycloalkyl), —(C$_0$-C$_5$ alkyl)(C$_1$-C$_9$ heteroaryl), —(C$_0$-C$_5$ alkyl)(C$_6$-C$_{10}$ aryl), wherein said alkyl is optionally substituted by R$^8$, and said aryl, cycloalkyl, heteroaryl and heterocyclyl are optionally substituted by R$^9$.

In another embodiment, R$^3$ and R$^4$ are taken together with the nitrogen to which they are attached to form a C$_1$-C$_5$ heterocyclyl optionally substituted by R$^{13}$.

In one embodiment of Formula I, R$^3$ and R$^4$ are taken together with the nitrogen to which they are attached to form a C$_4$-C$_5$ heterocyclyl optionally substituted by oxo, F, C$_1$-C$_3$ alkyl, —C(O)C$_1$-C$_6$ alkyl or —C(O)OR$^a$.

In one embodiment of Formula I, R$^4$ is phenyl, —(CH$_2$)phenyl, —(CH$_2$CH$_2$)phenyl, —CH(CH$_3$)phenyl, —C(CH$_3$)$_2$phenyl, —(C$_0$-C$_3$ alkyl)C$_4$-C$_5$ heterocyclyl or —(C$_0$-C$_3$ alkyl)C$_3$-C$_5$ heteroaryl, wherein said phenyl is optionally substituted by 1 or 2 substituents independently selected from methyl, ethyl, i-propyl, F, Cl, —OCH$_2$O—, —OCH$_2$CH$_2$O—, —OCH$_2$CH$_2$CH$_2$O—, —OCH$_2$CH$_2$NH$_2$, —OCH$_2$CH$_2$NMe$_2$, —OCH$_2$(C$_4$-C$_5$ heterocyclyl), —OH, —OCH$_3$, —OCH$_2$CH$_3$, —CF$_3$, —OCF$_3$ and —OCHF$_2$, said heterocyclyl is selected from tetrahydropyranyl, tetrahydrofuranyl, pyrrolidinyl, morpholinyl, piperazinyl and piperidinyl, said heterocyclyl is optionally substituted by halo, methyl or C(O)O(t-butyl), said heteroaryl is selected from pyrazolyl, imidazolyl, furanyl and thienyl, and said heteroaryl is optionally substituted by halo or methyl.

In one embodiment, R$^4$ is —(C$_0$-C$_5$ alkyl)(C$_6$-C$_{10}$ aryl) optionally substituted by R$^9$. In one example, R$^4$ is —(C$_0$-C$_5$ alkyl)(C$_6$-C$_{10}$ aryl) optionally substituted by (C$_1$-C$_3$ alkyl) or halo, and said aryl is phenyl, naphthalenyl, indenyl, indanyl, 1,2-dihydronapthalenyl and 1,2,3,4-tetrahydronaphthyl. In another example, R$^4$ is selected from:

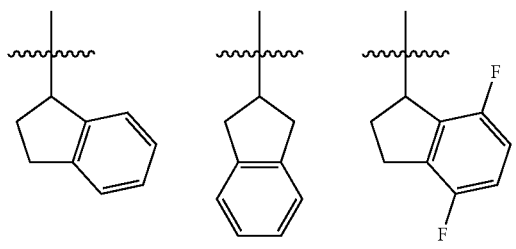

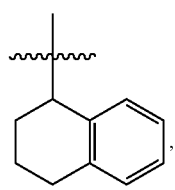

wherein the wavy lines represent the point of attachment of R⁴ in the compound of the invention.

In one embodiment, R⁴ is phenyl, —(CH₂)phenyl, —(CH₂CH₂)phenyl, —CH(CH₃)phenyl, —CH(CH₂CH₃)phenyl, —(R)—CH(CH₃)phenyl, —(S)—CH(CH₃)phenyl, —(R)—CH(CH₂CH₃)phenyl, —(S)—CH(CH₂CH₃)phenyl or —C(CH₃)₂phenyl, wherein said phenyl is optionally substituted by R⁹. In one example, said phenyl is optionally substituted by 1 or 2 R⁹, wherein R⁹ is independently selected from methyl, ethyl, i-propyl, cyclopropyl, F, Cl, —OCH₂O—, —OCH₂CH₂O—, —OCH₂CH₂CH₂O—, —OCH₂CH₂NH₂, —OCH₂CH₂NMe₂, —OCH₂)₁₋₃(C₄-C₅ heterocyclyl), C₃-C₅ heteroaryl, —(CH₂)₀₋₃C₃-C₅ heterocyclyl optionally substituted by C₁-C₃ alkyl or halo, —OH, —OCH₃, —OCH₂CH₃, —SH, —SCH₃, —SCH₂CH₃, —N(CH₃)₂—N(CH₂CH₃)₂, —CN, —CF₃, —OCF₃, —OCHF₂ and C(O)O(C₁-C₃ alkyl). In another example, R⁴ is selected from:

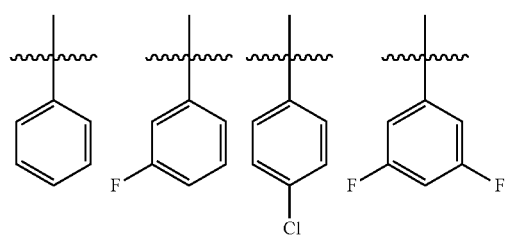

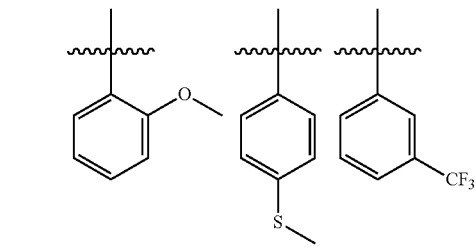

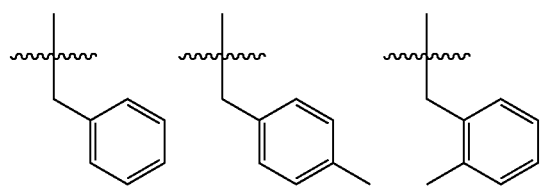

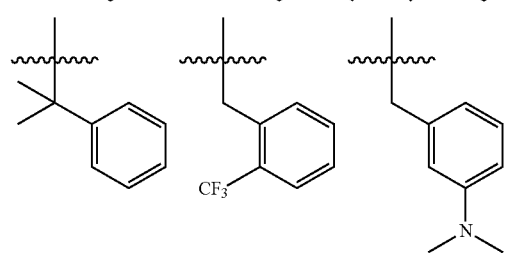

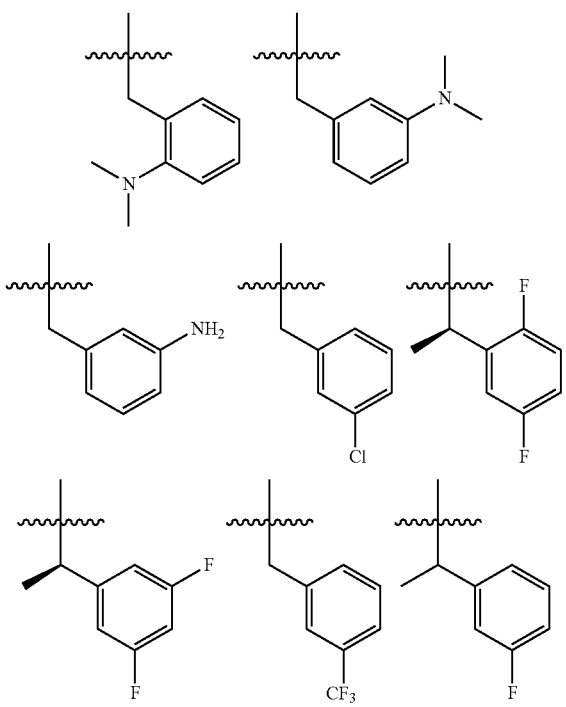

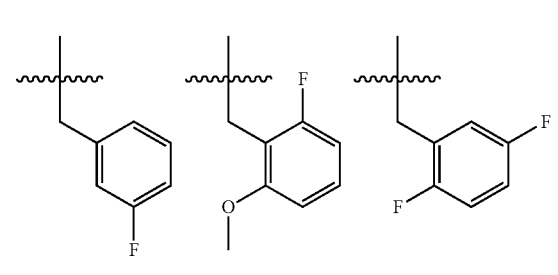

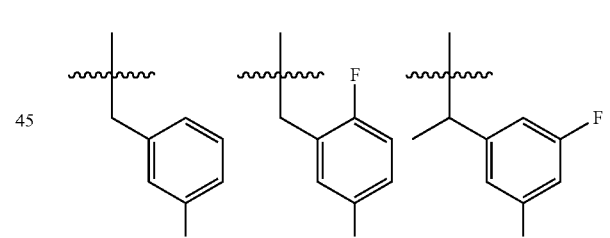

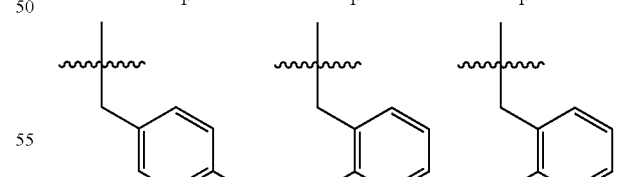

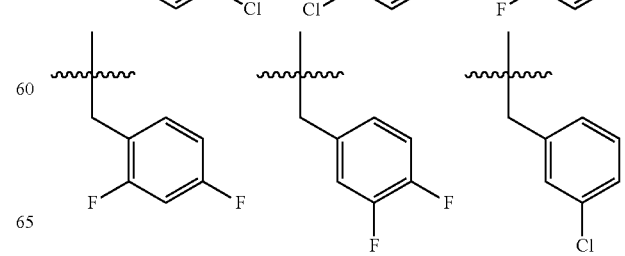

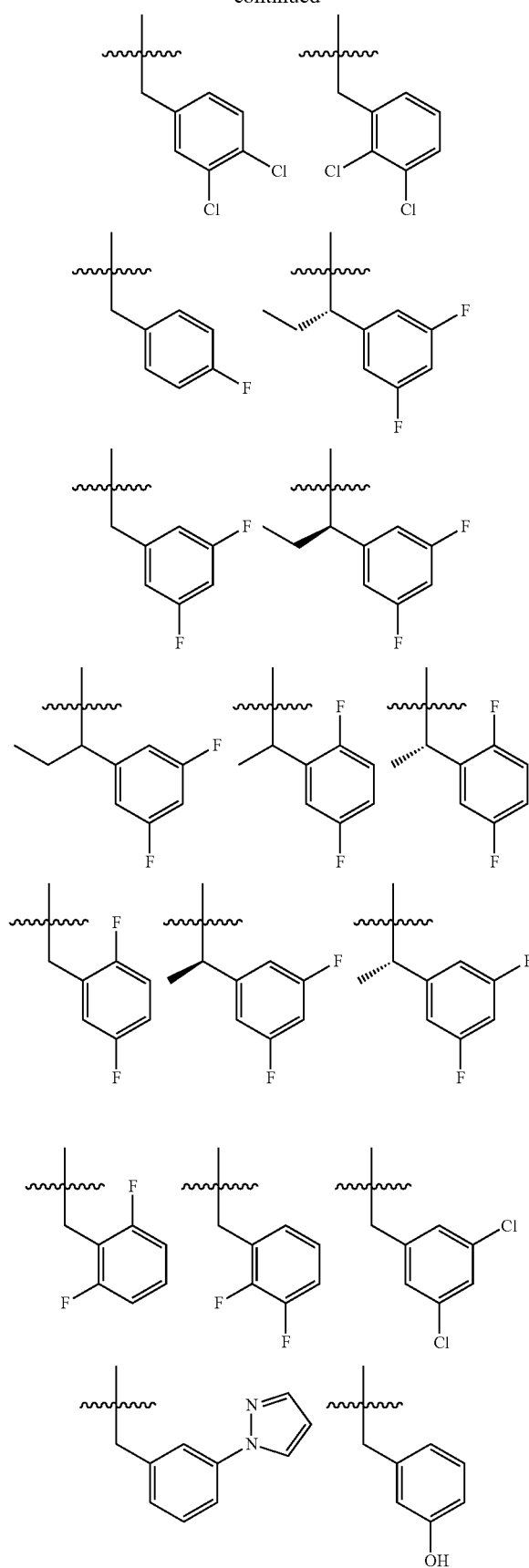

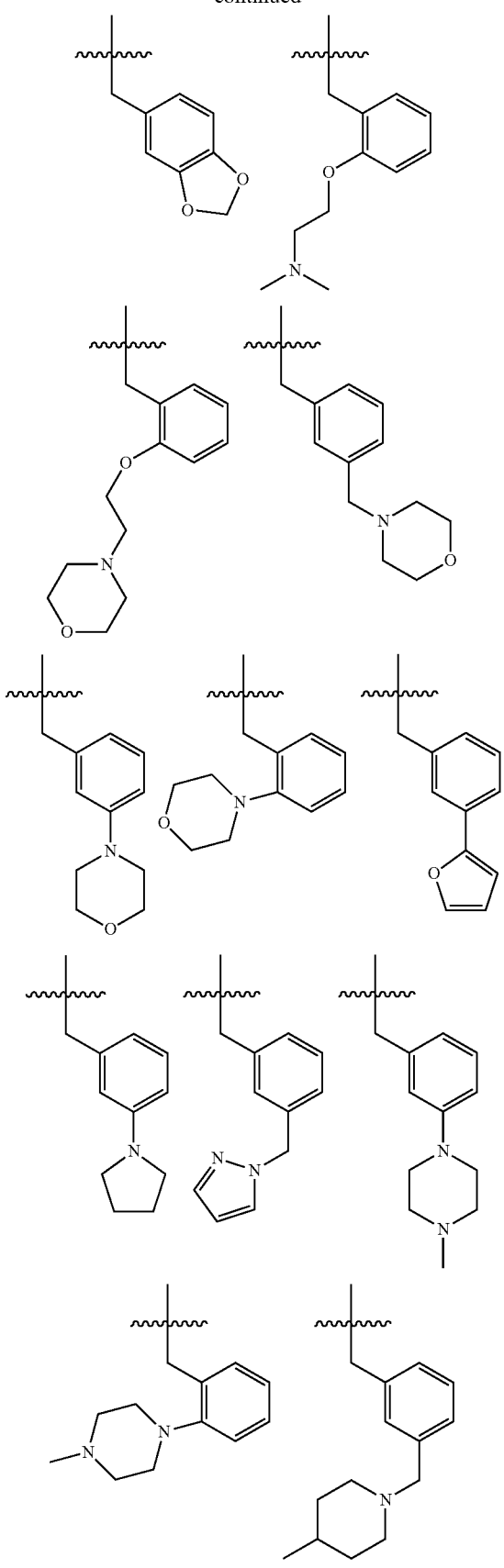
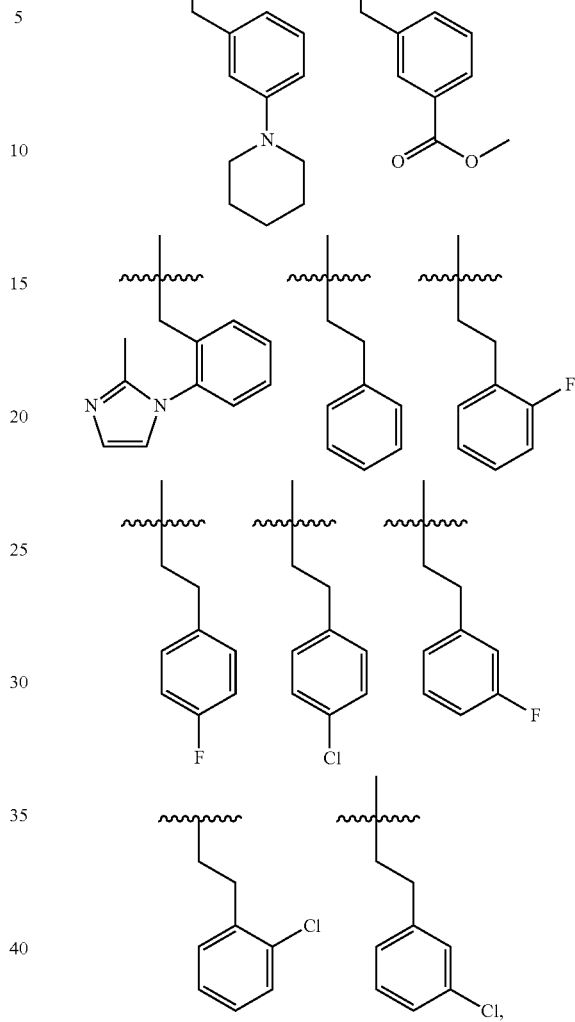

wherein the wavy lines represent the point of attachment of R⁴.

In another embodiment, R⁴ is —(C₀-C₅ alkyl)(C₁-C₉ heterocyclyl) or —(C₀-C₅ alkyl)(C₁-C₉ heteroaryl), wherein said heteroaryl and heterocyclyl are optionally substituted by R⁹. In one example, R⁴ is pyridinyl, —(CH₂)pyridinyl, —(CH₂CH₂)pyridinyl, —CH(CH₃)pyridinyl, pyrimidinyl, —(CH₂)pyrimidinyl, imidazolyl, —(CH₂)imidazolyl, pyrazolyl, —(CH₂)pyrazolyl, tetrahydropyranyl, tetrahydrofuranyl, pyrrolidinyl, morpholinyl, piperazinyl or piperidinyl optionally substituted by R⁹. In one example, R⁹ is methyl, ethyl, i-propyl, F, Cl, —NH₂, —NMe₂, —OCH₃, —OH, —OCH₂CH₃, —CF₃, —OCF₃ —OCHF₂, C(O)O(t-butyl) or phenyl. In another example, R⁴ is selected from:

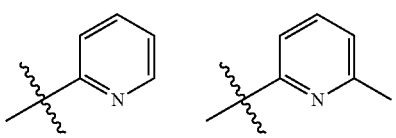

-continued

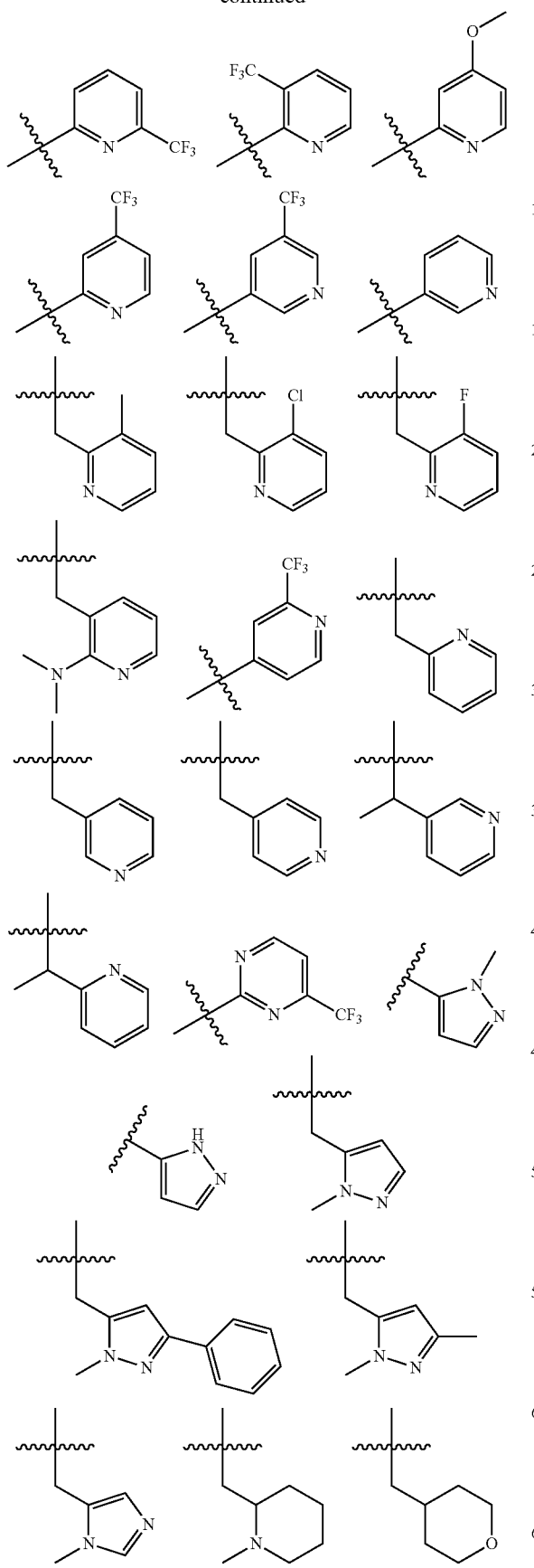

wherein the wavy lines represent the point of attachment of $R^4$.

In one embodiment of Formula I, $R^4$ is $C_4$-$C_5$ heterocyclyl or —$(CH_2)C_4$-$C_5$ heterocyclyl, wherein said heterocyclyl is tetrahydropyranyl, tetrahydrofuranyl, pyrrolidinyl, piperazinyl, piperidinyl or morpholinyl optionally substituted by methyl or C(O)O(t-butyl).

In one embodiment of Formula I, $R^3$ and $R^4$ are taken together with the nitrogen to which they are attached to form a pyrrolidinyl, piperazinyl, piperidinyl or morpholinyl optionally substituted by methyl.

In one embodiment, $R^3$ and $R^4$ are taken together with the nitrogen to which they are attached to form azetidinyl optionally substituted by $R^{13}$. In another embodiment, $R^3$ and $R^4$ are taken together with the nitrogen to which they are attached to form azetidinyl optionally substituted by phenyl.

In one embodiment of Formula I, $R^4$ is pyridinyl or —$(CH_2)$pyridinyl, wherein said pyridinyl is optionally substituted by methyl, F or Cl.

In one embodiment, $R^4$ is cyclopropyl, cyclobuytl, cyclopentyl, cyclohexyl, cycloheptyl, —$(CH_2)$cyclopropyl, —$(CH_2)$cyclobutyl, —$(CH_2)$cyclopentyl, —$(CH_2)$cyclohexyl, —$(CH_2)$cycloheptyl, indanyl or tetrahydronaphthalenyl and said $R^4$ is independently optionally substituted by $R^9$.

In one example, $R^9$ is F, oxo, methyl or $CH_2NH_2$.

In one embodiment of Formula I, $R^4$ is cyclohexyl, cycloheptyl, —$(CH_2)$cyclohexyl or —$(CH_2)$cycloheptyl and said cyclohexyl and cycloheptyl are independently optionally substituted by oxo, methyl or $CH_2NH_2$.

In one embodiment, Z is —$NR^5R^6$. In one embodiment, Z is —$NR^5R^6$, and $R^5$ is H. In one embodiment, Z is —$NR^5R^6$, $R^5$ is H and $R^6$ is H.

In one embodiment of Formula I, Z is —NR$^5$R$^6$.

In one embodiment of Formula I, Z is —OR$^6$.

In one embodiment of Formula I, Z is —NR$^5$R$^6$, and R$^5$ is H.

In one embodiment, R$^6$ is C$_1$-C$_{10}$ alkyl, —(C$_0$-C$_5$ alkyl)(C$_1$-C$_9$ heterocyclyl), —(C$_0$-C$_5$ alkyl)(C$_3$-C$_8$ cycloalkyl), —(C$_0$-C$_5$ alkyl)(C$_1$-C$_9$ heteroaryl), —(C$_0$-C$_5$ alkyl)(C$_6$-C$_9$ aryl), wherein alkyl is optionally substituted by R$^{10}$, and wherein aryl, cycloalkyl, heteroaryl and heterocyclyl are optionally substituted by R$^{11}$.

In one embodiment of Formula I, R$^6$ is C$_1$-C$_8$ alkyl, —(C$_0$-C$_3$ alkyl)(C$_3$-C$_5$ heterocyclyl), —(C$_0$-C$_3$ alkyl)(C$_3$-C$_8$ cycloalkyl), —(C$_0$-C$_3$ alkyl)(C$_3$-C$_5$ heteroaryl) or —(C$_0$-C$_1$ alkyl)(phenyl), wherein said alkyl is optionally substituted by oxo, F, OR$^a$ or NR$^a$R$^b$, and said phenyl, cycloalkyl, heteroaryl and heterocyclyl are optionally substituted by oxo, —CN, —CF$_3$, halo, —C(O)C$_1$-C$_6$ alkyl, —C(O)OR$^a$, —C(O)NR$^a$R$^b$, —(C$_0$-C$_5$ alkyl)NR$^a$R$^b$, —(C$_0$-C$_5$ alkyl)OR$^a$, C$_1$-C$_6$ alkyl optionally substituted by oxo or F, —(C$_0$-C$_2$ alkyl)C$_3$-C$_5$ heterocyclyl optionally substituted by halo, oxo, C$_1$-C$_3$ alkyl or C(O)C$_1$-C$_3$ alkyl, —(C$_0$-C$_2$ alkyl)C$_3$-C$_5$ heteroaryl optionally substituted by halo or C$_1$-C$_3$ alkyl, —(C$_0$-C$_2$ alkyl)phenyl optionally substituted by C$_1$-C$_3$ alkyl, —CF$_3$, halo, —CN, —OR$^a$ or —NR$^a$R$^b$, or —(C$_0$-C$_2$ alkyl)C$_6$-C$_8$ cycloalkyl optionally substituted by oxo, —NR$^c$R$^d$, C$_1$-C$_3$ alkyl or F.

In one embodiment, R$^6$ is C$_1$-C$_8$ alkyl, optionally substituted by R$^{10}$. In one embodiment, R$^6$ is methyl, ethyl, i-propyl, n-butyl, s-butyl, t-butyl, 3,3-dimethylbut-1-yl, pent-3-yl, octyl, —C(CH$_2$)$_2$CH$_2$OH, —CH$_2$CH$_2$OH or —CH$_2$CH$_2$OCH$_3$.

In one embodiment of Formula I, R$^6$ is C$_1$-C$_8$ alkyl, optionally substituted by oxo, F, OR$^a$ or NR$^a$R$^b$.

In one embodiment of Formula I, R$^6$ is methyl, ethyl, i-propyl, n-butyl, s-butyl, t-butyl, 3,3-dimethylbut-1-yl, pent-3-yl, octyl, —C(CH$_2$)$_2$CH$_2$OH, —CH$_2$CH$_2$OH or —CH$_2$CH$_2$OCH$_3$.

In one embodiment, R$^6$ is C$_3$-C$_5$ heterocyclyl or —(CH$_2$)C$_3$-C$_5$ heterocyclyl optionally substituted by R$^{11}$. In another embodiment, R$^6$ is C$_3$-C$_5$ heterocyclyl or —(CH$_2$)C$_3$-C$_5$ heterocyclyl optionally substituted by R$^{11}$, wherein said heterocyclyl is tetrahydrofuranyl, tetrahydropyranyl, piperazinyl, piperidinyl, morpholinyl, pyrazolyl, imidazolyl, oxazolyl, isoxazolyl, thiazolyl, isothiazolyl, pyridinyl, and wherein said R$^{11}$ is independently oxo, —CN, —CF$_3$, halo, —C(O)C$_1$-C$_6$ alkyl, —C(O)OR$^a$, —C(O)NR$^a$R$^b$, —(C$_0$-C$_5$ alkyl)NR$^a$R$^b$, —(C$_0$-C$_5$ alkyl)OR$^a$, C$_1$-C$_6$ alkyl optionally substituted by oxo or F, —(C$_0$-C$_5$ alkyl)C$_1$-C$_9$ heterocyclyl optionally substituted by halo, oxo, C$_1$-C$_3$ alkyl or C(O)C$_1$-C$_3$ alkyl, —(C$_0$-C$_5$ alkyl)C$_1$-C$_9$ heteroaryl optionally substituted by halo or C$_1$-C$_3$ alkyl, —(C$_0$-C$_5$ alkyl)phenyl optionally substituted by C$_1$-C$_3$ alkyl, —CF$_3$, halo, —CN, —OR$^a$ or —NR$^a$R$^b$, or —(C$_0$-C$_5$ alkyl)C$_3$-C$_6$ cycloalkyl optionally substituted by oxo, —NR$^c$R$^d$, C$_1$-C$_3$ alkyl or F. In one example, R$^6$ is C$_3$-C$_5$ heteroaryl optionally substituted by 1-4 R$^{11}$. In another example, R$^6$ is C$_3$-C$_5$ heteroaryl, wherein said heteroaryl is substituted with phenyl optionally substituted by C$_1$-C$_3$ alkyl, —CF$_3$, halo, —CN, —OR$^a$ or —NR$^a$R$^b$, and wherein said heteroaryl is further optionally substituted by 1-2 R$^{11}$ independently selected from halo, —CF$_3$ or C$_1$-C$_6$ alkyl optionally substituted by oxo or F In one embodiment of Formula I, R$^6$ is C$_3$-C$_5$ heterocyclyl or —(CH$_2$)C$_3$-C$_5$ heterocyclyl, wherein said heterocyclyl is tetrahydrofuranyl, piperazinyl, piperidinyl or morpholinyl optionally substituted by methyl, ethyl or C(O)Ot-butyl.

In one embodiment of Formula I, R$^6$ is —(C$_0$-C$_2$ alkyl)C$_3$-C$_8$ cycloalkyl, wherein said cycloalkyl is optionally substituted by C$_1$-C$_6$ alkyl, C(O)OCH$_3$, C(O)OH, OH, CN, C(O)cyclohexyl, C(O)(C$_4$-C$_5$ heterocyclyl) or —CH$_2$cyclohexyl optionally substituted by NH$_2$, and wherein said heterocyclyl is selected from piperazinyl, piperidinyl or morpholinyl, and said heterocyclyl is optionally substituted by methyl or CH$_2$NH$_2$.

In one embodiment, R$^6$ is cyclopropyl, cyclobutyl, cyclopentyl, cyclohexyl, cycloheptyl, cyclooctyl, —(CH$_2$)cyclohexyl, —(CH$_2$CH$_2$)cyclohexyl, —(CH$_2$)cycloheptyl, bicyclo[2.2.1]heptyl or —(CH$_2$)bicyclo[2.2.1]heptyl, and wherein R$^6$ is optionally substituted by 1 to 3 substituents selected from oxo, halo, C$_1$-C$_6$ alkyl, C(O)OCH$_3$, C(O)OH, OH, CN, C(O)cyclohexyl, C(O)(C$_4$-C$_5$ heterocyclyl) and —CH$_2$cyclohexyl optionally substituted by NH$_2$, and wherein said heterocyclyl is selected from piperazinyl, piperidinyl or morpholinyl, and said heterocyclyl is optionally substituted by methyl or CH$_2$NH$_2$.

In one embodiment of Formula I, R$^6$ is cyclopropyl, cyclobutyl, cyclopentyl, cyclohexyl, cycloheptyl, cyclooctyl, —(CH$_2$)cyclohexyl, —(CH$_2$CH$_2$)cyclohexyl, —(CH$_2$)cycloheptyl, bicyclo[2.2.1]heptyl or —(CH$_2$)bicyclo[2.2.1]heptyl, and wherein R$^6$ is optionally substituted by 1 to 3 C$_1$-C$_6$ alkyl, C(O)OCH$_3$, C(O)OH, OH, CN, C(O)cyclohexyl, C(O)(C$_4$-C$_5$ heterocyclyl) or —CH$_2$cyclohexyl optionally substituted by NH$_2$, and wherein said heterocyclyl is selected from piperazinyl, piperidinyl or morpholinyl, and said heterocyclyl is optionally substituted by methyl or CH$_2$NH$_2$.

In one embodiment, R$^6$ is C$_3$-C$_5$ heteroaryl or —(CH$_2$)C$_3$-C$_5$ heteroaryl, and wherein R$^6$ is optionally substituted by R$^{11}$.

In one embodiment of Formula I, R$^6$ is C$_3$-C$_5$ heteroaryl or —(CH$_2$)C$_3$-C$_5$ heteroaryl, and wherein R$^6$ is optionally substituted by one or more substituents selected from oxo, —CN, —CF$_3$, halo, —C(O)C$_1$-C$_6$ alkyl, —C(O)OR$^a$, —C(O)NR$^a$R$^b$, —(C$_0$-C$_5$ alkyl)NR$^a$R$^b$, —(C$_0$-C$_5$ alkyl)OR$^a$, C$_1$-C$_6$ alkyl optionally substituted by oxo or F, —(C$_0$-C$_2$ alkyl)C$_4$-C$_5$ heterocyclyl optionally substituted by halo, oxo, C$_1$-C$_3$ alkyl or C(O)C$_1$-C$_3$ alkyl, —(C$_0$-C$_2$ alkyl)C$_3$-C$_5$ heteroaryl optionally substituted by halo or C$_1$-C$_3$ alkyl, —(C$_0$-C$_2$ alkyl)phenyl optionally substituted by C$_1$-C$_3$ alkyl, —CF$_3$, halo, —CN, —OR$^a$ or —NR$^a$R$^b$, and —(C$_0$-C$_2$ alkyl)C$_6$-C$_7$ cycloalkyl optionally substituted by oxo, C$_1$-C$_3$ alkyl or F.

In one embodiment, R$^6$ is isoxazolyl, oxazolyl, isothiazolyl, thiazolyl, imidazolyl, pyrazolyl or pyridinyl, and wherein R$^6$ is optionally substituted by 1 to 3 substituents selected from —CF$_3$, halo, C$_1$-C$_6$ alkyl optionally substituted by oxo or F, —(C$_1$-C$_6$ alkyl)OR$^a$, phenyl optionally substituted by methyl, ethyl, isopropyl, —CF$_3$, —CN, OR$^a$, Cl, F, Br or I, and pyridinyl optionally substituted by methyl, ethyl, isopropyl, —CF$_3$, —CN, OR$^a$, Cl, F, Br or I.

In one embodiment of Formula I, R$^6$ is pyrazolyl or pyridinyl, and wherein R$^6$ is optionally substituted by 1 to 3 substituents selected from C$_1$-C$_6$ alkyl optionally substituted by oxo or F, halo and phenyl, and wherein said phenyl is optionally substituted by methyl, ethyl, isopropyl, —CF$_3$, —CN, OR$^a$, Cl or F.

In one embodiment of Formula I, R$^6$ is phenyl or —CH$_2$phenyl, and wherein said phenyl is optionally substituted by F, Cl, —OH, —OCH$_3$, —OCH$_2$CH$_3$, —Ophenyl, —C(O)NH$_2$, —C(O)OH, —C(O)OCH$_3$, cyclohexyl, methyl, ethyl or i-propyl.

In one embodiment, $R^7$ is halo. In one embodiment, $R^7$ is Cl. In one embodiment, $R^7$ is H.

In one embodiment, $R^8$ is independently oxo, halo, $OR^a$ or $NR^aR^b$. In one embodiment, $R^8$ is independently halo. In one embodiment, $R^8$ is F.

In one embodiment, $R^9$ is independently —$CF_3$, halo, —($C_0$-$C_5$ alkyl)$NR^aR^b$, —($C_0$-$C_5$ alkyl)$OR^a$, —($C_0$-$C_5$ alkyl)$SR^a$, —$O[C(R^a)_2]_{1-3}O$—, $C_1$-$C_3$ alkyl optionally substituted by oxo or F, —($C_0$-$C_5$ alkyl)($C_3$-$C_6$ cycloalkyl) optionally substituted by oxo or F, —($C_0$-$C_5$ alkyl)$C_1$-$C_9$ heterocyclyl optionally substituted by halo, oxo, $C_1$-$C_3$ alkyl or $C(O)C_1$-$C_3$ alkyl, —($C_0$-$C_5$ alkyl)$C_6$ aryl optionally substituted by halo or $C_1$-$C_3$ alkyl —$O(C_1$-$C_3$ alkyl), or —($C_0$-$C_5$ alkyl)$C_1$-$C_9$ heteroaryl optionally substituted by halo or $C_1$-$C_3$ alkyl. In one embodiment, $R^9$ is independently Cl, F, —$CF_3$, —$CH_3$, —OH, —$OCH_3$, —$OCH_2CH_3$, —$O(CH_2)_2O$—, —$O(CH_2)_3O$—, —$OCHF_2$, —$OCF_3$, —$N(CH_3)_2$, —$NH_2$, morpholinyl, pyrrolidinyl, pyrazolyl, —$OCH_2$(pyrazolyl), N-methyl-piperidinyl or —$O(CH_2)_2$(morpholinyl).

In one embodiment, $R^{10}$ is independently oxo, halo, $OR^a$ or $NR^aR^b$. In one embodiment, $R^{10}$ is independently halo. In one embodiment, $R^{10}$ is F.

In one embodiment, $R^{11}$ is independently oxo, —$CF_3$, halo, —$C(O)C_1$-$C_6$ alkyl, —$C(O)OR^a$, —$C(O)NR^aR^b$, —($C_0$-$C_5$ alkyl)$NR^aR^b$, —($C_0$-$C_5$ alkyl)$OR^a$, $C_1$-$C_6$ alkyl optionally substituted by oxo or F, —($C_0$-$C_5$ alkyl)$C_1$-$C_9$ heterocyclyl optionally substituted by halo, oxo, $C_1$-$C_3$ alkyl or $C(O)C_1$-$C_3$ alkyl, —($C_0$-$C_5$ alkyl)$C_1$-$C_9$ heteroaryl optionally substituted by halo or $C_1$-$C_3$ alkyl, —($C_0$-$C_5$ alkyl)phenyl optionally substituted by $C_1$-$C_4$ alkyl, $C_1$-$C_4$ alkenyl, $C_1$-$C_4$ alkynyl, $C_3$-$C_6$ cycloalkyl, —$CF_3$, halo, —CN, —$OR^a$ or —$NR^aR^b$, or —($C_0$-$C_5$ alkyl)$C_3$-$C_6$ cycloalkyl optionally substituted by oxo, —$NR^aR^d$, $C_1$-$C_3$ alkyl or F. In one embodiment, $R^{11}$ is independently Cl, F, —$CF_3$, —$CH_3$, —$CH_2CH_3$, —OH, —$OCH_3$, —$OCH_2CH_3$, 2-methyl-5-chlorophenyl, 2,5-dichlorophenyl, 2,5-difluorophenyl, 2,5-dimethylphenyl, gem-difluoro, gem-dimethyl, 2-hydroxyethyl, 2-methoxyethyl, 3,5-dimethylphenyl, 3,5-dichlorophenyl, 3,5-difluorophenyl, 2,4-difluorophenyl, 2-chloro-5-methylphenyl, 2-methylphenyl, 2-trifluoromethylphenyl, 2-chlorophenyl, 2-fluorophenyl, 3-methylphenyl, 3-fluorophenyl, 3-chlorophenyl, 3-cyanophenyl, 2-iodophenyl, 2-bromophenyl, phenyl, pyridyl, —$C(O)OCH_3$, —$CH_2$(4-aminocyclohex-1-yl), 2-chloro-6-iodophenyl, 2,6-dichlorophenyl, 2,6-dimethylphenyl, 2,6-dibromophenyl, 2-chloro-6-methylphenyl, 2-chloro-6-fluorophenyl, 2-bromo-6-fluorophenyl, 2-bromo-6-methylphenyl, 2-fluoro-6-methylphenyl, 2-chloro-6-trifluoromethylphenyl, 2-thiomethylphenyl, 2-ethylphenyl, 2-ethynyl-6-methylphenyl, 2-ethynyl-6-fluorophenyl, 2-chloro-5-cyanophenyl, 2-methoxyphenyl, 2-cyclopropylphenyl, 2-methoxy-6-methylphenyl2-ethynylphenyl, 2-chloro-4-cyanophenyl, 2-isopropylphenyl or 2-trifluoromethoxyphenyl.

In one embodiment of Formula I, $R^6$ is:
—($C_0$-$C_1$ alkyl)($C_6$-$C_8$ cycloalkyl) optionally substituted by oxo, —CN, —$CF_3$, halo, —$C(O)C_1$-$C_6$ alkyl, —$C(O)OR^a$, —$C(O)NR^aR^b$, —($C_0$-$C_5$ alkyl)$NR^aR^b$, —($C_0$-$C_5$ alkyl)$OR^a$ or $C_1$-$C_6$ alkyl optionally substituted by oxo or F,
—($C_0$-$C_2$ alkyl)$C_4$-$C_5$ heterocyclyl optionally substituted by halo, oxo, $C_1$-$C_3$ alkyl or $C(O)C_1$-$C_3$ alkyl,
—($C_0$-$C_2$ alkyl)$C_3$-$C_5$ heteroaryl optionally substituted by halo, $C_1$-$C_3$ alkyl or phenyl, wherein said phenyl is optionally substituted by $C_1$-$C_3$ alkyl, —$CF_3$, halo, —CN, —$OR^a$ or —$NR^aR^b$,
($C_0$-$C_2$ alkyl)phenyl optionally substituted by halo, —CN, —$OR^a$ or —$NR^aR^b$, or
—($C_0$-$C_2$ alkyl)$C_6$-$C_7$ cycloalkyl optionally substituted by oxo, $C_1$-$C_3$ alkyl or F; and
$R^4$ is H or —($C_0$-$C_3$ alkyl)phenyl, wherein said phenyl is optionally substituted by:
$C_1$-$C_3$ alkyl optionally substituted by F,
—$OCH_2O$—, —$OCH_2CH_2O$—, —$OCH_2CH_2CH_2O$—, —$CF_3$, —$OCF_3$, —$OCHF_2$, halo, —$C(O)C_1$-$C_6$ alkyl, —$C(O)OR^a$, —$C(O)NR^aR^b$, —($C_0$-$C_5$ alkyl)$NR^aR^b$, —($C_0$-$C_5$ alkyl)$OR^a$,
—($C_0$-$C_3$ alkyl)$C_4$-$C_4$ heterocyclyl optionally substituted by halo, oxo, $C_1$-$C_3$ alkyl or $C(O)C_1$-$C_3$ alkyl, or
—($C_0$-$C_3$ alkyl)$C_3$-$C_5$ heteroaryl optionally substituted by halo or $C_1$-$C_3$ alkyl.

In another embodiment, $R^6$ is cyclohexyl optionally substituted by 1 or 2 substituents independently selected from methyl, ethyl, pentyl, $C(O)OCH_3$, $C(O)OH$, OH, CN, $C(O)$cyclohexyl and $C(O)(C_4$-$C_5$ heterocyclyl), wherein said heterocyclyl is piperazinyl, piperidinyl or morpholinyl, optionally substituted by methyl, $CH_2NH_2$, or $CH_2$cyclohexyl optionally substituted by $NH_2$; and $R^4$ is —$(CH_2)$phenyl, wherein said phenyl is optionally substituted by 1 or 2 substituents independently selected from methyl, F, Cl, —$OCH_2O$—, —$OCH_2CH_2O$—, —$OCH_2CH_2CH_2O$—, —$OCH_2CH_2NMe_2$, —$OCH_2(C_4$-$C_5$ heterocyclyl), —OH, —$CF_3$, —$OCF_3$, —$OCH_3$, —$OCH_2CH_3$, —$OCHF_2$, —($C_0$-$C_1$ alkyl)$C_4$-$C_5$ heterocyclyl, wherein said heterocyclyl is selected from pyrrolidinyl, morpholinyl, piperazinyl or piperidinyl and is optionally substituted by methyl, and —($C_0$-$C_1$ alkyl)$C_4$-$C_5$ heteroaryl, wherein said heteroaryl is selected from pyrazolyl, imidazolyl, furanyl and thienyl and is optionally substituted by methyl. In an example of this embodiment, $R^2$ is —$NR^3R^4$, and $R^1$ and $R^3$ are H.

In one embodiment of Formula I, $R^6$ is —($C_0$-$C_1$ alkyl)($C_6$-$C_7$ cycloalkyl), wherein said cycloalkyl is optionally substituted by oxo, —CN, —$CF_3$, halo, —$C(O)C_1$-$C_6$ alkyl, —$C(O)OR^a$, —$C(O)NR^aR^b$, —($C_0$-$C_5$ alkyl)$NR^aR^b$, —($C_0$-$C_5$ alkyl)$OR^a$,
$C_1$-$C_6$ alkyl optionally substituted by oxo or F,
—($C_0$-$C_2$ alkyl)$C_4$-$C_5$ heterocyclyl optionally substituted by halo, oxo, $C_1$-$C_3$ alkyl or $C(O)C_1$-$C_3$ alkyl,
—($C_0$-$C_2$ alkyl)$C_3$-$C_5$ heteroaryl optionally substituted by halo or $C_1$-$C_3$ alkyl,
—($C_0$-$C_2$ alkyl)phenyl optionally substituted by halo, —CN, —$OR^a$ or —$NR^aR^b$, or
—($C_0$-$C_2$ alkyl)$C_6$-$C_7$ cycloalkyl optionally substituted by oxo, $C_1$-$C_3$ alkyl or F; and
$R^4$ is —($C_0$-$C_2$ alkyl)pyridinyl, wherein said pyridinyl is optionally substituted by —$OCH_2O$—, —$OCH_2CH_2O$—, —$OCH_2CH_2CH_2O$—, —$CF_3$, —$OCF_3$, —$OCHF_2$, halo, —$C(O)C_1$-$C_6$ alkyl, —$C(O)OR^a$, —$C(O)NR^aR^b$, —($C_0$-$C_5$ alkyl)$NR^aR^b$, —($C_0$-$C_5$ alkyl)$OR^a$,
$C_1$-$C_3$ alkyl optionally substituted by F,
—($C_0$-$C_3$ alkyl)$C_4$-$C_4$ heterocyclyl optionally substituted by halo, oxo, $C_1$-$C_3$ alkyl or $C(O)C_1$-$C_3$ alkyl, or
—($C_0$-$C_3$ alkyl)$C_3$-$C_5$ heteroaryl optionally substituted by halo or $C_1$-$C_3$ alkyl.

In one embodiment of Formula I, $R^6$ is cyclohexyl optionally substituted by 1 or 2 substituents independently selected from methyl, ethyl, pentyl, $C(O)OCH_3$, $C(O)OH$, OH, CN, $C(O)$cyclohexyl, $C(O)(C_4$-$C_5$ heterocyclyl), wherein said heterocyclyl is piperazinyl, piperidinyl or morpholinyl optionally substituted by methyl, $CH_2NH_2$, or $CH_2$cyclohexyl optionally substituted by $NH_2$; and $R^4$ is pyridinyl or —$(CH_2)$pyridinyl, wherein said pyridinyl is optionally substituted by methyl, F or Cl. In another example of this embodiment, $R^2$ is —$NR^3R^4$, and $R^1$ and $R^3$ are H.

In one embodiment, $R^6$ is $C_1$-$C_4$ alkyl optionally substituted by $R^{10}$, $C_3$-$C_5$ heterocyclyl, $C_3$-$C_5$ heteroaryl or $C_3$-$C_7$ cycloalkyl, wherein said heterocyclyl, heteroaryl and cycloalkyl are optionally substituted by $R^{11}$; and $R^4$ is H, —($C_0$-$C_5$ alkyl)($C_1$-$C_9$ heterocyclyl), —($C_0$-$C_5$ alkyl)($C_3$-$C_6$ cycloalkyl), —($C_0$-$C_5$ alkyl)($C_1$-$C_9$ heteroaryl), —($C_0$-$C_5$ alkyl)($C_6$-$C_{10}$ aryl), wherein said alkyl is optionally substituted by $R^8$, and said aryl, cycloalkyl, heteroaryl and heterocyclyl are optionally substituted by $R^9$.

In one embodiment of Formula I, $R^1$ is H; $R^2$ is —$NR^3R^4$; $R^3$ is H; and $R^6$ is $C_3$-$C_5$ heteroaryl, optionally substituted by one or more substituents selected from oxo, —$CF_3$, halo, —$C(O)C_1$-$C_6$ alkyl, $C_1$-$C_6$ alkyl optionally substituted by oxo or F, —($C_0$-$C_2$ alkyl)$C_4$-$C_5$ heterocyclyl optionally substituted by halo, oxo, $C_1$-$C_3$ alkyl or $C(O)C_1$-$C_3$ alkyl, —($C_0$-$C_2$ alkyl)$C_3$-$C_5$ heteroaryl optionally substituted by halo or $C_1$-$C_3$ alkyl, —($C_0$-$C_2$ alkyl)phenyl optionally substituted by $C_1$-$C_3$ alkyl, —$CF_3$, halo, —CN, —$OR^a$ or —$NR^aR^b$, and —($C_0$-$C_2$ alkyl)$C_6$-$C_7$ cycloalkyl optionally substituted by oxo, $C_1$-$C_3$ alkyl or F. And in one example of this embodiment, $R^4$ is H.

In an embodiment of Formula I, when $R^4$ is —($C_0$-$C_5$ alkyl)($C_1$-$C_5$ heterocyclyl), —($C_0$-$C_5$ alkyl)($C_3$-$C_5$ cycloalkyl), —($C_0$-$C_5$ alkyl)($C_1$-$C_9$ heteroaryl), —($C_0$-$C_5$ alkyl)($C_6$-$C_9$ aryl), then the aryl, cycloalkyl, heteroaryl and heterocyclyl are optionally substituted by 1-3 substitutents independently selected from oxo, $C_1$-$C_3$ alkyl optionally substituted by 1-3 substituents independently selected from oxo and F, —CN, —$CF_3$, halo, —$C(O)C_1$-$C_6$ alkyl, —$C(O)OR^a$, —$C(O)NR^aR^b$, —($C_0$-$C_5$ alkyl)$NR^aR^b$, —($C_0$-$C_5$ alkyl)$OR^a$, —($C_0$-$C_5$ alkyl)$C_1$-$C_9$ heterocyclyl optionally substituted by 1-3 substitutents independently selected from halo, oxo, $C_1$-$C_3$ alkyl and $C(O)C_1$-$C_3$ alkyl, —($C_0$-$C_5$ alkyl)$C_1$-$C_9$ heteroaryl optionally substituted by 1-3 substitutents independently selected from halo and $C_1$-$C_3$ alkyl, —$OCH_2O$—, —$OCH_2CH_2O$—, —$OCH_2CH_2CH_2O$— and —$OCH_2(C_4$-$C_5$ heterocyclyl). When $R^4$ is alkyl, alkenyl or alkynyl, then the alkyl, alkenyl and alkynyl are optionally substituted by 1-3 substituents independently selected from oxo, F, $OR^a$ and $NR^aR^b$.

In an embodiment of Formula I, when $R^3$ and $R^4$ are taken together with the nitrogen to which they are attached to form a $C_0$-$C_5$ heterocyclyl, then the heterocyclyl is optionally substituted by 1-3 substituents independently selected from oxo, F, $C_1$-$C_3$ alkyl, —$C(O)C_1$-$C_6$ alkyl and —$C(O)OR^a$.

In an embodiment of Formula I, when $R^6$ is $C_6$ aryl, $C_3$-$C_8$ cycloalkyl, $C_3$-$C_5$ heteroaryl and $C_3$-$C_5$ heterocyclyl, then the aryl, cycloalkyl, heteroaryl and heterocyclyl are optionally substituted by 1-3 substituents independently selected from oxo, $C_1$-$C_6$ alkyl optionally substituted by 1-3 substituents independently selected from oxo and F, —CN, —$CF_3$, halo, —$OCH_2O$—, —$OCH_2CH_2O$—, —$OCH_2CH_2CH_2O$—, —$C(O)C_1$-$C_6$ alkyl, —$C(O)OR^a$, —$C(O)NR^aR^b$, —($C_0$-$C_5$ alkyl)$NR^aR^b$, —($C_0$-$C_5$ alkyl)$OR^a$, —($C_0$-$C_5$ alkyl)$C_1$-$C_9$ heterocyclyl optionally substituted by 1-3 substituents independently selected from halo, oxo, $C_1$-$C_3$ alkyl and $C(O)C_1$-$C_3$ alkyl, —($C_0$-$C_5$ alkyl)$C_1$-$C_9$ heteroaryl optionally substituted by 1-3 substituents independently selected from halo and $C_1$-$C_3$ alkyl, —($C_0$-$C_5$ alkyl)phenyl optionally substituted by 1-3 substituents independently selected from halo, —CN, —$CF_3$, —$OR^a$ and —$NR^aR^b$, and —($C_0$-$C_5$ alkyl)$C_3$-$C_6$ cycloalkyl optionally substituted by 1-3 substituents independently selected from oxo, $C_1$-$C_3$ alkyl and F. When $R^6$ is alkyl, alkenyl or alkynyl, then alkyl, alkenyl and alkynyl are optionally substituted by 1-3 substituents independently selected from oxo, F, $OR^a$ and $NR^aR^b$.

In an embodiment of Formula I, when $R^a$ and $R^b$ are $C_1$-$C_6$ alkyl, $C_6$ aryl, $C_3$-$C_6$ cycloalkyl or $C_4$-$C_5$ heterocyclyl, then the alkyl, aryl, cycloalkyl and heterocyclyl are optionally substituted by 1-3 substituents independently selected from $C_1$-$C_4$ alkyl, ($C_0$-$C_3$ alkyl)$OR^c$, oxo, halo, $NR^cR^d$ and $C_4$-$C_5$ heterocyclyl. When $R^a$ and $R^b$ together with the atom to which they are attached form a $C_1$-$C_5$ heterocyclyl, then the heterocyclyl is optionally substituted by 1-3 substituents independently selected from oxo, F, $C_1$-$C_3$ alkyl, —$C(O)C_1$-$C_6$ alkyl and —$C(O)OR^a$.

In an embodiment of Formula I, when $R^c$ and $R^d$ are $C_1$-$C_3$ alkyl, $C_3$-$C_6$ cycloalkyl or phenyl, then the alkyl, cycloalkyl and phenyl are optionally substituted by 1-3 substituents independently selected from halo, $CH_3$ OH, $NH_2$, $C(O)O(C_1$-$C_6$ alkyl) and $C(O)NH(C_1$-$C_6$ alkyl).

In one embodiment, $R^a$ and $R^b$ are independently H, —$CF_3$, —$CHF_2$, —$CH_2F$, $C_1$-$C_6$ alkyl, phenyl, $C_3$-$C_6$ cycloalkyl or $C_4$-$C_5$ heterocyclyl; wherein said alkyl, aryl and cycloalkyl are optionally substituted by $C_1$-$C_4$ alkyl, —($C_0$-$C_3$ alkyl)$OR^c$, oxo, halo, $NR^cR^d$ or $C_4$-$C_5$ heterocyclyl. In one embodiment, $R^a$ and $R^b$ together with the atom to which they are attached form a $C_1$-$C_5$ heterocyclyl optionally substituted by oxo, F, $C_1$-$C_3$ alkyl, —$C(O)C_1$-$C_6$ alkyl or —$C(O)OR^a$. In one embodiment, $R^a$ and $R^b$ are independently H or $C_1$-$C_3$ alkyl.

In one embodiment, $R^c$ and $R^d$ are independently H, $C_1$-$C_3$ alkyl, $C_3$-$C_6$ cycloalkyl or phenyl, wherein said alkyl, cycloalkyl and phenyl are optionally substituted by halo, $CH_3$ OH, $NH_2$, $C(O)O(C_1$-$C_6$ alkyl) or $C(O)NH(C_1$-$C_6$ alkyl). In one embodiment, $R^c$ and $R^d$ are independently H or $C_1$-$C_3$ alkyl.

In one embodiment, $R^7$ is H; $R^2$ is —$NR^3S(O)_2R^4$; $R^3$ is H; and $R^4$ is phenyl optionally substituted by 1-3 $R^9$. In one embodiment, $R^2$ is —$NR^3S(O)_2R^4$; $R^3$ is H; $R^4$ is phenyl optionally substituted by 1-3 substituents selected from $C_1$-$C_3$ alkyl, —$CF_3$ and halo; Z is —$NR^5R^6$; $R^5$ is H; and $R^6$ is cyclopropyl, cyclobutyl, cyclopentyl, cyclohexyl, cycloheptyl or cyclooctyl, and wherein $R^6$ is optionally substituted by 1 to 3 substituents selected from oxo, halo and $C_1$-$C_6$ alkyl.

In one embodiment, $R^7$ is H; $R^2$ is —$NR^3R^4$; $R^3$ is H; $R^5$ is H; $R^6$ is pyrazolyl optionally substituted by methyl and substituted by phenyl, wherein said phenyl is optionally substituted by one or two methyl, halo, methoxy, cyano, trifluoromethyl, hydroxy or trifluoromethoxy.

In one embodiment, a compound of Formula I is at least 10 fold or more selective in inhibiting JAK2 kinase activity over inhibiting each of JAK1, JAK3 and Tyk-2 activity.

In one embodiment, a compound of the present invention is about 5 fold or more selective in inhibiting JAK3 kinase activity over inhibiting JAK2 kinase activity. In another embodiment, a compound of the present invention is about 10 fold or more selective in inhibiting JAK3 kinase activity over inhibiting JAK2 kinase activity.

The compounds of the present invention may contain asymmetric or chiral centers, and, therefore, exist in different stereoisomeric forms. It is intended that all stereoisomeric forms of the compounds of the present invention, including but not limited to: diastereomers, enantiomers, and atropisomers as well as mixtures thereof such as racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention. Both the single positional isomers and mixture of positional isomers, e.g., resulting from the N-oxidation of the pyrimidinyl and pyrrozolyl rings, or the E and Z forms of compounds of the present invention (for example oxime moieties), are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention, as defined by the claims, embrace both solvated and unsolvated forms.

In an embodiment, compounds of the present invention may exist in different tautomeric forms, and all such forms are embraced within the scope of the invention, as defined by the claims. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention, which are identical to those recited herein, but for the fact that one or more atoms are replaced by an atom having an atomic mass or mass number different from the atomic mass or mass number usually found in nature. All isotopes of any particular atom or element as specified are contemplated within the scope of the invention. Exemplary isotopes that can be incorporated into compounds of the present invention include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Synthesis of Pyrazolopyrimidine JAK Inhibitor Compounds

Compounds of the present invention may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or *Comprehensive Heterocyclic Chemistry*, Editors Katrizky and Rees, Pergamon Press, 1984.

Compounds of the present invention may be prepared singly or as compound libraries comprising at least 2, for example 5 to 1,000 compounds, or 10 to 100 compounds of the present invention. Libraries of compounds of the present invention may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the present invention, enantiomers, diasteriomers or pharmaceutically acceptable salts thereof.

For illustrative purposes, reaction scheme 1 depicted below provides routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Compounds of the invention may be prepared from commercially available starting materials using the general methods illustrated herein.

REACTION SCHEME 1

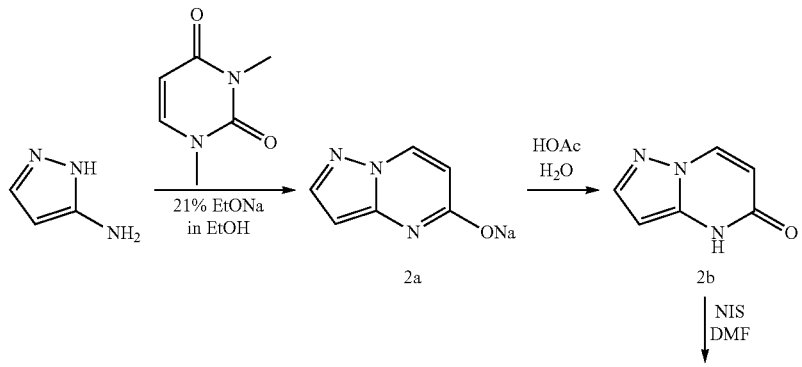

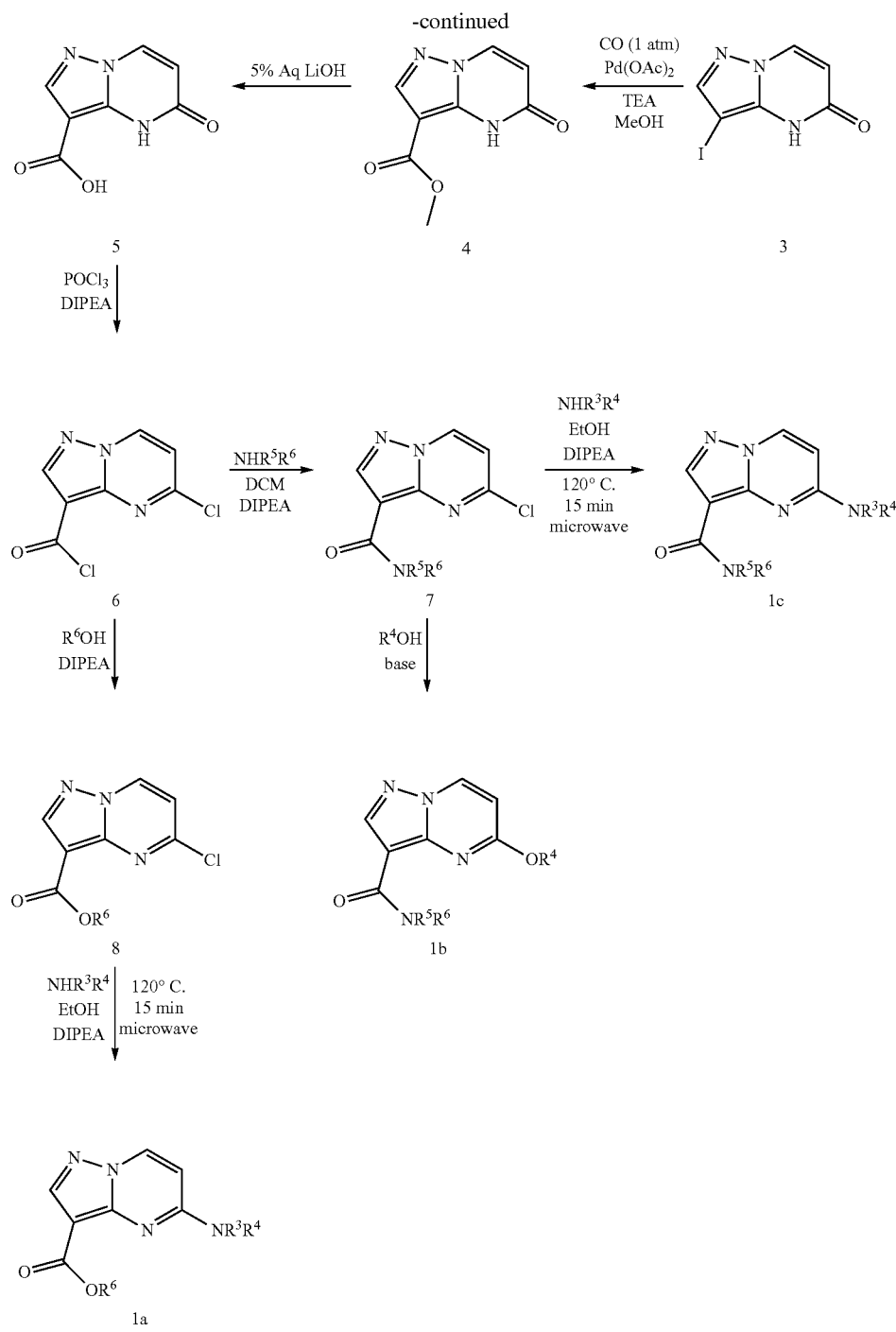

Compounds of Formula I can be synthesized as shown in Reaction Scheme 1. For example, commercially available compounds 3-aminopyrazole and 1,3-dimethyluracil can be reacted together in sodium ethoxide solution to give compound 2a, which can be converted from the sodium salt form to 2b by treatment with dilute acid. Compound 2b can be iodinated with N-iodosuccinimide (NIS) in DMF to give compound 3. Carbonylation of compound 3 under basic conditions (such as triethylamine (TEA)) with carbon monoxide and a palladium catalyst in methanol gives methyl ester compound 4, which can be hydrolyzed in aqueous lithium hydroxide to compound 5. Heating compound 5 in a mixture of phosphorous oxychloride and diisopropylethylamine (DIPEA) produces the dichlorinated compound 6, which is a common intermediate for the ultimate synthesis of compounds 1a, 1b and 1c. Thus, compound 6 can be reacted with a primary or secondary amine under mild conditions to give amide compound 7 then under more vigorous conditions with a second amine or an alkoxide to give compounds 1c or 1b respectively. Alternatively, compound 6 can be reacted under basic conditions with an alcohol to give esters of formula 8 which may then be further reacted with a primary or secondary amine to give compounds of formula 1a.

REACTION SCHEME 2

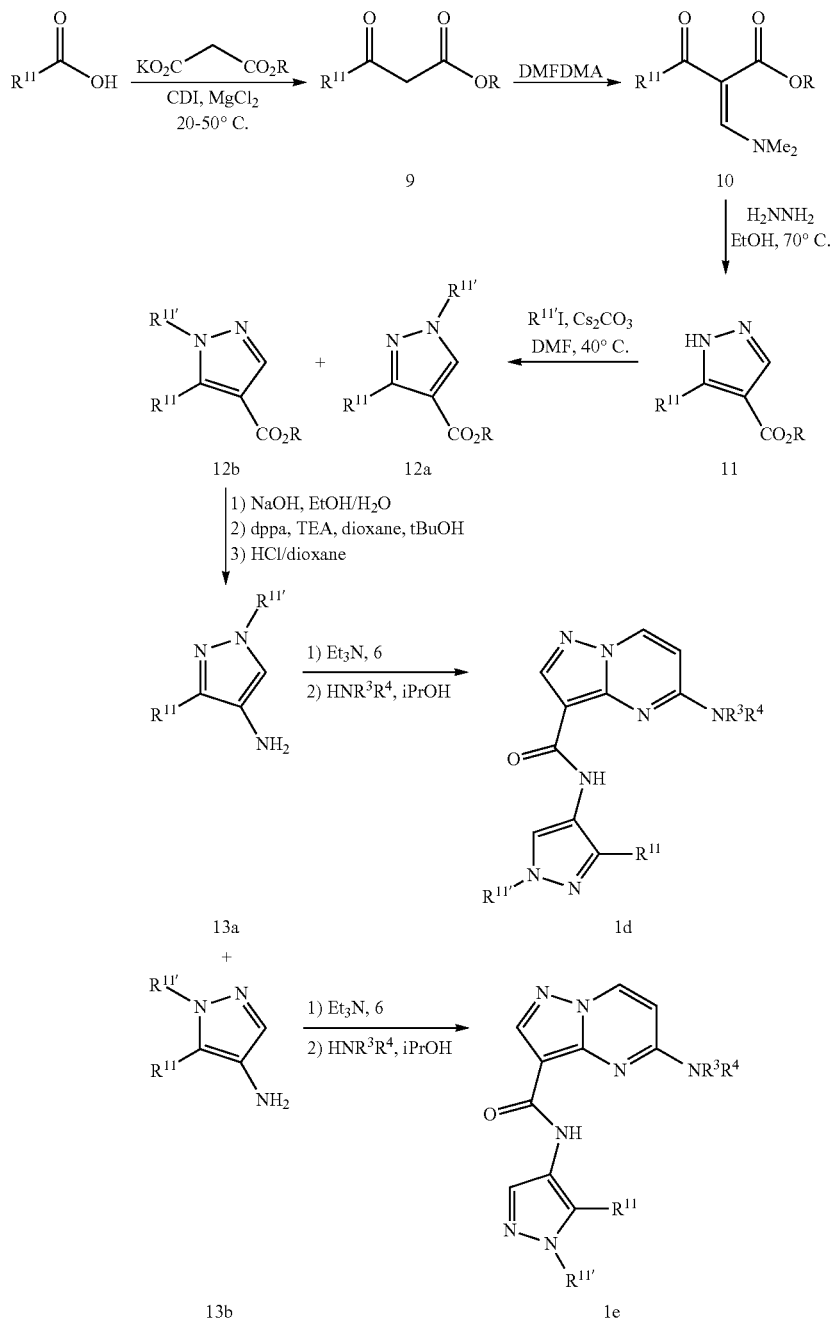

Compounds of the present invention can be synthesized as shown in Scheme 2. For example, commercially available benzoic acids can be reacted with potassium 3-ethoxy-3-oxopropanoate in the presence of carbonyldiimidazole (CDI) and magnesium chloride to give β-keto-ester 9 (where R is alkyl, for example ethyl). Compound 9 can be heated with 1,1-dimethoxy-N,N-dimethylmethanamine (N,N-dimethylformamideDMA) to give compound 10. Cyclization of compound 10 with hydrazine in ethanol provides pyrazole compound 11. Alkylation of compound 11 with alkyl halides in the presence of a base such as cesium carbonate affords a mixture of the regioisomers 12a and 12b (wherein $R^{11'}$, is optionally substituted alkyl). Hydrolysis of the ethyl ester, followed by Curtius rearrangement utilizing diphenylphosphonic azide (dppa) and t-butanol provides the t-butylcarbamate protected amino-pyrazole, which is unmasked with HCl to give amino-pyrazole compounds 13a and 13b. The regioisomers 13a and 13b can be separated using silica chromatography. Acylation of each regioisomer separately with 5-chloropyrazolo[1,5-a]pyrimidine-3-carbonyl chloride (compound 6) in the presence of triethylamine, followed by microwave assisted amination provides compounds of Formula 1d and 1e.

REACTION SCHEME 3

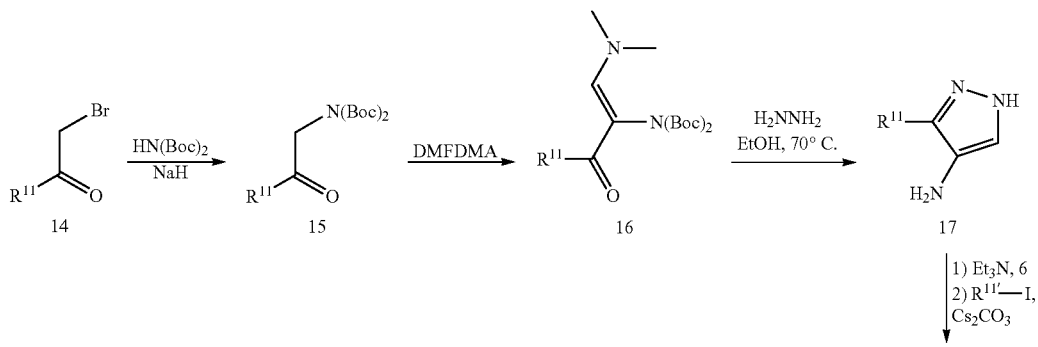

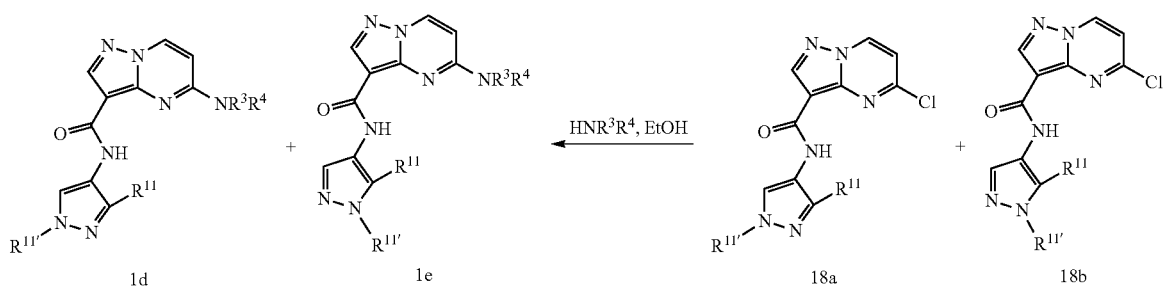

An alternative method for the synthesis of compounds of the present invention is illustrated in Reaction Scheme 3. Alkylation of di-tert-butyl iminodicarbonate with sodium hydride and various α-bromoketones 14 generates compound 15. Compound 15 can be heated with N,N-dimethylformamideDMA to give compound 16. Cyclization of compound 16 with hydrazine in ethanol provides pyrazole compound 17. Acylation of each regioisomer separately with compound 6 in the presence of triethylamine, followed by alkylation of the pyrazole with alkyl halides provides compounds 18a and 18b (where is optionally substituted alkyl). Microwave assisted amination yields compounds of Formula 1d and 1e.

REACTION SCHEME 4

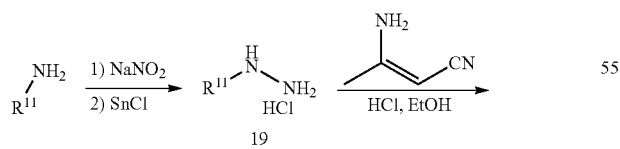

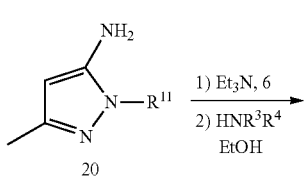

-continued

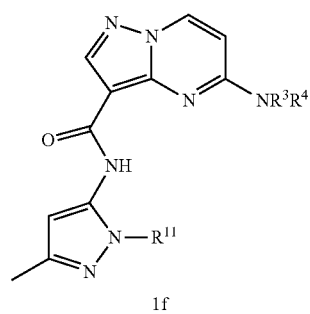

Reaction Scheme 4 illustrates the synthesis of compounds of Formula 1f. Subjection of commercially available anilines to diazotization and tin chloride mediated reduction provides compound 19. Condensation of compound 19 with 3-aminocrotonitrile in ethanolic hydrochloric acid generates aminopyrazole compound 20. Acylation with compound 6 in the presence of triethylamine, followed by microwave assisted amination provides compounds of Formula 1f.

REACTION SCHEME 5

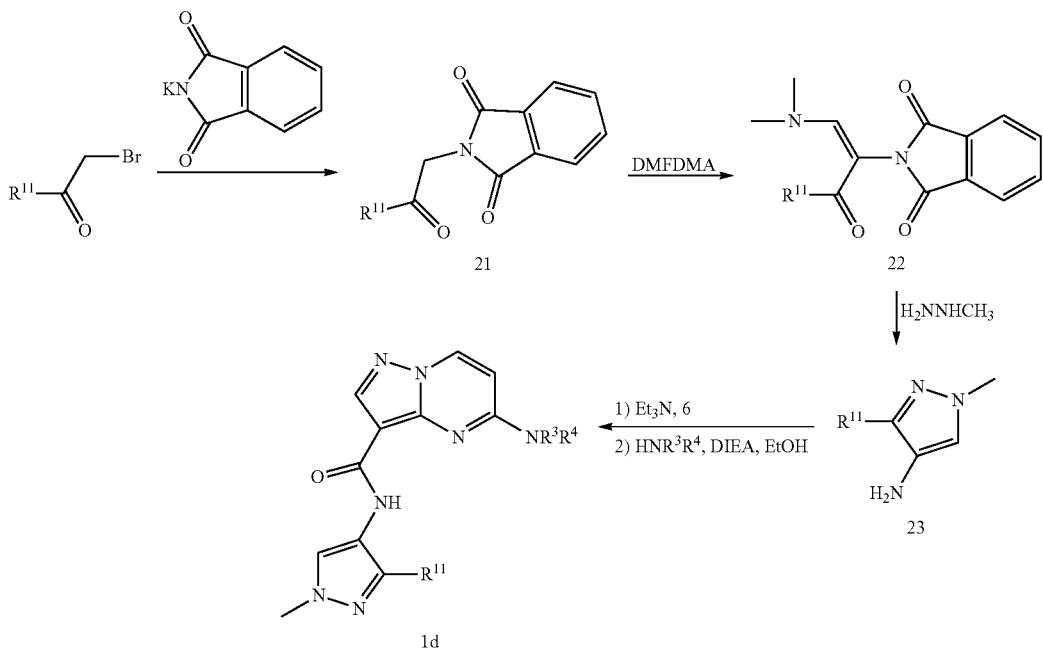

An alternative method for the synthesis of compounds of Formula I is described in Reaction Scheme 5. Alkylation of potassium phthalimide with α-bromoketones generates compound 21. Condensation with N,N-dimethylformamideDMA yields compounds 22. Compounds of Formula 22 may be cyclized with N-methylhydrazine to provide the alkylated pyrazole 23. Acylation of compound 23 with compound 6 in the presence of triethylamine, followed by microwave assisted amination with substituted amines provides compounds of Formula 1d.

REACTION SCHEME 6

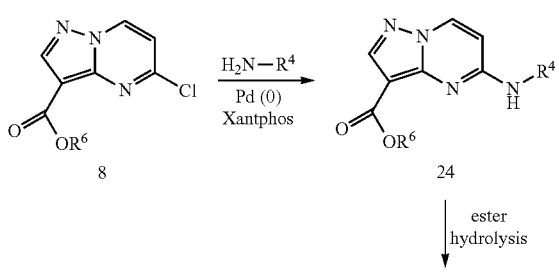

Compounds of Formula 1g can be synthesized as shown in Scheme 6. Addition of primary sulfonamides to 5-chloropyrazolo[1,5-a]pyrimidine intermediate 7 mediated by a base such as cesium carbonate in a polar aprotic solvent such as 1,2-dimethoxyethane affords compounds of Formula 1g.

REACTION SCHEME 7

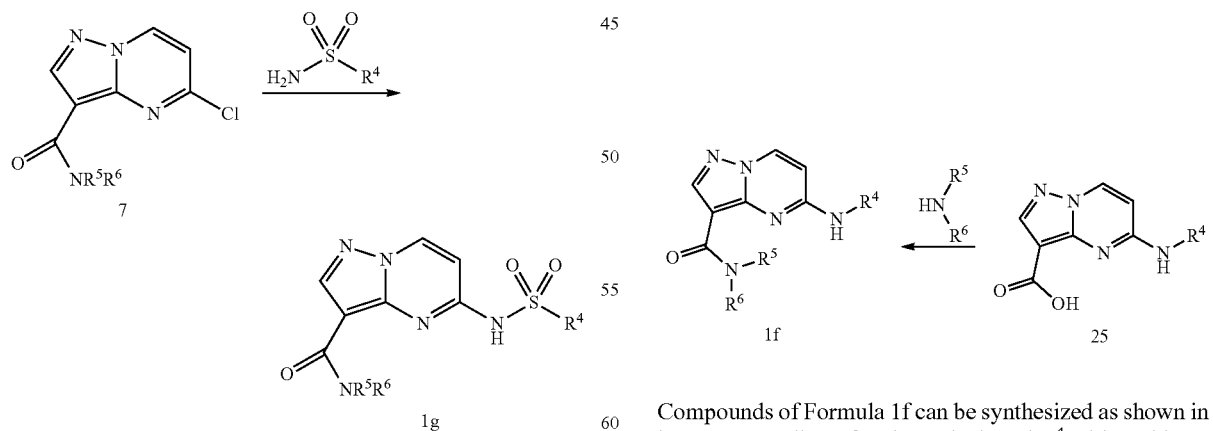

Compounds of Formula 1f can be synthesized as shown in Scheme 7. Coupling of amino substituted $R^4$ with 5-chloropyrazolo[1,5-a]pyrimidine intermediate 8 under palladium mediated conditions with a ligand such as Xantphos arrives at compound 24. Ester hydrolysis under basic conditions affords acid 25. Amide formation to arrive at compounds of formula 1f may occur via addition of amines to the acid chloride of acid 25.

REACTION SCHEME 8

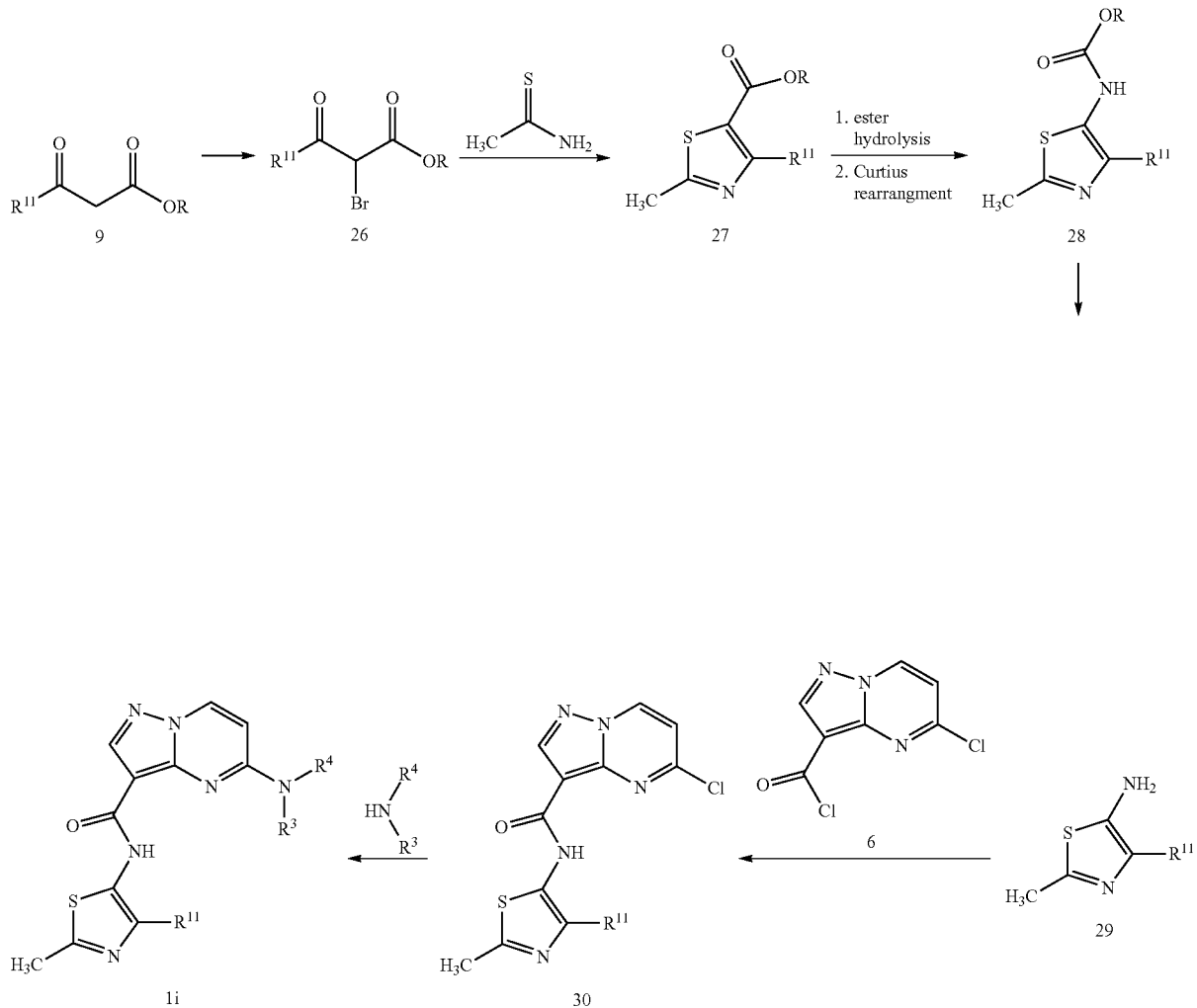

Compounds of Formula 1i can be synthesized as shown in Scheme 8. Bromination of aryl ketoester 9 (where R is alkyl, for example ethyl) furnishes bromide 26. Alkylation of bromide 26 with thioacetamide followed by cyclodehydration under thermal conditions affords thiazole 27. Hydrolysis of ester 27 under basic conditions followed by Curtius rearrangement using diphenyl phosphorylazide provides carbamate 28 after trapping with an alcohol such as t-butanol. Removal of the carbamate of 28 under acidic conditions arrives at 5-aminothiazole 29, which upon coupling with acid chloride 6 provides amide 30. Microwave assisted amination of chloride 30 affords compounds of Formula 1i.

REACTION SCHEME 9

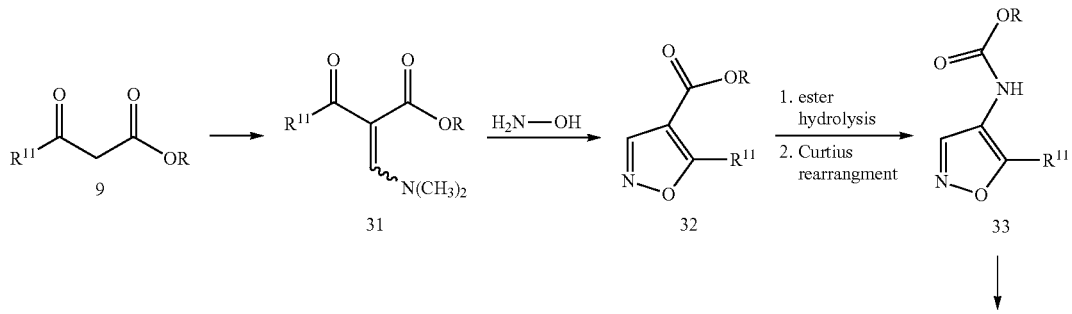

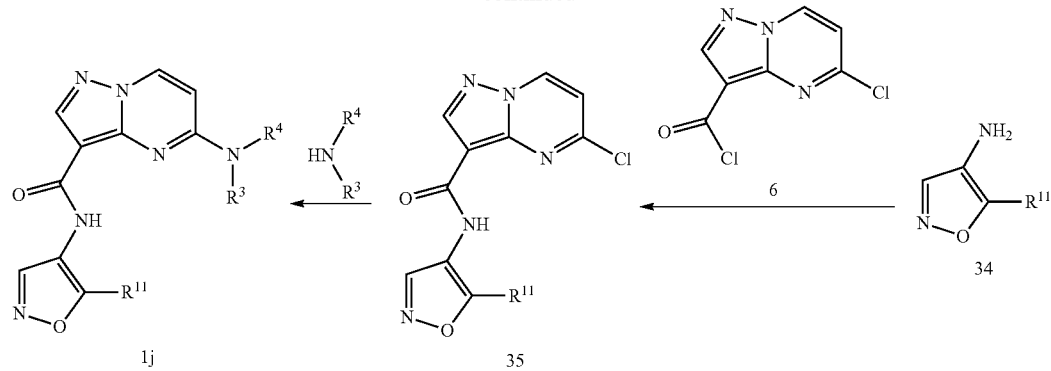

Compounds of formula 1j can be synthesized as shown in Scheme 9. Condensation of aryl ketoester 9 (where R is alkyl, for example ethyl) with 1,1-dimethoxy-N,N-dimethylmethanamine furnishes aminoester 31, which upon treatment with hydroxylamine and heat affords isoxazole 32. Hydrolysis of ester 32 under acidic conditions followed by Curtius rearrangement will provide carbamate 33 after trapping with an alcohol such as t-butanol. Removal of the carbamate of 33 under acidic conditions arrives at 4-aminoisoxazole 34, which upon coupling with acid chloride 6 provides amide 35. Microwave assisted amination of chloride 35 affords compounds of Formula 1j.

Compounds of Formula 1k can be synthesized according to Scheme 10. Chlorination of aryl oxime 36 with N-chlorosuccinimide provides α-chlorobenzaldoxime 37. Treatment of α-chlorobenzaldoxime 37 with a tertiary amine base such as triethylamine forms benzonitrile N-oxide that participate in dipolar cycloaddition with 3-pyrrolidin-1-yl-acrylic acid ester to afford isoxazole 38 (where R is alkyl, for example ethyl). Hydrolysis of ester 38 under acidic conditions followed by Curtius rearrangement using diphenyl phosphorylazide provides carbamate 39 after trapping with an alcohol such as t-butanol. Removal of the carbamate of 39 under acidic conditions arrives at 4-aminoisoxazole 40, which upon

REACTION SCHEME 10

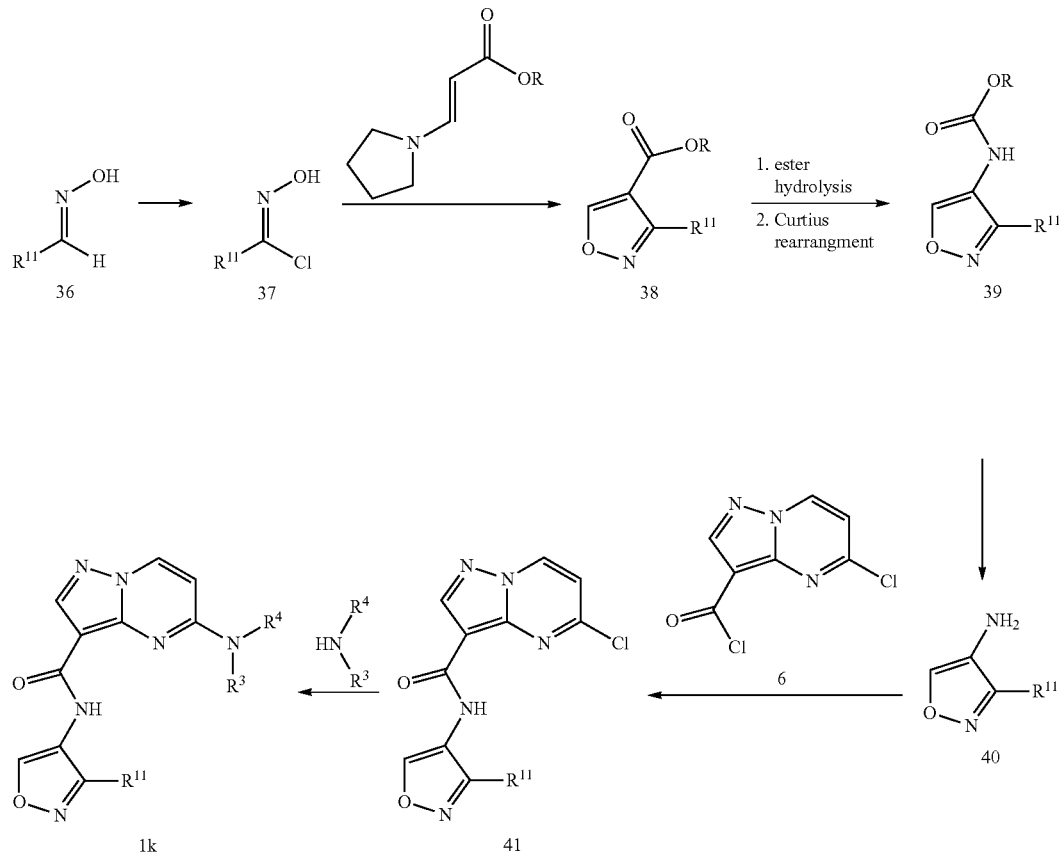

coupling with acid chloride 6 provides amide 41. Microwave assisted amination of chloride 41 affords compounds of Formula 1k.

REACTION SCHEME 11

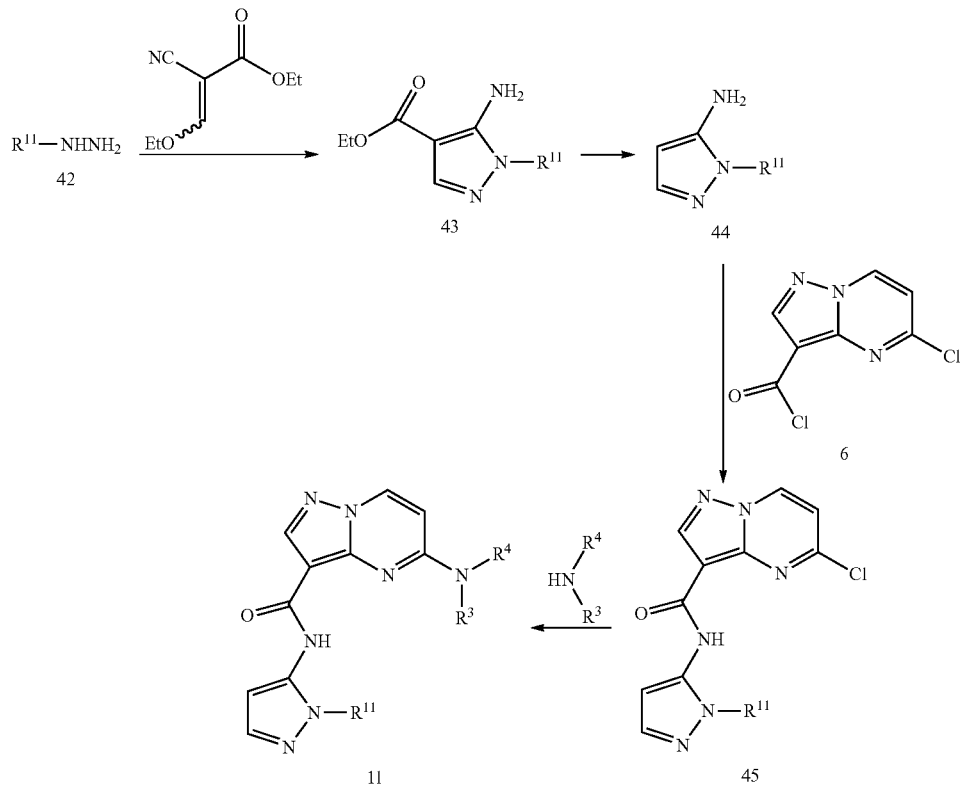

Compounds of Formula 11 can be synthesized according to Scheme 11. Addition of arylhydrazine 42 to ethyl 2-cyano-3-ethoxyacrylate provides 5-amino-1-arylpyrazole 43. Hydrolysis of ester 43 followed by decarboxylation of the resulting acid occurs under acidic conditions to afford 5-amino-1-arylpyrazole 44, which upon coupling with acid chloride 6 provides amide 45. Microwave assisted amination of chloride 45 affords compounds of Formula 11.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention may be prepared from readily available starting materials using the general methods illustrated herein.

Methods of Separation

In each of the exemplary Schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g. an enantiomer, substantially free of its stereoisomer may be obtained by resolution of the racemic mixture using a method such as formation of diastereomers using optically active resolving agents (Eliel, E. and Wilen, S., *Stereochemistry of Organic Compounds*, John Wiley & Sons, Inc., New York, 1994; Lochmuller, C. H., *J. Chromatogr.*, 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., *Stereochemistry of Organic Compounds*, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob, *J. Org. Chem.* 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* W. J. Lough, Ed., Chapman and Hall, New York, (1989); Okamoto, *J. of Chromatogr.* 513:375-378 (1990)). Enriched or purified enantiomers can be distinguished by methods used to distinguish other chiral molecules with asymmetric carbon atoms, such as optical rotation and circular dichroism.

Positional isomers, for example E and Z forms, of compounds of the present invention, and intermediates for their synthesis, may be observed by characterization methods such as NMR and analytical HPLC. For certain compounds where the energy barrier for interconversion is sufficiently high, the E and Z isomers may be separated, for example by preparatory HPLC.

Biological Evaluation

Previous studies have shown that the isolated kinase domain of human JAK2 phosphorylates peptide substrates in in vitro kinase assays. Saltzman et al., *Biochem. Biophys. Res. Commun.* 246:627-633 (2004). The catalytically active kinase domain of human JAK2 was purified from extracts of SF9 insect cells infected with a recombinant baculovirus expression vector encoding the human JAK2 kinase domain (amino acid residues D812-G1132 according to the numbering of GenBank sequence accession number NP_004963.1). The activity of the JAK2 kinase domain can be measured by a number of direct and indirect methods, including quantification of phosphorylation of peptide substrates derived from the human JAK3 protein Saltzman et al., *Biochem. Biophys. Res. Commun.* 246:627-633 (2004). The activity of the JAK2 kinase domain was measured in vitro by monitoring phosphorylation of JAK3 derived peptides using the Caliper Lab-Chip technology (see Examples).

Administration of Pyrazolopyrimidine Compounds

Another embodiment includes a method of treating or lessening the severity of a disease or condition responsive to the inhibition of JAK2 kinase activity in a patient. The method includes the step of administering to a patient a therapeutically effective amount of a compound of the present invention.

Another embodiment includes a method of treating or lessening the severity of a disease or condition responsive to the inhibition of JAK3 kinase activity in a patient. The method includes the step of administering to a patient a therapeutically effective amount of a compound of the present invention.

In one embodiment, a compound of the present invention is administered to a patient in a therapeutically effective amount to treat or lessen the severity of a disease or condition responsive to the inhibition of JAK2 kinase activity, and said compound is at least 10 fold or more selective in inhibiting JAK2 kinase activity over inhibiting each of JAK1, JAK3 and Tyk-2 activity.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the disease or condition is cancer.
In one embodiment, the disease is a myeloproliferative disorder.
In one embodiment, the myeloproliferative disorder is polycythemia vera, essential thrombocytosis, myelofibrosis or chronic myelogenous leukemia (CML).

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the cardiovascular disease is restenosis, cardiomegaly, atherosclerosis, myocardial infarction or congestive heart failure.

In one embodiment, the neurodegenerative disease is Alzheimer's disease, Parkinson's disease, amyotrophic lateral sclerosis, Huntington's disease, and cerebral ischemia, and neurodegenerative disease caused by traumatic injury, glutamate neurotoxicity or hypoxia.

In one embodiment, the inflammatory diseases is rheumatoid arthritis, psoriasis, contact dermatitis or delayed hypersensitivity reactions.

In one embodiment, the autoimmune disease is lupus or multiple sclerosis.

A compound of the present invention may be administered by any route appropriate to the disease or condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary, and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound of the present invention is administered orally, it may be formulated as a pill, capsule, tablet, etc. with a pharmaceutically acceptable carrier or excipient. Where the compound of the present invention is administered parenterally, it may be formulated with a pharmaceutically acceptable parenteral vehicle and in a unit dosage injectable form, as detailed below.

A dose to treat human patients may range from about 10 mg to about 1000 mg of a compound of the present invention. A typical dose may be about 100 mg to about 300 mg of a compound of the present invention. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Another embodiment includes a method of treating or preventing cancer in a mammal in need of such treatment, wherein the method comprises administering to said mammal a therapeutically effective amount of a compound of Formulas I-Ia, a stereoisomer, tautomer, prodrug or pharmaceutically acceptable salt thereof.

Another embodiment includes compounds of Formulas I-Ia, a stereoisomer, tautomer, prodrug or pharmaceutically acceptable salt thereof, for use in therapy.

Another embodiment includes the use of a compound of Formulas I-Ia, a stereoisomer, tautomer, prodrug or pharmaceutically acceptable salt thereof, in the manufacture of a medicament for the treatment of a disease described herein (e.g., cancer or inflammatory disease).

Pharmaceutical Formulations of Pyrazolopyrimidine Compounds

Another embodiment includes a pharmaceutical composition that includes a compound of the present invention and a pharmaceutically acceptable carrier, adjuvant or vehicle.

In one embodiment, the pharmaceutical composition also includes an additional therapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

In one embodiment, a compound of the present invention is present in a pharmaceutical formulation in an amount to detectably inhibit JAK2 kinase activity and a pharmaceutically acceptable carrier, adjuvant or vehicle.

In one embodiment, a compound of the present invention is present in a pharmaceutical formulation in an amount to detectably inhibit JAK3 kinase activity and a pharmaceutically acceptable carrier, adjuvant or vehicle.

In one embodiment, a compound of the present invention is present in a pharmaceutical formulation in an amount to detectably inhibit JAK2 kinase activity and is at least 10 fold or more selective in inhibiting JAK2 kinase activity over inhibiting each of JAK1, JAK3 and Tyk-2 activity.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound, such as a complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical, formulations of a compound of the present invention may be prepared for various routes and types of administration. A compound of the present invention having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are nontoxic to recipients at the dosages and concentrations employed. The pH of the formulation depends mainly on the particular use and the concentration of compound, but may range from about 3 to about 8. Formulation in an acetate buffer at pH 5 is a suitable embodiment.

In an embodiment, the compound of the present invention for use in a pharmaceutical composition is substantially sterile. The compound ordinarily will be stored as a solid composition, although lyophilized formulations or aqueous solutions are acceptable.

The pharmaceutical compositions of the invention will be formulated, dosed, and administered in a fashion, i.e. amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the disorder. Such amount is preferably below the amount that is toxic to the host.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing a compound of the present invention, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the administration routes detailed herein. The formulations may conveniently be presented in unit dosage form and may be prepared by any of the methods well known in the art of pharmacy. Techniques and formulations generally are found in *Remington Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of the present invention suitable for oral administration may be prepared as discrete units such as pills, capsules, cachets or tablets each containing a predetermined amount of the compound of the present invention.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of a compound of the present invention intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For infections of the eye or other external tissues e.g. mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkyl oxide (e.g. ethylene oxide, propylene oxide) with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The pharmaceutical composition of a compound of the present invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

A compound of the present invention may be combined in a pharmaceutical combination formulation, or dosing regimen as combination therapy, with a second compound that has anti-hyperproliferative or chemotherapeutic properties, that is useful for treating a disease or disorder responsive to the inhibition of a JAK kinase, for example a hyperproliferative disorder (e.g. cancer), or that is useful in treating another disorder named herein. The second compound of the pharmaceutical combination formulation or dosing regimen preferably has complementary activities to a compound of the present invention of the combination such that they do not adversely affect each other. Such molecules are suitably present in combination in amounts that are effective for the purpose intended.

Another embodiment, therefore, includes a method of treating or lessening the severity of a disease or condition responsive to the inhibition of JAK2 kinase activity in a patient, comprising administering to said patient a therapeutically effective amount of a compound of the present invention, and further comprising, administering a second chemotherapeutic agent.

Another embodiment, therefore, includes a method of treating or lessening the severity of a disease or condition responsive to the inhibition of JAK3 kinase activity in a patient, comprising administering to said patient a therapeutically effective amount of a compound of the present invention, and further comprising, administering a second chemotherapeutic agent.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Pyrazolopyrimidine Compounds

Another embodiment includes in vivo metabolic products of an administered compound of the present invention. Such products may result for example from the oxidation, reduction, hydrolysis, amidation, deamidation, esterification, deesterification, enzymatic cleavage, and the like, of the administered compound.

Metabolite products typically are identified by preparing a radiolabelled (e.g. $^{14}C$ or $^{3}H$) isotope of a compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of a compound of the present invention.

Articles of Manufacture

Another embodiment includes a kit for treating a disease or disorder responsive to the inhibition of a JAK kinase. The kit includes:

(a) a first pharmaceutical composition comprising a compound of the present invention; and
(b) instructions for use.

In another embodiment, the kit further includes:

(c) a second pharmaceutical composition, which includes a chemotherapeutic agent.

In one embodiment, the instructions include instructions for the simultaneous, sequential or separate administration of said first and second pharmaceutical compositions to a patient in need thereof.

In one embodiment, the first and second compositions are contained in separate containers.

In one embodiment, the first and second compositions are contained in the same container.

Containers for use include, for example, bottles, vials, syringes, blister pack, etc. The containers may be formed from a variety of materials such as glass or plastic. The container includes a compound of the present invention or formulation thereof which is effective for treating the condition and may have a sterile access port (for example the container may be an intravenous solution bag or a vial having a stopper pierceable by a hypodermic injection needle). The container includes a composition comprising at least one compound of the present invention. The label or package insert indicates that the composition is used for treating the condition of choice, such as cancer. In one embodiment, the label or package inserts indicates that the composition comprising the compound of the present invention can be used to treat a disorder. In addition, the label or package insert may indicate that the patient to be treated is one having a disorder characterized by overactive or irregular kinase activity. The label or package insert may also indicate that the composition can be used to treat other disorders.

The article of manufacture may comprise (a) a first container with a compound of the present invention contained therein; and (b) a second container with a second pharmaceutical formulation contained therein, wherein the second pharmaceutical formulation comprises a chemotherapeutic agent. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In an embodiment, the compounds of the present invention can be used to control JAK protein kinases, tyrosine kinases, additional serine/threonine kinases, and/or dual specificity kinases. Thus, they are useful as pharmacological standards for use in the development of new biological tests, assays and in the search for new pharmacological agents.

Compounds of the present invention may be assayed for the ability to modulate the activity of JAK protein kinases, tyrosine kinases, additional serine/threonine kinases, and/or dual specificity kinases in vitro and in vivo. In vitro assays include biochemical and cell-based assays that determine inhibition of the kinase activity. Alternate in vitro assays quantify the ability of the compound of the present invention to bind to kinases and may be measured either by radiolabelling the compound of the present invention prior to binding, isolating the compound of the present invention/kinase complex and determining the amount of radiolabel bound, or by running a competition experiment where a compound of the present invention is incubated with known radiolabeled ligands. These and other useful in vitro assays are well known to those of skill in the art.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of the present invention, and alternative methods for preparing the compounds of the present invention are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

BIOLOGICAL EXAMPLES

The activity of the isolated kinase domain of JAK2 can be measured by monitoring phosphorylation of peptide substrates derived from the human JAK3 kinase in vitro Saltzman et al., Biochem. Biophys. Res. Commun. 246:627-633 (2004). The human JAK2 kinase domain was expressed with an N-terminal His6 tag followed by a thrombin cleavage site using the baculovirus expression vector system. The kinase domain expressed is defined as amino acid residues D812-G1132 according to the numbering of GenBank sequence accession number NP_004963.1. Recombinant DNA transfer vectors were co-transfected with BakPAK6 linearized DNA (Clontech Laboratories, Inc., Mountain View, Calif.) and the resulting viral stocks were amplified using standard protocols. Protein was produced in SF9 cells grown to a cell density of 2E6/mL in ESF921 media (Expression Systems LLC, Woodland, Calif.) and infected at an M.O.I. of 1 in Wave bioreactors. The cells were harvested 72 hours post infection, and active JAK2 enzyme was purified from the lysates of infected cells by Ni-NTA (Qiagen, Valencia, Calif.) column chromatography followed by Sephacryl S-200 (GE Healthcare, Piscataway, N.J.) column chromatography.

Previous studies have shown that the isolated kinase domains of human JAK1, JAK2, JAK3 or TYK2 phosphorylate peptide substrates in in vitro kinase assays (Saltzman et al., Biochem. Biophys. Res. Commun. 246:627-633 (2004)). The catalytically active kinase domain of human JAK1, JAK2, JAK3 or TYK2 was purified from extracts of SF9 insect cells infected with a recombinant baculovirus expression vector encoding the human JAK1, JAK2, JAK3 or TYK2 kinase domains (JAK1 amino acid residues N852-D1154 according to the numbering of GenBank sequence accession number P23458, JAK2 amino acid residues D812-G1132 according to the numbering of GenBank sequence accession number NP_004963.1; JAK3 amino acid residues S783-S1124 according to the numbering of GenBank sequence accession number P52333, and TYK2 amino acid residues N873-C1187 according to the numbering of GenBank sequence accession number P29597). The activity of the JAK1, JAK2, JAK3 or TYK2 kinase domains can be measured by a number of direct and indirect methods, including quantification of phosphorylation of peptide substrates derived from the human JAK3 protein (Saltzman et al., Biochem. Biophys. Res. Commun. 246:627-633 (2004)). The activity of the JAK1, JAK2, JAK3 or TYK2 kinase domains was measured in vitro by monitoring phosphorylation of JAK3 derived peptides using the Caliper LabChip technology.

Example A

JAK2 Inhibition Assay Protocol

The activity of the isolated JAK2 kinase domain was measured by monitoring phosphorylation of a peptide derived from JAK3 (Val-Ala-Leu-Val-Asp-Gly-Tyr-Phe-Arg-Leu-Thr-Thr) fluorescently labeled on the N-terminus with 5-carboxyfluorescein using the Caliper LabChip technology (Caliper Life Sciences, Hopkinton, Mass.). To determine the inhibition constants ($K_i$), compounds were diluted serially in DMSO and added to 50 kinase reactions containing 0.2 nM purified JAK2 enzyme, 100 mM Hepes pH7.2, 0.015% Brij-35, 1.5 µM peptide substrate, 25 µM ATP, 10 mM $MgCl_2$, 4 mM DTT at a final DMSO concentration of 2%. Reactions were incubated at 22° C. in 384-well polypropylene microtiter plates for 30 minutes and then stopped by addition of 250 µL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. $K_i$ values were then determined using the Morrison tight binding model. Morrison, J. F., *Biochim. Biophys. Acta.* 185:269-296 (1969); William, J. W. and Morrison, J. F., *Meth. Enzymol.,* 63:437-467 (1979).

Example B

JAK1 and TYK2 Inhibition Assay Protocol

The activity of the isolated JAK1 or TYK2 kinase domain was measured by monitoring phosphorylation of a peptide derived from JAK3 (Val-Ala-Leu-Val-Asp-Gly-Tyr-Phe-Arg-Leu-Thr-Thr) fluorescently labeled on the N-terminus with 5-carboxyfluorescein using the Caliper LabChip technology (Caliper Life Sciences, Hopkinton, Mass.). To determine inhibition constants ($K_i$), compounds were diluted serially in DMSO and added to 50 uL kinase reactions containing 1.5 nM JAK1, 0.2 nM purified JAK2 or 1 nM purified TYK2 enzyme, 100 mM Hepes pH7.2, 0.015% Brij-35, 1.5 uM peptide substrate, 25 uM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)).

Example C

JAK3 Inhibition Assay Protocol

The activity of the isolated JAK3 kinase domain was measured by monitoring phosphorylation of a peptide derived from JAK3 (Leu-Pro-Leu-Asp-Lys-Asp-Tyr-Tyr-Val-Val-Arg) fluorescently labeled on the N-terminus with 5-carboxyfluorescein using the Caliper LabChip technology (Caliper Life Sciences, Hopkinton, Mass.). To determine inhibition constants ($K_i$), compounds were diluted serially in DMSO and added to 50 uL kinase reactions containing 5 nM purified JAK3 enzyme, 100 mM Hepes pH7.2, 0.015% Brij-35, 1.5 uM peptide substrate, 5 uM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)).

Example D

Cell-Based Pharmacology Assays

The activities of compounds were determined in cell-based assays that are designed to measure JAK2-dependent signaling or proliferation. Compounds were serially diluted in DMSO and incubated with Set-2 cells (German Collection of Microorganisms and Cell Cultures (DSMZ); Braunschweig, Germany), which express the JAK2V617F mutant protein, in 96-well microtiter plates for 1 hr at 37° C. in RPMI medium at a final cell density of 100,000 cells per well and a final DMSO concentration of 0.57%. Compound-mediated effects on STAT5 phosphorylation were then measured in the lysates of incubated cells using the Meso Scale Discovery (MSD) technology (Gaithersburg, Md.) according to the manufacturer's protocol and EC50 values were determined. Alternatively, serially diluted compounds were added to 384-well microtiter plates in RPMI medium with 10% fetal bovine serum (Invitrogen Corp.; Carlsbad, Calif.) at a final cell density of 2500 cells per well and a final DMSO concentration of 0.3% and incubated at 37° C. for 72 hours. Cell viability was then determined using the CellTiter-Glo® Luminescent Cell Viability Assay according to the manufacturer's protocol (Promega; Madison, Wis.) and EC50 values were determined.

The activities of compounds were determined in cell-based assays that are designed to measure TYK2-dependent signaling. Compounds were serially diluted in DMSO and incubated with NK92 cells (American Type Culture Collection (ATCC); Manassas, Va.) in 96-well microtiter plates in RPMI medium at a final cell density of 100,000 cells per well and a final DMSO concentration of 0.57%. Human recombinant IL-12 (R&D systems; Minneapolis, Minn.) was then added at a final concentration of 10 ng/mL to the microtiter plates containing the NK92 cells and compound and the plates were incubated for 1 hr at 37° C. Compound-mediated effects on STAT4 phosphorylation were then measured in the lysates of incubated cells using the Meso Scale Discovery (MSD) technology (Gaithersburg, Md.) according to the manufacturer's protocol and EC50 values were determined The activities of compounds were determined in cell-based assays that are designed to measure JAK1 or JAK2-dependent signaling. Compounds were serially diluted in DMSO and incubated with TF-1 cells (American Type Culture Collection (ATCC); Manassas, Va.) in 384-well microtiter plates in Opti-MEM medium without phenol red, 1% Charcoal/Dextran stripped FBS, 0.1 mM NEAA, 1 mM sodium pyruvate (Invitrogen Corp.; Carlsbad, Calif.) at a final cell density of 100,000 cells per well and a final DMSO concentration of 0.2%. Human recombinant IL-6 (R&D systems; Minneapolis, Minn.) or EPO (Invitrogen Corp.; Carlsbad, Calif.) was then added at a final concentration of 30 ng/mL or 10 Units/mL, respectively, to the microtiter plates containing the TF-1 cells and compound and the plates were incubated for 30 min at 37°

C. Compound-mediated effects on STAT3 or STAT5 phosphorylation were then measured in the lysates of cells incubated in the presence of IL-6 or EPO, respectively, using the Meso Scale Discovery (MSD) technology (Gaithersburg, Md.) according to the manufacturer's protocol and EC50 values were determined.

PREPARATIVE EXAMPLES

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of dry nitrogen (unless otherwise stated) in anhydrous solvents.

Column chromatography was conducted on a Combiflash system (Manufacturer: Teledyne Isco) having a silica gel column, by traditional flash chromatography on silica or by reversed phase HPLC chromatography on a C-18 column with acetonitrile/water containing either 0.1% trifluoroacetic acid (TFA) or 0.1% formic acid as the eluant. $^1$H NMR spectra were recorded on a Bruker instrument operating at 400 MHz or 500 MHz. $^1$H NMR spectra were obtained as CDCl$_3$ or d$_6$-DMSO solutions (reported in ppm), using tetramethylsilane as the reference standard (0.00 ppm). When peak multiplicities are reported, the following abbreviations are used: s (singlet), d (doublet), t (triplet), m (multiplet), br (broadened), dd (doublet of doublets), dt (doublet of triplets). Coupling constants (J), when given, are reported in Hertz (Hz).

Example 1

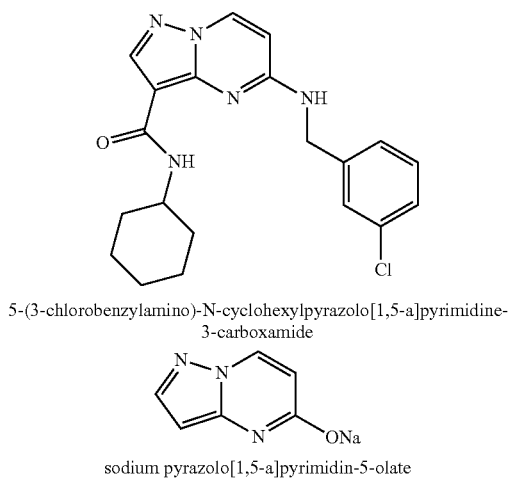

5-(3-chlorobenzylamino)-N-cyclohexylpyrazolo[1,5-a]pyrimidine-3-carboxamide

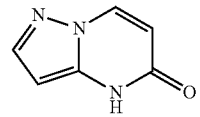

sodium pyrazolo[1,5-a]pyrimidin-5-olate

A mechanically stirred mixture of 3-aminopyrazole (9.38 g, 0.11 mM, 1.0 equiv), 1,3-dimethyluracil (14.7 g, 0.11 mM, 1.0 equiv) and 21% sodium ethoxide in ethanol (170 mL, 5.0 equiv) was heated to reflux. Within minutes, a heavy precipitate formed. After refluxing for 1 hour, 1,3-dimethyluracil could no longer be detected by thin layer chromatography (tlc) (92:8 dichloromethane (dichloromethane):MeOH). The reaction mixture was cooled, filtered, washed with cold ethanol and vacuum dried to give 13.47 g (95%) of sodium pyrazolo[1,5-a]pyrimidin-5-olate. LCMS (ESI) m+H=136.0; $^1$H NMR (400 MHz, DMSO-d$_6$) δ: 8.0 (d, 1H), 7.43 (d, 1H), 5.65 (d, 1H), 5.37 (d, 1H).

pyrazolo[1,5-a]pyrimidin-5(4H)-one

Sodium pyrazolo[1,5-a]pyrimidin-5-olate (13.47 g) was dissolved in 500 mL of acetic acid and 100 mL of water, stirred 15 minutes then evaporated to dryness under vacuum. The residue was suspended in 300 mL of 9:1 dichloromethane:methanol and vacuum filtered through silica gel to remove sodium acetate. The silica gel pad was washed with 700 mL of additional dichloromethane:methanol solution. The combined dichloromethane:methanol solution was concentrated to dryness. The solid product was suspended in 1:1 hexane:dichloromethane and filtered to yield 9.9 g (85%) pyrazolo[1,5-c]pyrimidin-5(4H)-one. LCMS (ESI) m+H=136.0; $^1$H NMR (400 MHz, DMSO-d$_6$) δ: 12.1 (s broad exchangeable, 1H), 8.47 (d, 1H, J=7.9), 7.75 (d, 1H, J=1.9), 5.94 (d, 1H, J=7.5), 5.81 (d, 1H, J=1.7).

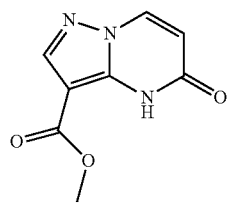

3-iodopyrazolo[1,5-a]pyrimidin-5(4H)-one

Pyrazolo[1,5-c]pyrimidin-5(4H)-one (1.0 g, 7.4 mM, 1.0 equiv) and N-iodosuccinimide (1.67 g, 7.4 mM, 1.0 equiv) were combined with 20 mL of DMF and warmed slightly. Within minutes a heavy precipitate formed. The reaction mixture was stirred an additional 1 h at ambient temperature then cooled on an icewater bath and filtered. The collected solid was washed with 20 mL of dichloromethane and air dried to give 1.66 g (86%) of 3-iodopyrazolo[1,5-c]pyrimidin-5(4H)-one. LCMS (ESI) m+H=262.2; $^1$H NMR (400 MHz, DMSO-d$_6$) δ: 12.1 (s, 1H), 8.5 (d, 1H, J=7.6), 7.84 (s, 1H), 6.01 (d, 1H, J=7.1).

methyl 5-oxo-4,5-dihydropyrazolo[1,5-a]pyrimidine-3-carboxylate

A mixture of 3-iodopyrazolo[1,5-c]pyrimidin-5(4H)-one (1.5 g, 5.7 mM, 1.0 equiv), palladium acetate (0.27 g, 1.2 mM, 0.2 equiv), triethylamine (2.3 mL, 17 mM, 3.0 equiv) and 75 mL of methanol was stirred, degassed twice under vacuum (with a nitrogen break) then blanketed with carbon monoxide under a balloon. The reaction mixture was heated to 55° C. for 5 hours. TLC (95:5 dichloromethane:methanol) indicated complete reaction. The reaction mixture was filtered through celite and concentrated under vacuum. The residue was recrystallized from water and filtered to give 0.81 g (73%) of methyl 5-oxo-4,5-dihydropyrazolo[1,5-a]pyrimidine-3-carboxylate which was 97.6% pure by HPLC. $^1$H NMR (400 MHz, DMSO-$d_6$) δ: 11.0 (br s, 1H), 8.58 (d, 1H), 8.19 (s, 1H), 6.19 (d, 1H), 3.80 (s, 3H).

5-oxo-4,5-dihydropyrazolo[1,5-a]pyrimidine-3-carboxylic acid

A solution of methyl 5-oxo-4,5-dihydropyrazolo[1,5-c]pyrimidine-3-carboxylate (0.75 g 3.89 mM, 1.0 equiv), lithium hydroxide (0.466 g, 19.4 mM, 5.0 equiv) and 20 mL of water was stirred at ambient temperature for 3 hours. HPLC indicated complete reaction. Acetic acid (5 mL) was added and the precipitated solid was collected by vacuum filtration to give 0.65 g (93%) 5-oxo-4,5-dihydropyrazolo[1,5-a]pyrimidine-3-carboxylic acid. $^1$H NMR (400 MHz, DMSO-$d_6$) δ: 12.5 (br s, 1H,), 11.3 (br s, 1H), 8.57 (d, 1H), 8.08 (d, 1H), 6.15 (d, 1H).

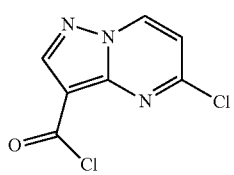

5-chloropyrazolo[1,5-a]pyrimidine-3-carbonyl chloride

A mixture of 5-oxo-4,5-dihydropyrazolo[1,5-c]pyrimidine-3-carboxylic acid (371 mg, 2.1 mM, 1.0 equiv), phosphorus oxychloride (20 mL) and N,N-diisopropylethylamine (1.2 mL, 6.9 mM, 3.3 equiv) was refluxed for 2 hours. The reaction mixture was cooled and concentrated under reduced pressure. The residue was taken up in dichloromethane and concentrated again 3 times. The residue was partitioned between water and dichloromethane. The dichloromethane layer was dried with sodium sulfate, vacuum filtered through a bed of silica gel and concentrated to give 390 mg (87%) of 5-chloropyrazolo[1,5-c]pyrimidine-3-carbonyl chloride as a yellow solid which was used immediately without further purification.

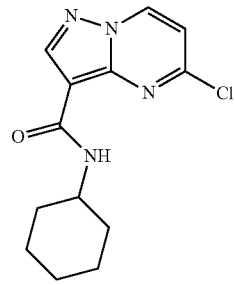

5-chloro-N-cyclohexylpyrazolo[1,5-a]pyrimidine-3-carboxamide

To a stirred solution of crude 5-chloropyrazolo[1,5-c]pyrimidine-3-carbonyl chloride (200 mg, 0.9 mM, 1.0 equiv) in 15 mL of dichloromethane was added cyclohexylamine (400 ul, 4.0 mM, 4 equiv). The reaction mixture was stirred for 15 minutes then quenched with 0.4 mL of acetic acid. The reaction mixture was concentrated under reduced pressure and the residue partitioned between water and dichloromethane. The dichloromethane phase was concentrated, and the crude product purified by flash chromatography on silica gel (97:3 dichloromethane:methanol) to yield 310 mg (100%) of 5-chloro-N-cyclohexylpyrazolo[1,5-c]pyrimidine-3-carboxamide. LCMS (ESI) m+H=279.1; $^1$H NMR (400 MHz, CDCl$_3$) δ: 8.66 (s, 1H), 8.65 (d, 1H), 7.47 (d (broad exchangeable) 1H), 6.93 (d, 1H), 4.08 (m, 1H), 2.02 (m, 2H), 1.80 (m, 2H), 1.62 (m, 1H), 1.40 (m, 5H).

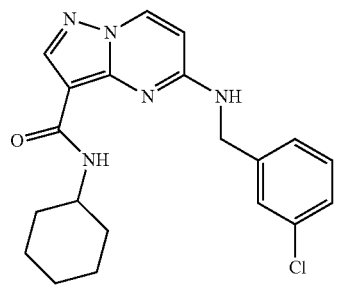

5-(3-chlorobenzylamino)-N-cyclohexylpyrazolo[1,5-a]pyrimidine-3-carboxamide

A solution of 5-chloro-N-cyclohexylpyrazolo[1,5-c]pyrimidine-3-carboxamide (28 mg, 0.09 mM, 1.0 equiv), 3-chlorobenzylamine (28 mg, 0.18 mM, 2.0 equiv), N,N-diisopropylethylamine (26 mg, 0.18 mM, 2.0 equiv) and 2 mL of ethanol were microwaved at 120° C. for 10 minutes. TLC (95:5 dichloromethane:methanol) showed reaction complete. The reaction mixture was cooled, the crystalline product collected by filtration, washed with cold ethanol and air dried to yield 29.7 mg (77%) of 5-(3-chlorobenzylamino)-N-cyclohexylpyrazolo[1,5-c]pyrimidine-3-carboxamide. LCMS (ESI) m+H=384.2; $^1$H NMR (400 MHz, DMSO-$d_6$) δ: 8.61

(overlapping d and t, 2H), 8.06 (s, 1H), 7.60 (d, 1H), 7.4-7.25 (m, 4H), 6.49 (d, 1H), 3.70 (m, 1H), 1.75-1.5 (m, 5H), 1.4-0.8 (m, 5H).

Example 2

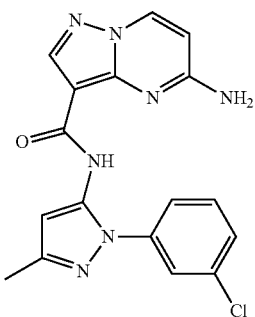

5-amino-N-(1-(3-chlorophenyl)-3-methyl-1H-pyrazol-5-yl)pyrazolo[1,5-a]pyrimidine-3-carboxamide

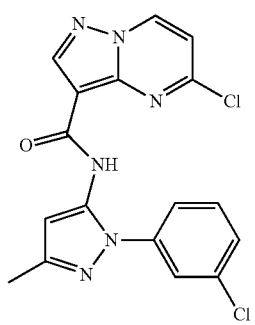

5-chloro-N-(1-(3-chlorophenyl)-3-methyl-1H-pyrazol-5-yl)pyrazolo[1,5-a]pyrimidine-3-carboxamide A solution of 5-chloropyrazolo[1,5-a]pyrimidine-3-carbonyl chloride (150 mg, 0.69 mM, 1.0 equiv), 1-(3-chlorophenyl)-3-methyl-1H-pyrazol-5-amine (140 mg, 0.69 mM, 1.0 equiv, available from Enamine, Ltd, Cincinnati, Ohio Cat# EN300-02447), N,N-diisopropylethylamine (0.18 mL, 1.0 mM, 1.0 equiv), and 15 mL of dichloromethane was stirred at ambient temperature for 3 days. The reaction was partitioned between dichloromethane and water. The dichloromethane phase was dried over sodium sulfate and vacuum filtered through silica gel. The silica gel pad was washed with 95:5 dichloromethane:methanol. The combined filtrates were concentrated to give 250 mg (93%) of 5-chloro-N-(1-(3-chlorophenyl)-3-methyl-1H-pyrazol-5-yl)pyrazolo[1,5-a]pyrimidine-3-carboxamide which was 74% pure by HPLC and used without further purification. LCMS (ESI) m+H=387.2, (two chlorine isotope pattern).

A mixture of 74% pure 5-chloro-N-(1-(3-chlorophenyl)-3-methyl-1H-pyrazol-5-yl)pyrazolo[1,5-a]pyrimidine-3-carboxamide (55 mg, 0.14 mM, 1.0 equiv) and 3 mL of concentrated ammonium hydroxide was sealed and heated in a microwave reactor at 105° C. for 30 minutes. The reaction mixture was cooled and the precipitated product collected by filtration to give 25 mg (48%) of 5-amino-N-(1-(3-chlorophenyl)-3-methyl-1H-pyrazol-5-yl)pyrazolo[1,5-a]pyrimidine-3-carboxamide which was purified by reverse phase chromatography on C-18 with acetonitrile/water (0 to 60 gradient, 0.1% TFA) and lyophilized. LCMS (ESI) m+H=368.3 (one chlorine isotope pattern), $^1$H NMR (400 MHz, DMSO-$d_6$) δ: 9.94 (s, 1H), 8.66 (d, 1H), 8.20 (s, 1H) 7.67 (s, 1H), 7.57 (d, 1H), 7.49 (dd, 1H), 7.44 (d, 1H), 6.89 (br s, 1H), 6.40 (overlapping d and s, 2H), 2.26 (s, 3H).

Example 3

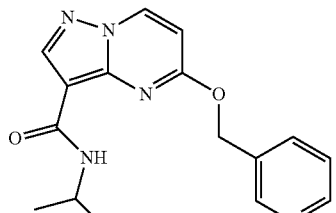

N-isopropyl-5-(pyridin-3-ylmethoxy)pyrazolo[1,5-a]pyrimidine-3-carboxamide

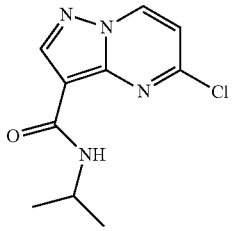

5-chloro-N-isopropylpyrazolo[1,5-a]pyrimidine-3-carboxamide

A mixture of 5-oxo-4,5-dihydropyrazolo[1,5-c]pyrimidine-3-carboxylic acid (2.0 g, 10 mM, 1.0 equiv), 30 mL of phosphorus oxychloride (300 mM, 30 equiv) and N,N-diisopropylethylamine (8 mL, 40 mM, 4 equiv) was heated with stirring to reflux for 2 hours. The reaction mixture was cooled and concentrated under vacuum. The brown oil was taken up in dichloromethane and isopropylamine added (3 mL, 30 mM, 3 equiv). The reaction mixture was stirred 5 minutes then partitioned between ethyl acetate and water. The organic phase was washed with brine, dried over sodium sulfate and vacuum filtered through a pad of silica gel. The filtrate was concentrated and cooled and the crystallized product collected by filtration to give 2.31 g (90%) of 5-chloro-N-isopropylpyrazolo[1,5-c]pyrimidine-3-carboxamide. LCMS (ESI) m+H=239.1 (mono chlorinated isotope pattern) $^1$H NMR (400 MHz, DMSO-$d_6$) δ: 9.33 (d, 1H), 8.60 (s, 1H), 7.47 (d, 1H), 7.36 (d, 1H), 4.09 (m, 1H), 1.20 (d, 6H).

To a degassed solution of 3-pyridylcarbinol (17.6 mg, 0.16 mM, 1.5 equiv) in 0.8 mL of DMF was added a one molar solution of lithium hexamethyldisilazide (215 uL, 0.22 mM, 2.0 equiv). This mixture was stirred for 10 minutes then added dropwise to a stirred solution of 5-chloro-N-isopropylpyrazolo[1,5-c]pyrimidine-3-carboxamide (25.7 mg, 0.11 mM, 1.0 equiv) in one mL of DMF. The reaction mixture was purified using reversed phase HPLC (5 to 30% acetonitrile/water, 0.1% formic acid) and the product lyophilized to give 22.7 mg (68%) of N-isopropyl-5-(pyridin-3-ylmethoxy)pyrazolo[1,5-a]pyrimidine-3-carboxamide. LCMS (ESI) m+H=312.2, $^1$H NMR (400 MHz, DMSO-$d_6$) δ: 9.09 (d, 1H), 8.76 (d, 1H), 8.59 (dd, 1H), 8.38 (s, 1H), 7.95 (d, 1H), 7.45 (dd 2H), 6.81 (d, 1H), 5.61 (s, 1H), 4.08 (m, 1H), 1.19 (d, 6H).

Example 4

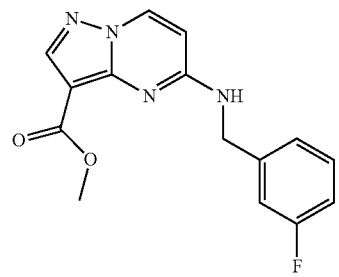

methyl 5-(3-fluorobenzylamino)pyrazolo[1,5-a]pyrimidine-3-carboxylate

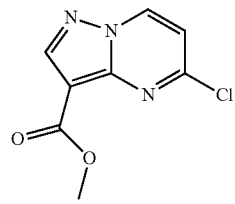

methyl 5-chloropyrazolo[1,5-a]pyrimidine-3-carboxylate

A mixture of 5-oxo-4,5-dihydropyrazolo[1,5-c]pyrimidine-3-carboxylic acid (151 mg, 0.84 mM, 1.0 equiv), phosphorus oxychloride (20 mL) and N,N-diisopropylethylamine (440 uL, 2.5 mM, 3.0 equiv), were heated under reflux for 2 hours. The reaction mixture was cooled to ambient temperature overnight then concentrated under reduced pressure. The residue was dissolved in 20 mL of methanol, stirred for 30 minutes and concentrated under vacuum. The residue was partitioned between ethyl acetate and water. The organic phase was washed with brine, dried over sodium sulfate, filtered through a pad of silica gel and concentrated to give 160 mg (90%) of methyl 5-chloropyrazolo[1,5-c]pyrimidine-3-carboxylate LCMS (ESI) m+H=212.2, $^1$H NMR (400 MHz, DMSO-$d_6$) δ: 9.34 (d, 1H), 8.68 (s, 1H), 7.42 (d, 1H), 3.83 (s, 3H).

A solution of methyl 5-chloropyrazolo[1,5-c]pyrimidine-3-carboxylate (240 mg, 1.1 mM, 1.0 equiv), 3-fluorobenzylamine (200 uL, 2.0 mM, 2.0 equiv), 30 mL of ethanol and 400 uL of N,N-diisopropylethylamine (2.0 mM, 2 equiv) were combined and heated under reflux for 4 hours. The mixture was concentrated and the product collected by filtration and washed with cold ethanol to give 271 mg (80%) of methyl 5-(3-fluorobenzylamino)pyrazolo[1,5-a]pyrimidine-3-carboxylate LCMS (ESI) m+H=301.2, $^1$H NMR (400 MHz, DMSO-$d_6$) δ: 8.56 (d, 1H), 8.41 (m 1H), 8.17 (s, 1H), 7.35 (m, 3H), 7.08 (td, 1H), 6.44 (d, 1H), 4.61 (d, 2H), 3.74 (s, 3H).

Examples 5-221 shown in Table 1 were prepared according to the above-described methods.

TABLE 1

| Ex # | Structure | Name | CMS, M + H/1 |
|---|---|---|---|
| 5 | 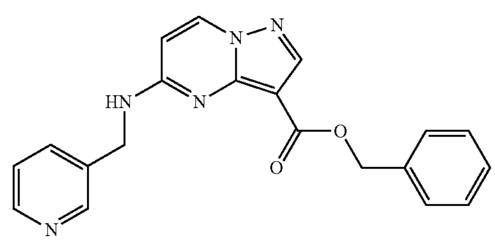 [SMILES: O=C(OCc1ccccc1)c1cnn2ccc(NCc3cccnc3)nc12] | benzyl 5-(pyridin-3-ylmethylamino)pyrazolo[1,5-a]pyrimidine-3-carboxylate | 360.2 |
| 6 | 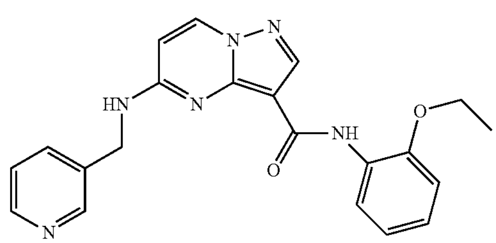 [SMILES: CCOc1ccccc1NC(=O)c1cnn2ccc(NCc3cccnc3)nc12] | N-(2-ethoxyphenyl)-5-(pyridin-3-ylmethylamino)pyrazolo[1,5-a]pyrimidine-3-carboxamide | 389.2 |
| 7 | 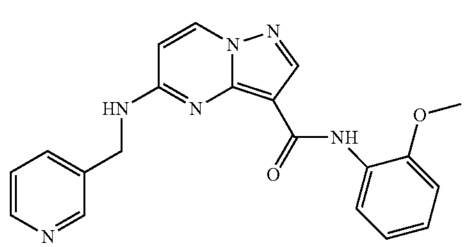 [SMILES: COc1ccccc1NC(=O)c1cnn2ccc(NCc3cccnc3)nc12] | N-(2-methoxyphenyl)-5-(pyridin-3-ylmethylamino)pyrazolo[1,5-a]pyrimidine-3-carboxamide | 375.1 |

TABLE 1-continued

| Ex # | Structure | Name | CMS, M + H/1 |
|---|---|---|---|
| 8 | 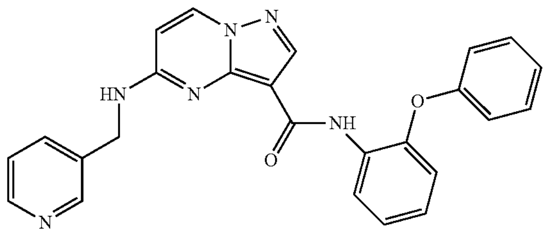 [SMILES: O=C(Nc1ccccc1Oc1ccccc1)c1cnn2ccc(NCc3cccnc3)nc12] | N-(2-phenoxyphenyl)-5-(pyridin-3-ylmethylamino)pyrazolo[1,5-a]pyrimidine-3-carboxamide | 437.1 |
| 9 | 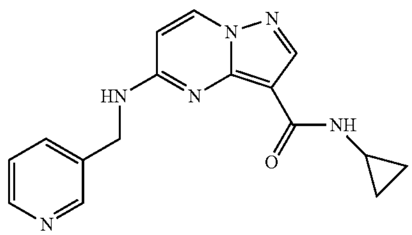 [SMILES: O=C(NC1CC1)c1cnn2ccc(NCc3cccnc3)nc12] | N-cyclopropyl-5-(pyridin-3-ylmethylamino)pyrazolo[1,5-a]pyrimidine-3-carboxamide | 309.2 |
| 10 | 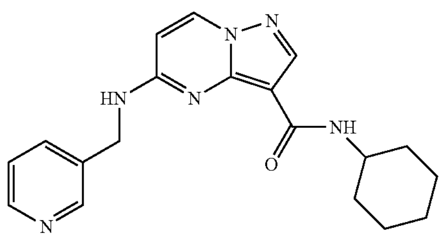 [SMILES: O=C(NC1CCCCC1)c1cnn2ccc(NCc3cccnc3)nc12] | N-cyclohexyl-5-(pyridin-3-ylmethylamino)pyrazolo[1,5-a]pyrimidine-3-carboxamide | 351.2 |
| 11 | 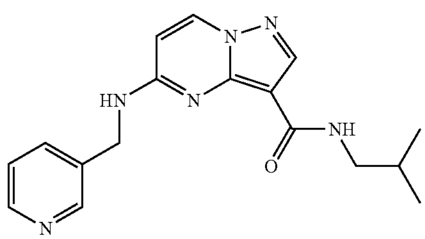 [SMILES: CC(C)CNC(=O)c1cnn2ccc(NCc3cccnc3)nc12] | N-isobutyl-5-(pyridin-3-ylmethylamino)pyrazolo[1,5-a]pyrimidine-3-carboxamide | 325.2 |
| 12 | 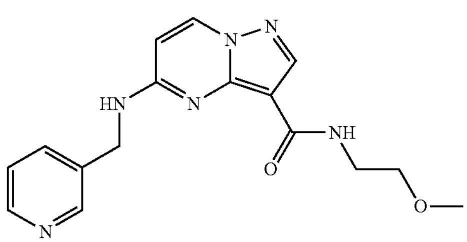 [SMILES: COCCNC(=O)c1cnn2ccc(NCc3cccnc3)nc12] | N-(2-methoxyethyl)-5-(pyridin-3-ylmethylamino)pyrazolo[1,5-a]pyrimidine-3-carboxamide | 327.2 |
| 13 | 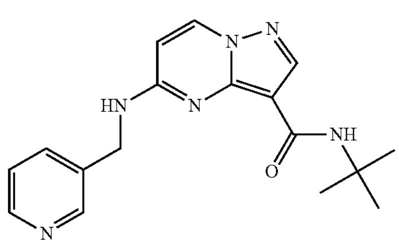 [SMILES: CC(C)(C)NC(=O)c1cnn2ccc(NCc3cccnc3)nc12] | N-tert-butyl-5-(pyridin-3-ylmethylamino)pyrazolo[1,5-a]pyrimidine-3-carboxamide | 325.2 |

TABLE 1-continued

| Ex # | Structure | Name | CMS, M + H/1 |
|---|---|---|---|
| 14 | 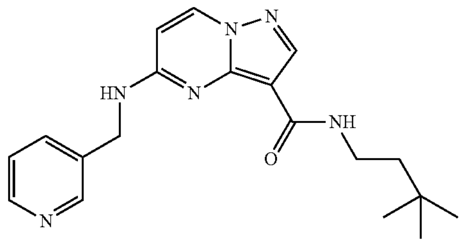 [SMILES: CC(C)(C)CCNC(=O)c1cnn2ccc(NCc3cccnc3)nc12] | N-(3,3-dimethylbutyl)-5-(pyridin-3-ylmethylamino)pyrazolo[1,5-a]pyrimidine-3-carboxamide | 353.5 |
| 15 | 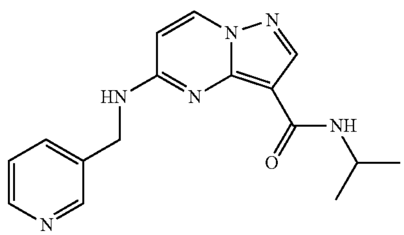 [SMILES: CC(C)NC(=O)c1cnn2ccc(NCc3cccnc3)nc12] | N-isopropyl-5-(pyridin-3-ylmethylamino)pyrazolo[1,5-a]pyrimidine-3-carboxamide | 311.2 |
| 16 | 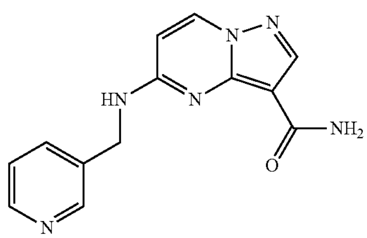 [SMILES: NC(=O)c1cnn2ccc(NCc3cccnc3)nc12] | 5-(pyridin-3-ylmethylamino)pyrazolo[1,5-a]pyrimidine-3-carboxamide | 269.1 |
| 17 | 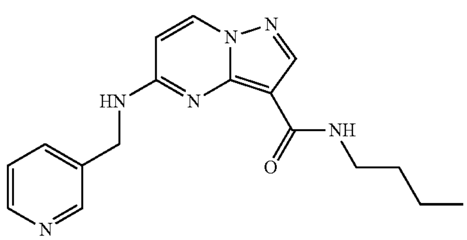 [SMILES: CCCCNC(=O)c1cnn2ccc(NCc3cccnc3)nc12] | N-butyl-5-(pyridin-3-ylmethylamino)pyrazolo[1,5-a]pyrimidine-3-carboxamide | 325.2 |
| 18 | 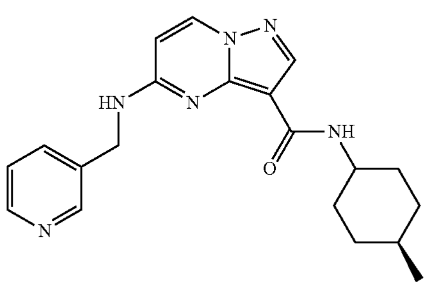 | N-(4-methylcyclohexyl)-5-(pyridin-3-ylmethylamino)pyrazolo[1,5-a]pyrimidine-3-carboxamide | 365.3 |
| 19 | 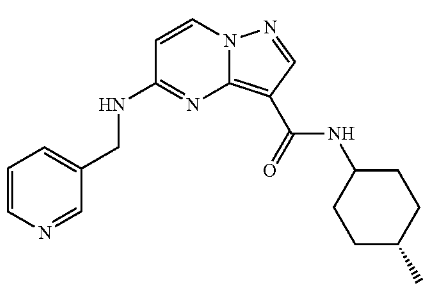 | N-(4-methylcyclohexyl)-5-(pyridin-3-ylmethylamino)pyrazolo[1,5-a]pyrimidine-3-carboxamide | 365.3 |

TABLE 1-continued

| Ex # | Structure | Name | CMS, M + H/1 |
|---|---|---|---|
| 20 | 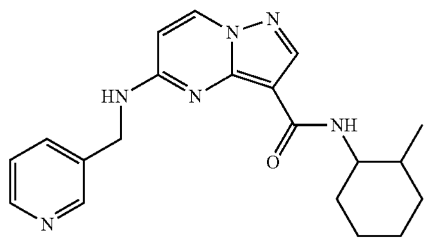 [SMILES: CC1CCCCC1NC(=O)c1cnn2ccc(NCc3cccnc3)nc12] | N-(2-methylcyclohexyl)-5-(pyridin-3-ylmethylamino)pyrazolo[1,5-a]pyrimidine-3-carboxamide | 365.3 |
| 21 | 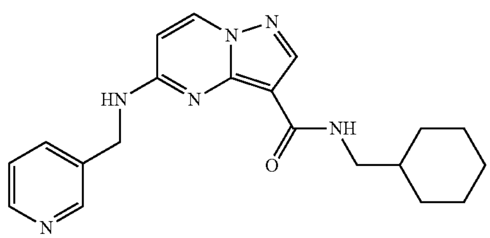 [SMILES: O=C(NCC1CCCCC1)c1cnn2ccc(NCc3cccnc3)nc12] | N-(cyclohexylmethyl)-5-(pyridin-3-ylmethylamino)pyrazolo[1,5-a]pyrimidine-3-carboxamide | 365.3 |
| 22 | 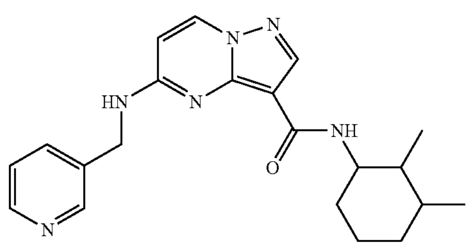 [SMILES: CC1CCCC(NC(=O)c2cnn3ccc(NCc4cccnc4)nc23)C1C] | N-(2,3-dimethylcyclohexyl)-5-(pyridin-3-ylmethylamino)pyrazolo[1,5-a]pyrimidine-3-carboxamide | 379.3 |
| 23 | 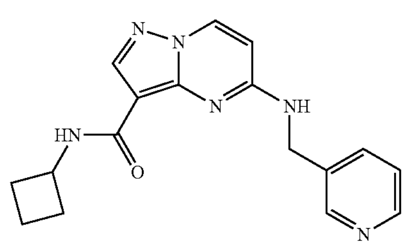 [SMILES: O=C(NC1CCC1)c1cnn2ccc(NCc3cccnc3)nc12] | N-cyclobutyl-5-(pyridin-3-ylmethylamino)pyrazolo[1,5-a]pyrimidine-3-carboxamide | 323.2 |
| 24 | 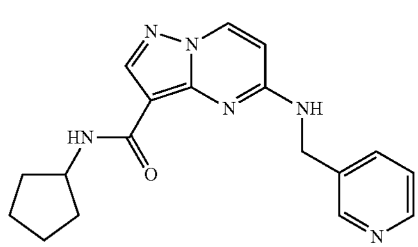 [SMILES: O=C(NC1CCCC1)c1cnn2ccc(NCc3cccnc3)nc12] | N-cyclopentyl-5-(pyridin-3-ylmethylamino)pyrazolo[1,5-a]pyrimidine-3-carboxamide | 337.2 |
| 25 | 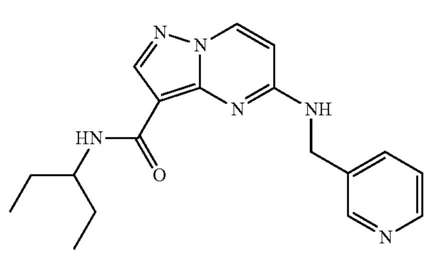 [SMILES: CCC(CC)NC(=O)c1cnn2ccc(NCc3cccnc3)nc12] | N-(pentan-3-yl)-5-(pyridin-3-ylmethylamino)pyrazolo[1,5-a]pyrimidine-3-carboxamide | 339.2 |

TABLE 1-continued

| Ex # | Structure | Name | CMS, M + H/1 |
|---|---|---|---|
| 26 | 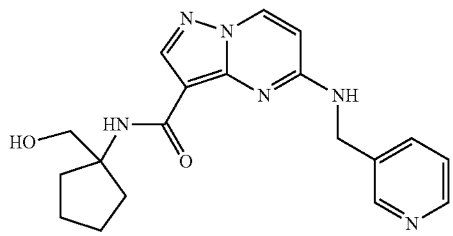 [SMILES: O=C(NC1(CO)CCCC1)c1cnn2ccc(NCc3cccnc3)nc12] | N-(1-(hydroxymethyl)cyclopentyl)-5-(pyridin-3-ylmethylamino)pyrazolo[1,5-a]pyrimidine-3-carboxamide | 367.2 |
| 27 | 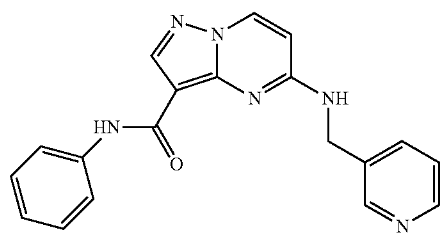 [SMILES: O=C(Nc1ccccc1)c1cnn2ccc(NCc3cccnc3)nc12] | N-phenyl-5-(pyridin-3-ylmethylamino)pyrazolo[1,5-a]pyrimidine-3-carboxamide | 345.2 |
| 28 | 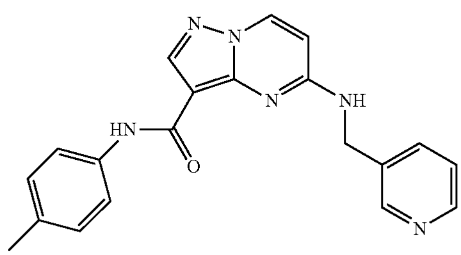 [SMILES: Cc1ccc(NC(=O)c2cnn3ccc(NCc4cccnc4)nc23)cc1] | 5-(pyridin-3-ylmethylamino)-N-p-tolylpyrazolo[1,5-a]pyrimidine-3-carboxamide | 359.2 |
| 29 | 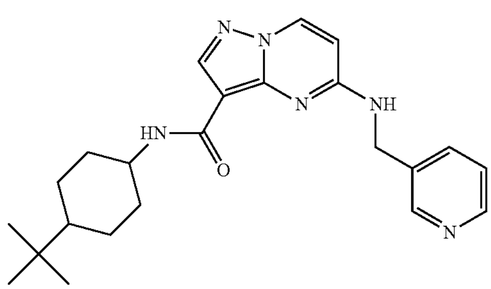 [SMILES: CC(C)(C)C1CCC(NC(=O)c2cnn3ccc(NCc4cccnc4)nc23)CC1] | N-(4-tert-butylcyclohexyl)-5-(pyridin-3-ylmethylamino)pyrazolo[1,5-a]pyrimidine-3-carboxamide | 407.3 |
| 30 | 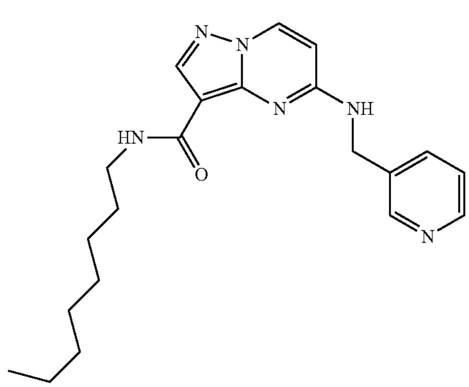 [SMILES: CCCCCCCCNC(=O)c1cnn2ccc(NCc3cccnc3)nc12] | N-octyl-5-(pyridin-3-ylmethylamino)pyrazolo[1,5-a]pyrimidine-3-carboxamide | 381.3 |

TABLE 1-continued

| Ex # | Structure | Name | CMS, M + H/1 |
|---|---|---|---|
| 31 | 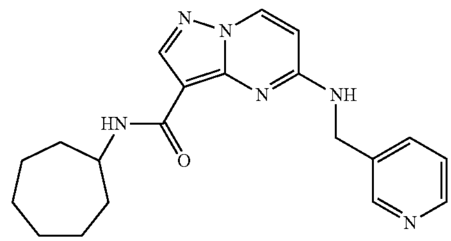 [SMILES: O=C(NC1CCCCCC1)c1cnn2ccc(NCc3cccnc3)nc12] | N-cycloheptyl-5-(pyridin-3-ylmethylamino)pyrazolo[1,5-a]pyrimidine-3-carboxamide | 365.3 |
| 32 | 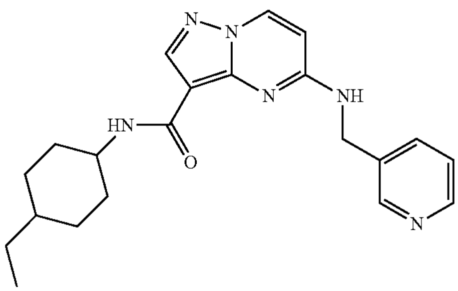 [SMILES: CCC1CCC(NC(=O)c2cnn3ccc(NCc4cccnc4)nc23)CC1] | N-(4-ethylcyclohexyl)-5-(pyridin-3-ylmethylamino)pyrazolo[1,5-a]pyrimidine-3-carboxamide | 379.3 |
| 33 | 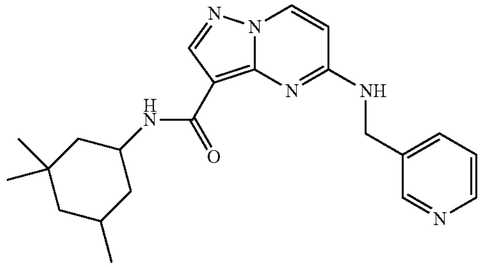 [SMILES: CC1CC(NC(=O)c2cnn3ccc(NCc4cccnc4)nc23)CC(C)(C)C1] | 5-(pyridin-3-ylmethylamino)-N-(3,3,5-trimethylcyclohexyl)pyrazolo[1,5-a]pyrimidine-3-carboxamide | 393.3 |
| 34 | 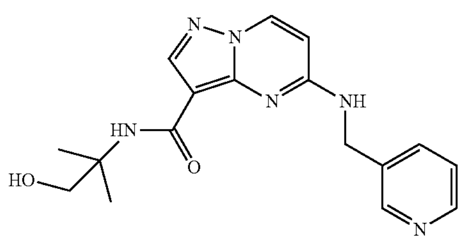 [SMILES: CC(C)(CO)NC(=O)c1cnn2ccc(NCc3cccnc3)nc12] | N-(1-hydroxy-2-methylpropan-2-yl)-5-(pyridin-3-ylmethylamino)pyrazolo[1,5-a]pyrimidine-3-carboxamide | 341.2 |
| 35 | 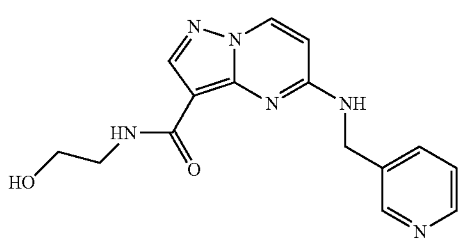 [SMILES: O=C(NCCO)c1cnn2ccc(NCc3cccnc3)nc12] | N-(2-hydroxyethyl)-5-(pyridin-3-ylmethylamino)pyrazolo[1,5-a]pyrimidine-3-carboxamide | 313.2 |
| 36 | 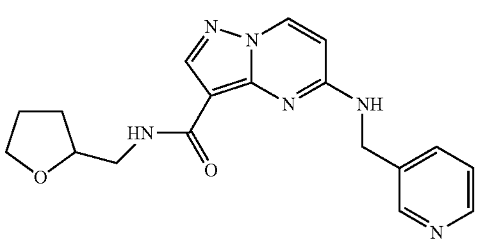 [SMILES: O=C(NCC1CCCO1)c1cnn2ccc(NCc3cccnc3)nc12] | 5-(pyridin-3-ylmethylamino)-N-((tetrahydrofuran-2-yl)methyl)pyrazolo[1,5-a]pyrimidine-3-carboxamide | 353.2 |

TABLE 1-continued

| Ex # | Structure | Name | CMS, M + H/1 |
|---|---|---|---|
| 37 | 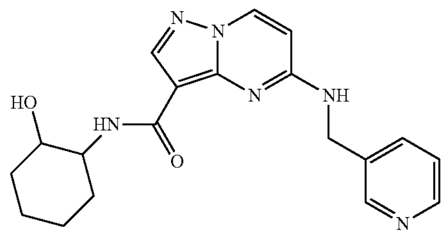 [SMILES: O=C(NC1CCCCC1O)c1cnn2ccc(NCc3cccnc3)nc12] | N-(2-hydroxycyclohexyl)-5-(pyridin-3-ylmethylamino)pyrazolo[1,5-a]pyrimidine-3-carboxamide | 367.3 |
| 38 | 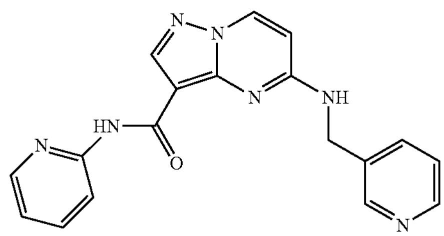 [SMILES: O=C(Nc1ccccn1)c1cnn2ccc(NCc3cccnc3)nc12] | N-(pyridin-2-yl)-5-(pyridin-3-ylmethylamino)pyrazolo[1,5-a]pyrimidine-3-carboxamide | 346.2 |
| 39 | 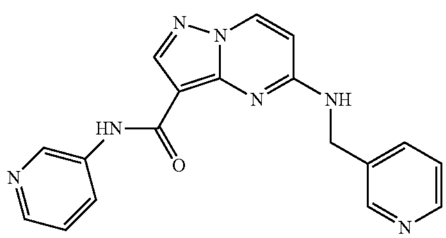 [SMILES: O=C(Nc1cccnc1)c1cnn2ccc(NCc3cccnc3)nc12] | N-(pyridin-3-yl)-5-(pyridin-3-ylmethylamino)pyrazolo[1,5-a]pyrimidine-3-carboxamide | 346.3 |
| 40 | 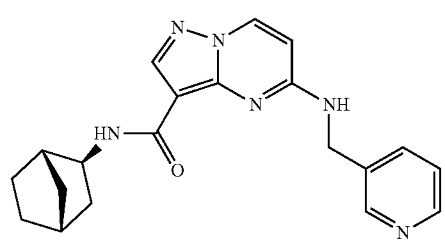 [SMILES: O=C(N[C@H]1C[C@@H]2CC[C@H]1C2)c1cnn2ccc(NCc3cccnc3)nc12] | N-((1S,2S,4R)-bicyclo[2.2.1]heptan-2-yl)-5-(pyridin-3-ylmethylamino)pyrazolo[1,5-a]pyrimidine-3-carboxamide | 363.2 |
| 41 | 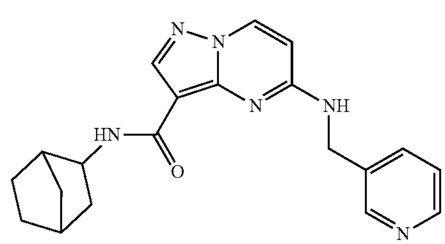 [SMILES: O=C(NC1CC2CCC1C2)c1cnn2ccc(NCc3cccnc3)nc12] | N-(bicyclo[2.2.1]heptan-2-yl)-5-(pyridin-3-ylmethylamino)pyrazolo[1,5-a]pyrimidine-3-carboxamide | 363.2 |
| 42 | 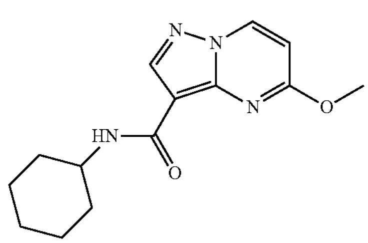 [SMILES: COc1ccn2ncc(C(=O)NC3CCCCC3)c2n1] | N-cyclohexyl-5-methoxypyrazolo[1,5-a]pyrimidine-3-carboxamide | 275.2 |

TABLE 1-continued

| Ex # | Structure | Name | CMS, M + H/1 |
|---|---|---|---|
| 43 | 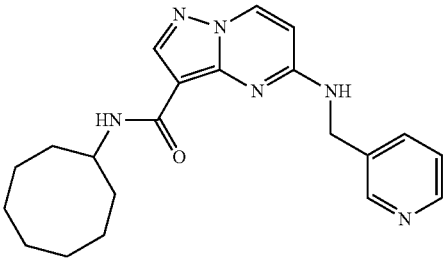 [SMILES: O=C(NC1CCCCCCC1)c1cnn2ccc(NCc3cccnc3)nc12] | N-cyclooctyl-5-(pyridin-3-ylmethylamino)pyrazolo[1,5-a]pyrimidine-3-carboxamide | 379.3 |
| 44 | 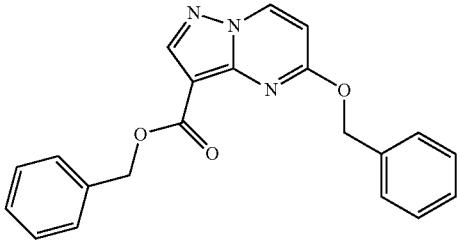 [SMILES: O=C(OCc1ccccc1)c1cnn2ccc(OCc3ccccc3)nc12] | benzyl 5-(benzyloxy)pyrazolo[1,5-a]pyrimidine-3-carboxylate | 360.2 |
| 45 | 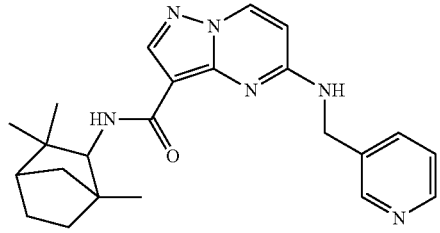 [SMILES: CC12CCC(C1)C(C)(C)C2NC(=O)c1cnn2ccc(NCc3cccnc3)nc12] | 5-(pyridin-3-ylmethylamino)-N-(1,3,3-trimethylbicyclo[2.2.1]heptan-2-yl)pyrazolo[1,5-a]pyrimidine-3-carboxamide | 405.4 |
| 46 | 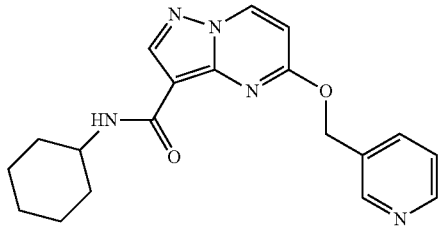 [SMILES: O=C(NC1CCCCC1)c1cnn2ccc(OCc3cccnc3)nc12] | N-cyclohexyl-5-(pyridin-3-ylmethoxy)pyrazolo[1,5-a]pyrimidine-3-carboxamide | 352.2 |
| 47 | 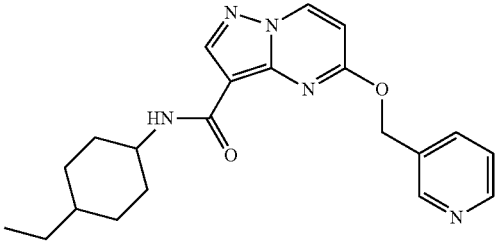 [SMILES: CCC1CCC(NC(=O)c2cnn3ccc(OCc4cccnc4)nc23)CC1] | N-(4-ethylcyclohexyl)-5-(pyridin-3-ylmethoxy)pyrazolo[1,5-a]pyrimidine-3-carboxamide | 380.4 |
| 48 | 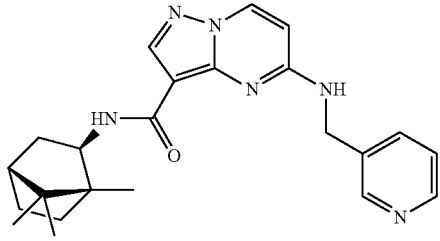 [SMILES: CC1(C)[C@@H]2CC[C@@]1(C)[C@H](NC(=O)c1cnn3ccc(NCc4cccnc4)nc13)C2] | 5-(pyridin-3-ylmethylamino)-N-((1R,2R,4R)-1,7,7-trimethylbicyclo[2.2.1]heptan-2-yl)pyrazolo[1,5-a]pyrimidine-3-carboxamide | 405.3 |

TABLE 1-continued

| Ex # | Structure | Name | CMS, M + H/1 |
|---|---|---|---|
| 49 | 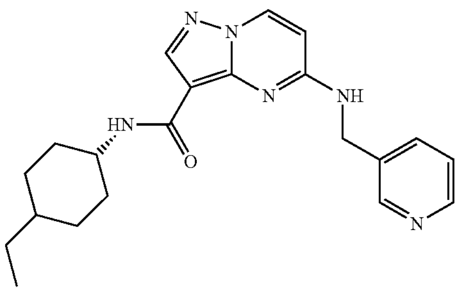 | N-(4-ethylcyclohexyl)-5-(pyridin-3-ylmethylamino)pyrazolo[1,5-a]pyrimidine-3-carboxamide | 379.4 |
| 50 | 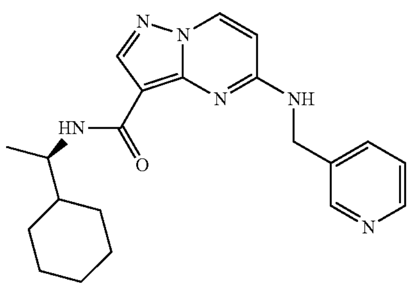 [SMILES: C[C@@H](NC(=O)c1cnn2ccc(NCc3cccnc3)nc12)C1CCCCC1] | (R)-N-(1-cyclohexylethyl)-5-(pyridin-3-ylmethylamino)pyrazolo[1,5-a]pyrimidine-3-carboxamide | 379.3 |
| 51 | 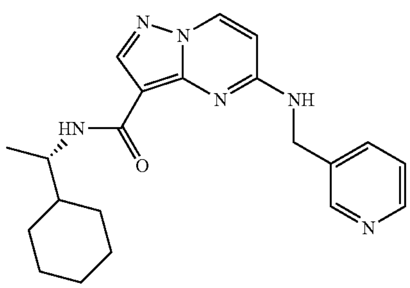 [SMILES: C[C@H](NC(=O)c1cnn2ccc(NCc3cccnc3)nc12)C1CCCCC1] | (S)-N-(1-cyclohexylethyl)-5-(pyridin-3-ylmethylamino)pyrazolo[1,5-a]pyrimidine-3-carboxamide | 379.4 |
| 52 | 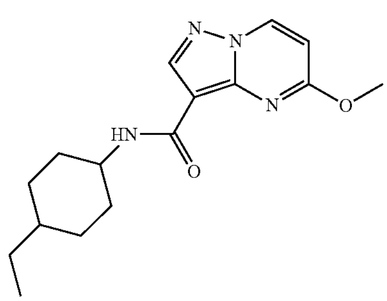 [SMILES: CCC1CCC(NC(=O)c2cnn3ccc(OC)nc23)CC1] | N-(4-ethylcyclohexyl)-5-methoxypyrazolo[1,5-a]pyrimidine-3-carboxamide | 303.2 |
| 53 | 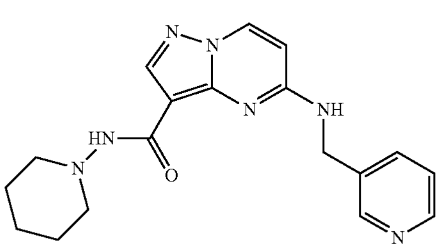 [SMILES: O=C(NN1CCCCC1)c1cnn2ccc(NCc3cccnc3)nc12] | N-(piperidin-1-yl)-5-(pyridin-3-ylmethylamino)pyrazolo[1,5-a]pyrimidine-3-carboxamide | 352.2 |

TABLE 1-continued

| Ex # | Structure | Name | CMS, M + H/1 |
|---|---|---|---|
| 54 | 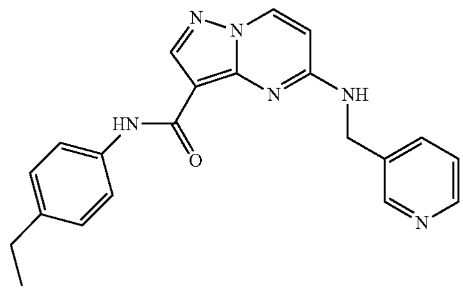 [SMILES: CCc1ccc(NC(=O)c2cnn3ccc(NCc4cccnc4)nc23)cc1] | N-(4-ethylphenyl)-5-(pyridin-3-ylmethylamino)pyrazolo[1,5-a]pyrimidine-3-carboxamide | 373.2 |
| 55 | 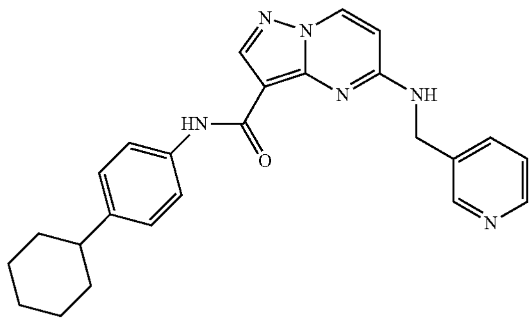 [SMILES: O=C(Nc1ccc(C2CCCCC2)cc1)c1cnn2ccc(NCc3cccnc3)nc12] | N-(4-cyclohexylphenyl)-5-(pyridin-3-ylmethylamino)pyrazolo[1,5-a]pyrimidine-3-carboxamide | 427.2 |
| 56 | 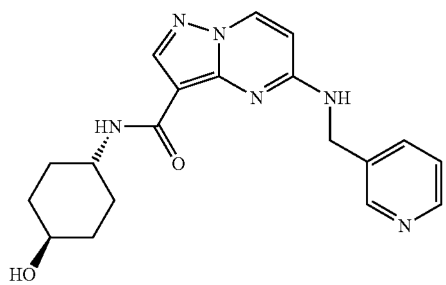 | N-((1R,4R)-4-hydroxycyclohexyl)-5-(pyridin-3-ylmethylamino)pyrazolo[1,5-a]pyrimidine-3-carboxamide | 367.2 |
| 57 | 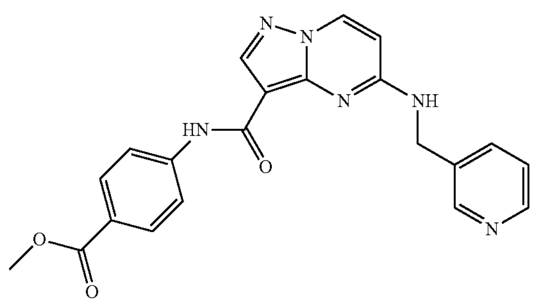 [SMILES: COC(=O)c1ccc(NC(=O)c2cnn3ccc(NCc4cccnc4)nc23)cc1] | methyl 4-(5-(pyridin-3-ylmethylamino)pyrazolo[1,5-a]pyrimidine-3-carboxamido)benzoate | 403.2 |
| 58 | 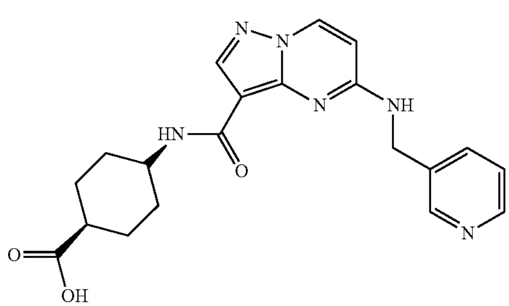 | (1R,4R)-4-(5-(pyridin-3-ylmethylamino)pyrazolo[1,5-a]pyrimidine-3-carboxamido)-cyclohexanecarboxylic acid | 395.2 |

TABLE 1-continued

| Ex # | Structure | Name | CMS, M + H/1 |
|---|---|---|---|
| 59 | 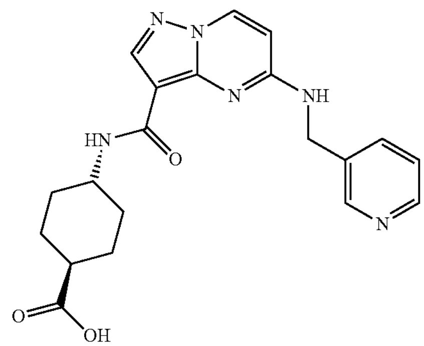 | (1R,4R)-4-(5-(pyridin-3-ylmethylamino)pyrazolo[1,5-a]pyrimidine-3-carboxamido)-cyclohexanecarboxylic acid | 395.2 |
| 60 | 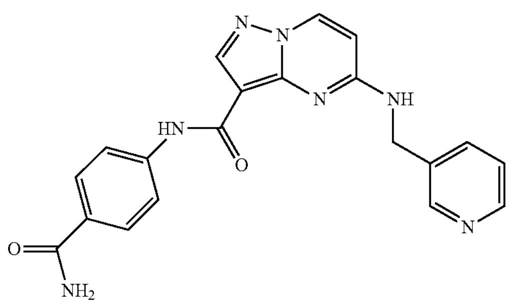 [SMILES: NC(=O)c1ccc(NC(=O)c2cnn3ccc(NCc4cccnc4)nc23)cc1] | N-(4-carbamoylphenyl)-5-(pyridin-3-ylmethylamino)pyrazolo[1,5-a]pyrimidine-3-carboxamide | 388.2 |
| 61 | 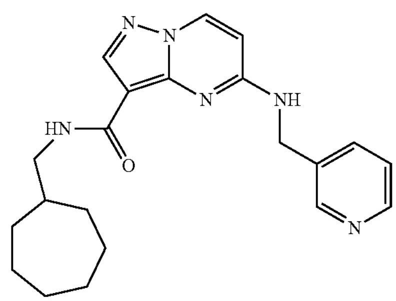 [SMILES: O=C(NCC1CCCCCC1)c1cnn2ccc(NCc3cccnc3)nc12] | N-(cycloheptylmethyl)-5-(pyridin-3-ylmethylamino)pyrazolo[1,5-a]pyrimidine-3-carboxamide | 379.3 |
| 62 | 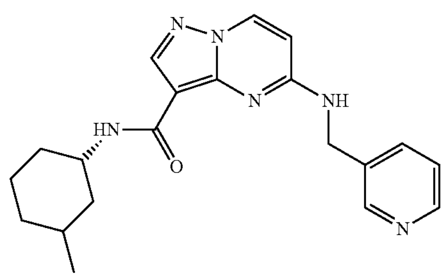 | N-((1S)-3-methylcyclohexyl)-5-(pyridin-3-ylmethylamino)pyrazolo[1,5-a]pyrimidine-3-carboxamide | 365.3 |
| 63 | 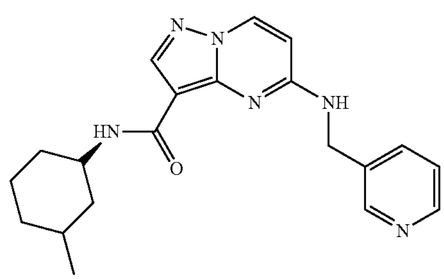 | N-((1S)-3-methylcyclohexyl)-5-(pyridin-3-ylmethylamino)pyrazolo[1,5-a]pyrimidine-3-carboxamide | 365.3 |

TABLE 1-continued

| Ex # | Structure | Name | CMS, M + H/1 |
|---|---|---|---|
| 64 | 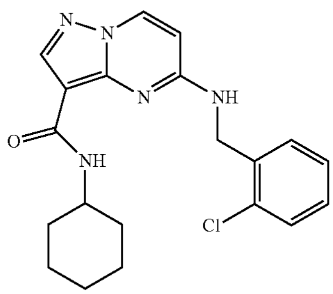 [SMILES: O=C(NC1CCCCC1)c1cnn2ccc(NCc3ccccc3Cl)nc12] | 5-(2-chlorobenzylamino)-N-cyclohexylpyrazolo[1,5-a]pyrimidine-3-carboxamide | 384.2 |
| 65 | 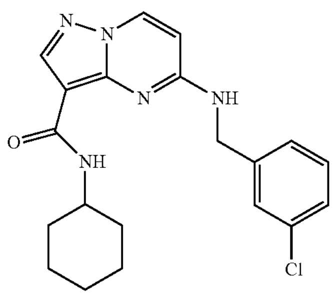 [SMILES: O=C(NC1CCCCC1)c1cnn2ccc(NCc3cccc(Cl)c3)nc12] | 5-(3-chlorobenzylamino)-N-cycyclohexylpyrazolo[1,5-a]pyrimidine-3-carboxamide | 384.2 |
| 66 | 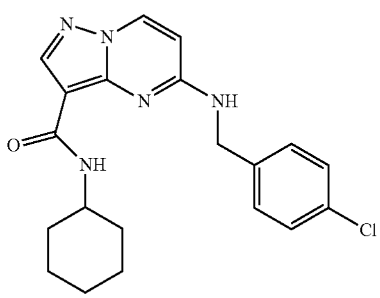 [SMILES: O=C(NC1CCCCC1)c1cnn2ccc(NCc3ccc(Cl)cc3)nc12] | 5-(4-chlorobenzylamino)-N-cycyclohexylpyrazolo[1,5-a]pyrimidine-3-carboxamide | 384.2 |
| 67 | 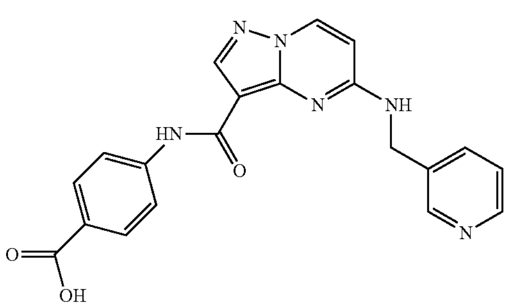 [SMILES: O=C(O)c1ccc(NC(=O)c2cnn3ccc(NCc4cccnc4)nc23)cc1] | 4-(5-(pyridin-3-ylmethylamino)pyrazolo[1,5-a]pyrimidine-3-carboxamido)benzoic acid | 389.2 |
| 68 | 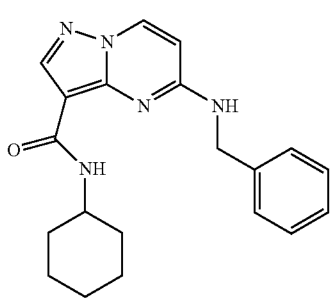 [SMILES: O=C(NC1CCCCC1)c1cnn2ccc(NCc3ccccc3)nc12] | 5-(benzylamino)-N-cyclohexylpyrazolo[1,5-a]pyrimidine-3-carboxamide | 350.2 |

TABLE 1-continued

| Ex # | Structure | Name | CMS, M + H/1 |
|---|---|---|---|
| 69 | 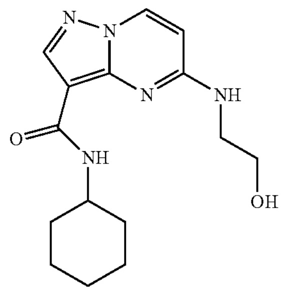 [SMILES: O=C(NC1CCCCC1)c1cnn2ccc(NCCO)nc12] | N-cyclohexyl-5-(2-hydroxyethylamino)pyrazolo[1,5-a]pyrimidine-3-carboxamide | 304.2 |
| 70 | 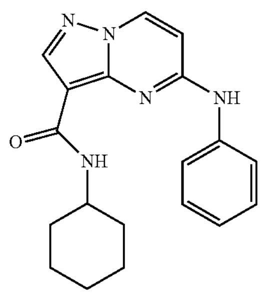 [SMILES: O=C(NC1CCCCC1)c1cnn2ccc(Nc3ccccc3)nc12] | N-cyclohexyl-5-(phenylamino)pyrazolo[1,5-a]pyrimidine-3-carboxamide | 336.2 |
| 71 | 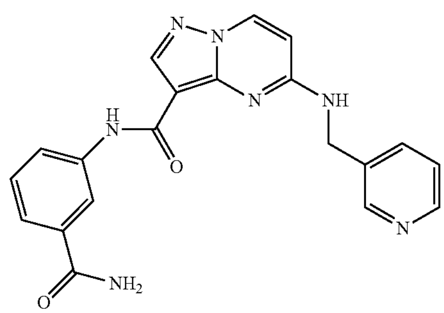 [SMILES: NC(=O)c1cccc(NC(=O)c2cnn3ccc(NCc4cccnc4)nc23)c1] | N-(3-carbamoylphenyl)-5-(pyridin-3-ylmethylamino)pyrazolo[1,5-a]pyrimidine-3-carboxamide | 388.2 |
| 72 | 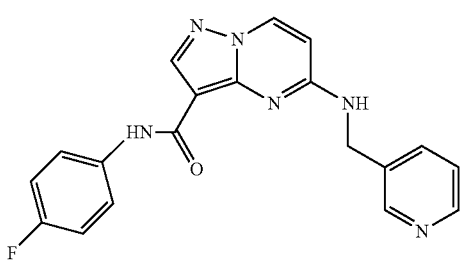 [SMILES: O=C(Nc1ccc(F)cc1)c1cnn2ccc(NCc3cccnc3)nc12] | N-(4-fluorophenyl)-5-(pyridin-3-ylmethylamino)pyrazolo[1,5-a]pyrimidine-3-carboxamide | 363.2 |
| 73 | 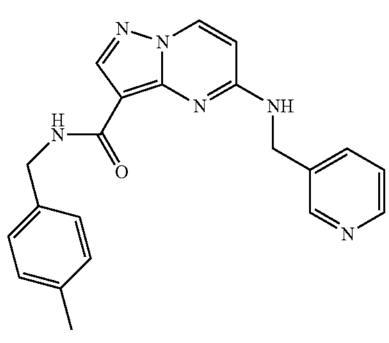 [SMILES: Cc1ccc(CNC(=O)c2cnn3ccc(NCc4cccnc4)nc23)cc1] | N-(4-methylbenzyl)-5-(pyridin-3-ylmethylamino)pyrazolo[1,5-a]pyrimidine-3-carboxamide | 373.2 |

TABLE 1-continued

| Ex # | Structure | Name | CMS, M + H/1 |
|---|---|---|---|
| 74 | 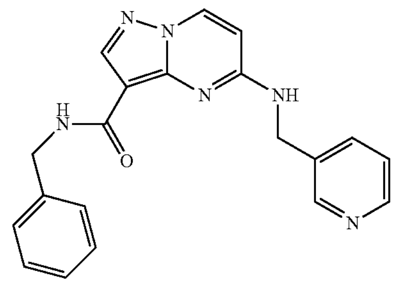 [SMILES: O=C(NCc1ccccc1)c1cnn2ccc(NCc3cccnc3)nc12] | N-benzyl-5-(pyridin-3-ylmethylamino)pyrazolo[1,5-a]pyrimidine-3-carboxamide | 359.2 |
| 75 | 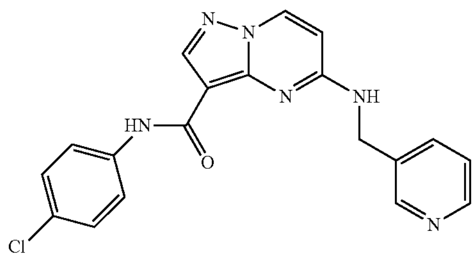 [SMILES: O=C(Nc1ccc(Cl)cc1)c1cnn2ccc(NCc3cccnc3)nc12] | N-(4-chlorophenyl)-5-(pyridin-3-ylmethylamino)pyrazolo[1,5-a]pyrimidine-3-carboxamide | 379.2 |
| 76 | 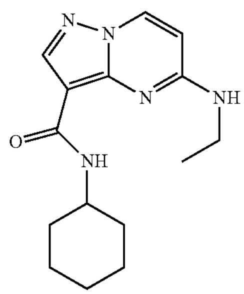 [SMILES: CCNc1ccn2ncc(C(=O)NC3CCCCC3)c2n1] | N-cyclohexyl-5-(ethylamino)pyrazolo[1,5-a]pyrimidine-3-carboxamide | 288.2 |
| 77 | 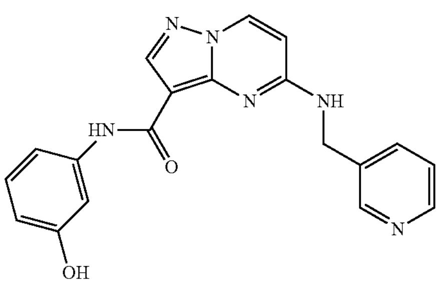 [SMILES: O=C(Nc1cccc(O)c1)c1cnn2ccc(NCc3cccnc3)nc12] | N-(3-hydroxyphenyl)-5-(pyridin-3-ylmethylamino)pyrazolo[1,5-a]pyrimidine-3-carboxamide | 361.2 |
| 78 | 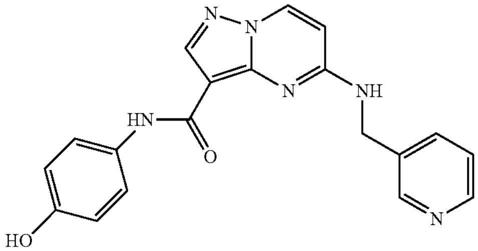 [SMILES: O=C(Nc1ccc(O)cc1)c1cnn2ccc(NCc3cccnc3)nc12] | N-(4-hydroxyphenyl)-5-(pyridin-3-ylmethylamino)pyrazolo[1,5-a]pyrimidine-3-carboxamide | 361.2 |

TABLE 1-continued

| Ex # | Structure | Name | CMS, M + H/1 |
|---|---|---|---|
| 79 | 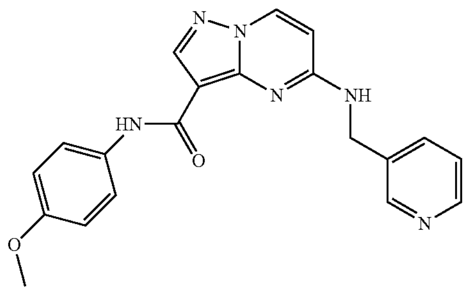 [SMILES: COc1ccc(NC(=O)c2cnn3ccc(NCc4cccnc4)nc23)cc1] | N-(4-methoxyphenyl)-5-(pyridin-3-ylmethylamino)pyrazolo[1,5-a]pyrimidine-3-carboxamide | 375.2 |
| 80 | 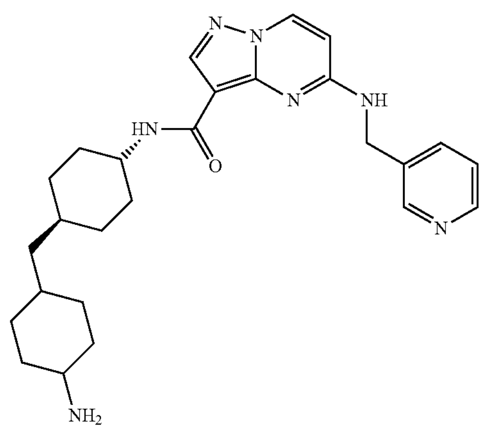 | N-((1R,4R)-4-((4-aminocyclohexyl)methyl)-cyclohexyl)-5-(pyridin-3-ylmethylamino)pyrazolo[1,5-a]pyrimidine-3-carboxamide | 462.3 |
| 81 | 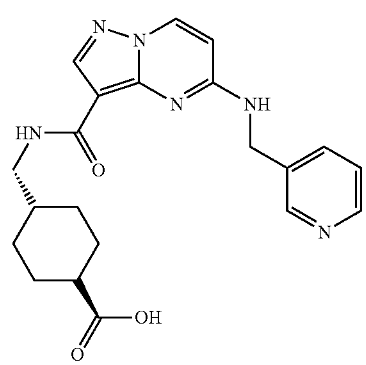 | (1S,4S)-4-((5-(pyridin-3-ylmethylamino)pyrazolo[1,5-a]pyrimidine-3-carboxamido)methyl)-cyclohexanecarboxylic acid | 409.2 |
| 82 | 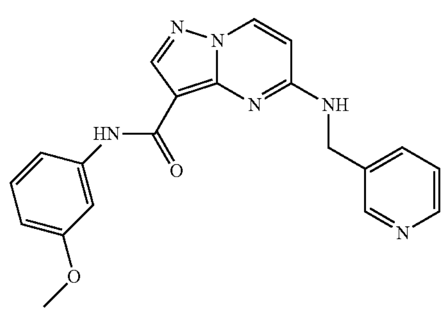 [SMILES: COc1cccc(NC(=O)c2cnn3ccc(NCc4cccnc4)nc23)c1] | N-(3-methoxyphenyl)-5-(pyridin-3-ylmethylamino)pyrazolo[1,5-a]pyrimidine-3-carboxamide | 375.2 |

TABLE 1-continued

| Ex # | Structure | Name | CMS, M + H/1 |
|---|---|---|---|
| 83 | 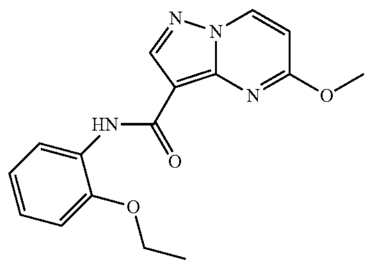 [SMILES: CCOc1ccccc1NC(=O)c1cnn2ccc(OC)nc12] | N-(2-ethoxyphenyl)-5-methoxypyrazolo[1,5-a]pyrimidine-3-carboxamide | 313.2 |
| 84 | 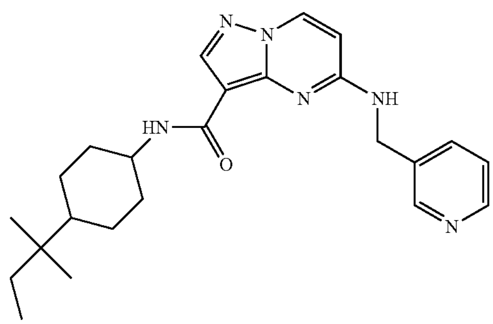 [SMILES: CCC(C)(C)C1CCC(NC(=O)c2cnn3ccc(NCc4cccnc4)nc23)CC1] | N-(4-tert-pentylcyclohexyl)-5-(pyridin-3-ylmethylamino)pyrazolo[1,5-a]pyrimidine-3-carboxamide | 421.3 |
| 85 | 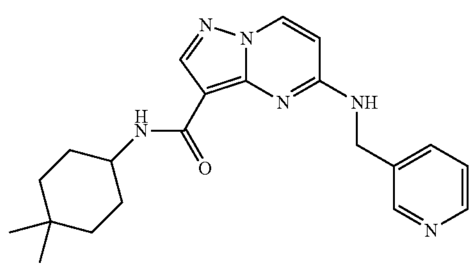 [SMILES: CC1(C)CCC(NC(=O)c2cnn3ccc(NCc4cccnc4)nc23)CC1] | N-(4,4-dimethylcyclohexyl)-5-(pyridin-3-ylmethylamino)pyrazolo[1,5-a]pyrimidine-3-carboxamide | 379.3 |
| 86 | 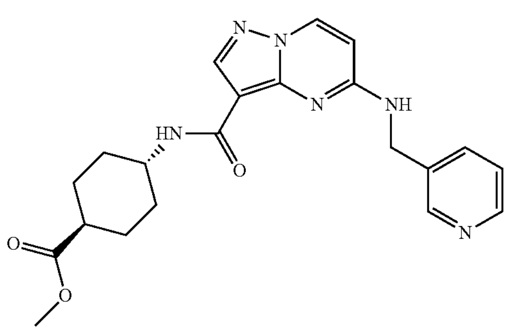 [SMILES: COC(=O)[C@H]1CC[C@H](NC(=O)c2cnn3ccc(NCc4cccnc4)nc23)CC1] | (1R,4R)-methyl 4-(5-(pyridin-3-ylmethylamino)pyrazolo[1,5-a]pyrimidine-3-carboxamido)cyclohexanecarboxylate | 409.2 |
| 87 | 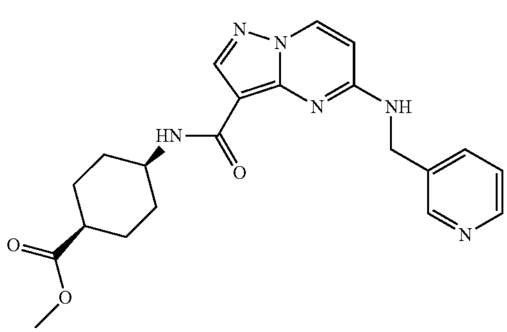 [SMILES: COC(=O)[C@H]1CC[C@@H](NC(=O)c2cnn3ccc(NCc4cccnc4)nc23)CC1] | (1S,4S)-methyl 4-(5-(pyridin-3-ylmethylamino)pyrazolo[1,5-a]pyrimidine-3-carboxamido)cyclohexanecarboxylate | 409.4 |

TABLE 1-continued

| Ex # | Structure | Name | CMS, M + H/1 |
|---|---|---|---|
| 88 | 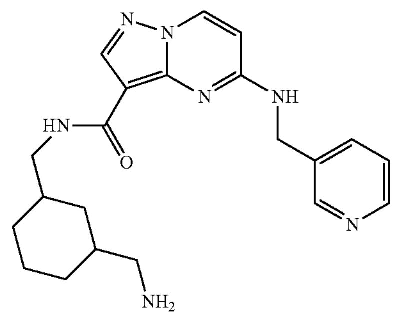 [SMILES: NCC1CCCC(CNC(=O)c2cnn3ccc(NCc4cccnc4)nc23)C1] | N-((3-(aminomethyl)cyclohexyl)methyl)-5-(pyridin-3-ylmethylamino)pyrazolo[1,5-a]pyrimidine-3-carboxamide | 394.3 |
| 89 | 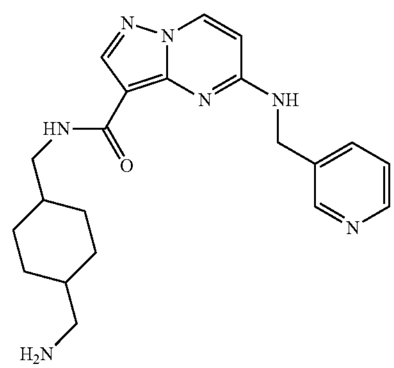 [SMILES: NCC1CCC(CNC(=O)c2cnn3ccc(NCc4cccnc4)nc23)CC1] | N-((4-(aminomethyl)cyclohexyl)methyl)-5-(pyridin-3-ylmethylamino)pyrazolo[1,5-a]pyrimidine-3-carboxamide | 394.0 |
| 90 | 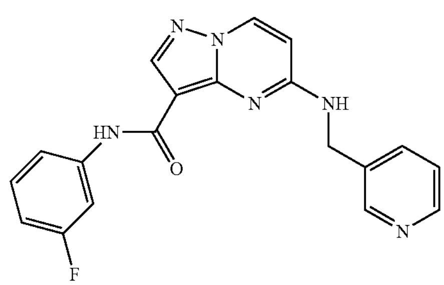 [SMILES: O=C(Nc1cccc(F)c1)c1cnn2ccc(NCc3cccnc3)nc12] | N-(3-fluorophenyl)-5-(pyridin-3-ylmethylamino)pyrazolo[1,5-a]pyrimidine-3-carboxamide | 363.2 |
| 91 | 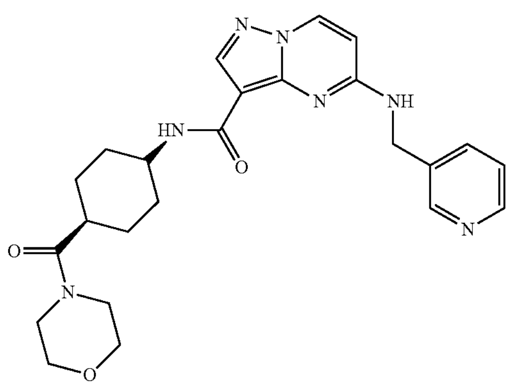 | N-((1R,4R)-4-(morpholine-4-carbonyl)cyclohexyl)-5-(pyridin-3-ylmethylamino)pyrazolo[1,5-a]pyrimidine-3-carboxamide | 464.2 |

TABLE 1-continued

| Ex # | Structure | Name | CMS, M + H/1 |
|---|---|---|---|
| 92 | 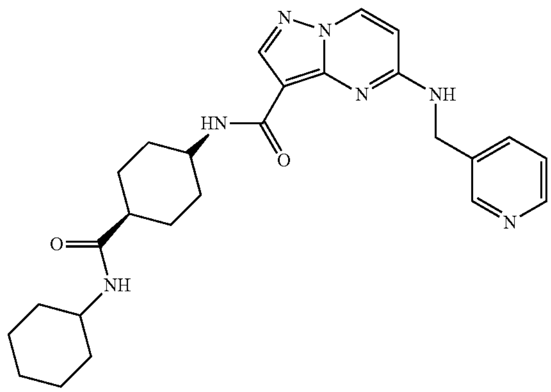 | N-((1R,4R)-4-(cyclohexylcarbamoyl)cyclohexyl)-5-(pyridin-3-ylmethylamino)pyrazolo[1,5-a]pyrimidine-3-carboxamide | 476.3 |
| 93 | 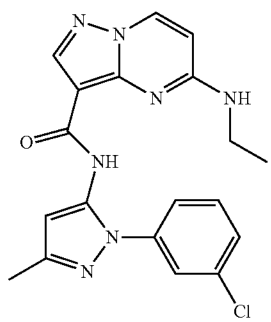 [SMILES: CCNc1ccn2ncc(C(=O)Nc3cc(C)nn3-c3cccc(Cl)c3)c2n1] | N-(1-(3-chlorophenyl)-3-methyl-1H-pyrazol-5-yl)-5-(ethylamino)pyrazolo[1,5-a]pyrimidine-3-carboxamide | 396.2 |
| 94 | 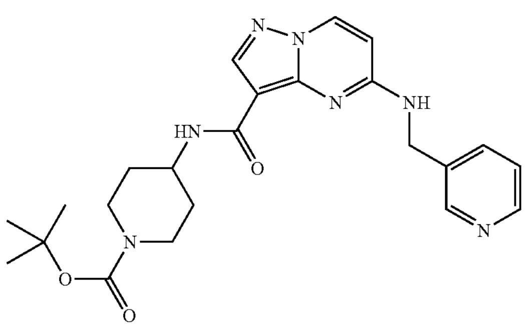 [SMILES: CC(C)(C)OC(=O)N1CCC(NC(=O)c2cnn3ccc(NCc4cccnc4)nc23)CC1] | tert-butyl 4-(5-(pyridin-3-ylmethylamino)pyrazolo[1,5-a]pyrimidine-3-carboxamido)piperidine-1-carboxylate | 452.3 |
| 95 | 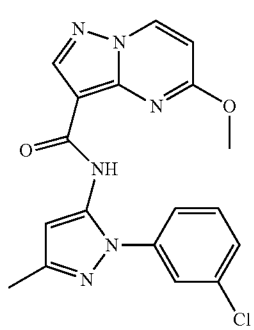 [SMILES: COc1ccn2ncc(C(=O)Nc3cc(C)nn3-c3cccc(Cl)c3)c2n1] | N-(1-(3-chlorophenyl)-3-methyl-1H-pyrazol-5-yl)-5-methoxypyrazolo[1,5-a]pyrimidine-3-carboxamide | 383.2 |

| Ex # | Structure | Name | CMS, M + H/1 |
|---|---|---|---|
| 96 | 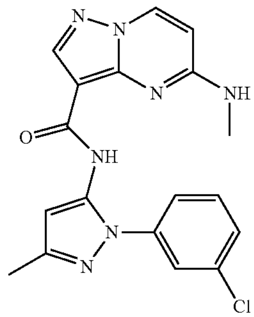 [SMILES: CNc1ccn2ncc(C(=O)Nc3cc(C)nn3-c3cccc(Cl)c3)c2n1] | N-(1-(3-chlorophenyl)-3-methyl-1H-pyrazol-5-yl)-5-(methylamino)pyrazolo[1,5-a]pyrimidine-3-carboxamide | 382.2 |
| 97 | 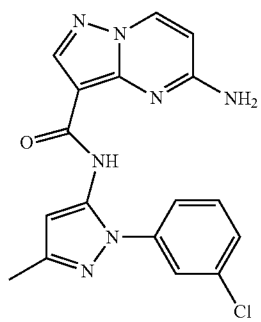 [SMILES: Cc1cc(NC(=O)c2cnn3ccc(N)nc23)n(-c2cccc(Cl)c2)n1] | 5-amino-N-(1-(3-chlorophenyl)-3-methyl-1H-pyrazol-5-yl)pyrazolo[1,5-a]pyrimidine-3-carboxamide | 368.2 |
| 98 | 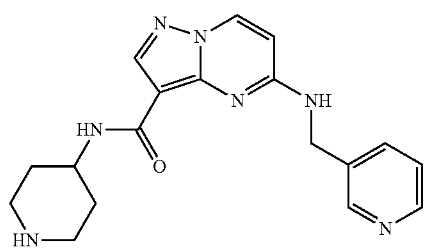 [SMILES: O=C(NC1CCNCC1)c1cnn2ccc(NCc3cccnc3)nc12] | N-(piperidin-4-yl)-5-(pyridin-3-ylmethylamino)pyrazolo[1,5-a]pyrimidine-3-carboxamide | 352.2 |
| 99 | 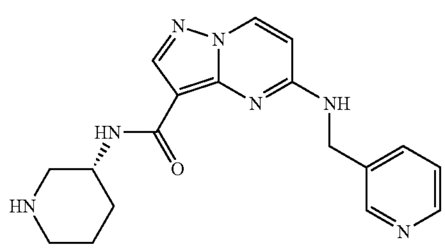 [SMILES: O=C(N[C@@H]1CCCNC1)c1cnn2ccc(NCc3cccnc3)nc12] | (R)-N-(piperidin-3-yl)-5-(pyridin-3-ylmethylamino)pyrazolo[1,5-a]pyrimidine-3-carboxamide | 352.2 |
| 100 | 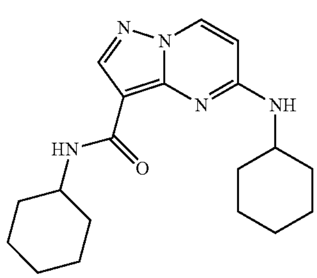 [SMILES: O=C(NC1CCCCC1)c1cnn2ccc(NC3CCCCC3)nc12] | N-cyclohexyl-5-(cyclohexylamino)pyrazolo[1,5-a]pyrimidine-3-carboxamide | 342.3 |

TABLE 1-continued

| Ex # | Structure | Name | CMS, M + H/1 |
|---|---|---|---|
| 101 | 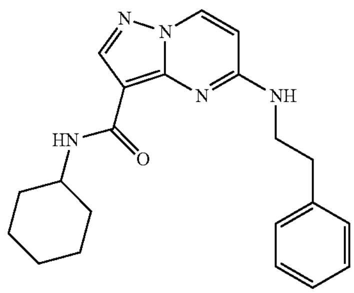 [SMILES: O=C(NC1CCCCC1)c1cnn2ccc(NCCc3ccccc3)nc12] | N-cyclohexyl-5-(phenethylamino)pyrazolo[1,5-a]pyrimidine-3-carboxamide | 364.3 |
| 102 | 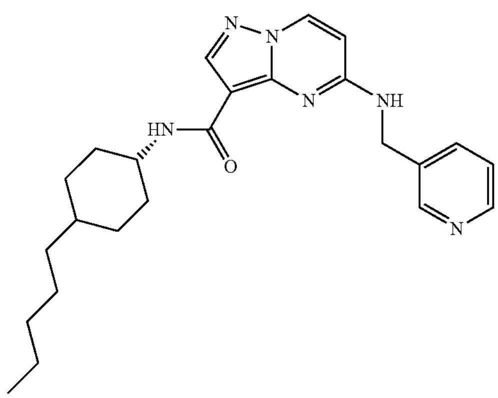 | N-(4-pentylcyclohexyl)-5-(pyridin-3-ylmethylamino)pyrazolo[1,5-a]pyrimidine-3-carboxamide | 421.3 |
| 103 | 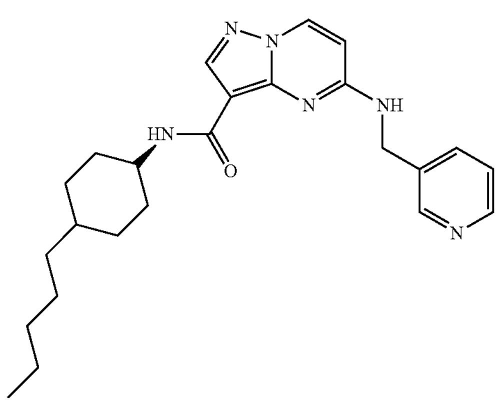 | N-(4-pentylcyclohexyl)-5-(pyridin-3-ylmethylamino)pyrazolo[1,5-a]pyrimidine-3-carboxamide | 421.3 |
| 104 | 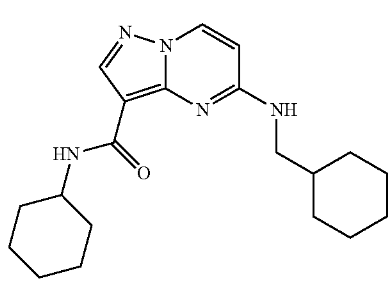 [SMILES: O=C(NC1CCCCC1)c1cnn2ccc(NCC3CCCCC3)nc12] | N-cyclohexyl-5-(cyclohexylmethylamino)pyrazolo-[1,5-a]pyrimidine-3-carboxamide | 356.3 |

TABLE 1-continued

| Ex # | Structure | Name | CMS, M + H/1 |
|---|---|---|---|
| 105 | 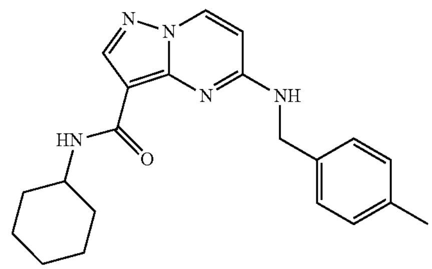 [SMILES: Cc1ccc(CNc2ccn3ncc(C(=O)NC4CCCCC4)c3n2)cc1] | N-cyclohexyl-5-(4-methylbenzylamino)pyrazolo[1,5-a]pyrimidine-3-carboxamide | 364.3 |
| 106 | 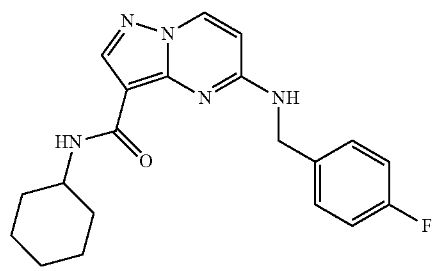 [SMILES: O=C(NC1CCCCC1)c1cnn2ccc(NCc3ccc(F)cc3)nc12] | N-cyclohexyl-5-(4-fluorobenzylamino)pyrazolo[1,5-a]pyrimidine-3-carboxamide | 368.2 |
| 107 | 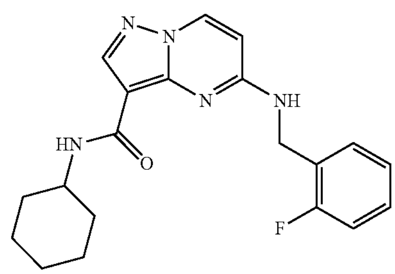 [SMILES: O=C(NC1CCCCC1)c1cnn2ccc(NCc3ccccc3F)nc12] | N-cyclohexyl-5-(2-fluorobenzylamino)pyrazolo[1,5-a]pyrimidine-3-carboxamide | 368.2 |
| 108 | 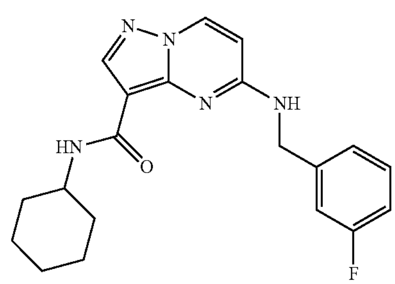 [SMILES: O=C(NC1CCCCC1)c1cnn2ccc(NCc3cccc(F)c3)nc12] | N-cyclohexyl-5-(3-fluorobenzylamino)pyrazolo[1,5-a]pyrimidine-3-carboxamide | 368.2 |
| 109 | 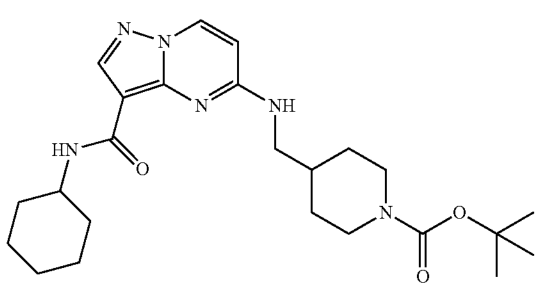 [SMILES: CC(C)(C)OC(=O)N1CCC(CNc2ccn3ncc(C(=O)NC4CCCCC4)c3n2)CC1] | tert-butyl 4-((3-(cyclohexylcarbamoyl)pyrazolo-[1,5-a]pyrimidin-5-ylamino)methyl)piperidine-1-carboxylate | 457.3 |

TABLE 1-continued

| Ex # | Structure | Name | CMS, M + H/1 |
|---|---|---|---|
| 110 | 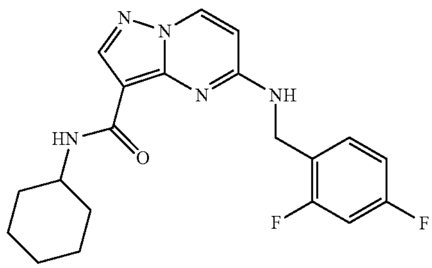 [SMILES: O=C(NC1CCCCC1)c1cnn2ccc(NCc3ccc(F)cc3F)nc12] | N-cyclohexyl-5-(2,4-difluorobenzylamino)pyrazolo[1,5-a]pyrimidine-3-carboxamide | 386.2 |
| 111 | 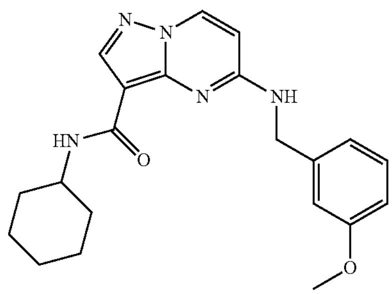 [SMILES: COc1cccc(CNc2ccn3ncc(C(=O)NC4CCCCC4)c3n2)c1] | N-cyclohexyl-5-(3-methoxybenzylamino)pyrazolo-[1,5-a]pyrimidine-3-carboxamide | 380.3 |
| 112 | 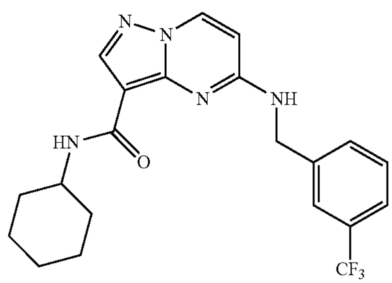 [SMILES: O=C(NC1CCCCC1)c1cnn2ccc(NCc3cccc(C(F)(F)F)c3)nc12] | N-cyclohexyl-5-(3-(trifluoromethyl)benzylamino)-pyrazolo[1,5-a]pyrimidine-3-carboxamide | 418.2 |
| 113 | 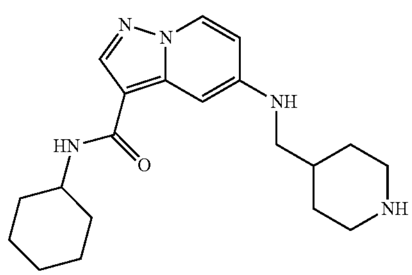 [SMILES: O=C(NC1CCCCC1)c1cnn2ccc(NCC3CCNCC3)cc12] | N-cyclohexyl-5-(piperidin-4-ylmethylamino)pyrazolo[1,5-a]pyridine-3-carboxamide | 357.3 |
| 114 | 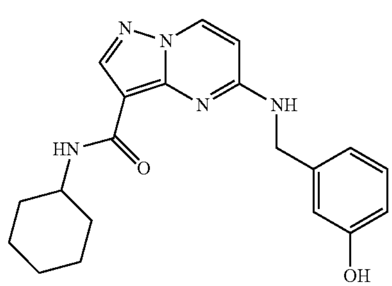 [SMILES: O=C(NC1CCCCC1)c1cnn2ccc(NCc3cccc(O)c3)nc12] | N-cyclohexyl-5-(3-hydroxybenzylamino)pyrazolo-[1,5-a]pyrimidine-3-carboxamide | 366.2 |

TABLE 1-continued

| Ex # | Structure | Name | CMS, M + H/1 |
|---|---|---|---|
| 115 | 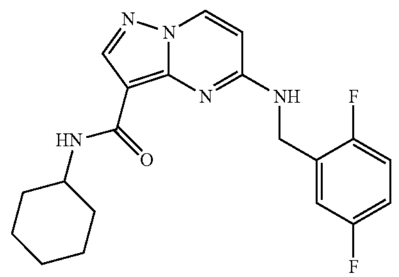 [SMILES: O=C(NC1CCCCC1)c1cnn2ccc(NCc3cc(F)ccc3F)nc12] | N-cyclohexyl-5-(2,5-difluorobenzylamino)pyrazolo-[1,5-a]pyrimidine-3-carboxamide | 386.2 |
| 116 | 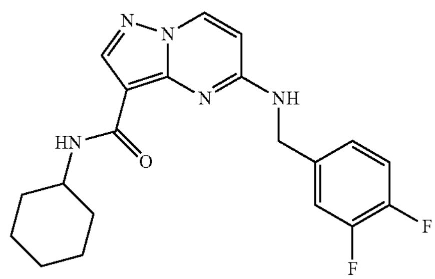 [SMILES: O=C(NC1CCCCC1)c1cnn2ccc(NCc3ccc(F)c(F)c3)nc12] | N-cyclohexyl-5-(3,4-difluorobenzylamino)pyrazolo-[1,5-a]pyrimidine-3-carboxamide | 386.2 |
| 117 | 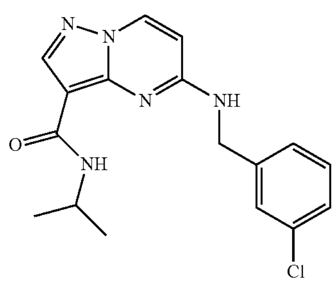 [SMILES: CC(C)NC(=O)c1cnn2ccc(NCc3cccc(Cl)c3)nc12] | 5-(3-chlorobenzylamino)-N-isopropylpyrazolo[1,5-a]pyrimidine-3-carboxamide | 344.2 |
| 118 | 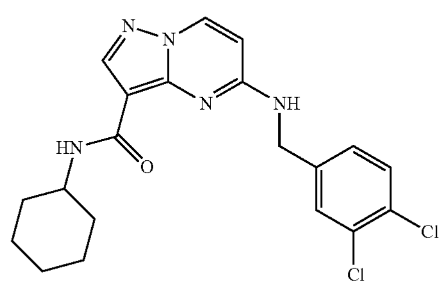 [SMILES: O=C(NC1CCCCC1)c1cnn2ccc(NCc3ccc(Cl)c(Cl)c3)nc12] | N-cyclohexyl-5-(3,4-dichlorobenzylamino)pyrazolo-[1,5-a]pyrimidine-3-carboxamide | 418.1 |
| 119 | 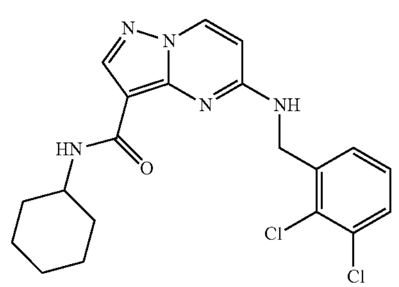 [SMILES: O=C(NC1CCCCC1)c1cnn2ccc(NCc3cccc(Cl)c3Cl)nc12] | N-cyclohexyl-5-(2,3-dichlorobenzylamino)pyrazolo-[1,5-a]pyrimidine-3-carboxamide | 418.1 |

| Ex # | Structure | Name | CMS, M + H/1 |
|---|---|---|---|
| 120 | 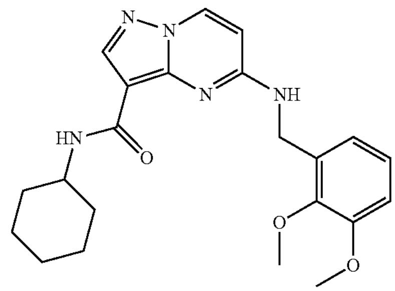 [SMILES: COc1cccc(CNc2ccn3ncc(C(=O)NC4CCCCC4)c3n2)c1OC] | N-cyclohexyl-5-(2,3-dimethoxybenzylamino)pyrazolo-[1,5-a]pyrimidine-3-carboxamide | 410.2 |
| 121 | 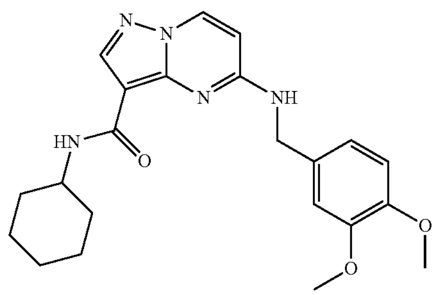 [SMILES: COc1ccc(CNc2ccn3ncc(C(=O)NC4CCCCC4)c3n2)cc1OC] | N-cyclohexyl-5-(3,4-dimethoxybenzylamino)pyrazolo-[1,5-a]pyrimidine-3-carboxamide | 410.2 |
| 122 | 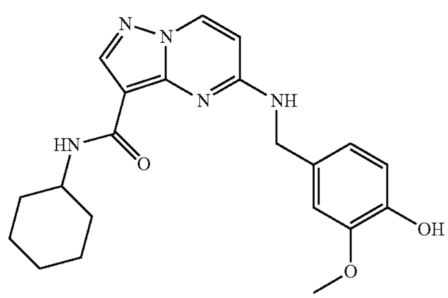 [SMILES: COc1cc(CNc2ccn3ncc(C(=O)NC4CCCCC4)c3n2)ccc1O] | N-cyclohexyl-5-(4-hydroxy-3-methoxybenzylamino)pyrazolo-[1,5-a]pyrimidine-3-carboxamide | 396.2 |
| 123 | 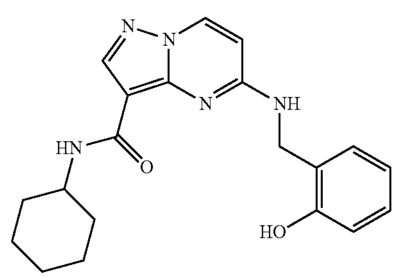 [SMILES: O=C(NC1CCCCC1)c1cnn2ccc(NCc3ccccc3O)nc12] | N-cyclohexyl-5-(2-hydroxybenzylamino)pyrazolo-[1,5-a]pyrimidine-3-carboxamide | 366.2 |
| 124 | 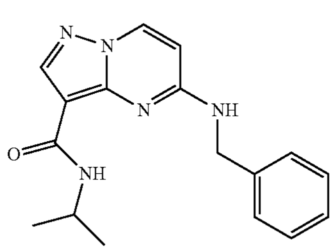 [SMILES: CC(C)NC(=O)c1cnn2ccc(NCc3ccccc3)nc12] | 5-(benzylamino)-N-isopropylpyrazolo[1,5-a]pyrimidine-3-carboxamide | 310.2 |

| Ex # | Structure | Name | CMS, M + H/1 |
|---|---|---|---|
| 125 | 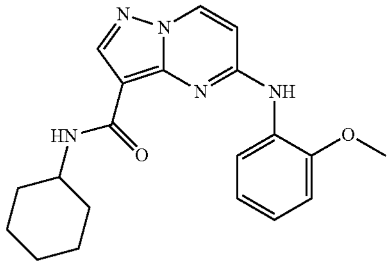 [SMILES: COc1ccccc1Nc1ccn2ncc(C(=O)NC3CCCCC3)c2n1] | N-cyclohexyl-5-(2-methoxyphenylamino)pyrazolo-[1,5-a]pyrimidine-3-carboxamide | 366.2 |
| 126 | 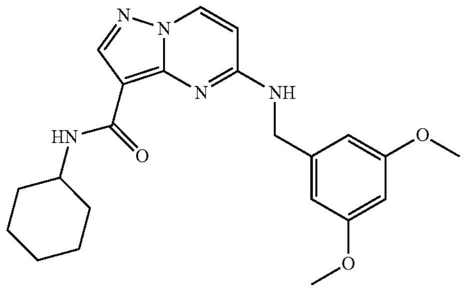 [SMILES: COc1cc(CNc2ccn3ncc(C(=O)NC4CCCCC4)c3n2)cc(OC)c1] | N-cyclohexyl-5-(3,5-dimethoxybenzylamino)pyrazolo-[1,5-a]pyrimidine-3-carboxamide | 410.2 |
| 127 | 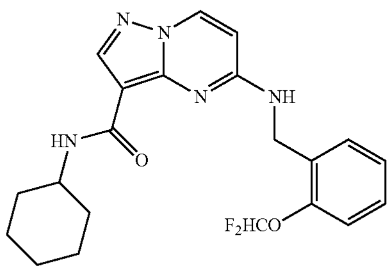 [SMILES: O=C(NC1CCCCC1)c1cnn2ccc(NCc3ccccc3OC(F)F)nc12] | N-cyclohexyl-5-(2-(difluoromethoxy)benzylamino)-pyrazolo[1,5-a]pyrimidine-3-carboxamide | 416.2 |
| 128 | 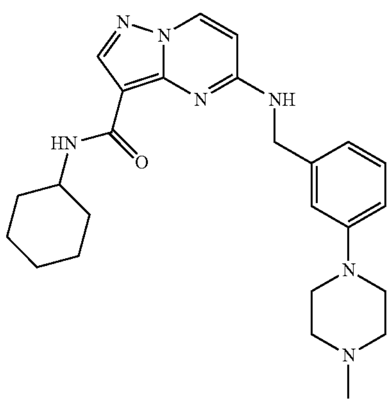 [SMILES: CN1CCN(c2cccc(CNc3ccn4ncc(C(=O)NC5CCCCC5)c4n3)c2)CC1] | N-cyclohexyl-5-(3-(4-methylpiperazin-1-yl)benzylamino)pyrazolo[1,5-a]pyrimidine-3-carboxamide | 448.3 |
| 129 | 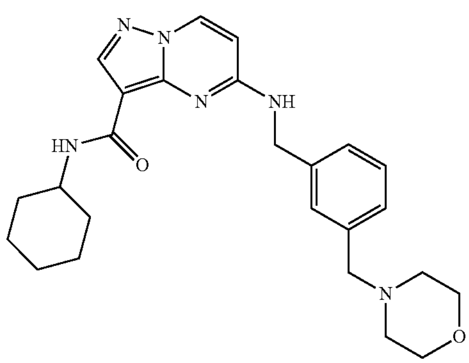 [SMILES: O=C(NC1CCCCC1)c1cnn2ccc(NCc3cccc(CN4CCOCC4)c3)nc12] | N-cyclohexyl-5-(3-(morpholinomethyl)benzylamino)-pyrazolo[1,5-a]pyrimidine-3-carboxamide | 449.3 |

TABLE 1-continued

| Ex # | Structure | Name | CMS, M + H/1 |
|---|---|---|---|
| 130 | 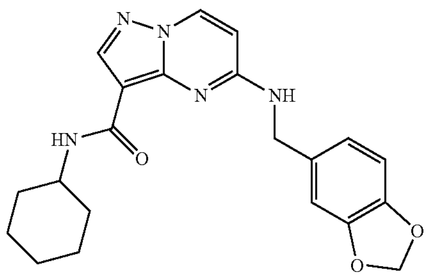 [SMILES: O=C(NC1CCCCC1)c1cnn2ccc(NCc3ccc4c(c3)OCO4)nc12] | 5-(benzo[d][1,3]dioxol-5-ylmethylamino)-N-cyclohexylpyrazolo[1,5-a]pyrimidine-3-carboxamide | 394.2 |
| 131 | 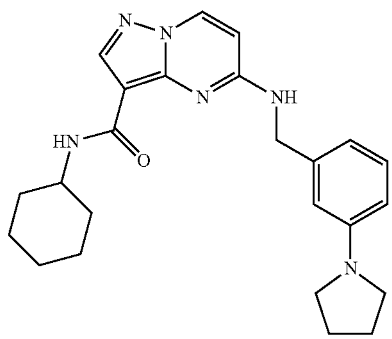 [SMILES: O=C(NC1CCCCC1)c1cnn2ccc(NCc3cccc(N4CCCC4)c3)nc12] | N-cyclohexyl-5-(3-(pyrrolidin-1-yl)benzylamino)pyrazolo[1,5-a]pyrimidine-3-carboxamide | 419.3 |
| 132 | 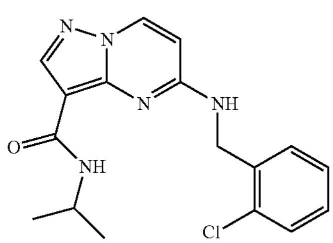 [SMILES: CC(C)NC(=O)c1cnn2ccc(NCc3ccccc3Cl)nc12] | 5-(2-chlorobenzylamino)-N-isopropylpyrazolo[1,5-a]pyrimidine-3-carboxamide | 344.2 |
| 133 | 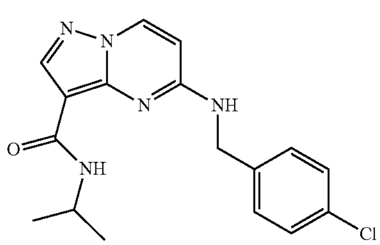 [SMILES: CC(C)NC(=O)c1cnn2ccc(NCc3ccc(Cl)cc3)nc12] | 5-(4-chlorobenzylamino)-N-isopropylpyrazolo[1,5-a]pyrimidine-3-carboxamide | 344.2 |
| 134 | 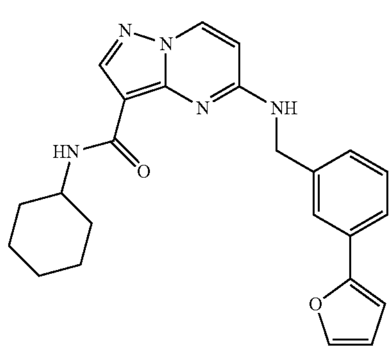 [SMILES: O=C(NC1CCCCC1)c1cnn2ccc(NCc3cccc(-c4ccco4)c3)nc12] | N-cyclohexyl-5-(3-(furan-2-yl)benzylamino)pyrazolo[1,5-a]pyrimidine-3-carboxamide | 416.2 |

TABLE 1-continued

| Ex # | Structure | Name | CMS, M + H/1 |
|---|---|---|---|
| 135 | 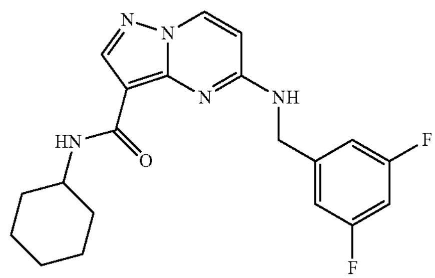 [SMILES: O=C(NC1CCCCC1)c1cnn2ccc(NCc3cc(F)cc(F)c3)nc12] | N-cyclohexyl-5-(3,5-difluorobenzylamino)pyrazolo-[1,5-a]pyrimidine-3-carboxamide | 386.2 |
| 136 | 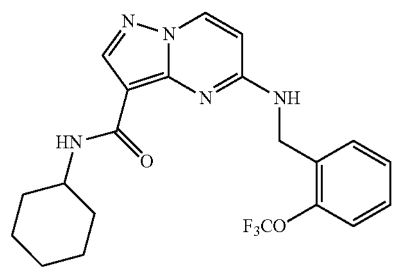 [SMILES: O=C(NC1CCCCC1)c1cnn2ccc(NCc3ccccc3OC(F)(F)F)nc12] | N-cyclohexyl-5-(2-(trifluoromethoxy)benzylamino)-pyrazolo[1,5-a]pyrimidine-3-carboxamide | 434.2 |
| 137 | 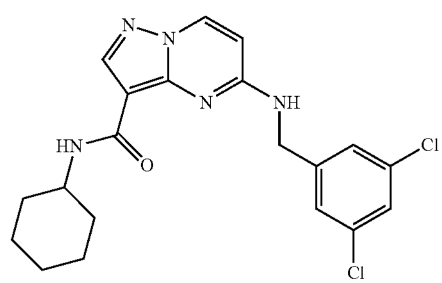 [SMILES: O=C(NC1CCCCC1)c1cnn2ccc(NCc3cc(Cl)cc(Cl)c3)nc12] | N-cyclohexyl-5-(3,5-dichlorobenzylamino)pyrazolo-[1,5-a]pyrimidine-3-carboxamide | 418.1 |
| 138 | 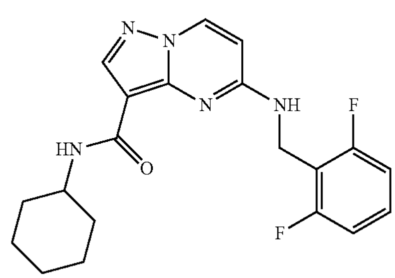 [SMILES: O=C(NC1CCCCC1)c1cnn2ccc(NCc3c(F)cccc3F)nc12] | N-cyclohexyl-5-(2,6-difluorobenzylamino)pyrazolo-[1,5-a]pyrimidine-3-carboxamide | 386.2 |
| 139 | 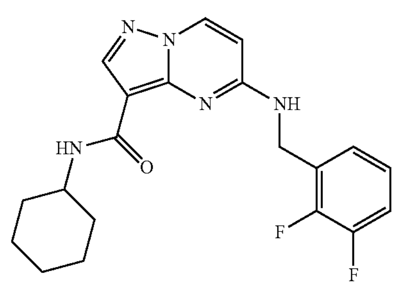 [SMILES: O=C(NC1CCCCC1)c1cnn2ccc(NCc3cccc(F)c3F)nc12] | N-cyclohexyl-5-(2,3-difluorobenzylamino)pyrazolo[1,5-a]pyrimidine-3-carboxamide | 386.2 |

TABLE 1-continued

| Ex # | Structure | Name | CMS, M + H/1 |
|---|---|---|---|
| 140 | 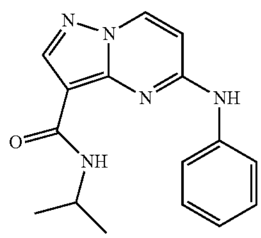 [SMILES: CC(C)NC(=O)c1cnn2ccc(Nc3ccccc3)nc12] | N-isopropyl-5-(phenylamino)pyrazolo[1,5-a]pyrimidine-3-carboxamide | 296.2 |
| 141 | 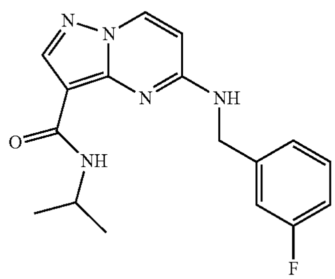 [SMILES: CC(C)NC(=O)c1cnn2ccc(NCc3cccc(F)c3)nc12] | 5-(3-fluorobenzylamino)-N-isopropylpyrazolo[1,5-a]pyrimidine-3-carboxamide | 328.2 |
| 142 | 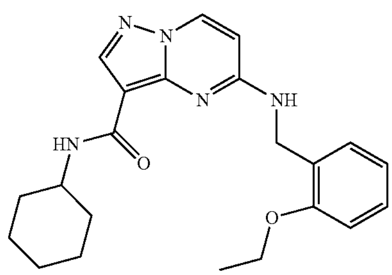 [SMILES: CCOc1ccccc1CNc1ccn2ncc(C(=O)NC3CCCCC3)c2n1] | N-cyclohexyl-5-(2-ethoxybenzylamino)pyrazolo[1,5-a]pyrimidine-3-carboxamide | 394.3 |
| 143 | 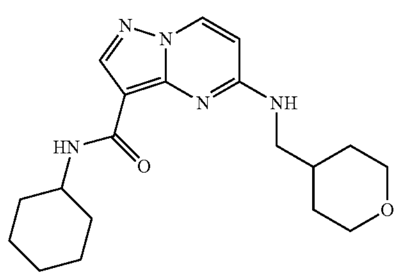 [SMILES: O=C(NC1CCCCC1)c1cnn2ccc(NCC3CCOCC3)nc12] | N-cyclohexyl-5-((tetrahydro-2H-pyran-4-yl)methylamino)pyrazolo[1,5-a]pyrimidine-3-carboxamide | 358.3 |
| 144 | 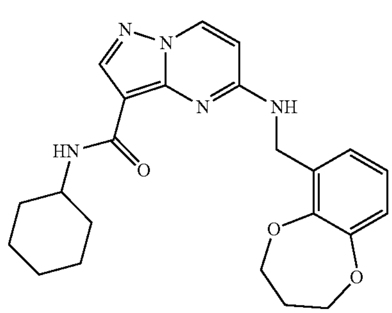 [SMILES: O=C(NC1CCCCC1)c1cnn2ccc(NCc3cccc4c3OCCCO4)nc12] | N-cyclohexyl-5-((3,4-dihydro-2H-benzo[b][1,4]dioxepin-6-yl)methylamino)pyrazolo[1,5-a]pyrimidine-3-carboxamide | 422.2 |

| Ex # | Structure | Name | CMS, M + H/1 |
| --- | --- | --- | --- |
| 145 | 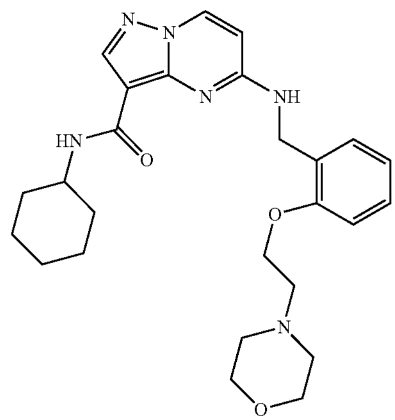 [SMILES: O=C(NC1CCCCC1)c1cnn2ccc(NCc3ccccc3OCCN3CCOCC3)nc12] | N-cyclohexyl-5-(2-(2-morpholinoethoxy)benzylamino)-pyrazolo[1,5-a]pyrimidine-3-carboxamide | 479.3 |
| 146 | 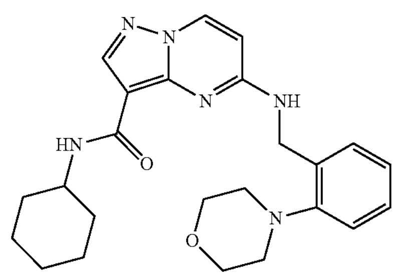 [SMILES: O=C(NC1CCCCC1)c1cnn2ccc(NCc3ccccc3N3CCOCC3)nc12] | N-cyclohexyl-5-(2-morpholinobenzylamino)pyrazolo-[1,5-a]pyrimidine-3-carboxamide | 435.3 |
| 147 | 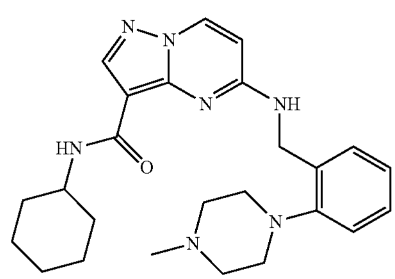 [SMILES: CN1CCN(c2ccccc2CNc2ccn3ncc(C(=O)NC4CCCCC4)c3n2)CC1] | N-cyclohexyl-5-(2-(4-methylpiperazin-1-yl)benzylamino)pyrazolo[1,5-a]pyrimidine-3-carboxamide | 448.3 |
| 148 | 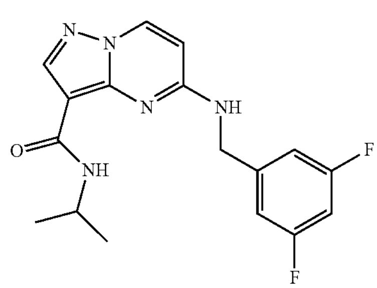 [SMILES: CC(C)NC(=O)c1cnn2ccc(NCc3cc(F)cc(F)c3)nc12] | 5-(3,5-difluorobenzylamino)-N-isopropylpyrazolo[1,5-a]pyrimidine-3-carboxamide | 346.2 |

TABLE 1-continued

| Ex # | Structure | Name | CMS, M + H/1 |
|---|---|---|---|
| 149 | 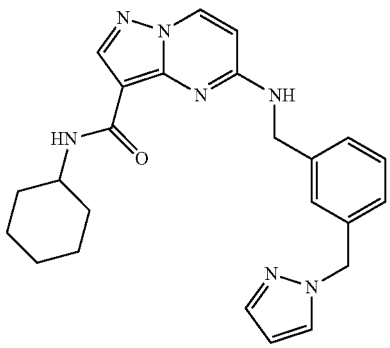 [SMILES: O=C(NC1CCCCC1)c1cnn2ccc(NCc3cccc(Cn4cccn4)c3)nc12] | 5-(3-((1H-pyrazol-1-yl)methyl)benzylamino)-N-cyclohexylpyrazolo[1,5-a]pyrimidine-3-carboxamide | 430.2 |
| 150 | 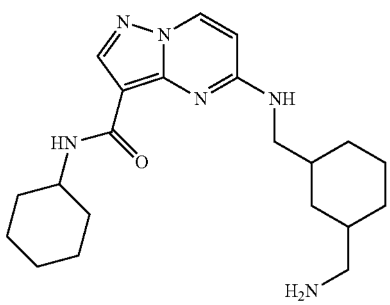 [SMILES: NCC1CCCC(CNc2ccn3ncc(C(=O)NC4CCCCC4)c3n2)C1] | 5-((3-(aminomethyl)cyclohexyl)-methylamino)-N-cyclohexyl-pyrazolo[1,5-a]pyrimidine-3-carboxamide | 385.2 |
| 151 | 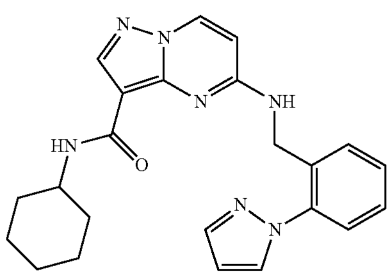 [SMILES: O=C(NC1CCCCC1)c1cnn2ccc(NCc3ccccc3-n3cccn3)nc12] | 5-(2-(1H-pyrazol-1-yl)benzylamino)-N-cyclohexylpyrazolo[1,5-a]pyrimidine-3-carboxamide | 416.2 |
| 152 | 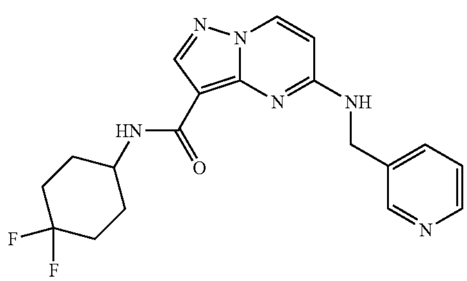 [SMILES: O=C(NC1CCC(F)(F)CC1)c1cnn2ccc(NCc3cccnc3)nc12] | N-(4,4-difluorocyclohexyl)-5-(pyridin-3-ylmethylamino)pyrazolo[1,5-a]pyrimidine-3-carboxamide | 387.1 |
| 153 | 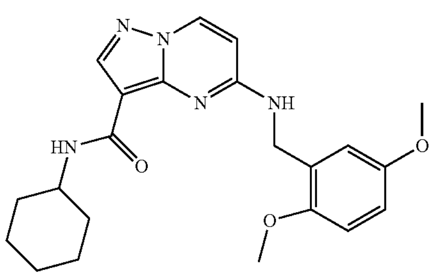 [SMILES: COc1ccc(OC)c(CNc2ccn3ncc(C(=O)NC4CCCCC4)c3n2)c1] | N-cyclohexyl-5-(2,5-dimethoxybenzylamino)pyrazolo-[1,5-a]pyrimidine-3-carboxamide | 410.2 |

TABLE 1-continued

| Ex # | Structure | Name | CMS, M + H/1 |
|---|---|---|---|
| 154 | 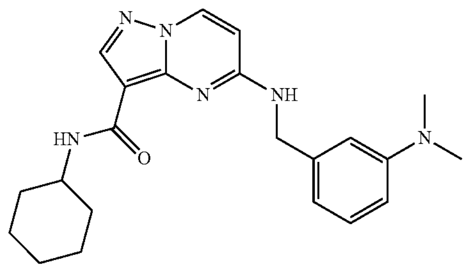 [SMILES: CN(C)c1cccc(CNc2ccn3ncc(C(=O)NC4CCCCC4)c3n2)c1] | N-cyclohexyl-5-(3-(dimethylamino)benzylamino)-pyrazolo[1,5-a]pyrimidine-3-carboxamide | 393.2 |
| 155 | 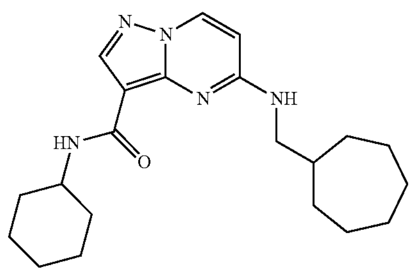 [SMILES: O=C(NC1CCCCC1)c1cnn2ccc(NCC3CCCCCC3)nc12] | 5-(cycloheptylmethylamino)-N-cyclohexylpyrazolo[1,5-a]pyrimidine-3-carboxamide | 370.2 |
| 156 | 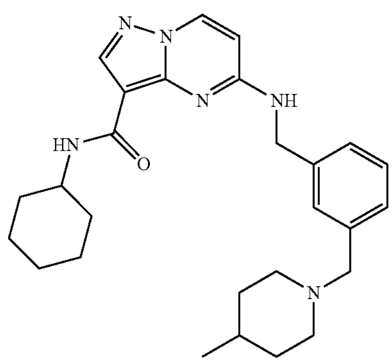 [SMILES: CC1CCN(Cc2cccc(CNc3ccn4ncc(C(=O)NC5CCCCC5)c4n3)c2)CC1] | N-cyclohexyl-5-(3-((4-methylpiperidin-1-yl)methyl)benzylamino)pyrazolo-[1,5-a]pyrimidine-3-carboxamide | 461.3 |
| 157 | 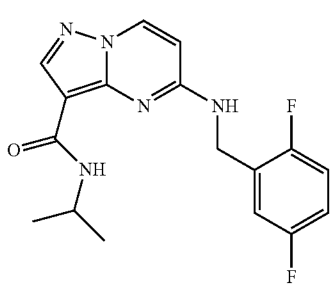 [SMILES: CC(C)NC(=O)c1cnn2ccc(NCc3cc(F)ccc3F)nc12] | 5-(2,5-difluorobenzylamino)-N-isopropylpyrazolo[1,5-a]pyrimidine-3-carboxamide | 346.1 |
| 158 | 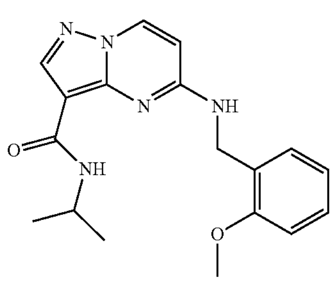 [SMILES: COc1ccccc1CNc1ccn2ncc(C(=O)NC(C)C)c2n1] | N-isopropyl-5-(2-methoxybenzylamino)pyrazolo-[1,5-a]pyrimidine-3-carboxamide | 340.2 |

TABLE 1-continued

| Ex # | Structure | Name | CMS, M + H/1 |
|---|---|---|---|
| 159 | 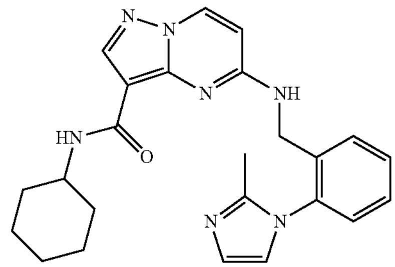 [SMILES: Cc1nccn1-c1ccccc1CNc1ccn2ncc(C(=O)NC3CCCCC3)c2n1] | N-cyclohexyl-5-(2-(2-methyl-1H-imidazol-1-yl)benzylamino)pyrazolo[1,5-a]pyrimidine-3-carboxamide | 430.2 |
| 160 | 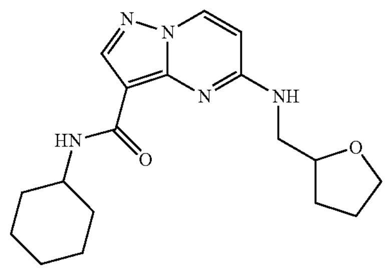 [SMILES: O=C(NC1CCCCC1)c1cnn2ccc(NCC3CCCO3)nc12] | N-cyclohexyl-5-((tetrahydrofuran-2-yl)methylamino)pyrazolo[1,5-a]pyrimidine-3-carboxamide | 344.2 |
| 161 | 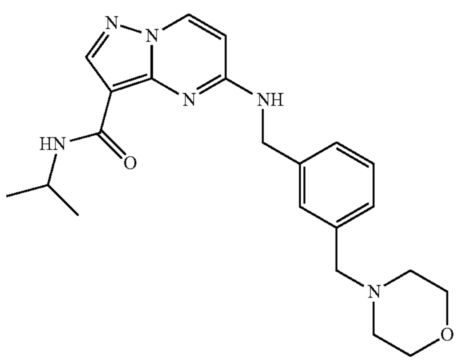 [SMILES: CC(C)NC(=O)c1cnn2ccc(NCc3cccc(CN4CCOCC4)c3)nc12] | N-isopropyl-5-(3-(morpholinomethyl)benzylamino)-pyrazolo[1,5-a]pyrimidine-3-carboxamide | 409.2 |
| 162 | 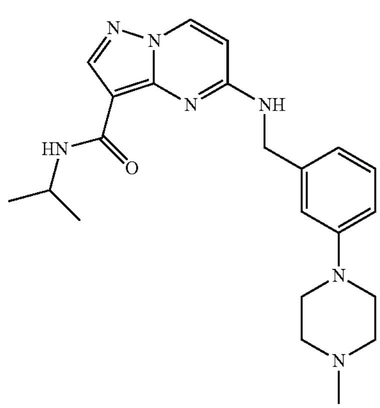 [SMILES: CC(C)NC(=O)c1cnn2ccc(NCc3cccc(N4CCN(C)CC4)c3)nc12] | N-isopropyl-5-(3-(4-methylpiperazin-1-yl)benzylamino)pyrazolo[1,5-a]pyrimidine-3-carboxamide | 408.3 |

TABLE 1-continued

| Ex # | Structure | Name | CMS, M + H/1 |
|---|---|---|---|
| 163 | 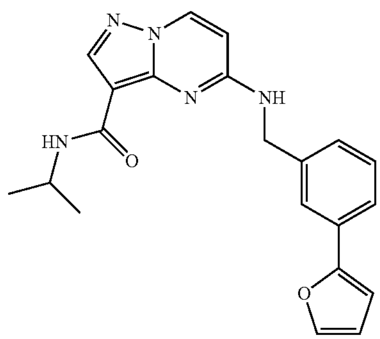 [SMILES: CC(C)NC(=O)c1cnn2ccc(NCc3cccc(-c4ccco4)c3)nc12] | 5-(3-(furan-2-yl)benzylamino)-N-isopropylpyrazolo[1,5-a]pyrimidine-3-carboxamide | 376.2 |
| 164 | 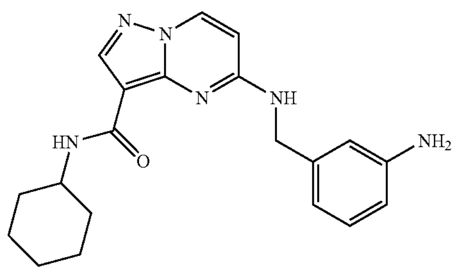 [SMILES: Nc1cccc(CNc2ccn3ncc(C(=O)NC4CCCCC4)c3n2)c1] | 5-(3-aminobenzylamino)-N-cyclohexylpyrazolo[1,5-a]pyrimidine-3-carboxamide | 365.2 |
| 165 | 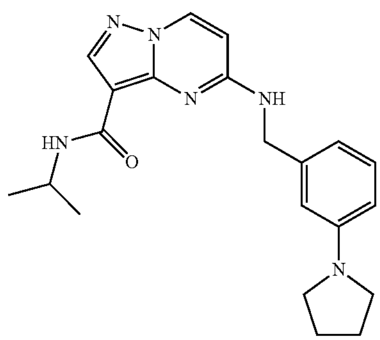 [SMILES: CC(C)NC(=O)c1cnn2ccc(NCc3cccc(N4CCCC4)c3)nc12] | N-isopropyl-5-(3-(pyrrolidin-1-yl)benzylamino)pyrazolo[1,5-a]pyrimidine-3-carboxamide | 379.2 |
| 166 | 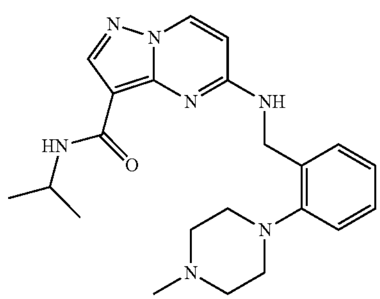 [SMILES: CC(C)NC(=O)c1cnn2ccc(NCc3ccccc3N3CCN(C)CC3)nc12] | N-isopropyl-5-(2-(4-methylpiperazin-1-yl)benzylamino)pyrazolo[1,5-a]pyrimidine-3-carboxamide | 408.2 |
| 167 | 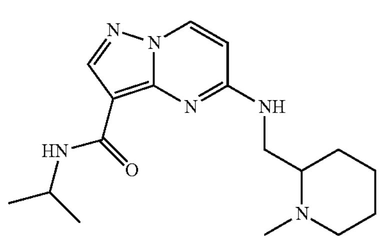 [SMILES: CC(C)NC(=O)c1cnn2ccc(NCC3CCCCN3C)nc12] | N-isopropyl-5-((1-methylpiperidin-2-yl)methylamino)pyrazolo[1,5-a]pyrimidine-3-carboxamide | 331.2 |

TABLE 1-continued

| Ex # | Structure | Name | CMS, M + H/1 |
|---|---|---|---|
| 168 | 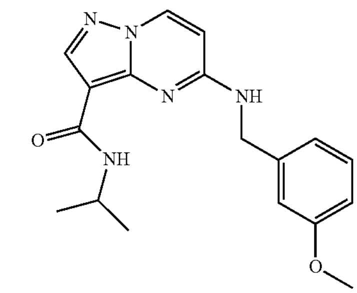 [SMILES: COc1cccc(CNc2ccn3ncc(C(=O)NC(C)C)c3n2)c1] | N-isopropyl-5-(3-methoxybenzylamino)pyrazolo-[1,5-a]pyrimidine-3-carboxamide | 340.1 |
| 169 | 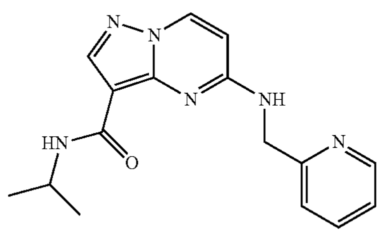 [SMILES: CC(C)NC(=O)c1cnn2ccc(NCc3ccccn3)nc12] | N-isopropyl-5-(pyridin-2-ylmethylamino)pyrazolo[1,5-a]pyrimidine-3-carboxamide | 311.1 |
| 170 | 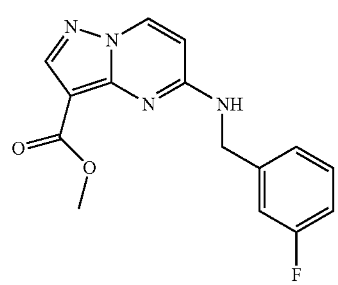 [SMILES: COC(=O)c1cnn2ccc(NCc3cccc(F)c3)nc12] | methyl 5-(3-fluorobenzylamino)pyrazolo-[1,5-a]pyrimidine-3-carboxylate | 301.1 |
| 171 | 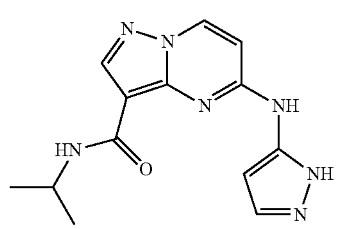 [SMILES: CC(C)NC(=O)c1cnn2ccc(Nc3ccn[nH]3)nc12] | 5-(1H-pyrazol-5-ylamino)-N-isopropylpyrazolo[1,5-a]-pyrimidine-3-carboxamide | 286.1 |
| 172 | 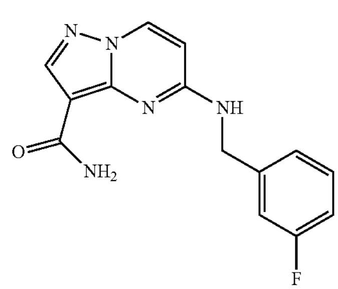 [SMILES: NC(=O)c1cnn2ccc(NCc3cccc(F)c3)nc12] | 5-(3-fluorobenzylamino)pyrazolo-[1,5-a]pyrimidine-3-carboxamide | 286.1 |

TABLE 1-continued

| Ex # | Structure | Name | CMS, M + H/1 |
|---|---|---|---|
| 173 | 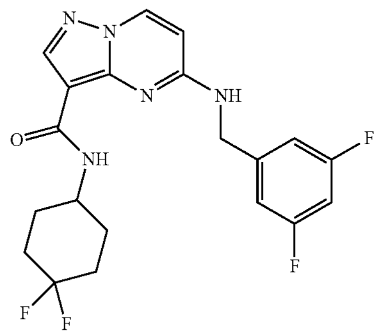 [SMILES: O=C(NC1CCC(F)(F)CC1)c1cnn2ccc(NCc3cc(F)cc(F)c3)nc12] | 5-(3,5-difluorobenzylamino)-N-(4,4-difluorocyclohexyl)-pyrazolo[1,5-a]-pyrimidine-3-carboxamide | 422.2 |
| 174 | 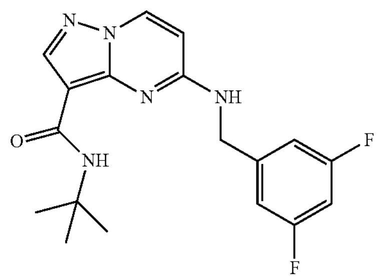 [SMILES: CC(C)(C)NC(=O)c1cnn2ccc(NCc3cc(F)cc(F)c3)nc12] | N-tert-butyl-5-(3,5-difluorobenzylamino)pyrazolo-[1,5-a]pyrimidine-3-carboxamide | 360.2 |
| 175 | 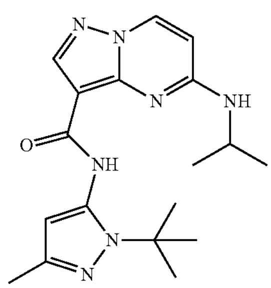 [SMILES: Cc1cc(NC(=O)c2cnn3ccc(NC(C)C)nc23)n(C(C)(C)C)n1] | N-tert-butyl-5-(3,5-difluorobenzylamino)pyrazolo-[1,5-a]pyrimidine-3-carboxamide | 356.2 |
| 176 | 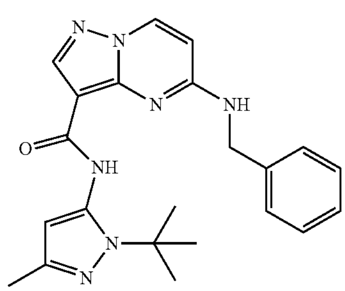 [SMILES: Cc1cc(NC(=O)c2cnn3ccc(NCc4ccccc4)nc23)n(C(C)(C)C)n1] | 5-(benzylamino)-N-(1-tert-butyl-3-methyl-1H-pyrazol-5-yl)pyrazolo[1,5-a]pyrimidine-3-carboxamide | 404.2 |
| 177 | 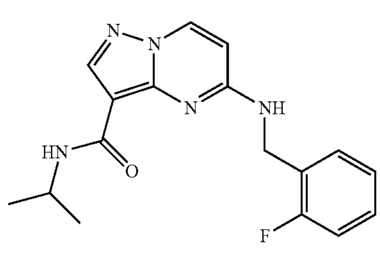 [SMILES: CC(C)NC(=O)c1cnn2ccc(NCc3ccccc3F)nc12] | 5-(2-fluorobenzylamino)-N-isopropylpyrazolo[1,5-a]pyrimidine-3-carboxamide | 328.1 |

TABLE 1-continued

| Ex # | Structure | Name | CMS, M + H/1 |
|---|---|---|---|
| 178 | 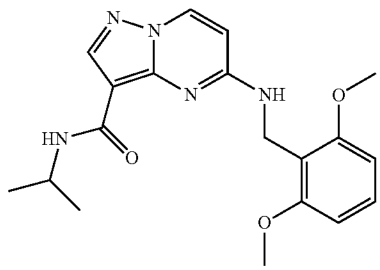 [SMILES: COc1cccc(OC)c1CNc1ccn2ncc(C(=O)NC(C)C)c2n1] | 5-(2,6-dimethoxybenzylamino)-N-isopropylpyrazolo[1,5-a]pyrimidine-3-carboxamide | 370.2 |
| 179 | 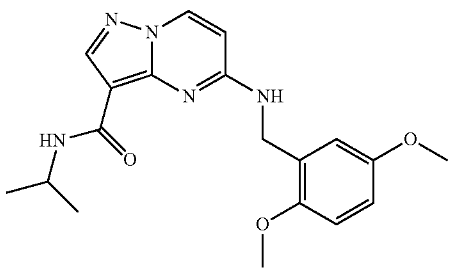 [SMILES: COc1ccc(OC)c(CNc2ccn3ncc(C(=O)NC(C)C)c3n2)c1] | 5-(2,5-dimethoxybenzylamino)-N-isopropylpyrazolo[1,5-a]pyrimidine-3-carboxamide | 370.2 |
| 180 | 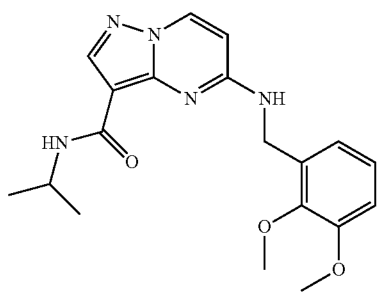 [SMILES: COc1cccc(CNc2ccn3ncc(C(=O)NC(C)C)c3n2)c1OC] | 5-(2,3-dimethoxybenzylamino)-N-isopropylpyrazolo[1,5-a]pyrimidine-3-carboxamide | 370.2 |
| 181 | 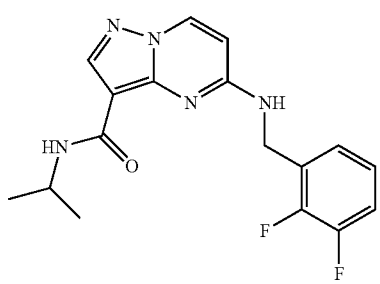 [SMILES: CC(C)NC(=O)c1cnn2ccc(NCc3cccc(F)c3F)nc12] | 5-(2,3-difluorobenzylamino)-N-isopropylpyrazolo[1,5-a]pyrimidine-3-carboxamide | 346.1 |
| 182 | 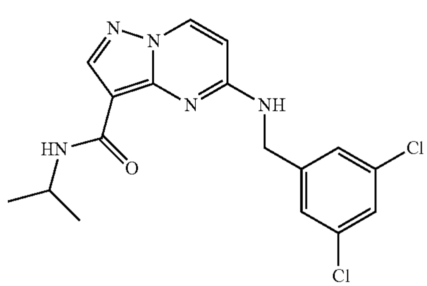 [SMILES: CC(C)NC(=O)c1cnn2ccc(NCc3cc(Cl)cc(Cl)c3)nc12] | 5-(3,5-dichlorobenzylamino)-N-isopropylpyrazolo[1,5-a]pyrimidine-3-carboxamide | 378.1 |

TABLE 1-continued

| Ex # | Structure | Name | CMS, M + H/1 |
|---|---|---|---|
| 183 | 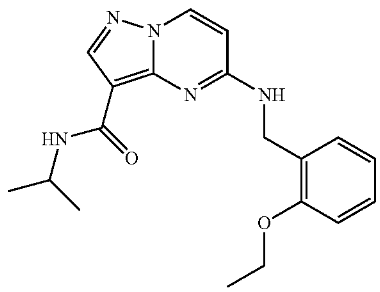 [SMILES: CCOc1ccccc1CNc1ccn2ncc(C(=O)NC(C)C)c2n1] | 5-(2-ethoxybenzylamino)-N-isopropylpyrazolo[1,5-a]pyrimidine-3-carboxamide | 354.2 |
| 184 | 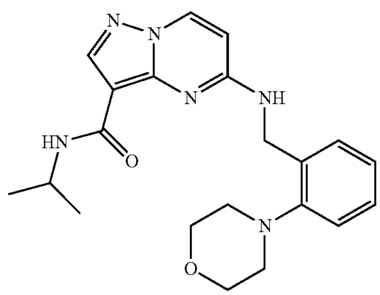 [SMILES: CC(C)NC(=O)c1cnn2ccc(NCc3ccccc3N3CCOCC3)nc12] | N-isopropyl-5-(2-morpholinobenzylamino)pyrazolo-[1,5-a]pyrimidine-3-carboxamide | 395.2 |
| 185 | 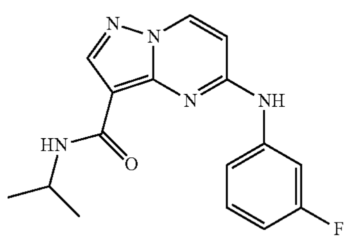 [SMILES: CC(C)NC(=O)c1cnn2ccc(Nc3cccc(F)c3)nc12] | 5-(3-fluorophenylamino)-N-isopropylpyrazolo[1,5-a]pyrimidine-3-carboxamide | 314.1 |
| 186 | 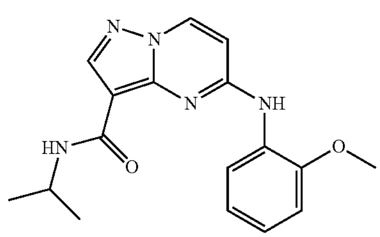 [SMILES: COc1ccccc1Nc1ccn2ncc(C(=O)NC(C)C)c2n1] | N-isopropyl-5-(2-methoxyphenylamino)pyrazolo-[1,5-a]pyrimidine-3-carboxamide | 326.1 |
| 187 | 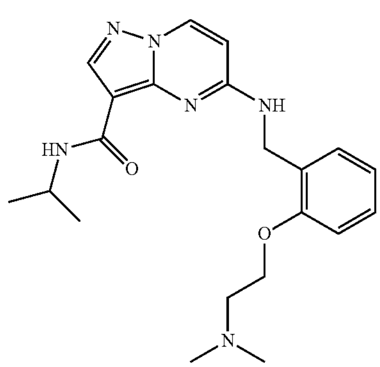 [SMILES: CC(C)NC(=O)c1cnn2ccc(NCc3ccccc3OCCN(C)C)nc12] | 5-(2-(2-(dimethylamino)ethoxy)-benzylamino)-N-isopropylpyrazolo[1,5-a]pyrimidine-3-carboxamide | 397.2 |

TABLE 1-continued

| Ex # | Structure | Name | CMS, M + H/1 |
|---|---|---|---|
| 188 | 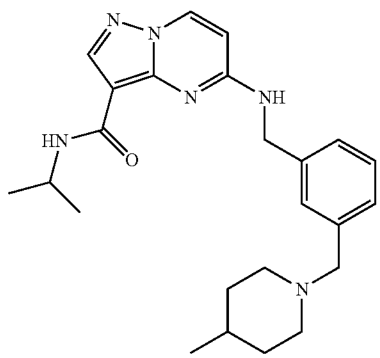 [SMILES: CC1CCN(Cc2cccc(CNc3ccn4ncc(C(=O)NC(C)C)c4n3)c2)CC1] | N-isopropyl-5-(3-((4-methylpiperidin-1-yl)methyl)benzylamino)pyrazolo-[1,5-a]pyrimidine-3-carboxamide | 421.2 |
| 189 | 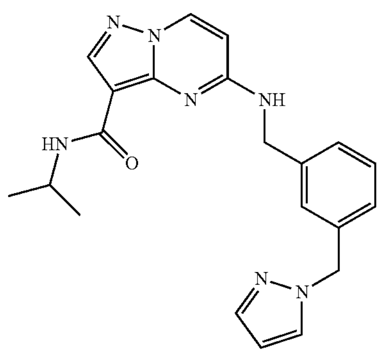 [SMILES: CC(C)NC(=O)c1cnn2ccc(NCc3cccc(Cn4cccn4)c3)nc12] | 5-(3-((1H-pyrazol-1-yl)methyl)benzylamino)-N-isopropylpyrazolo[1,5-a]pyrimidine-3-carboxamide | 390.2 |
| 190 | 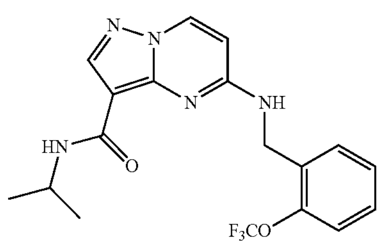 [SMILES: CC(C)NC(=O)c1cnn2ccc(NCc3ccccc3OC(F)(F)F)nc12] | N-isopropyl-5-(2-(trifluoromethoxy)benzylamino)-pyrazolo[1,5-a]pyrimidine-3-carboxamide | 394.1 |
| 191 | 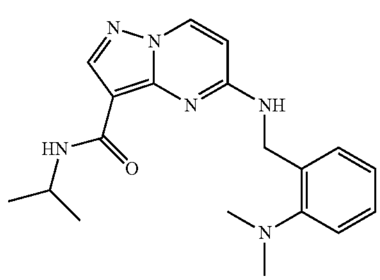 [SMILES: CC(C)NC(=O)c1cnn2ccc(NCc3ccccc3N(C)C)nc12] | 5-(2-(dimethylamino)benzylamino)-N-isopropylpyrazolo[1,5-a]pyrimidine-3-carboxamide | 353.2 |
| 192 | 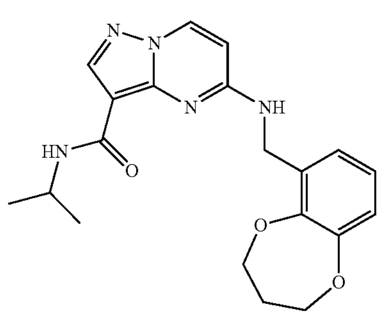 [SMILES: CC(C)NC(=O)c1cnn2ccc(NCc3cccc4c3OCCCO4)nc12] | 5-((3,4-dihydro-2H-benzo[b][1,4]dioxepin-6-yl)methylamino)-N-isopropylpyrazolo[1,5-a]pyrimidine-3-carboxamide | 382.2 |

TABLE 1-continued

| Ex # | Structure | Name | CMS, M + H/1 |
|---|---|---|---|
| 193 | 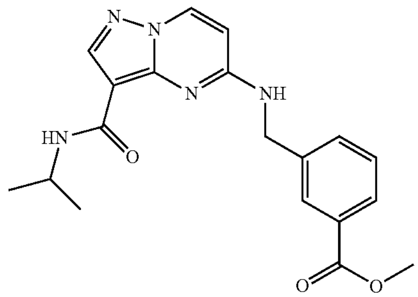 [SMILES: COC(=O)c1cccc(CNc2ccn3ncc(C(=O)NC(C)C)c3n2)c1] | methyl 3-((3-(isopropylcarbamoyl)pyrazolo-[1,5-a]pyrimidin-5-ylamino)methyl)benzoate | 368.2 |
| 194 | 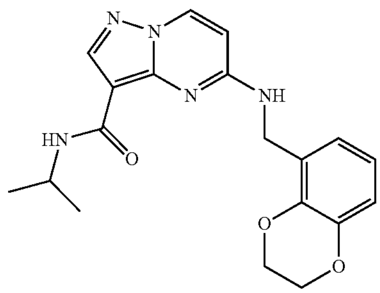 [SMILES: CC(C)NC(=O)c1cnn2ccc(NCc3cccc4c3OCCO4)nc12] | 5-((2,3-dihydrobenzo[b][1,4]dioxin-5-yl)methylamino)-N-isopropylpyrazolo[1,5-a]pyrimidine-3-carboxamide | 368.2 |
| 195 | 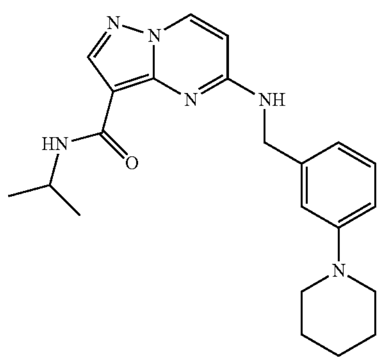 [SMILES: CC(C)NC(=O)c1cnn2ccc(NCc3cccc(N4CCCCC4)c3)nc12] | N-isopropyl-5-(3-(piperidin-1-yl)benzylamino)pyrazolo[1,5-a]pyrimidine-3-carboxamide | 393.2 |
| 196 | 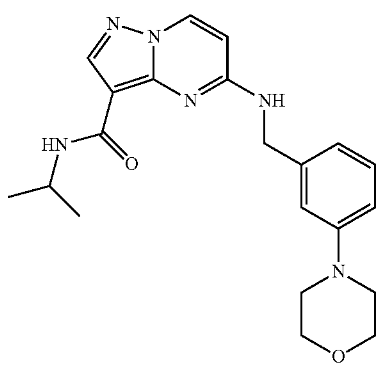 [SMILES: CC(C)NC(=O)c1cnn2ccc(NCc3cccc(N4CCOCC4)c3)nc12] | N-isopropyl-5-(3-morpholinobenzylamino)pyrazolo-[1,5-a]pyrimidine-3-carboxamide | 395.2 |
| 197 | 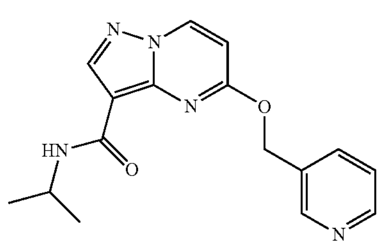 [SMILES: CC(C)NC(=O)c1cnn2ccc(OCc3cccnc3)nc12] | N-isopropyl-5-(pyridin-3-ylmethoxy)pyrazolo[1,5-a]pyrimidine-3-carboxamide | 312.2 |

TABLE 1-continued

| Ex # | Structure | Name | CMS, M + H/1 |
|---|---|---|---|
| 198 | 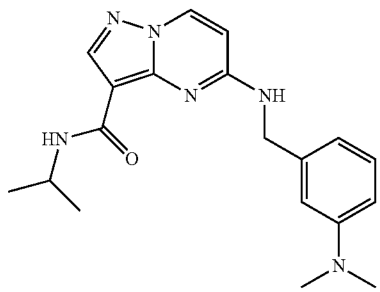 [SMILES: CC(C)NC(=O)c1cnn2ccc(NCc3cccc(N(C)C)c3)nc12] | 5-(3-(dimethylamino)benzylamino)-N-isopropylpyrazolo[1,5-a]pyrimidine-3-carboxamide | 353.2 |
| 199 | 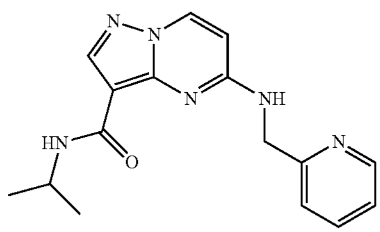 [SMILES: CC(C)NC(=O)c1cnn2ccc(NCc3ccccn3)nc12] | N-isopropyl-5-(pyridin-2-ylmethylamino)pyrazolo[1,5-a]pyrimidine-3-carboxamide | 311.2 |
| 200 | 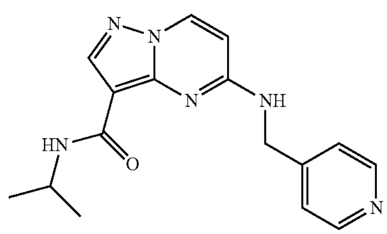 [SMILES: CC(C)NC(=O)c1cnn2ccc(NCc3ccncc3)nc12] | N-isopropyl-5-(pyridin-4-ylmethylamino)pyrazolo[1,5-a]pyrimidine-3-carboxamide | 311.2 |
| 201 | 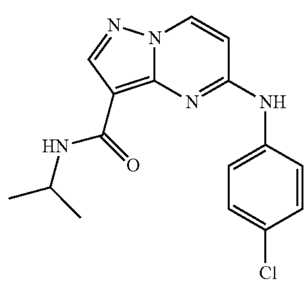 [SMILES: CC(C)NC(=O)c1cnn2ccc(Nc3ccc(Cl)cc3)nc12] | 5-(4-chlorophenylamino)-N-isopropylpyrazolo[1,5-a]pyrimidine-3-carboxamide | 330.2 |
| 202 | 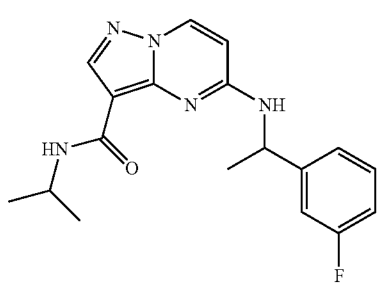 [SMILES: CC(C)NC(=O)c1cnn2ccc(NC(C)c3cccc(F)c3)nc12] | 5-(1-(3-fluorophenyl)ethylamino)-N-isopropylpyrazolo[1,5-a]pyrimidine-3-carboxamide | 342.2 |

TABLE 1-continued

| Ex # | Structure | Name | CMS, M + H/1 |
|---|---|---|---|
| 203 | 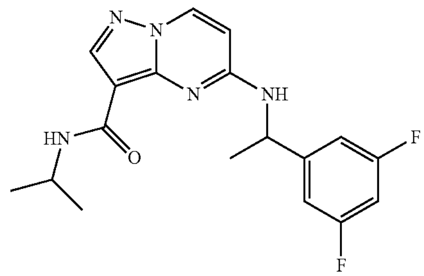 [SMILES: CC(C)NC(=O)c1cnn2ccc(NC(C)c3cc(F)cc(F)c3)nc12] | 5-(1-(3,5-difluorophenyl)ethylamino)-N-isopropylpyrazolo[1,5-a]pyrimidine-3-carboxamide | 360.2 |
| 204 | 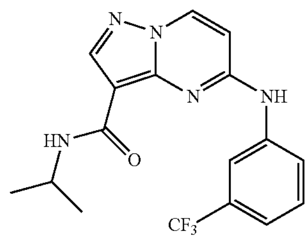 [SMILES: CC(C)NC(=O)c1cnn2ccc(Nc3cccc(C(F)(F)F)c3)nc12] | N-isopropyl-5-(3-(trifluoromethyl)phenylamino)-pyrazolo[1,5-a]pyrimidine-3-carboxamide | 364.2 |
| 205 | 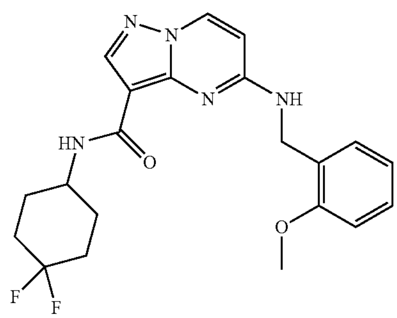 [SMILES: COc1ccccc1CNc1ccn2ncc(C(=O)NC3CCC(F)(F)CC3)c2n1] | N-(4,4-difluorocyclohexyl)-5-(2-methoxybenzylamino)pyrazolo-[1,5-a]pyrimidine-3-carboxamide | 416.2 |
| 206 | 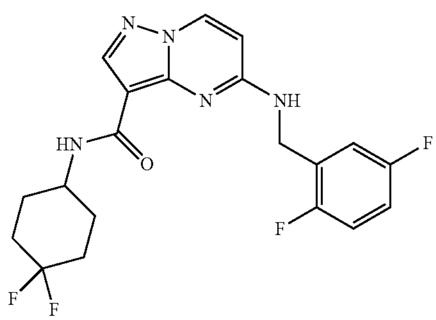 [SMILES: O=C(NC1CCC(F)(F)CC1)c1cnn2ccc(NCc3cc(F)ccc3F)nc12] | 5-(2,5-difluorobenzylamino)-N-(4,4-difluorocyclohexyl)pyrazolo[1,5-a]pyrimidine-3-carboxamide | 422.2 |
| 207 | 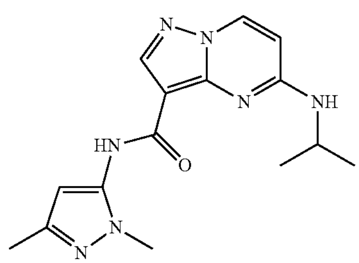 [SMILES: Cc1cc(NC(=O)c2cnn3ccc(NC(C)C)nc23)n(C)n1] | N-(1,3-dimethyl-1H-pyrazol-5-yl)-5-(isopropylamino)pyrazolo[1,5-a]pyrimidine-3-carboxamide | 314.1 |

TABLE 1-continued

| Ex # | Structure | Name | CMS, M + H/1 |
|---|---|---|---|
| 208 | 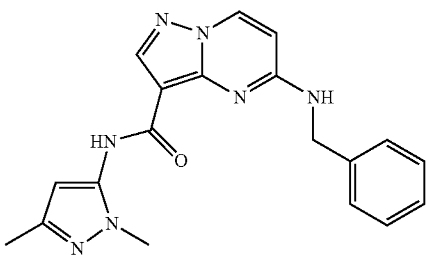 [SMILES: Cc1cc(NC(=O)c2cnn3ccc(NCc4ccccc4)nc23)n(C)n1] | 5-(benzylamino)-N-(1,3-dimethyl-1H-pyrazol-5-yl)pyrazolo[1,5-a]pyrimidine-3-carboxamide | 362.2 |
| 209 | 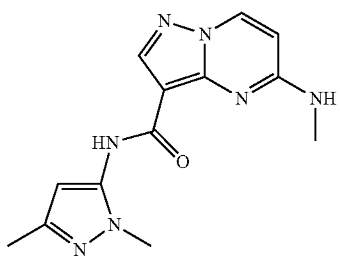 | N-(1,3-dimethyl-1H-pyrazol-5-yl)-5-(methylamino)pyrazolo[1,5-a]pyrimidine-3-carboxamide | 286.1 |
| 210 | 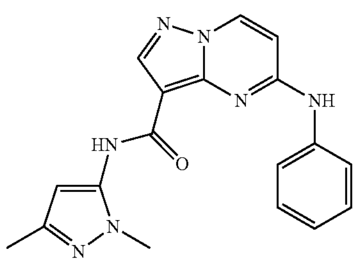 [SMILES: Cc1cc(NC(=O)c2cnn3ccc(Nc4ccccc4)nc23)n(C)n1] | N-(1,3-dimethyl-1H-pyrazol-5-yl)-5-(phenylamino)pyrazolo[1,5-a]pyrimidine-3-carboxamide | 348.2 |
| 211 | 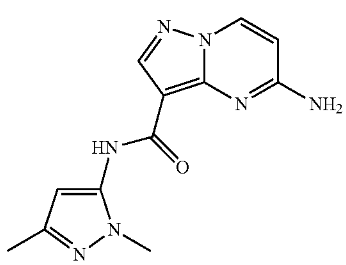 [SMILES: Cc1cc(NC(=O)c2cnn3ccc(N)nc23)n(C)n1] | 5-amino-N-(1,3-dimethyl-1H-pyrazol-5-yl)pyrazolo[1,5-a]pyrimidine-3-carboxamide | 272.1 |
| 212 | 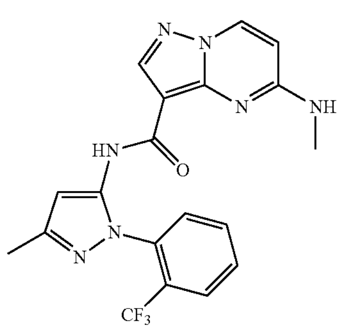 | 5-(isopropylamino)-N-(3-methyl-1-(3-(trifluoromethyl)phenyl)-1H-pyrazol-5-yl)pyrazolo[1,5-a]pyrimidine-3-carboxamide | 444.2 |

TABLE 1-continued

| Ex # | Structure | Name | CMS, M + H/1 |
|---|---|---|---|
| 213 | 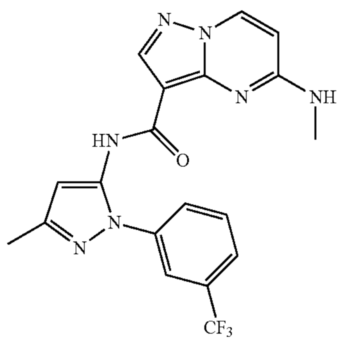 | N-isopropyl-5-(2-phenylpropan-2-ylamino)pyrazolo[1,5-a]pyrimidine-3-carboxamide | 338.2 |
| 214 | 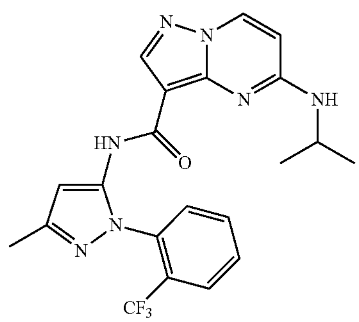 [SMILES: Cc1cc(NC(=O)c2cnn3ccc(NC(C)C)nc23)n(-c2ccccc2C(F)(F)F)n1] | (R)-N-isopropyl-5-(1-phenylethylamino)pyrazolo[1,5-a]pyrimidine-3-carboxamide | 324.2 |
| 215 | 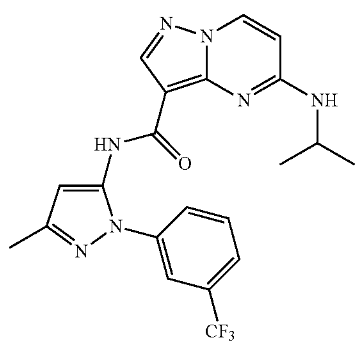 [SMILES: Cc1cc(NC(=O)c2cnn3ccc(NC(C)C)nc23)n(-c2cccc(C(F)(F)F)c2)n1] | 5-amino-N-(3-methyl-1-(2-(trifluoromethyl)phenyl)-1H-pyrazol-5-yl)pyrazolo[1,5-a]pyrimidine-3-carboxamide | 402.1 |
| 216 | 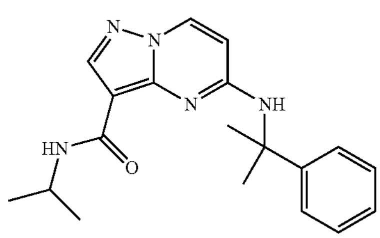 [SMILES: CC(C)NC(=O)c1cnn2ccc(NC(C)(C)c3ccccc3)nc12] | 5-amino-N-(3-methyl-1-(3-(trifluoromethyl)phenyl)-1H-pyrazol-5-yl)pyrazolo[1,5-a]pyrimidine-3-carboxamide | 402.1 |
| 217 | 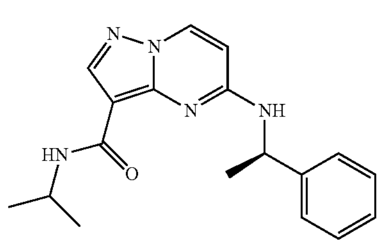 [SMILES: CC(C)NC(=O)c1cnn2ccc(N[C@H](C)c3ccccc3)nc12] | (S)-N-isopropyl-5-(1-phenylethylamino)pyrazolo[1,5-a]pyrimidine-3-carboxamide | 324.2 |

TABLE 1-continued

| Ex # | Structure | Name | CMS, M + H/1 |
|---|---|---|---|
| 218 | 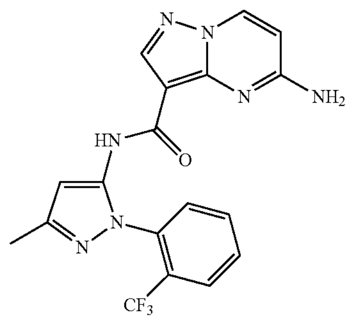 [SMILES: Cc1cc(NC(=O)c2cnn3ccc(N)nc23)n(-c2ccccc2C(F)(F)F)n1] | 5-(isopropylamino)-N-(3-methyl-1-(3-(trifluoromethyl)phenyl)-1H-pyrazol-5-yl)pyrazolo[1,5-a]pyrimidine-3-carboxamide | 444.2 |
| 219 | 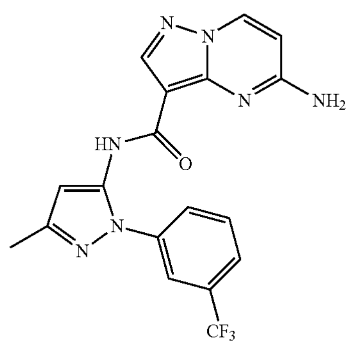 [SMILES: Cc1cc(NC(=O)c2cnn3ccc(N)nc23)n(-c2cccc(C(F)(F)F)c2)n1] | N-isopropyl-5-(2-phenylpropan-2-ylamino)pyrazolo[1,5-a]pyrimidine-3-carboxamide | 338.2 |
| 220 | 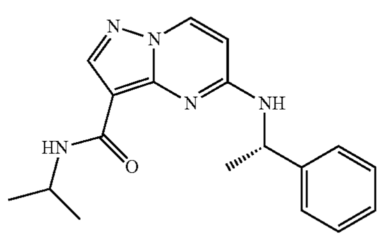 [SMILES: CC(C)NC(=O)c1cnn2ccc(N[C@@H](C)c3ccccc3)nc12] | (R)-N-isopropyl-5-(1-phenylethylamino)pyrazolo[1,5-a]pyrimidine-3-carboxamide | 324.2 |
| 221 | 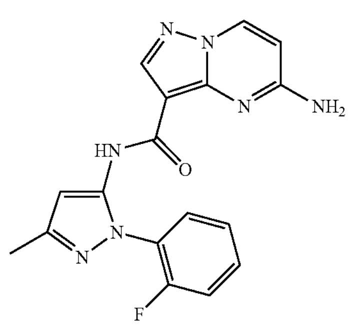 [SMILES: Cc1cc(NC(=O)c2cnn3ccc(N)nc23)n(-c2ccccc2F)n1] | 5-amino-N-(1-(2-fluorophenyl)-3-methyl-1H-pyrazol-5-yl)pyrazolo[1,5-a]pyrimidine-3-carboxamide | 353.1 |

Example 222

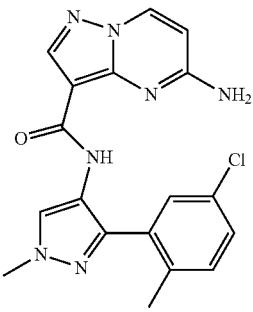

5-Amino-N-(3-(5-chloro-2-methylphenyl)-1-methyl-1H-pyrazol-4-yl)pyrazolo[1,5-a]pyrimidine-3-carboxamide

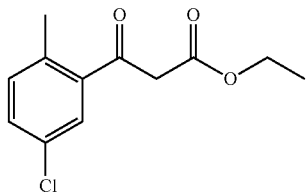

Ethyl 3-(5-chloro-2-methylphenyl)-3-oxopropanoate

To a stirring solution of 5-chloro-2-methylbenzoic acid (4.85 g, 28.4 mmol) in tetrahydrofuran (30 mL) was added N,N-carbonyldiimidazole (4.87 g, 30.0 mmol, 1.06 equiv). After 30 minutes, the reaction mixture was added to a suspension of potassium ethyl malonate (11.61 g, 68.22 mmol, 2.40 equiv) and magnesium chloride (3.27 g, 34.3 mmol, 1.21 equiv) in tetrahydrofuran (50 mL). The resultant suspension was heated at 50° C. After hours, the reaction mixture was partitioned between ethyl acetate and water. The organic portion was dried over magnesium sulfate, filtered, and concentrated to provide 8.07 g (118%) of ethyl 3-(5-chloro-2-methoxyphenyl)-3-oxopropanoate which was used without purification. LCMS (ESI) m+H=241.2

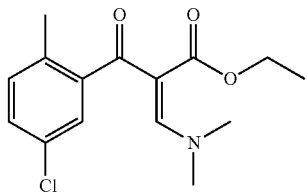

Ethyl 2-(5-chloro-2-methylbenzoyl)-3-(dimethylamino)acrylate

A solution of ethyl 3-(5-chloro-2-methylphenyl)-3-oxopropanoate (28.4 mmol) in 1,1-dimethoxy-N,N-dimethylmethanamine (10.0 mL, 75.3 mmol, 2.6 equiv) was heated at 90° C. After 3 hours, the reaction mixture was concentrated in vacuo, and the resultant residue was purified by flash column chromatography on silica gel (0 to 80% ethyl acetate in dichloromethane) to yield 2.87 g (34%) of ethyl 2-(5-chloro-2-methylbenzoyl)-3-(dimethylamino)acrylate. LCMS (ESI) m+H=296.3.

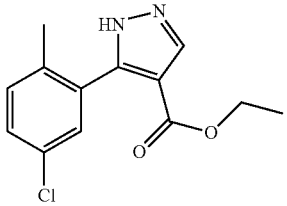

Ethyl 5-(5-chloro-2-methylphenyl)-1H-pyrazole-4-carboxylate

A solution of ethyl 2-(5-chloro-2-methylbenzoyl)-3-(dimethylamino)acrylate (2.87 g, 9.70 mmol) and hydrazine (0.50 mL, 16.0 mmol, 1.6 equiv) in 30 mL ethanol was heated at 70° C. for 2 hours. Solvent and excess hydrazine were then evaporated to provide 2.57 g (100%) of ethyl 5-(5-chloro-2-methoxyphenyl)-1H-pyrazole-4-carboxylate, which was used without further purification. LCMS (ESI) m+H=265.2.

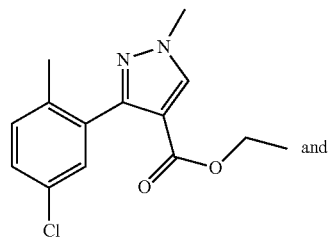

Ethyl 3-(5-chloro-2-methylphenyl)-1-methyl-1H-pyrazole-4-carboxylate

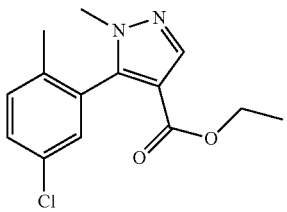

Ethyl 5-(5-chloro-2-methylphenyl)-1-methyl-1H-pyrazole-4-carboxylate

A solution of ethyl 5-(5-chloro-2-methylphenyl)-1H-pyrazole-4-carboxylate (9.70 mmol), cesium carbonate (3.83 g, 11.8 mmol, 1.2 equiv) and iodomethane (0.90 mL, 14.0 mmol, 1.5 equiv) in N,N-dimethylformamide (35 mL) was heated at 40° C. After 7 hours, the reaction mixture was partitioned between ethyl acetate and water. The organic portion was dried over magnesium sulfate, filtered, and concentrated. The crude product was purified by flash column chromatography on silica gel (0 to 40% ethyl acetate in dichloromethane) to yield 2.18 g (81%) of a 1:1 mixture of regioisomeric products, ethyl 3-(5-chloro-2-methylphenyl)-1-methyl-1H-pyrazole-4-carboxylate and ethyl 5-(5-chloro-2-methylphenyl)-1-methyl-1H-pyrazole-4-carboxylate. LCMS (ESI) m+H=279.2.

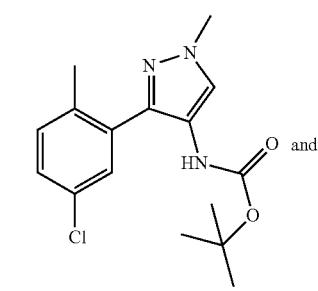

tert-Butyl 3-(5-chloro-2-methylphenyl)-
1-methyl-1H-pyrazol-4-ylcarbamate

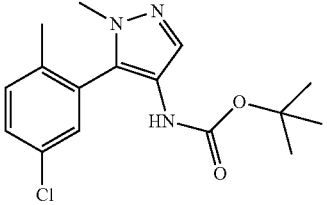

tert-Butyl 5-(5-chloro-2-methylphenyl)-
1-methyl-1H-pyrazol-4-ylcarbamate

A solution of ethyl 3-(5-chloro-2-methylphenyl)-1-methyl-1H-pyrazole-4-carboxylate and ethyl 5-(5-chloro-2-methylphenyl)-1-methyl-1H-pyrazole-4-carboxylate (1:1 mixture of regioisomers, 2.179 g, 7.818 mmol) and 1.0 M aqueous sodium hydroxide (14 mL, 20 mmol, 4 equiv) in ethanol (10 mL) was heated at 50° C. for 16 hours. After evaporation of the ethanol, the residue was diluted with water. The resultant aqueous solution was acidified to about pH 2 with 1.0 M aqueous phosphoric acid. This solution was extracted with dichloromethane (3×). The combined organic extracts were dried over MgSO₄, filtered, and concentrated to yield 1.936 g (99%) of the corresponding carboxylic acids which were carried forward immediately without further purification. LCMS (ESI) m+H=251.1.

To a solution of the intermediate carboxylic acids in dioxane (15 mL) was added triethylamine (2.2 mL, 15.8 mmol, 4.1 equiv) and diphenylphosphonic azide (1.9 mL, 8.82 mmol, 2.3 equiv). After 1 hour, the reaction was heated to 90° C. and t-butyl alcohol (15 mL) was added. After 2 hours, the reaction mixture was concentrated in vacuo, and the resultant residue was partitioned between ethyl acetate and water. The organic portion was washed with saturated aqueous sodium chloride solution, dried over magnesium sulfate, filtered, and concentrated. The crude product was purified by flash column chromatography on silica gel (0 to 50% ethyl acetate in dichloromethane) to obtain 1.64 g (66%) of a 1:1 mixture of the regioisomeric products. LCMS (ESI) m+H=322.2.

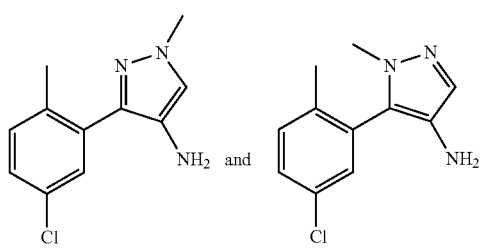

3-(5-Chloro-2-methylphenyl)-     5-(5-Chloro-2-methylphenyl)-
1-methyl-1H-pyrazol-4-amine      1-methyl-1H-pyrazol-4-amine To a solution of tert-butyl 3-(5-chloro-2-methylphenyl)-1-methyl-1H-pyrazol-4-ylcarbamate and tert-butyl 5-(5-chloro-2-methylphenyl)-1-methyl-1H-pyrazol-4-ylcarbamate (1:1 mixture of regioisomers, 1.64 g, 5.09 mmol) in dichloromethane (10 mL) was added hydrogen chloride (10.0 mL, 40 mmol, 16 equiv, 4.0 M in 1,4-dioxane). After 16 hours, the reaction mixture was concentrated in vacuo. The resultant solid residue was partitioned between dichloromethane and saturated aqueous sodium bicarbonate solution. The aqueous portion was extracted once more with dichloromethane, and the combined organic extracts were dried over magnesium sulfate and concentrated. The crude product was purified and regioisomers separated by flash column chromatography on silica gel (0 to 100% ethyl acetate in dichloromethane) to yield: 429.7 mg of 3-(5-chloro-2-methylphenyl)-1-methyl-1H-pyrazol-4-amine. LCMS (ESI) m+H=222.1; ¹H NMR (400 MHz, CDCl₃) δ: 7.35 (d, J=1.8, 1H), 7.24-7.17 (m, 2H), 7.04 (s, 1H), 3.84 (s, 3H), 2.76 (s, 2H), 2.30 (s, 3H), and 420.2 mg of 5-(5-chloro-2-methylphenyl)-1-methyl-1H-pyrazol-4-amine. LCMS (ESI) m+H=222.2; ¹H NMR (400 MHz, CDCl₃) δ: 7.33 (dd, J=8.3, 2.1, 1H), 7.28 (s, 1H), 7.24-7.19 (m, 2H), 3.57 (s, 3H), 2.71 (s, 2H), 2.15 (s, 3H).

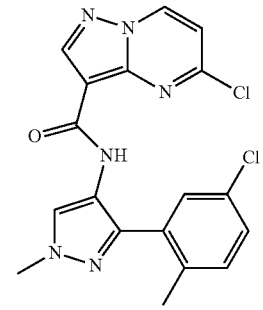

5-Chloro-N-(3-(5-chloro-2-methylphenyl)-1-methyl-1H-
pyrazol-4-yl)pyrazolo[1,5-a]pyrimidine-3-carboxamide To a solution of 3-(5-chloro-2-methylphenyl)-1-methyl-1H-pyrazol-4-amine (182.9 mg, 0.4826 mmol, 1.2 equiv) in dichloromethane (5 mL) was added 5-chloropyrazolo[1,5-a]pyrimidine-3-carbonyl chloride (91.2 mg, 0.411 mmol, 1.0 equiv) and triethylamine (0.30 mL, 2.2 mmol, 5.2 equiv) at room temperature. After 16 hours, the reaction mixture was partitioned between ethyl acetate and saturated aqueous sodium bicarbonate solution. The organic layer was dried over magnesium sulfate, filtered, and concentrated to give 143.1 mg (87%) of 5-chloro-N-(3-(5-chloro-2-methylphenyl)-1-methyl-1H-pyrazol-4-yl)pyrazolo[1,5-a]pyrimidine-3-carboxamide which was carried forward without purification. LCMS (ESI) m+H=401.0.

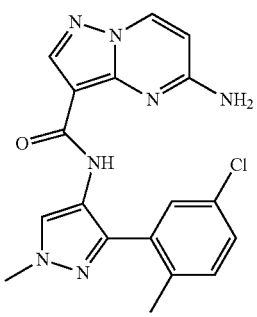

5-amino-N-(3-(5-chloro-2-methylphenyl)-1-methyl-1H-pyrazol-4-yl)pyrazolo[1,5-a]pyrimidine-3-carboxamide Ammonia gas was bubbled through an ice-cooled suspension of 5-chloro-N-(3-(5-chloro-2-methylphenyl)-1-methyl-1H-pyrazol-4-yl)pyrazolo[1,5-a]pyrimidine-3-carboxamide (143.1 mg, 0.3566 mmol) in 3.0 mL isopropanol for 20 minutes. The reaction vessel was capped and heated by microwave irradiation at 110° C. for 30 minutes. The reaction mixture was concentrated to dryness. The crude product was purified by reverse phase HPLC and lyophilized to give 76.4 mg (56%) of 5-amino-N-(3-(5-chloro-2-methylphenyl)-1-methyl-1H-pyrazol-4-yl)pyrazolo[1,5-a]pyrimidine-3-carboxamide. LCMS (ESI) m+H=382.1; $^1$H NMR (400 MHz, DMSO) δ 9.34 (s, 1H), 8.63 (d, J=7.6, 1H), 8.16 (d, J=9.6, 2H), 7.41 (m, 3H), 6.37 (d, J=7.6, 1H), 3.89 (s, 3H), 2.26 (s, 3H).

Example 223

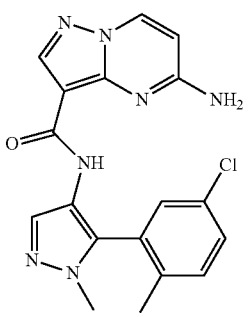

5-Amino-N-(5-(5-chloro-2-methylphenyl)-1-methyl-1H-pyrazol-4-yl)pyrazolo[1,5-a]pyrimidine-3-carboxamide Using 5-(5-chloro-2-methylphenyl)-1-methyl-1H-pyrazol-4-amine and following the procedures described for Example 222, the title compound 5-amino-N-(5-(5-chloro-2-methylphenyl)-1-methyl-1H-pyrazol-4-yl)pyrazolo[1,5-a]pyrimidine-3-carboxamide was obtained. LCMS (ESI) m+H=382.1; $^1$H NMR (400 MHz, DMSO) δ 9.16 (s, 1H), 8.61 (d, J=7.6, 1H), 8.13 (s, 1H), 7.83 (s, 1H), 7.50 (m 3H), 6.35 (d, J=7.6, 1H), 3.60 (s, 3H), 2.13 (s, 3H).

Example 224

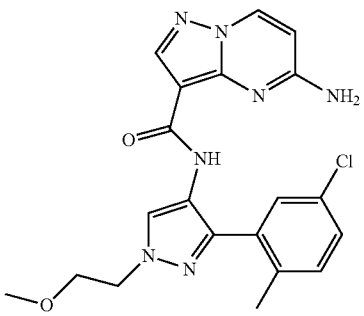

5-Amino-N-(3-(5-chloro-2-methylphenyl)-1-(2-methoxyethyl)-1H-pyrazol-4-yl)pyrazolo[1,5-a]pyrimidine-3-carboxamide

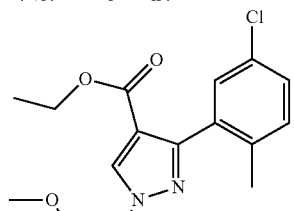

Ethyl 3-(5-chloro-2-methylphenyl)-1-(2-methoxyethyl)-1H-pyrazole-4-carboxylate

A solution of ethyl 5-(5-chloro-2-methylphenyl)-1H-pyrazole-4-carboxylate (0.2286 g, 0.8636 mmol), cesium carbonate (359.1 mg, 1.102 mmol, 1.276 equiv) and 1-bromo-2-methoxyethane in N,N-dimethylformamide (6 mL) was heated at 50° C. After 2.5 hours, the reaction mixture was partitioned between ethyl acetate and water. The organic layer was dried over magnesium sulfate, filtered, and concentrated to yield 257.7 mg (92%) of ethyl 3-(5-chloro-2-methylphenyl)-1-(2-methoxyethyl)-1H-pyrazole-4-carboxylate, which was carried forward without purification. LCMS (ESI) m+H=323.2.

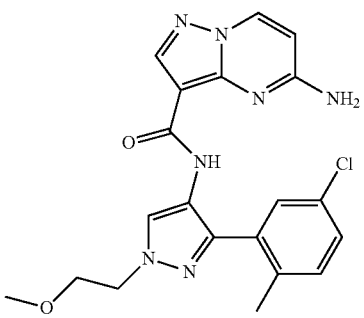

5-Amino-N-(3-(5-chloro-2-methylphenyl)-1-(2-methoxyethyl)-1H-pyrazol-4-yl)pyrazolo[1,5-a]pyrimidine-3-carboxamide The title compound was prepared using ethyl 3-(5-chloro-2-methylphenyl)-1-(2-methoxyethyl)-1H-pyrazole-4-carboxylate and following the procedures described for Example 222. LCMS (ESI) m+H=426.2; $^1$H NMR (400 MHz, DMSO) δ 9.34 (s, 1H), 8.63 (d, J=7.5, 1H), 8.16 (d, J=1.6, 2H), 7.41

(m, 3H), 6.37 (d, J=7.6, 1H), 4.31 (t, J=5.2, 2H), 3.74 (t, J=5.2, 2H), 3.27 (s, 3H), 2.26 (s, 3H).

Example 225

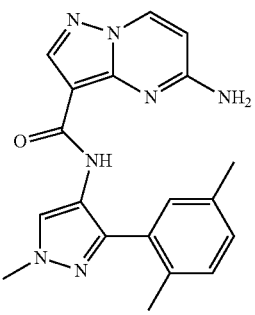

5-Amino-N-(3-(2,5-dimethylphenyl)-1-methyl-1H-pyrazol-4-yl)pyrazolo[1,5-a]pyrimidine-3-carboxamide

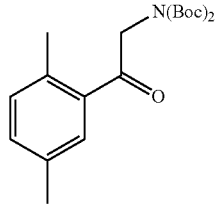

Di-tert-butyl 2-(2,5-dimethylphenyl)-2-oxoethyliminodicarbonate

To an oven-dried flask charged with di-tert-butyl iminodicarboxylate (2.566 g, 11.81 mmol, 1.10 equiv) in N,N-dimethylformamide (30 mL) was added sodium hydride (0.586 g, 14.6 mmol, 1.37 equiv, 60% in mineral oil) at room temperature. After 1.5 hours, 2-bromo-1-(2,5-dimethylphenyl)ethanone (2.432 g, 10.71 mmol, 1.00 equiv) was added to the reaction mixture at room temperature. After an additional 1.5 hours, the reaction mixture was partitioned between ethyl acetate and water. The organic portion was washed with water and saturated aqueous sodium chloride solution, dried over magnesium sulfate, filtered, and concentrated. The crude product was purified by flash column chromatography on silica gel (0 to 40% ethyl acetate in heptanes) to obtain 3.01 g (77%) of di-tert-butyl 2-(2,5-dimethylphenyl)-2-oxoethyliminodicarbonate. LCMS (ESI) m+Na=386.2.

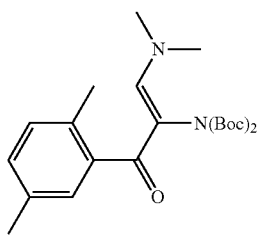

Di-tert-butyl 1-(dimethylamino)-3-(2,5-dimethylphenyl)-3-oxoprop-1-en-2-yliminodicarbonate A solution of di-tert-butyl 2-(2,5-dimethylphenyl)-2-oxoethyliminodicarbonate (3.0076 g, 8.2752 mmol, 1 equiv) and 1,1-dimethoxy-N,N-dimethylmethanamine (6.0 mL, 45 mmol, 5.4 equiv) was heated at 70° C. for 17 hours and then 100° C. for 24 hours. After the evaporation of excess 1,1-dimethoxy-N,N-dimethylmethanamine, the crude product was purified by flash column chromatography on silica gel (0 to 50% ethyl acetate in heptanes) to yield 1.305 g (38%) of di-tert-butyl 1-(dimethylamino)-3-(2,5-dimethylphenyl)-3-oxoprop-1-en-2-yliminodicarbonate. LCMS (ESI) m+H=419.3.

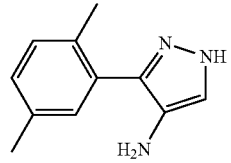

3-(2,5-Dimethylphenyl)-1H-pyrazol-4-amine

Di-tert-butyl 1-(dimethylamino)-3-(2,5-dimethylphenyl)-3-oxoprop-1-en-2-yliminodicarbonate (1.305 g, 3.118 mmol, 1.0 equiv) and hydrazine (0.20 mL, 6.4 mmol, 2.0 equiv) were dissolved together in ethanol (15 mL). The reaction mixture was heated at 70° C. for 1 hour and then evaporated to dryness. The solid residue was dissolved in dichloromethane (8 mL) and hydrogen chloride (8.0 mL, 100 mmol, 40 equiv, 4.0 M in 1,4-dioxane) and stirred at room temperature for 3.5 hours. The solvent and excess hydrogen chloride were evaporated, and the crude product was partitioned between saturated aqueous sodium bicarbonate solution and dichloromethane. The aqueous layer was extracted once with dichloromethane, and the combined organic extracts were dried over magnesium sulfate and concentrated to yield 605.4 mg (104%) of 3-(2,5-dimethylphenyl)-1H-pyrazol-4-amine, which was carried forward without purification. LCMS (ESI) m+H=188.3.

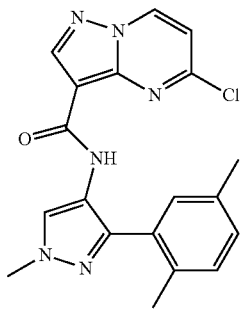

5-Chloro-N-(3-(2,5-dimethylphenyl)-1-methyl-1H-pyrazol-4-yl)pyrazolo[1,5-a]pyrimidine-3-carboxamide To a solution of 5-chloropyrazolo[1,5-a]pyrimidine-3-carbonyl chloride (400.4 mg, 1.853 mmol, 1.16 equiv) in dichloromethane (6 mL) was added 3-(2,5-dimethylphenyl)-1H-pyrazol-4-amine (300.0 mg, 1.602 mmol, 1.0 equiv) and triethylamine (0.70 mL, 5.0 mmol, 3.1 equiv) at room temperature. After 14 hours, the reaction mixture was partitioned between dichloromethane and half-saturated aqueous sodium bicarbonate solution. The aqueous layer was extracted once with dichloromethane. The combined organic portions are dried over magnesium sulfate, filtered, and concentrated to yield 5-chloro-N-(3-(2,5-dimethylphenyl)-1H-pyrazol-4-yl)pyrazolo[1,5-a]pyrimidine-3-carboxamide, which was carried forward without purification. LCMS (ESI) m+H=367.1.

To a solution of the above crude material in N,N-dimethylformamide (12 mL) was added cesium carbonate (0.890 g, 2.73 mmol, 2.0 equiv) and methyl iodide (0.135 mL, 2.17 mmol, 1.61 equiv). The reaction mixture was then heated at 40° C. After 5 hours, the reaction mixture was partitioned between ethyl acetate and water. The organic portion was washed with water and saturated aqueous sodium chloride solution, dried over magnesium sulfate, filtered, and concentrated. The crude product was purified by flash column chromatography on silica gel (20 to 90% ethyl acetate in dichloromethane) to obtain 45.5 mg (9%) of 5-chloro-N-(3-(2,5-dimethylphenyl)-1-methyl-1H-pyrazol-4-yl)pyrazolo[1,5-a]pyrimidine-3-carboxamide. LCMS (ESI) m+H=381.2.

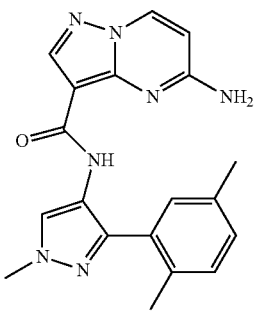

5-Amino-N-(3-(2,5-dimethylphenyl)-1-methyl-1H-pyrazol-4-yl)-pyrazolo[1,5-a]pyrimidine-3-carboxamide Ammonia gas was bubbled through an ice-cooled suspension of 5-chloro-N-(3-(2,5-dimethylphenyl)-1-methyl-1H-pyrazol-4-yl)pyrazolo[1,5-a]pyrimidine-3-carboxamide (45.5 mg, 0.119 mmol) in ethanol (3.0 mL) for 20 minutes. The reaction vessel was capped and heated at 100° C. by microwave irradiation for 30 minutes. The reaction mixture was concentrated to dryness, and the crude product was purified by reverse phase HPLC and lyophilized to give 4.0 mg (9.3%) of 5-amino-N-(3-(2,5-dimethylphenyl)-1-methyl-1H-pyrazol-4-yl)pyrazolo[1,5-a]pyrimidine-3-carboxamide. LCMS (ESI) m+H=362.1; $^1$H NMR (400 MHz, DMSO) δ 9.47 (s, 1H), 8.62 (d, J=7.5, 1H), 8.16 (d, J=7.1, 2H), 7.30 (d, J=8.2, 1H), 7.19 (d, J=6.2, 2H), 6.36 (d, J=7.6, 1H), 5.75 (s, 2H), 3.88 (s, 3H), 2.29 (s, 3H), 2.21 (s, 3H).

Example 226

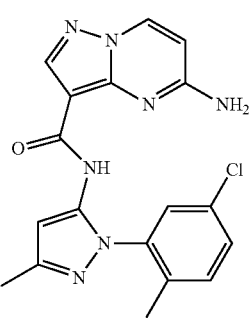

5-Amino-N-(1-(5-chloro-2-methylphenyl)-3-methyl-1H-pyrazol-5-yl)pyrazolo[1,5-a]pyrimidine-3-carboxamide

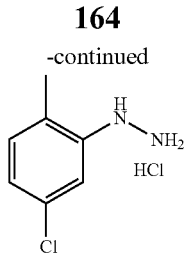

(5-Chloro-2-methylphenyl)hydrazine hydrochloride

To an ice-cooled suspension of 5-chloro-2-methylaniline (1.4362 g, 10.143 mmol, 1.00 equiv) in water (10 mL) was added concentrated hydrochloric acid (10 mL). To this reaction mixture was added dropwise a solution of sodium nitrite (0.791 g, 11.5 mmol, 1.13 equiv) in water (5 mL) at 0° C. After 2 hours, the reaction mixture was slowly added to a stirring ice-cooled solution of tin chloride dihydrate (5.88 g, 25.8 mmol, 2.55 equiv) in concentrated hydrochloric acid (8 mL). Water was added as needed to maintain the stirring while solids formed. The reaction was kept at 0° C. for 45 minutes. The white solids were filtered and rinsed with diethyl ether (2×50 mL). The solids were dried under vacuum to provide 1.49 g (76%) of (5-chloro-2-methylphenyl)hydrazine hydrochloride. $^1$H NMR (400 MHz, DMSO-d$_6$) δ: 10.08 (s, 3H), 7.98 (s, 1H), 7.13 (d, 1H), 6.97 (s, 1H), 6.91 (d, 1H), 2.14 (s, 3H).

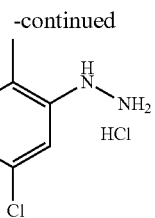

1-(5-Chloro-2-methylphenyl)-3-methyl-1H-pyrazol-5-amine

To a solution of (5-chloro-2-methylphenyl)hydrazine hydrochloride (1.49 g, 7.72 mmol, 1.00 equiv) in ethanol (8 mL) was added hydrogen chloride (4.0 mL, 20 mmol, 2 equiv, 5 M aqueous solution) and 3-aminocrotonitrile (0.664 g, 8.09 mmol, 1.05 equiv). The reaction mixture was stirred at 80° C. for 16 hours and then brought to neutral pH with saturated aqueous sodium bicarbonate solution. The resultant solution was extracted twice with dichloromethane, and the combined extracts were dried over magnesium sulfate, filtered, and concentrated to yield 1.41 g (82%) of 1-(5-chloro-2-methylphenyl)-3-methyl-1H-pyrazol-5-amine, which was carried forward without further purification. LCMS (ESI) m+H=222.2; $^1$H NMR (400 MHz, DMSO-d$_6$) δ: 7.39 (d, 1H), 7.37 (d, 1H), 7.25 (s, 1H), 5.22 (s, 1H), 5.00 (s, 2H), 2.04 (overlapping s and s, 6H).

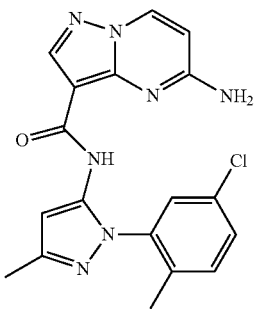

5-Amino-N-(1-(5-chloro-2-methylphenyl)-3-methyl-1H-pyrazol-5-yl)pyrazolo[1,5-a]pyrimidine-3-carboxamide The title compound was prepared using 1-(5-chloro-2-methylphenyl)-3-methyl-1H-pyrazol-5-amine and following the procedures described for Example 222. LCMS (ESI) m+H=382.1; $^1$H NMR (400 MHz, DMSO) δ 9.73 (s, 1H), 8.63 (d, J=7.5, 1H), 8.18 (s, 1H), 7.58-7.45 (m, 3H), 6.41 (s, 1H), 6.37 (d, J=7.6, 1H), 2.22 (s, 3H), 2.04 (s, 3H).

Example 227

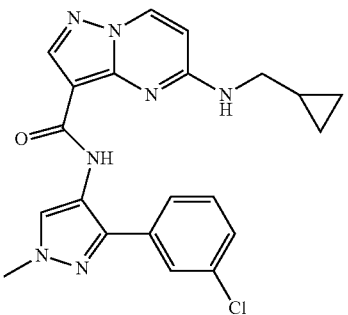

N-(3-(3-Chlorophenyl)-1-methyl-1H-pyrazol-4-yl)-5-(cyclopropylmethylamino)pyrazolo[1,5-a]pyrimidine-3-carboxamide

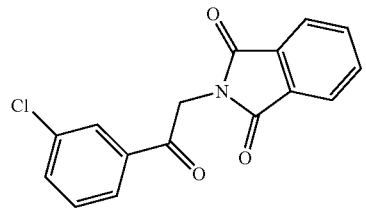

2-(2-(3-Chlorophenyl)-2-oxoethyl)isoindoline-1,3-dione

A solution of 2-bromo-3'-chloroacetophenone (0.9271 g, 3.971 mmol, 1.0 equiv) and potassium phthalimide (0.8129 g, 4.389 mmol, 1.1 equiv) in N,N-dimethylformamide (15 mL) was heated at 50° C. After 1 hour, the solvent was removed by rotary evaporation. The resultant solids were triturated with ethyl acetate and filtered. The collected solids were dried under vacuum to yield 1.19 g (117%) of 2-(2-(3-chlorophenyl)-2-oxoethyl)isoindoline-1,3-dione, which was carried forward without purification. $^1$H NMR (400 MHz, DMSO-d$_6$) δ: 8.13 (s, 1H), 8.05 (d, 1H), 7.96 (m, 2H), 7.93 (m, 2H), 7.83 (d, 1H), 7.65 (t, 1H), 5.29 (s, 2H).

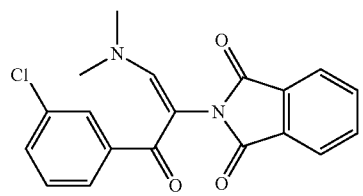

2-(3-(3-Chlorophenyl)-1-(dimethylamino)-3-oxoprop-1-en-2-yl)isoindoline-1,3-dione A stirred mixture of 2-(2-(3-chlorophenyl)-2-oxoethyl)isoindoline-1,3-dione (782.2 mg, 2.610 mmol, 1 equiv) and 1,1-dimethoxy-N,N-dimethylmethanamine (1.5 mL, 11 mmol, 4.3 equiv) was heated at 100° C. for 18 hours. Excess 1,1-dimethoxy-N,N-dimethylmethanamine was removed by rotary evaporation. The crude product was purified by flash column chromatography on silica gel (50 to 100% ethyl acetate in heptane) to yield 740 mg (80%) of 2-(3-(3-chlorophenyl)-1-(dimethylamino)-3-oxoprop-1-en-2-yl)isoindoline-1,3-dione. LCMS (ESI) m+H=355.2; $^1$H NMR (400 MHz, CDCl$_3$) δ: 7.90 (d of d, 2H), 7.77 (d of d, 2H), 7.57 (s, 1H), 7.44 (d, 1H), 7.37 (overlapping d and s, 2H), 7.31 (t, 1H), 3.00 (s, 6H).

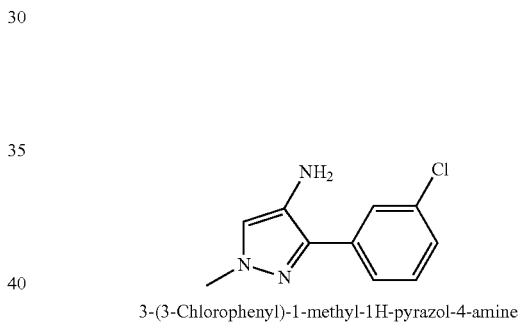

3-(3-Chlorophenyl)-1-methyl-1H-pyrazol-4-amine

A solution of 2-(3-(3-chlorophenyl)-1-(dimethylamino)-3-oxoprop-1-en-2-yl)isoindoline-1,3-dione (2.30 g, 6.48 mmol, 1.0 equiv) and N-methylhydrazine (1.4 mL, 26 mmol, 4.0 equiv) in ethanol (50 mL) was heated at 80° C. After 2 hours, the reaction mixture was concentrated, and the resultant crude mixture of regioisomers was separated and purified by flash column chromatography on silica gel (0 to 80% ethyl acetate in dichloromethane) to yield: 715.0 mg (53%) of 3-(3-chlorophenyl)-1-methyl-1H-pyrazol-4-amine. LCMS (ESI) m+H=208.2; $^1$H NMR (400 MHz, CDCl$_3$) δ: 7.78 (s, 1H), 7.63 (d, 1H), 7.33 (t, 1H), 7.25 (overlapping with CDCl$_3$, 1H), 7.04 (s, 1H), 3.84 (s, 3H), and 274.6 mg (20%) of 5-(3-chlorophenyl)-1-methyl-1H-pyrazol-4-amine. LCMS (ESI) m+H=208.2; $^1$H NMR (400 MHz, CDCl$_3$) δ: 7.43 (t, 1H), 7.38 (overlapping d and s, 2H), 7.27 (d, 1H), 7.23 (s, 1H), 3.76 (s, 3H).

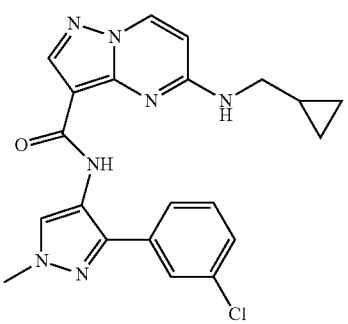

N-(3-(3-Chlorophenyl)-1-methyl-1H-pyrazol-4-yl)-5-(cyclopropylmethylamino)pyrazolo[1,5-a]pyrimidine-3-carboxamide To a solution of 5-chloropyrazolo[1,5-a]pyrimidine-3-carbonyl chloride (0.166 g, 0.768 mmol) in dichloromethane (8 mL) was added 3-(3-chlorophenyl)-1-methyl-1H-pyrazol-4-amine (73.6 mg, 0.354 mmol) and triethylamine (0.20 mL, 1.4 mmol) at room temperature. After 1 hour, the reaction mixture was partitioned between dichloromethane and half-saturated aqueous sodium bicarbonate solution. The organic layer was dried over magnesium sulfate and concentrated to yield 5-chloro-N-(3-(3-chlorophenyl)-1-methyl-1H-pyrazol-4-yl)pyrazolo[1,5-a]pyrimidine-3-carboxamide, which is carried forward without purification. LCMS (ESI) m+H=387.1.

A solution of the above crude 5-chloro-N-(3-(3-chlorophenyl)-1-methyl-1H-pyrazol-4-yl)pyrazolo[1,5-a]pyrimidine-3-carboxamide, cyclopropylmethylamine (0.1 mL, 1.0 mmol), and N,N-diisopropylethylamine (0.20 mL, 1.1 mmol) in ethanol (5 mL) was heated at 120° C. by microwave irradiation. After 30 minutes, the reaction mixture was concentrated to dryness, and the resultant crude product was purified by reverse phase HPLC and lyophilized to give 95.7 mg (64%) of N-(3-(3-chlorophenyl)-1-methyl-1H-pyrazol-4-yl)-5-(cyclopropylmethylamino)pyrazolo[1,5-a]pyrimidine-3-carboxamide. LCMS (ESI) m+H=422.1; $^1$H NMR (500 MHz, DMSO) δ 9.62 (s, 1H), 8.58 (d, J=7.6, 1H), 8.20 (s, 1H), 8.14 (s, 2H), 7.75-7.59 (m, 2H), 7.46 (t, J=7.8, 1H), 7.42-7.34 (m, 1H), 6.41 (d, J=7.6, 1H), 3.90 (s, 3H), 2.62-2.54 (m, 2H), 0.76 (s, 1H), 0.38-0.24 (m, 2H), −0.14 (m, 2H).

Example 228

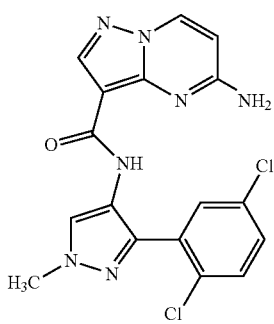

5-Amino-pyrazolo[1,5-a]pyrimidine-3-carboxylic acid [3-(2,5-dichloro-phenyl)-1-methyl-1H-pyrazol-4-yl]-amine

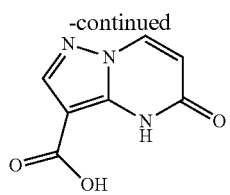

5-oxo-4,5-dihydropyrazolo[1,5-a]pyrimidine-3-carboxylic acid

To a stirred solution of 5-amino-1H-pyrazole-4-carboxylic acid (10.0 g, 71.4 mmol) in ethanol (100 mL), was added sodium ethoxide (17.0 g, 245 mmol) followed by 1,3-dimethyluracil (11.0 g, 78.6 mmol). The reaction mixture was then stirred at reflux overnight under an argon atmosphere. The mixture was poured into ice-water, and the resultant solution was acidified to about pH 3-4 with concentrated HCl. The suspension was stirred for 2 hours and then filtered to afford the intermediate, which was used without further purification (10.0 g, 58% yield). $^1$H NMR (400 MHz, DMSO-d$_6$): 8.54 (d, J=9.2 Hz, 1H), 8.06 (s, 1H), 6.11 (d, J=7.2 Hz, 1H).

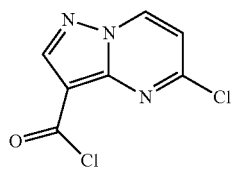

5-Chloropyrazolo[1,5-a]pyrimidine-3-carbonyl chloride

A suspension of 5-oxo-4,5-dihydropyrazolo[1,5-a]pyrimidine-3-carboxylic acid (9.5 g, 53.1 mmol) and diisopropylethylamine (17.1 g, 132.6 mmol) in phosphorus(V) oxychloride (250 mL) was heated at 130° C. under an argon atmosphere for 3.5 hours. The mixture was concentrated in vacuum and passed through a silica gel column (dichloromethane) to afford 5-chloropyrazolo[1,5-a]pyrimidine-3-carbonyl chloride as a solid (8.0 g, 70% yield). $^1$H NMR (400 MHz, CDCl$_3$): 8.72 (d, J=7.2 Hz, 1H), 8.65 (s, 1H), 7.17 (d, J=7.6 Hz, 1H).

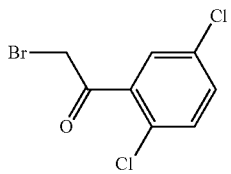

2-Bromo-1-(2,5-dichlorophenyl)ethanone

To an ice-cooled solution of 2',5'-dichloroacetophenone (1.0 g, 5.0 mmol) in acetic acid (10 mL) was added HBr (~1%) followed by a solution of bromine (0.80 g, 5.0 mmol) in acetic acid (3 mL). The resultant mixture was warmed to room temperature and stirred overnight. The mixture was poured into ice water and then neutralized with saturated aqueous sodium carbonate solution. Saturated aqueous sodium thiosulfate solution was then added to the mixture. The resultant mixture was extracted with ethyl acetate. The organic phase was washed with saturated aqueous sodium chloride solution, dried over anhydrous sodium sulfate, filtered, and concentrated. Purification by flash column chromatography afforded 2-bromo-1-(2,5-dichlorophenyl)ethanone as an oil (0.70 g, 50% yield). ¹H NMR (400 MHz, CDCl₃): 7.54 (d, J=2.4 Hz, 1H), 7.43 (m, 1H), 7.40 (m, 1H), 4.68 (s, 2H).

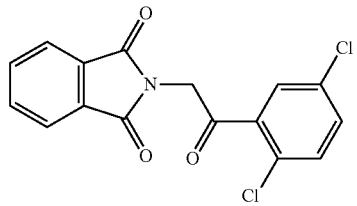

2-(2-(2,5-Dichlorophenyl)-2-oxoethyl)isoindoline-1,3-dione

To an ice-cooled solution of 2-bromo-1-(2,5-dichlorophenyl)ethanone (0.10 g, 0.37 mmol) in N,N-dimethylformamide (8 mL) was added potassium phthalimide (76 mg, 0.41 mmol). The mixture was warmed to room temperature for 2 hours. The resultant mixture was then poured into water and extracted with ethyl acetate. The organic layer was dried over anhydrous sodium sulfate, filtered, and concentrated. Recrystallization with diethyl ether afforded 2-(2-(2,5-dichlorophenyl)-2-oxoethyl)isoindoline-1,3-dione as a white solid. (110 mg, 88% yield). ¹H NMR (400 MHz, CDCl₃): 7.92-7.94 (m, 2H), 7.78-7.80 (m, 2H), 7.72 (m, 1H), 7.45-7.46 (m, 2H), 5.08 (s, 2H).

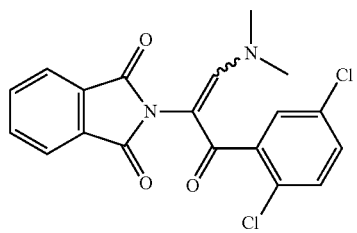

2-(3-(2,5-Dichlorophenyl)-1-(dimethylamino)-3-oxoprop-1-en-2-yl)isoindoline-1,3-dione A solution of 2-(2-(2,5-dichlorophenyl)-2-oxoethyl)isoindoline-1,3-dione (0.10 g, 0.30 mmol) in 1,1-dimethoxy-N,N-dimethylmethanamine (8 mL) was heated at reflux for 2 hours. The resultant mixture was then concentrated. Purification by flash column chromatography afforded 2-(3-(2,5-dichlorophenyl)-1-(dimethylamino)-3-oxoprop-1-en-2-yl)isoindoline-1,3-dione as a solid (0.90 g, 77% yield).

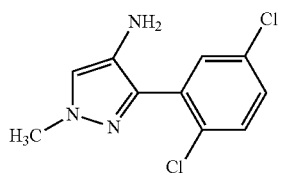

3-(2,5-Dichlorophenyl)-1-methyl-1H-pyrazol-4-amine

To an ice-cooled solution of 2-(3-(2,5-Dichlorophenyl)-1-(dimethylamino)-3-oxoprop-1-en-2-yl)isoindoline-1,3-dione (0.050 g, 0.13 mmol) in ethanol (6 mL) was added 40% aqueous methylhydrazine solution (45 mg, 0.39 mmol). The mixture was then heated at reflux for 3 hours. The reaction mixture was then concentrated and purified by flash column chromatography to afford 3-(2,5-dichlorophenyl)-1-methyl-1H-pyrazol-4-amine as a solid (12 mg, 38% yield). ¹H NMR (400 MHz, CDCl₃): 7.50 (d, J=3.6 Hz, 1H), 7.38 (d, J=8.8 Hz, 1H), 7.28 (m, 1H), 7.06 (s, 1H), 3.86 (s, 3H), 2.98 (s, 2H).

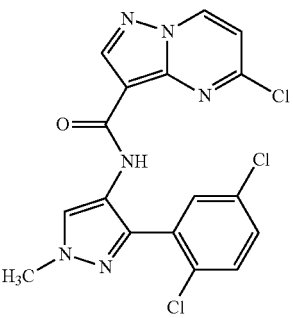

5-Chloro-N-(3-(2,5-dichlorophenyl)-1-methyl-1H-pyrazol-4-yl)-pyrazolo[1,5-a]pyrimidine-3-carboxamide To an ice-cooled solution of 3-(2,5-dichlorophenyl)-1-methyl-1H-pyrazol-4-amine (121 mg, 0.50 mmol) and triethylamine (101 mg, 1.00 mmol) in dichloromethane (15 mL) was added 5-chloropyrazolo[1,5-a]pyrimidine-3-carbonyl chloride (162 mg, 1.5 mmol). The reaction mixture was warmed to room temperature for 3 hours. The mixture was then washed with saturated aqueous sodium chloride solution. The collected organics were dried over anhydrous sodium sulfate, filtered, and concentrated. Purification by preparative HPLC afforded 5-chloro-N-(3-(2,5-dichlorophenyl)-1-methyl-1H-pyrazol-4-yl)pyrazolo[1,5-a]pyrimidine-3-carboxamide as a solid (110 mg, 52% yield). ¹H NMR (400 MHz, DMSO-d₆): 9.34 (d, J=7.6 Hz, 1H), 9.21 (s, 1H), 8.69 (s, 1H), 8.33 (s, 1H), 7.71 (d, J=9.2 Hz, 1H), 7.60 (d, J=9.2 Hz, 1H), 7.54 (s, 1H), 7.36 (d, J=6.8 Hz, 1H), 3.93 (s, 3H).

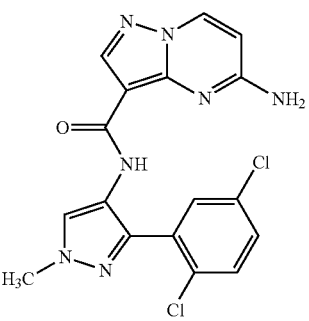

5-Amino-pyrazolo[1,5-a]pyrimidine-3-carboxylic acid [3-(2,5-dichloro-phenyl)-1-methyl-1H-pyrazol-4-yl]-amide A solution of 5-chloro-N-(3-(2,5-dichlorophenyl)-1-methyl-1H-pyrazol-4-yl)pyrazolo[1,5-a]pyrimidine-3-carboxamide (110 mg, 0.26 mmol) in ethanol saturated with ammonia (4 mL) was heated at 95° C. for 30 minutes with microwave irradiation. The mixture was concentrated. Purification by flash column chromatography afforded 5-amino-pyrazolo[1,5-a]pyrimidine-3-carboxylic acid [3-(2,5-dichloro-phenyl)-1-methyl-1H-pyrazol-4-yl]-amide as a solid (80 mg, 77% yield). ¹H NMR (400 MHz, DMSO-d₆): 9.37 (s, 1H), 8.63 (d, J=7.6 Hz, 1H), 8.14-8.16 (m, 2H), 7.70 (m, 1H), 7.52-7.55 (m, 2H), 6.39 (d, J=8.0 Hz, 1H), 3.91 (s, 3H).

Example 229

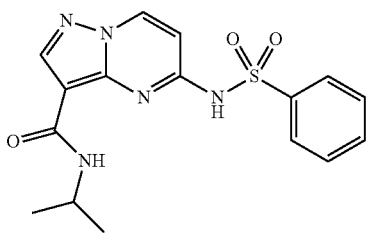

5-Benzenesulfonylamino-pyrazolo[1,5-a]pyrimidine-3-carboxylic acid isopropylamide A mixture of 5-chloro-N-isopropylpyrazolo[1,5-a]pyrimidine-3-carboxamide (95.5 mg, 0.40 mmol, 1.0 equiv), benzenesulfonamide (62.0 mg, 0.40 mmol, 1.0 equiv) and cesium carbonate (312 mg, 0.96 mmol, 2.4 equiv) in 1,2-dimethoxyethane (8 mL) was heated to 85° C. for 72 hours. The solvent was removed in vacuo, and the resultant residue dissolved in water. The pH of the solution was then adjusted to about 5 by the addition of 1M HCl aqueous solution and extracted with dichloromethane (2×30 mL). The organic extracts were concentrated under vacuum and the residue purified by flash column chromatography on silica gel (gradient: 0 to 10% methanol in dichloromethane) to afford 57.0 mg (40%) of 5-benzenesulfonylamino-pyrazolo[1,5-a]pyrimidine-3-carboxylic acid isopropylamide as a solid. LCMS (ESI) m+H=360.3; $^1$H NMR (400 MHz, DMSO-$d_6$) δ: 12.2 (s, 1H), 8.97 (d, 1H), 8.30 (s, 1H), 8.01 (d, 2H), 7.64 (m, 4H), 6.64 (m, 1H), 4.13 (m, 1H), 1.21 (d, 6H).

Example 230

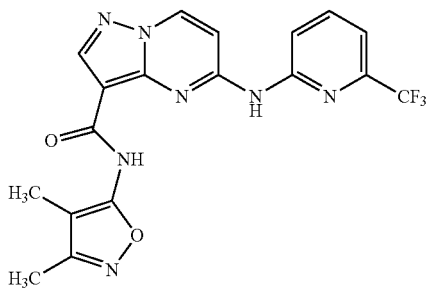

5-(6-Trifluoromethyl-pyridin-2-ylamino)-pyrazolo[1,5-a]pyrimidine-3-carboxylic acid (5-methyl-isoxazol-3-yl)-amide

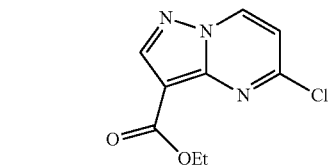

Ethyl 5-Chloropyrazolo[1,5-a]pyrimidine-3-carboxylate

To a suspension of 5-oxo-4,5-dihydro-pyrazolo[1,5-a]pyrimidine-3-carboxylic acid ethyl ester (prepared according to Gavrin, L. K. et al, *J. Org. Chem.* 2007, 72, 1043-1046) (3.00 g, 14.5 mmol, 1 equiv) in phosphorus oxychloride (30 mL) was added diisopropylethylamine (2.00 mL, 11.6 mmol, 0.8 equiv). The mixture was heated to 90° C. for 4.5 hours. After cooling, the mixture was carefully quenched with ice-water and extracted with dichloromethane. The organic extract was washed with saturated aqueous sodium bicarbonate solution, dried over anhydrous sodium sulphate, filtered, and concentrated under vacuum to give a solid. Trituration (diethyl ether) afforded 2.38 g (73%) of ethyl 5-chloropyrazolo[1,5-a]pyrimidine-3-carboxylate as a solid. LCMS (ESI) m+H=226.2 (mono chlorinated isotope pattern); $^1$H NMR (400 MHz, CDCl$_3$) δ: 8.63 (d, 1H), 8.56 (s, 1H), 6.99 (d, 1H), 4.43 (q, 2H), 1.42 (t, 3H).

Ethyl 5-(6-(Trifluoromethyl)pyridin-2-ylamino)pyrazolo[1,5-a]pyrimidine-3-carboxylate A 20-mL microwave vial was charged with ethyl 5-chloropyrazolo[1,5-a]pyrimidine-3-carboxylate (1.28 g, 5.67 mmol, 1 equiv), 2-amino-6-(trifluoromethyl)pyridine (1.10 g, 6.81 mmol, 1.2 equiv), 4,5-bis(diphenylphosphino)-9,9-dimethylxanthene (132 mg, 0.22 mmol, 4 mol %), tris(dibenzylideneacetone) dipalladium(0) (104 mg, 0.11 mmol, 2 mol %), sodium tert-butoxide (652 mg, 6.81 mmol, 1.2 equiv) and toluene (12 mL). The vial was sealed and the contents degassed, purged with argon and then heated in a microwave reactor at 140° C. for 20 minutes. After cooling, the mixture was diluted with ethyl acetate and filtered through a pad of Celite®. The filtrate was washed with water and saturated aqueous sodium chloride solution, dried over anydrous sodium sulphate, filtered, and concentrated under vacuum. The resultant residue was purified by flash column chromatography on silica gel (gradient: 0 to 20% ethyl acetate in dichloromethane) to give 344 mg (17%) of ethyl 5-(6-(trifluoromethyl)pyridin-2-ylamino)pyrazolo[1,5-a]pyrimidine-3-carboxylate as an orange solid. LCMS (ESI) m+H=352.1; $^1$H NMR (300 MHz, DMSO-$d_6$) δ: 11.06 (s, 1H), 9.16 (d, 1H), 8.94 (d, 1H), 8.39 (s, 1H), 8.10 (t, 1H), 7.57 (d, 1H), 7.05 (d, 1H), 4.31 (q, 2H), 1.40 (t, 3H).

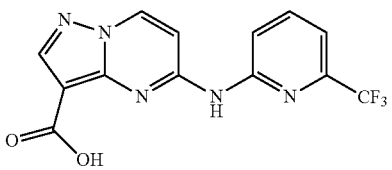

5-(6-Trifluoromethyl-pyridin-2-ylamino)-pyrazolo[1,5-a]pyrimidine-3-carboxylic acid A mixture of ethyl 5-(6-(trifluoromethyl)pyridin-2-ylamino)pyrazolo[1,5-a]pyrimidine-3-carboxylate (344 mg, 0.98 mmol, 1.0 equiv), 2M aqueous sodium hydroxide solution (1.50 mL, 3.0 equiv) and ethanol (15 mL) was heated to reflux for 5 hours. After cooling, the precipitate was collected by filtration, washed with ethanol, and air dried. The resultant solid was suspended in 1.25 M HCl in methanol (16 mL) and then concentrated under vacuum. The residue was triturated (diethyl ether) to afford 355 mg (quant. yield) of 5-(6-trifluoromethyl-pyridin-2-ylamino)-pyrazolo[1,5-a]pyrimidine-3-carboxylic acid which was used without further purification. LCMS (ESI) m+H=324.2; $^1$H NMR (300 MHz, DMSO-d$_6$) δ: 11.03 (s, 1H), 9.01 (d, 1H), 8.95 (d, 1H), 8.35 (s, 1H), 8.10-8.02 (m, 1H), 7.54 (d, 1H), 7.16 (d, 1H).

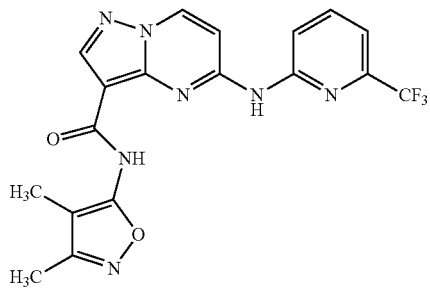

5-(6-Trifluoromethyl-pyridin-2-ylamino)-pyrazolo[1,5-a]-pyrimidine-3-carboxylic acid (5-methyl-isoxazol-3-yl)-amide Diisopropylethylamine (101 mg, 0.78 mmol, 0.8 equiv) was added to a suspension of 5-(6-trifluoromethyl-pyridin-2-ylamino)-pyrazolo[1,5-a]pyrimidine-3-carboxylic acid (0.98 mmol, 1.0 equiv) in phosphorus oxychloride (6 mL) at 0° C. The mixture was then heated to 90° C. for 20 hours. After cooling, the solvent was removed under vacuum and the residue azeotroped with dichloromethane, and then concentrated to yield the crude acid chloride as a solid. Half of this crude material (assumed to be 0.49 mmol) was used directly in the next step.

A mixture of acid chloride (0.49 mmol, 1.0 equiv) and 5-amino-3,4-dimethyl-1,2-isoxazole (66.0 mg, 0.59 mmol, 1.2 equiv) in pyridine (4 mL) was heated to 60° C. for 90 minutes. After cooling, the solvent was removed under vacuum, and the isolated residue triturated (water) and re-triturated (methanol) and the resultant solid was dried under vacuum to give 56.3 mg (28%) of 5-(6-trifluoromethyl-pyridin-2-ylamino)-pyrazolo[1,5-a]pyrimidine-3-carboxylic acid (5-methyl-isoxazol-3-yl)-amide. LCMS (ESI) m+H=418.1; $^1$H NMR (400 MHz, DMSO-d$_6$) δ: 11.12 (s, 1H), 10.04 (s, 1H), 9.04 (d, 1H), 8.50 (s, 1H), 8.41 (d, 1H), 8.02 (t, 1H), 7.58 (d, 1H), 7.30 (d, 1H), 2.19 (s, 3H), 1.88 (s, 3H).

Example 231

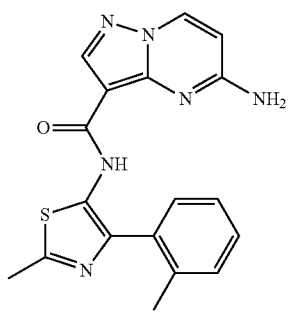

5-Amino-pyrazolo[1,5-a]pyrimidine-3-carboxylic acid (2-methyl-4-o-tolyl-thiazol-5-yl)-amide

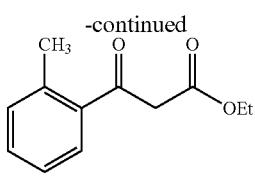

3-Oxo-3-o-tolyl-propionic acid ethyl ester

To a stirred suspension of sodium hydride (60% dispersion in mineral oil, 7.20 g, 180 mmol, 3.6 equiv) in toluene (300 mL) was slowly added diethyl carbonate (23.6 g, 200 mmol, 4.0 equiv) at ambient temperature. After stirring for 15 minutes, 2-methyl acetophenone (6.70 g, 50.0 mmol, 1.0 equiv) was added, and the resultant mixture heated to reflux for 18 hours. Glacial acetic acid (15 mL) was then added drop-wise over 10 minutes, followed by the cautious addition of ice cold water (150 mL). The resultant mixture was extracted with ethyl acetate and the combined organic extracts dried over magnesium sulfate and concentrated under vacuum. The resultant residue was purified by flash column chromatography on silica gel (gradient: 0 to 5% ethyl acetate in pentane) to afford 7.94 g (77%) of 3-oxo-3-o-tolyl-propionic acid ethyl ester as an oil (4:1 mixture of keto/enol tautomers). $^1$H NMR (Keto tautomer) (400 MHz, CDCl$_3$) δ: 7.66 (s, 1H), 7.41 (s, 1H), 7.30-7.25 (m, 2H), 4.22-4.15 (m, 2H), 3.96-3.94 (m, 2H), 2.55 (s, 3H), 1.28-1.22 (m, 3H).

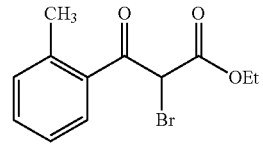

2-Bromo-3-oxo-3-o-tolyl-propionic acid ethyl ester

Bromine (1.65 g, 10.3 mmol, 1.03 equiv) was added drop-wise to a stirred solution of 3-oxo-3-o-tolyl-propionic acid ethyl ester (2.06 g, 10.0 mmol, 1.0 equiv) in 1,4-dioxane (25 mL) at ambient temperature. The mixture was stirred for 1 hour and then diluted with tert-butyl methyl ether (50 mL). The resultant solution was washed sequentially with water, aqueous potassium carbonate solution and saturated aqueous sodium chloride solution. The collected organic was dried over magnesium sulphate, filtered, and concentrated under vacuum to afford 2.74 g (96%) of 2-bromo-3-oxo-3-o-tolyl-propionic acid ethyl ester as a dark brown residue. $^1$H NMR (400 MHz, CDCl$_3$) δ: 7.66 (d, 1H), 7.46-7.37 (m, 1H), 7.28 (m, 2H), 5.62 (s, 1H), 4.29-4.22 (q, 2H), 2.52 (s, 3H), 1.28-1.19 (t, 3H).

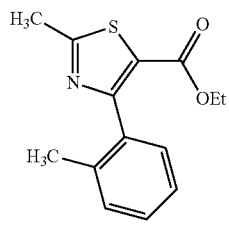

2-Methyl-4-o-tolyl-thiazole-5-carboxylic acid ethyl ester

A stirred mixture of 2-bromo-3-oxo-3-o-tolyl-propionic acid ethyl ester (2.74 g, 9.60 mmol, 1.0 equiv) and thioacetamide (0.76 g, 10.1 mmol, 1.05 equiv) in ethanol (30 mL) was heated to reflux for 4 hours. The cooled mixture was filtered and concentrated under vacuum. The residue was partitioned between ethyl acetate and water and the organic phase was separated and then washed with saturated aqueous sodium chloride solution. The collected organic was dried over magnesium sulphate, filtered, and concentrated under vacuum. The resultant residue was purified by flash column chromatography on silica gel (gradient: 0 to 20% ethyl acetate in pentane) to afford 0.84 g (34%) of 2-methyl-4-o-tolyl-thiazole-5-carboxylic acid ethyl ester as an oil. LCMS (ESI) m+H=261.9; $^1$H NMR (400 MHz, CDCl$_3$) δ: 7.31-7.18 (m, 4H), 4.16 (q, 2H), 2.76 (s, 3H), 2.18 (s, 3H), 1.14 (t, 3H).

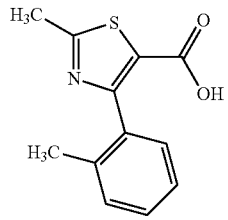

2-Methyl-4-o-tolyl-thiazole-5-carboxylic acid

A mixture of 2-methyl-4-o-tolyl-thiazole-5-carboxylic acid ethyl ester (0.84 g, 3.20 mmol, 1.0 equiv) and potassium hydroxide (0.36 g, 6.40 mmol, 2.0 equiv) in 50% aqueous methanol (10 mL) was heated to 50° C. for 5 hours. The mixture was concentrated, and the residue diluted with water and acidified to about pH 1 by the addition of 6N HCl solution. The resultant solution was extracted with ethyl acetate (3×). The combined extracts were dried over magnesium sulphate, filtered, and concentrated under vacuum to afford 0.61 g (81%) of 2-methyl-4-o-tolyl-thiazole-5-carboxylic acid as a solid. LCMS (ESI) m+H=234.0; $^1$H NMR (400 MHz, CDCl$_3$) δ: 7.32-7.17 (m, 4H), 2.75 (s, 3H), 2.17 (s, 3H).

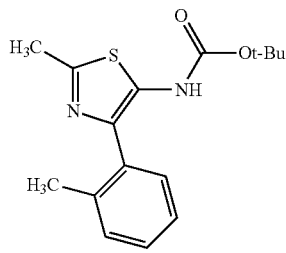

(2-Methyl-4-o-tolyl-thiazol-5-yl)-carbamic acid tert-butyl ester

A mixture of 2-methyl-4-o-tolyl-thiazole-5-carboxylic acid (300 mg, 1.29 mmol, 1.0 equiv), diphenyl phosphorylazide (DPPA) (354 mg, 1.29 mmol, 1.0 equiv), and triethylamine (130 mg, 1.29 mmol, 1.0 equiv) in tert-butanol (10 mL) was heated to 85° C. for 4 hours. After cooling, the mixture was diluted with water and extracted with ethyl acetate (3×). The combined organic extracts were dried over magnesium sulphate, filtered, and concentrated under vacuum. The residue was purified by flash column chromatography on silica gel (gradient: 2 to 25% ethyl acetate in pentane) to give 352 mg (90%) of (2-methyl-4-o-tolyl-thiazol-5-yl)-carbamic acid tert-butyl ester as an oil. LCMS (ESI) m+H=305.1; $^1$H NMR (400 MHz, CDCl$_3$) δ: 7.33-7.24 (m, 4H), 6.58 (s, 1H), 2.64 (s, 3H), 2.24 (s, 3H), 1.48 (s, 9H).

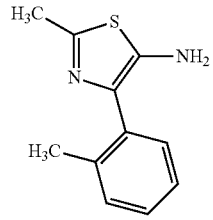

2-Methyl-4-o-tolyl-thiazol-5-ylamine

A solution of (2-methyl-4-o-tolyl-thiazol-5-yl)-carbamic acid tert-butyl ester (340 mg, 1.12 mmol, 1.0 equiv) in dichloromethane (10 mL) was treated with trifluoroacetic acid (0.7 mL, 9.00 mmol, 8.0 equiv) for 24 hours at ambient temperature. The mixture was concentrated under vacuum and the resultant residue dissolved in dichloromethane and washed sequentially with 10% aqueous potassium carbonate solution and saturated aqueous sodium chloride solution. The collected organic was dried over magnesium sulfate and filtered. The filtrate was passed through an Isolute® SCX-2 cartridge (eluting with dichloromethane, dichloromethane/methanol (1:1) and 2M ammonia in methanol) to afford 62.0 mg (27%) of 2-methyl-4-o-tolyl-thiazol-5-ylamine as a brown residue. LCMS (ESI) m+H=205.0; $^1$H NMR (400 MHz, CDCl$_3$) δ: 7.33-7.18 (m, 4H), 3.54-3.45 (br, 2H), 2.58 (s, 3H), 2.29 (s, 3H).

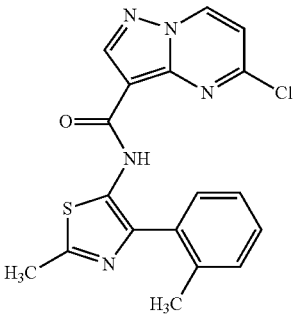

5-Chloro-pyrazolo[1,5-a]pyrimidine-3-carboxylic acid (2-methyl-4-o-tolyl-thiazol-5-yl)-amide To an ice-cooled solution of 2-methyl-4-o-tolyl-thiazol-5-ylamine (55.0 mg, 0.27 mmol, 1.0 equiv) and diisopropylethylamine (52.0 mg, 0.41 mmol, 1.5 equiv) in dichloromethane (10 mL) was added a solution of 5-chloropyrazolo[1,5-c]pyrimidine-3-carbonyl chloride (58.0 mg, 0.27 mmol, 1.0 equiv) in dichloromethane (5 mL). The reaction mixture was warmed to ambient temperature and stirred overnight. The mixture was washed with water and saturated aqueous sodium chloride solution, dried over magnesium sulfate, filtered, and concentrated under vacuum. Purification by flash column chromatography on silica gel (gradient: 0 to 3% methanol in dichloromethane) afforded 74.0 mg (73%) of 5-chloro-pyrazolo[1,5-a]pyrimidine-3-carboxylic acid (2-methyl-4-o-tolyl-thiazol-5-yl)-amide as a solid. LCMS (ESI) m+H=384.0 (mono chlorinated isotope pattern); $^1$H NMR (400 MHz, CDCl$_3$) δ: 9.73 (s, 1H), 8.70 (s, 1H), 8.63 (d, 1H), 7.44-7.30 (m, 4H), 6.93 (d, 1H), 2.72 (s, 3H), 2.31 (s, 3H).

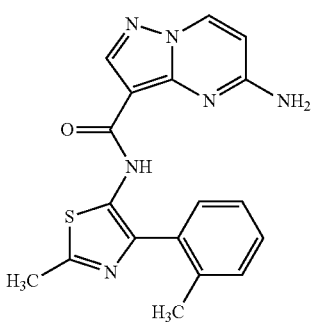

5-Amino-pyrazolo[1,5-a]pyrimidine-3-carboxylic acid
(2-methyl-4-o-tolyl-thiazol-5-yl)-amide A mixture of 5-chloro-pyrazolo[1,5-a]pyrimidine-3-carboxylic acid (2-methyl-4-o-tolyl-thiazol-5-yl)-amide (74.0 mg, 0.19 mmol, 1.0 equiv) and 2M ammonia in propan-2-ol (3 mL) was sealed and heated in a microwave reactor at 120° C. for 1 hour. The solvent was removed under vacuum, and the resultant residue purified by flash column chromatography on silica gel (gradient: 0 to 5% methanol in dichloromethane) to afford 11.0 mg (16%) of 5-amino-pyrazolo[1,5-a]pyrimidine-3-carboxylic acid (2-methyl-4-o-tolyl-thiazol-5-yl)-amide. LCMS (ESI) m+H=365.1; $^1$H NMR (400 MHz, DMSO-d$_6$) δ: 10.35 (s, 1H), 8.66 (d, 1H), 8.23 (s, 1H), 7.47-7.37 (m, 4H), 6.38 (d, 1H), 2.61 (s, 3H), 2.20 (s, 3H).

Example 232

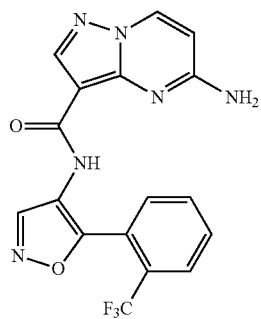

5-Amino-pyrazolo[1,5-a]pyrimidine-3-carboxylic acid
[5-(2-trifluoromethyl-phenyl)-isoxazol-4-yl]-amide

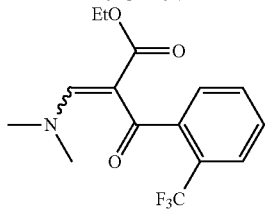

3-Dimethylamino-2-(2-trifluoromethyl-benzoyl)-acrylic acid
ethyl ester

A solution of 3-oxo-3-(2-trifluoromethyl-phenyl)-propionic acid ethyl ester, prepared following an analogous procedure to that outlined in Example 231, (3.14 g, 12.1 mmol, 1.0 equiv) and 1,1-dimethoxy-N,N-dimethylmethanamine (5.60 mL, 42.2 mmol, 3.5 equiv) in N,N-dimethylformamide was heated to reflux for 5 hours. After cooling, the mixture was partitioned between ethyl acetate and water. The organic phase was separated and washed sequentially with water (4×) and saturated aqueous sodium chloride. The collected organic was dried over anhydrous sodium sulfate, filtered, and concentrated under vacuum to give 3.20 g (83%) of 3-dimethylamino-2-(2-trifluoromethyl-benzoyl)-acrylic acid ethyl ester as an orange waxy solid. $^1$H NMR (400 MHz, CDCl$_3$) δ: 7.86 (s, 1H), 7.67-7.64 (m, 1H), 7.51-7.41 (m, 2H), 7.35 (d, 1H), 3.81 (q, 2H), 3.42-3.17 (m, 3H), 3.11-2.93 (m, 3H), 0.78-0.69 (t, 3H).

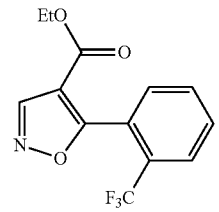

5-(2-Trifluoromethyl-phenyl)-isoxazole-4-carboxylic
acid ethyl ester

A mixture of 3-dimethylamino-2-(2-trifluoromethyl-benzoyl)-acrylic acid ethyl ester (3.10 g, 9.80 mmol, 1.0 equiv) and hydroxylamine hydrochloride (683 mg, 9.80 mmol, 1.0 equiv) in methanol (25 mL) was heated to reflux for 90 minutes. After cooling, the mixture was partitioned between water and ethyl acetate and separated. The aqueous layer was extracted with ethyl acetate. The combined organic extracts was washed with saturated aqueous sodium chloride, dried over anhydrous sodium sulfate, filtered, and concentrated under vacuum. Purification by flash column chromatography on silica gel (gradient: 0 to 30% ethyl acetate in cyclohexane) gave 1.43 g (51%) of 5-(2-trifluoromethyl-phenyl)-isoxazole-4-carboxylic acid ethyl ester. $^1$H NMR (300 MHz, CDCl$_3$) δ: 8.38 (s, 1H), 7.69 (d, 1H), 7.61-7.47 (m, 2H), 7.27 (d, 1H), 3.93 (br, 2H), 0.87 (br, 3H).

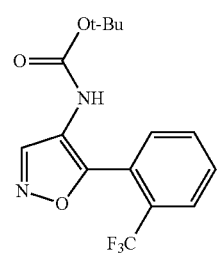

[5-(2-Trifluoromethyl-phenyl)-isoxazol-4-yl]-carbamic acid
tert-butyl ester

A mixture of 5-(2-trifluoromethyl-phenyl)-isoxazole-4-carboxylic acid ethyl ester (1.43 g, 5.01 mmol, 1.0 equiv), 6M HCl aqueous solution (34 mL) and acetic acid (20 mL) were heated to reflux for 5.5 hours. After cooling, the mixture was partitioned between water and ethyl acetate and separated. The organic phase was washed sequentially with water and saturated aqueous sodium chloride solution, dried over anhydrous sodium sulfate, and concentrated under vacuum to give 745 mg (58%) of crude 5-(2-trifluoromethyl-phenyl)-isoxazole-4-carboxylic acid which was used without purification.

A mixture of 5-(2-trifluoromethyl-phenyl)-isoxazole-4-carboxylic acid (745 mg, 2.90 mmol, 1.0 equiv) and thionyl chloride (8 mL) was heated to reflux for 3 hours. The mixture was cooled to room temperature and concentrated under vacuum. The residue was dissolved in acetone (8 mL), cooled with an ice bath and sodium azide (339 mg, 5.20 mmol, 1.8 equiv) was added. The mixture was stirred for 1 hour at this temperature, then 1 hour at ambient temperature. The reaction mixture was diluted with ethyl acetate, and the resultant solution was washed sequentially with water and saturated aqueous sodium chloride solution. The collected organic was dried over anhydrous sodium sulfate, filtered, and concentrated under vacuum. The resultant residue was dissolved in tert-butanol (8 mL) and heated to reflux for 16 hours. The reaction mixture was concentrated under vacuum. Purification by flash column chromatography on silica gel (gradient: 0 to 20% ethyl acetate in cyclohexane) gave 345 mg (36%) of [5-(2-trifluoromethyl-phenyl)-isoxazol-4-yl]-carbamic acid tert-butyl ester. $^1$H NMR (300 MHz, CDCl$_3$) δ: 8.89 (s, 1H), 7.88-7.84 (m, 1H), 7.72-7.66 (m, 2H), 7.54-7.49 (m, 1H), 5.98 (s, 1H), 1.48 (s, 9H).

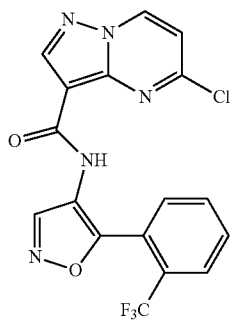

5-Chloro-pyrazolo[1,5-a]pyrimidine-3-carboxylic acid [5-(2-trifluoromethyl-phenyl)-isoxazol-4-yl]-amide A mixture of [5-(2-trifluoromethyl-phenyl)-isoxazol-4-yl]-carbamic acid tert-butyl ester (345 mg, 1.05 mmol, 1.0 equiv), 4M HCl in dioxane (2 mL) in 1,4-dioxane (3 mL) was heated to 40° C. for 20 hours. The mixture was concentrated under vacuum affording a residue which was dissolved in dichloromethane (12 mL) and treated with diisopropylethylamine (271 mg, 2.10 mmol, 2.0 equiv). The mixture was cooled with an ice-bath, and a solution of 5-chloropyrazolo[1,5-a]pyrimidine-3-carbonyl chloride (1.05 mmol, 1.0 equiv) in dichloromethane (6 mL) was added dropwise. The resultant mixture was stirred at ambient temperature for 18 hours. The solution was washed sequentially with 1M HCl aqueous solution, saturated aqueous sodium bicarbonate solution and water. The collected organic was dried over anhydrous sodium sulfate, filtered, and concentrated under vacuum. The residue was triturated (methanol), and the isolated solid was washed with methanol and diethyl ether before drying under vacuum to give 367 mg (86%) of 5-chloro-pyrazolo[1,5-a]pyrimidine-3-carboxylic acid [5-(2-trifluoromethyl-phenyl)-isoxazol-4-yl]-amide. LCMS (ESI) m+H=408.0 (mono Cl); $^1$H NMR (400 MHz, DMSO-d$_6$) δ: 9.50 (s, 1H), 9.35 (d, 1H), 9.22 (s, 1H), 8.71 (s, 1H), 8.03 (d, 1H), 7.97-7.82 (m, 3H), 7.38 (d, 1H).

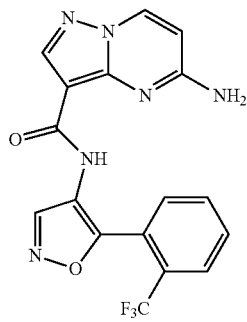

5-Amino-pyrazolo[1,5-a]pyrimidine-3-carboxylic acid [5-(2-trifluoromethyl-phenyl)-isoxazol-4-yl]-amide A mixture of 5-chloro-pyrazolo[1,5-a]pyrimidine-3-carboxylic acid [5-(2-trifluoromethyl-phenyl)-isoxazol-4-yl]-amide (200 mg, 0.49 mmol, 1.0 equiv) and 2M ammonia in propan-2-ol (4 mL) was sealed and heated in a microwave reactor at 120° C. for 40 minutes. The solvent was removed under vacuum and the resultant residue was purified by flash column chromatography on silica gel (gradient: 0 to 5% methanol in dichloromethane) to afford 58.6 mg (31%) of 5-amino-pyrazolo[1,5-a]pyrimidine-3-carboxylic acid [5-(2-trifluoromethyl-phenyl)-isoxazol-4-yl]-amide. LCMS (ESI) m+H=389.1; $^1$H NMR (400 MHz, DMSO-d$_6$) δ: 9.60 (s, 1H), 9.07 (s, 1H), 8.63 (d, 1H), 8.18 (s, 1H), 7.99 (d, 1H), 7.95-7.77 (m, 3H), 7.70-6.60 (br, 2H), 6.39 (d, 1H).

Example 233

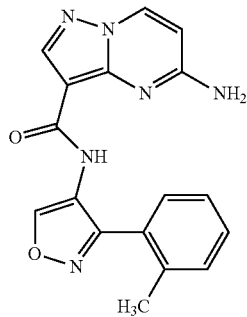

5-Amino-pyrazolo[1,5-a]pyrimidine-3-carboxylic acid (3-o-tolyl-isoxazol-4-yl)-amide

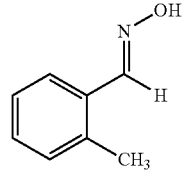

2-Methyl-benzaldehyde oxime

A mixture of o-tolualdehyde (5.00 g, 41.6 mmol, 1.0 equiv), hydroxylamine hydrochloride (3.18 g, 45.8 mmol, 1.1 equiv) and pyridine (3.29 g, 41.6 mmol, 1.0 equiv) in ethanol (100 mL) was stirred at ambient temperature for 2 hours. The pH of the mixture was adjusted to about 1 by the addition of 1M HCl aqueous solution. The resultant solution was extracted with dichloromethane. The collected organic extracts were dried over anhydrous sodium sulfate, filtered, and concentrated under vacuum to give an oil (6.30 g), which was used directly for the next step. LCMS (ESI) m+H+ MeOH=168.0; ¹H NMR (400 MHz, CDCl₃) δ: 8.42 (s, 1H), 7.70-7.63 (d, 1H), 7.29-7.16 (m, 3H), 2.43 (s, 3H).

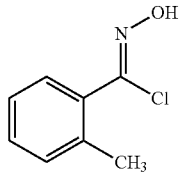

N-Hydroxy-2-methylbenzenecarboximidoyl chloride

N-Chlorosuccinimide (2.22 g, 16.6 mmol, 1.0 equiv) was added to a stirred solution of 2-methyl-benzaldehyde oxime (2.25 g, 16.6 mmol, 1.0 equiv) in N,N-dimethylformamide (30 mL) at ambient temperature. Stirring was continued for 2 hours and the reaction quenched (ice-water). The resultant mixture was extracted with ethyl acetate. The combined organic extracts were washed sequentially with water (6×) and saturated aqueous sodium chloride solution (2×). The organic was then dried over anhydrous sodium sulfate, filtered, and concentrated under vacuum to give 2.07 g (74%) of N-hydroxy-2-methylbenzenecarboximidoyl chloride as a green oil. ¹H NMR (300 MHz, CDCl₃) δ: 8.14 (s, 1H), 7.48-7.44 (m, 1H), 7.37-7.20 (m, 3H), 2.43 (s, 3H).

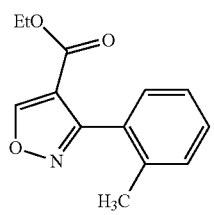

3-o-Tolyl-isoxazole-4-carboxylic acid ethyl ester

To a stirred solution of N-hydroxy-2-methylbenzenecarboximidoyl chloride (2.07 g, 12.2 mmol, 1.0 equiv) in diethyl ether (15 mL) was added a solution of 3-pyrrolidin-1-yl-acrylic acid ethyl ester (prepared according to the procedure described in U.S. Pat. No. 4,187,099) (2.06 g, 12.2 mmol, 1.0 equiv) and triethylamine (1.48 g, 12.2 mmol, 1.0 equiv) in diethyl ether (30 mL) dropwise over 15 minutes. The resultant mixture was stirred at ambient temperature for 16 hours, partitioned between water and diethyl ether and separated. The aqueous phase was extracted with diethyl ether (2×), and the combined ethereal extracts were dried over anhydrous sodium sulfate, filtered, and concentrated under vacuum. Purification by flash column chromatography on silica gel (gradient: 0 to 20% ethyl acetate in cyclohexane) gave 1.32 g (47%) of 3-o-tolyl-isoxazole-4-carboxylic acid ethyl ester. ¹H NMR (400 MHz, CDCl₃) δ: 9.02 (s, 1H), 7.39-7.34 (m, 1H), 7.32-7.24 (m, 3H), 4.19 (q, 2H), 2.23 (s, 3H), 1.17 (t, 3H).

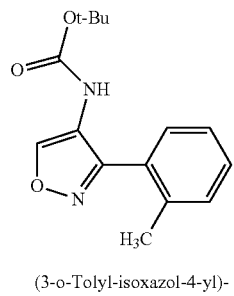

(3-o-Tolyl-isoxazol-4-yl)-carbamic acid tert-butyl ester

A solution of 3-o-tolyl-isoxazole-4-carboxylic acid ethyl ester (1.32 g, 5.71 mmol, 1.0 equiv), 6M HCl aqueous solution (40 mL) and acetic acid (24 mL) was heated to reflux for 5 hours. After cooling, the mixture was partitioned between water and ethyl acetate and separated. The organic phase was sequentially washed with water and saturated aqueous sodium chloride solution. The collected organic was then dried over anhydrous sodium sulfate, filtered, and concentrated under vacuum to give 930 mg (80%) of crude 3-o-tolyl-isoxazole-4-carboxylic acid which was used without purification.

A mixture of 3-o-tolyl-isoxazole-4-carboxylic acid (930 mg, 4.58 mmol, 1.0 equiv), diphenylphosphonic azide (1.26 g, 4.58 mmol, 1.0 equiv) and triethylamine (463 mg, 4.58 mmol, 1.0 equiv) in tert-butanol (40 mL) was heated to 85° C. for 16 hours. The mixture was concentrated under vacuum and the residue taken up into ethyl acetate and sequentially washed with 1M HCl aqueous solution, saturated aqueous sodium bicarbonate solution, water, and saturated aqueous sodium chloride solution. The collected organic was dried over anhydrous sodium sulfate, filtered, and concentrated under vacuum. The residue was purified by flash column chromatography on silica gel (gradient: 0 to 15% ethyl acetate in cyclohexane) to afford 943 mg (75%) of (3-o-tolyl-isoxazol-4-yl)-carbamic acid tert-butyl ester. LCMS (ESI) m+H=275.0; ¹H NMR (300 MHz, CDCl₃) δ: 8.92 (s, 1H), 7.47-7.29 (m, 4H), 5.87 (s, 1H), 2.29 (s, 3H), 1.48 (s, 9H).

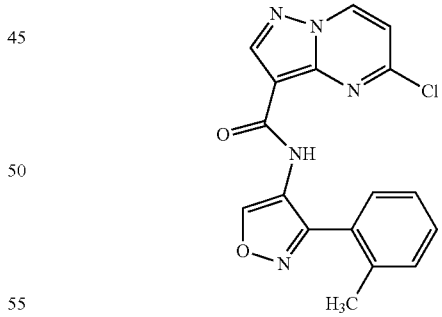

5-Chloro-pyrazolo[1,5-a]pyrimidine-3-carboxylic acid (3-o-tolyl-isoxazol-4-yl)-amide A mixture of (3-o-tolyl-isoxazol-4-yl)-carbamic acid tert-butyl ester (500 mg, 1.82 mmol, 1.0 equiv), 4M HCl in dioxane (4 mL) in 1,4-dioxane (5 mL) was stirred at ambient temperature for 22 hours and at 40° C. for 1 hour. The mixture was concentrated under vacuum affording a residue which was dissolved in dichloromethane (15 mL) and treated with diisopropylethylamine (523 mg, 4.05 mmol, 2.2 equiv). The mixture was cooled with an ice-bath and a solution of 5-chloropyrazolo[1,5-a]pyrimidine-3-carbonyl chloride (1.82 mmol, 1.0 equiv) in dichloromethane (10 mL) was added dropwise. The reaction mixture was warmed to room temperature after the addition. After 65 hours, the solution was sequentially washed with 1M HCl aqueous solution, saturated aqueous sodium bicarbonate solution, water, and saturated aqueous sodium chloride solution. The organic was dried over anhydrous sodium sulfate, filtered, and concentrated under vacuum. The residue was triturated (methanol) to give 444 mg (70%) of 5-chloro-pyrazolo[1,5-a]pyrimidine-3-carboxylic acid (3-o-tolyl-isoxazol-4-yl)-amide. LCMS (ESI) m+H=354.2 (mono Cl); $^1$H NMR (300 MHz, DMSO-$d_6$) δ: 9.47 (s, 1H), 9.36 (d, 1H), 9.11 (s, 1H), 8.72 (s, 1H), 7.53-7.40 (m, 4H), 7.37 (d, 1H), 2.31 (s, 3H).

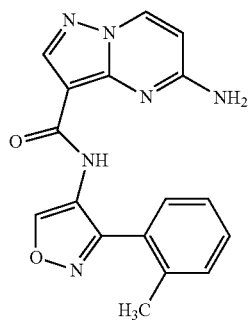

5-Amino-pyrazolo[1,5-a]pyrimidine-3-carboxylic acid (3-o-tolyl-isoxazol-4-yl)-amide A mixture of 5-chloro-pyrazolo[1,5-a]pyrimidine-3-carboxylic acid (3-o-tolyl-isoxazol-4-yl)-amide (200 mg, 0.57 mmol, 1.0 equiv) and 2M ammonia in propan-2-ol (3 mL) was heated in a sealed vial at 65° C. for 18 hours and then in a microwave reactor at 100° C. for 30 minutes. After cooling, the resultant precipitate was isolated by filtration. The solids were sequentially washed with propan-2-ol and diethyl ether, and dried under vacuum at 55° C. to yield 153 mg (80%) of 5-amino-pyrazolo[1,5-a]pyrimidine-3-carboxylic acid (3-o-tolyl-isoxazol-4-yl)-amide as a solid. LCMS (ESI) m+H=335.1; $^1$H NMR (400 MHz, DMSO-$d_6$) δ: 9.51 (s, 1H), 9.34 (s, 1H), 8.65 (d, 1H), 8.21 (s, 1H), 7.58-7.44 (m, 4H), 7.01 (br, 1H), 6.39 (d, 1H), 2.27 (s, 3H).

Example 234

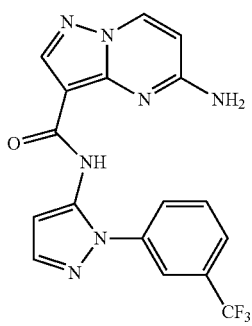

5-Amino-pyrazolo[1,5-a]pyrimidine-3-carboxylic acid [2-(3-trifluoromethyl-phenyl)-2H-pyrazol-3-yl]-amide

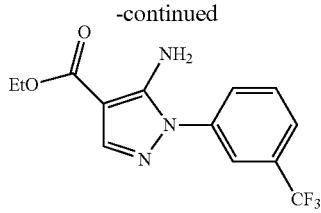

Ethyl 5-amino-1-(3-(trifluoromethyl)phenyl)-1H-pyrazole-4-carboxylate

To a solution of ethyl 2-cyano-3-ethoxyacrylate (0.81 g, 4.8 mmol) in ethanol (50 mL) was added 3-(trifluoromethyl)phenylhydrazine (0.85 g, 4.8 mmol). The resultant reaction mixture was refluxed for 24 hours under a nitrogen atmosphere. The mixture was cooled to room temperature and concentrated under reduced pressure to afford 0.94 g (yield: 66%), which was used without further purification. MS (ESI) m/z:300.3

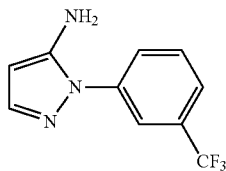

1-(3-(Trifluoromethyl)phenyl)-1H-pyrazol-5-amide

A solution of ethyl 5-amino-1-(3-(trifluoromethyl)phenyl)-1H-pyrazole-4-carboxylate (0.9 g, 3 mmol) in dioxane (20 mL) saturated with HCl was heated to 150° C. for 5 hours in a sealed tube. The reaction mixture was then cooled and concentrated in vacuo. The residue diluted with water, and the aqueous solution was extracted with ethyl acetate (3×50 mL). The combined organic extracts was dried over magnesium sulfate, filtered, and concentrated. The resultant residue was purified by flash column chromatography (5:1 ethyl acetate/petroleum ether) to afford product (430 mg, 63%). MS (ESI) m/z: 228.1

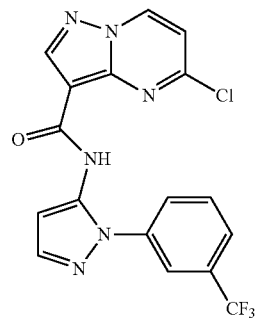

5-Chloro-N-(1-(3-(trifluoromethyl)phenyl)-1H-pyrazol-5-yl)pyrazolo[1,5-a]pyrimidine-3-carboxamide To a stirred solution of 1-(3-(trifluoromethyl)phenyl)-1H-pyrazol-5-amine (200 mg, 0.88 mmol) in dichloromethane (30 mL) was added 5-chloropyrazolo[1,5-a]pyrimidine-3-carbonyl chloride (215 mg, 1.0 mmol) and diisopropylethylamine (130 mg, 1.0 mmol). The mixture was heated to 50° C.

overnight. After cooling to room temperature, the mixture was concentrated to afford crude 5-chloro-N-(1-(3-(trifluoromethyl)phenyl)-1H-pyrazol-5-yl)pyrazolo[1,5-a]pyrimidine-3-carboxamide (210 mg, yield 58%), which was used for the next step without further purification. MS (ESI) m/z: 407.2

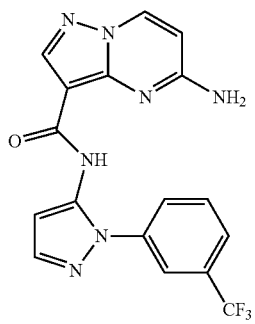

5-Amino-pyrazolo[1,5-a]pyrimidine-3-carboxylic acid [2-(3-trifluoromethyl-phenyl)-2H-pyrazol-3-yl]-amide A solution of 5-chloro-N-(1-(3-(trifluoromethyl)phenyl)-1H-pyrazol-5-yl)pyrazolo[1,5-a]pyrimidine-3-carboxamide (210 mg, 0.52 mmol) in ethanol (20 mL) saturated with ammonia was heated to 100° C. overnight in a sealed tube. After cooling to room temperature, solvent was removed under reduced pressure, and the resultant residue was purified by preparative HPLC to afford 5-amino-pyrazolo[1,5-a]pyrimidine-3-carboxylic acid [2-(3-trifluoromethyl-phenyl)-2H-pyrazol-3-yl]-amide (8 mg, yield: 4%). $^1$H NMR (DMSO, 400 MHz): δ 9.94 (s, 1H), 8.62 (d, J=7.6 Hz, 1H), 8.16 (s, 1H), 7.49-7.69 (m, 8H), 6.53 (s, 1H), 6.37 (d, J=7.6 Hz, 1H). MS (ESI) m/z: 388.1

Examples 235-452 shown in Table 2 were prepared according to the above methods.

TABLE 2

| Ex # | Structure | Name | LCMS (ESI) m/z |
|---|---|---|---|
| 235 | 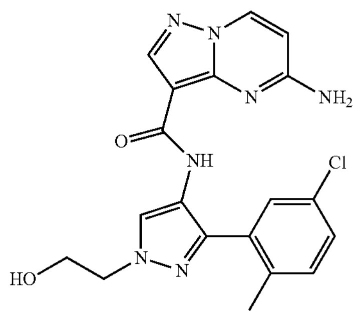 [SMILES: Cc1ccc(Cl)cc1-c1nn(CCO)cc1NC(=O)c1cnn2ccc(N)nc12] | 5-Amino-pyrazolo[1,5-a]-pyrimidine-3-carboxylic acid [3-(5-chloro-2-methyl-phenyl)-1-(2-hydroxy-ethyl)-1H-pyrazol-4-yl]-amide | 412.2 |
| 236 | 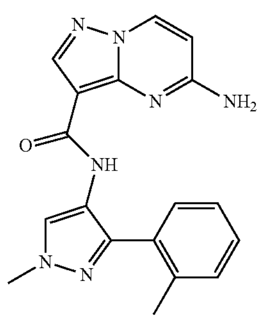 [SMILES: Cc1ccccc1-c1nn(C)cc1NC(=O)c1cnn2ccc(N)nc12] | 5-Amino-pyrazolo[1,5-a]-pyrimidine-3-carboxylic acid (1-methyl-3-o-tolyl-1H-pyrazol-4-yl)-amide | 348.1 |
| 237 | 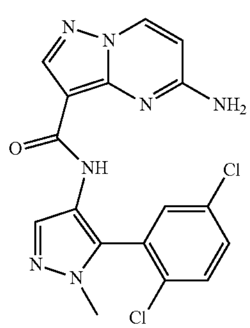 [SMILES: Cn1ncc(NC(=O)c2cnn3ccc(N)nc23)c1-c1cc(Cl)ccc1Cl] | 5-Amino-pyrazolo[1,5-a]-pyrimidine-3-carboxylic acid [5-(2,5-dichloro-phenyl)-1-methyl-1H-pyrazol-4-yl]-amide | 402.0 |

| Ex # | Structure | Name | LCMS (ESI) m/z |
|---|---|---|---|
| 238 | 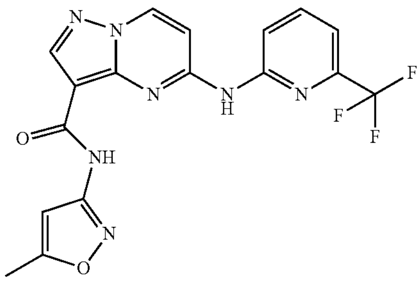 [SMILES: Cc1cc(NC(=O)c2cnn3ccc(Nc4cccc(C(F)(F)F)n4)nc23)no1] | 5-(6-Trifluoromethyl-pyridin-2-ylamino)-pyrazolo[1,5-a]-pyrimidine-3-carboxylic acid (5-methyl-isoxazol-3-yl)-amide | 404.0 |
| 239 | 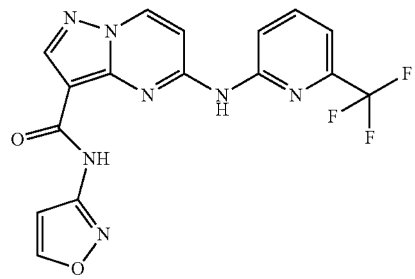 [SMILES: O=C(Nc1ccon1)c1cnn2ccc(Nc3cccc(C(F)(F)F)n3)nc12] | 5-(6-Trifluoromethyl-pyridin-2-ylamino)-pyrazolo[1,5-a]-pyrimidine-3-carboxylic acid isoxazol-3-ylamide | 390.0 |
| 240 | 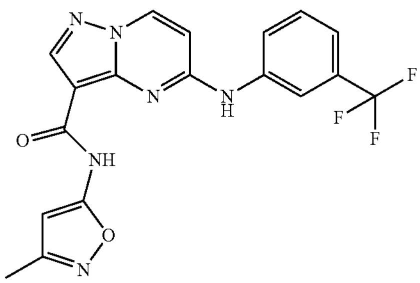 [SMILES: Cc1cc(NC(=O)c2cnn3ccc(Nc4cccc(C(F)(F)F)c4)nc23)on1] | 5-(3-Trifluoromethyl-phenylamino)-pyrazolo-[1,5-a]pyrimidine-3-carboxylic acid (3-methyl-isoxazol-5-yl)-amide | 403.0 |
| 241 | 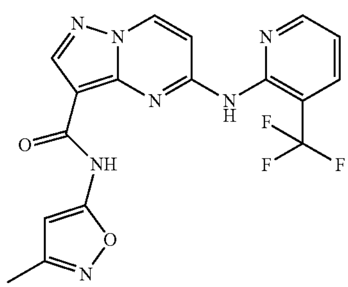 [SMILES: Cc1cc(NC(=O)c2cnn3ccc(Nc4ncccc4C(F)(F)F)nc23)on1] | 5-(3-Trifluoromethyl-pyridin-2-ylamino)-pyrazolo[1,5-a]-pyrimidine-3-carboxylic acid (3-methyl-isoxazol-5-yl)-amide | 404.0 |
| 242 | 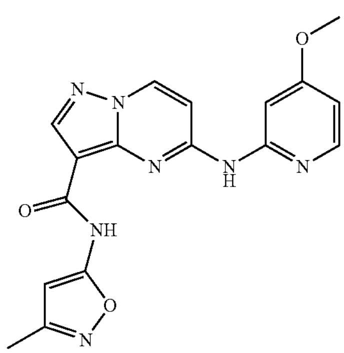 | 5-(4-Methoxy-pyridin-2-ylamino)-pyrazolo-[1,5-a]pyrimidine-3-carboxylic acid (3-methyl-isoxazol-5-yl)-amide | 366.1 |

TABLE 2-continued

| Ex # | Structure | Name | LCMS (ESI) m/z |
|---|---|---|---|
| 243 | 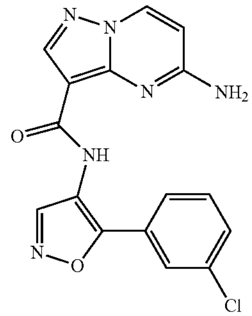 [SMILES: Nc1ccn2ncc(C(=O)Nc3cnoc3-c3cccc(Cl)c3)c2n1] | 5-Amino-pyrazolo[1,5-a]-pyrimidine-3-carboxylic acid [5-(3-chloro-phenyl)-isoxazol-4-yl]-amide | 355.1 |
| 244 | 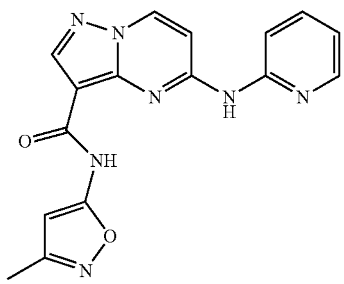 [SMILES: Cc1cc(NC(=O)c2cnn3ccc(Nc4ccccn4)nc23)on1] | 5-(Pyridin-2-ylamino)-pyrazolo[1,5-a]pyrimidine-3-carboxylic acid (3-methyl-isoxazol-5-yl)-amide | 336.2 |
| 245 | 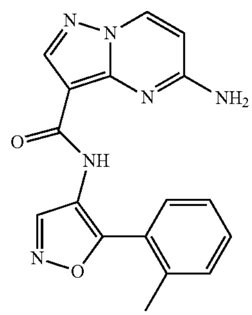 [SMILES: Cc1ccccc1-c1oncc1NC(=O)c1cnn2ccc(N)nc12] | 5-Amino-pyrazolo[1,5-a]-pyrimidine-3-carboxylic acid (5-o-tolyl-isoxazol-4-yl)-amide | 335.2 |
| 246 | 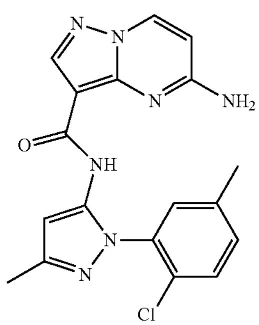 | 5-Amino-pyrazolo[1,5-a]-pyrimidine-3-carboxylic acid [2-(2-chloro-5-methyl-phenyl)-5-methyl-2H-pyrazol-3-yl]-amide | 382.1 |
| 247 | 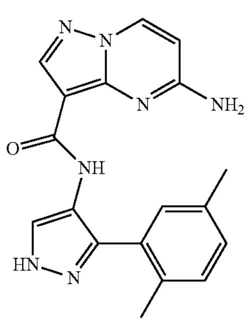 [SMILES: Cc1ccc(C)c(-c2n[nH]cc2NC(=O)c2cnn3ccc(N)nc23)c1] | 5-Amino-pyrazolo[1,5-a]-pyrimidine-3-carboxylic acid [3-(2,5-dimethyl-phenyl)-1H-pyrazol-4-yl]-amide | 348.1 |

TABLE 2-continued

| Ex # | Structure | Name | LCMS (ESI) m/z |
|---|---|---|---|
| 248 | 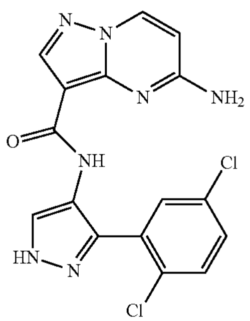 [SMILES: Nc1ccn2ncc(C(=O)Nc3c[nH]nc3-c3cc(Cl)ccc3Cl)c2n1] | 5-Amino-pyrazolo[1,5-a]-pyrimidine-3-carboxylic acid [3-(2,5-dichloro-phenyl)-1H-pyrazol-4-yl]-amide | 388.0 |
| 249 | 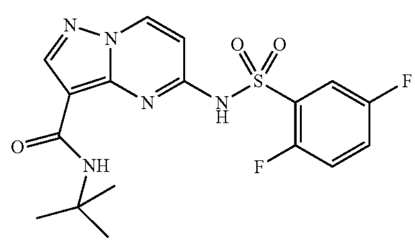 [SMILES: CC(C)(C)NC(=O)c1cnn2ccc(NS(=O)(=O)c3cc(F)ccc3F)nc12] | 5-(2,5-Difluoro-benzene-sulfonylamino)-pyrazolo[1,5-a]-pyrimidine-3-carboxylic acid tert-butylamide | 410.1 |
| 250 | 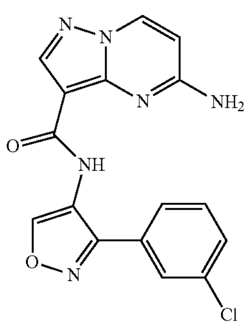 [SMILES: Nc1ccn2ncc(C(=O)Nc3conc3-c3cccc(Cl)c3)c2n1] | 5-Amino-pyrazolo[1,5-a]-pyrimidine-3-carboxylic acid [3-(3-chloro-phenyl)-isoxazol-4-yl]-amide | 355.1 |
| 251 | 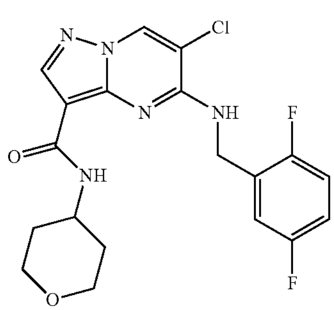 [SMILES: O=C(NC1CCOCC1)c1cnn2cc(Cl)c(NCc3cc(F)ccc3F)nc12] | 6-Chloro-5-(2,5-difluoro-benzylamino)-pyrazolo-[1,5-a]pyrimidine-3-carboxylic acid (tetrahydro-pyran-4-yl)-amide | 422.1 |
| 252 | 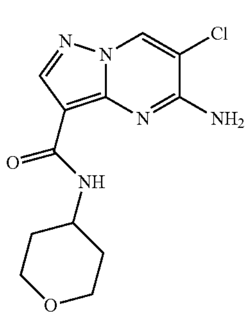 [SMILES: Nc1nc2c(C(=O)NC3CCOCC3)cnn2cc1Cl] | 5-Amino-6-chloro-pyrazolo-[1,5-a]pyrimidine-3-carboxylic acid (tetrahydro-pyran-4-yl)-amide | 296.1 |

TABLE 2-continued

| Ex # | Structure | Name | LCMS (ESI) m/z |
|---|---|---|---|
| 253 | 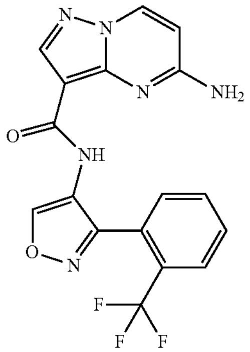 [SMILES: Nc1ccn2ncc(C(=O)Nc3conc3-c3ccccc3C(F)(F)F)c2n1] | 5-Amino-pyrazolo[1,5-a]-pyrimidine-3-carboxylic acid [3-(2-trifluoromethyl-phenyl)-isoxazol-4-yl]-amide | 389.1 |
| 254 | 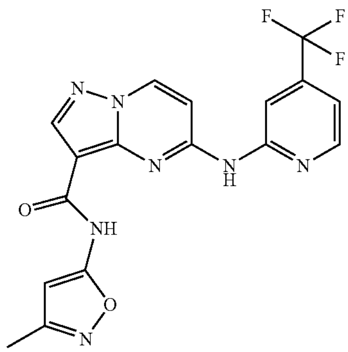 [SMILES: Cc1cc(NC(=O)c2cnn3ccc(Nc4cc(C(F)(F)F)ccn4)nc23)on1] | 5-(4-Trifluoromethyl-pyridin-2-ylamino)-pyrazolo[1,5-a]pyrimidine-3-carboxylic acid (3-methyl-isoxazol-5-yl)-amide | 404.1 |
| 255 | 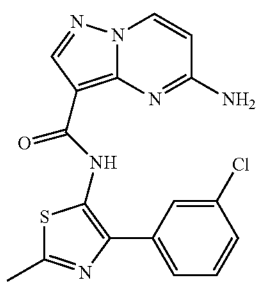 [SMILES: Cc1nc(-c2cccc(Cl)c2)c(NC(=O)c2cnn3ccc(N)nc23)s1] | 5-Amino-pyrazolo[1,5-a]-pyrimidine-3-carboxylic acid [4-(3-chloro-phenyl)-2-methyl-thiazol-5-yl]-amide | 385.1 |
| 256 | 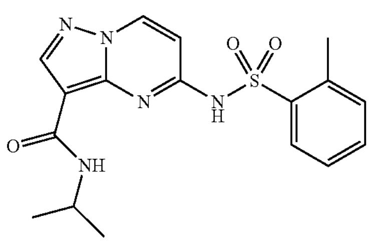 [SMILES: Cc1ccccc1S(=O)(=O)Nc1ccn2ncc(C(=O)NC(C)C)c2n1] | 5-(Toluene-2-sulfonyl-amino)-pyrazolo[1,5-a]-pyrimidine-3-carboxylic acid isopropylamide | 374.1 |
| 257 | 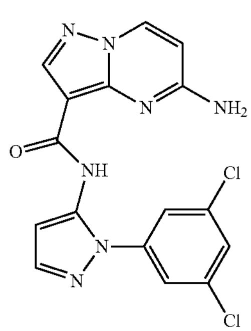 [SMILES: Nc1ccn2ncc(C(=O)Nc3ccnn3-c3cc(Cl)cc(Cl)c3)c2n1] | 5-Amino-pyrazolo[1,5-a]-pyrimidine-3-carboxylic acid [2-(3,5-dichloro-phenyl)-2H-pyrazol-3-yl]-amide | 388.1 |

TABLE 2-continued

| Ex # | Structure | Name | LCMS (ESI) m/z |
|---|---|---|---|
| 258 | 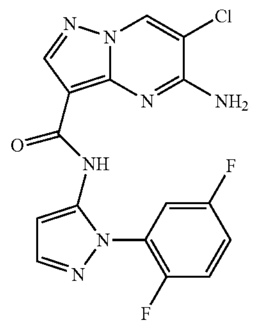 [SMILES: Nc1nc2c(C(=O)Nc3ccnn3-c3cc(F)ccc3F)cnn2cc1Cl] | 5-Amino-6-chloro-pyrazolo-[1,5-a]pyrimidine-3-carboxylic acid [2-(2,5-difluoro-phenyl)-2H-pyrazol-3-yl]-amide | |
| 259 | 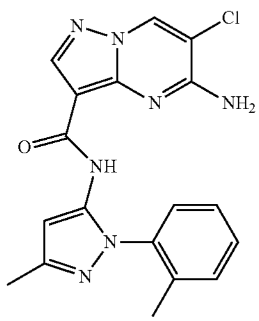 [SMILES: Cc1cc(NC(=O)c2cnn3cc(Cl)c(N)nc23)n(-c2ccccc2C)n1] | 5-Amino-6-chloro-pyrazolo-[1,5-a]pyrimidine-3-carboxylic acid (5-methyl-2-o-tolyl-2H-pyrazol-3-yl)-amide | 382.0 |
| 260 | 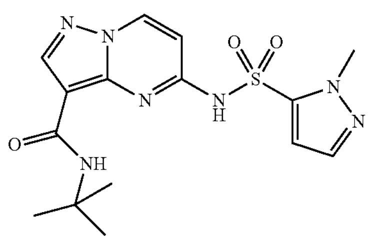 [SMILES: Cn1nccc1S(=O)(=O)Nc1ccn2ncc(C(=O)NC(C)(C)C)c2n1] | 5-(2-Methyl-2H-pyrazole-3-sulfonylamino)-pyrazolo-[1,5-a]pyrimidine-3-carboxylic acid tert-butylamide | 378.1 |
| 261 | 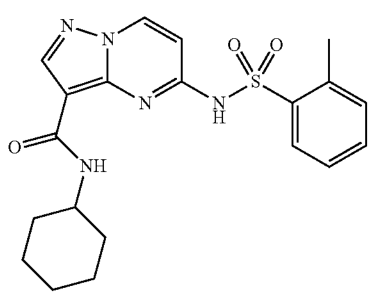 [SMILES: Cc1ccccc1S(=O)(=O)Nc1ccn2ncc(C(=O)NC3CCCCC3)c2n1] | 5-(Toluene-2-sulfonyl-amino)-pyrazolo-[1,5-a]pyrimidine-3-carboxylic acid cyclohexylamide | 414.1 |
| 262 | 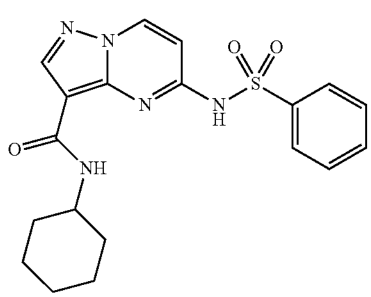 [SMILES: O=C(NC1CCCCC1)c1cnn2ccc(NS(=O)(=O)c3ccccc3)nc12] | 5-Benzenesulfonyl-amino-pyrazolo[1,5-a]-pyrimidine-3-carboxylic acid cyclohexylamide | 400.1 |

TABLE 2-continued

| Ex # | Structure | Name | LCMS (ESI) m/z |
|---|---|---|---|
| 263 | 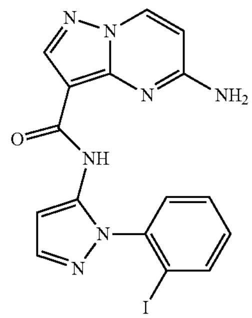 [SMILES: Nc1ccn2ncc(C(=O)Nc3ccnn3-c3ccccc3I)c2n1] | 5-Amino-pyrazolo[1,5-a]-pyrimidine-3-carboxylic acid [2-(2-iodo-phenyl)-2H-pyrazol-3-yl]-amide | 446.0 |
| 264 | 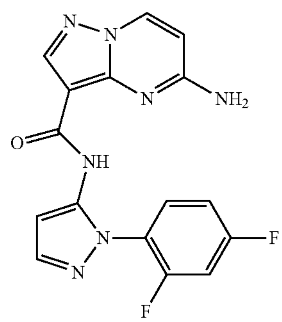 [SMILES: Nc1ccn2ncc(C(=O)Nc3ccnn3-c3ccc(F)cc3F)c2n1] | 5-Amino-pyrazolo[1,5-a]-pyrimidine-3-carboxylic acid [2-(2,4-difluoro-phenyl)-2H-pyrazol-3-yl]-amide | 355.7 |
| 265 | 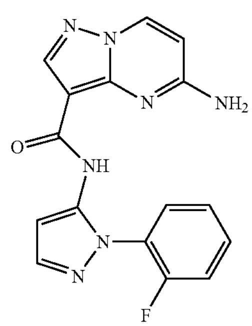 [SMILES: Nc1ccn2ncc(C(=O)Nc3ccnn3-c3ccccc3F)c2n1] | 5-Amino-pyrazolo[1,5-a]-pyrimidine-3-carboxylic acid [2-(2-fluoro-phenyl)-2H-pyrazol-3-yl]-amide | 338.2 |
| 266 | 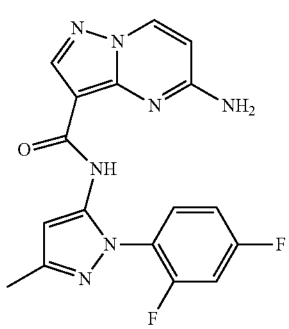 [SMILES: Cc1cc(NC(=O)c2cnn3ccc(N)nc23)n(-c2ccc(F)cc2F)n1] | 5-Amino-pyrazolo[1,5-a]-pyrimidine-3-carboxylic acid [2-(2,4-difluoro-phenyl)-5-methyl-2H-pyrazol-3-yl]-amide | 369.9 |
| 267 | 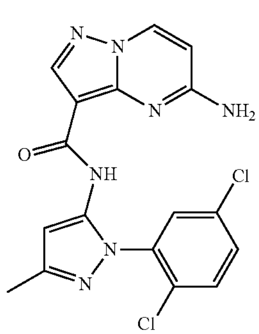 [SMILES: Cc1cc(NC(=O)c2cnn3ccc(N)nc23)n(-c2cc(Cl)ccc2Cl)n1] | 5-Amino-pyrazolo[1,5-a]-pyrimidine-3-carboxylic acid [2-(2,5-dichloro-phenyl)-5-methyl-2H-pyrazol-3-yl]-amide | 402.2 |

| Ex # | Structure | Name | LCMS (ESI) m/z |
|---|---|---|---|
| 268 | 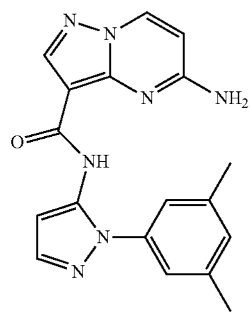 [SMILES: Cc1cc(C)cc(-n2nccc2NC(=O)c2cnn3ccc(N)nc23)c1] | 5-Amino-pyrazolo[1,5-a]-pyrimidine-3-carboxylic acid [2-(3,5-dimethyl-phenyl)-2H-pyrazol-3-yl]-amide | 347.9 |
| 269 | 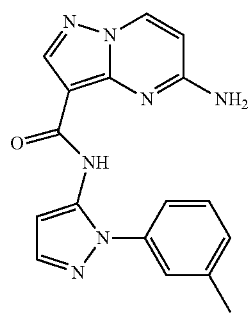 [SMILES: Cc1cccc(-n2nccc2NC(=O)c2cnn3ccc(N)nc23)c1] | 5-Amino-pyrazolo[1,5-a]-pyrimidine-3-carboxylic acid (2-m-tolyl-2H-pyrazol-3-yl)-amide | 333.9 |
| 270 | 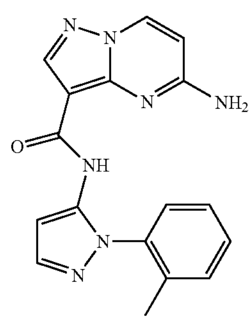 [SMILES: Cc1ccccc1-n1nccc1NC(=O)c1cnn2ccc(N)nc12] | 5-Amino-pyrazolo[1,5-a]-pyrimidine-3-carboxylic acid (2-o-tolyl-2H-pyrazol-3-yl)-amide | 334.0 |
| 271 | 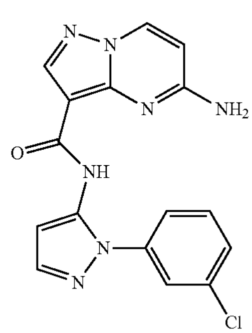 [SMILES: Nc1ccn2ncc(C(=O)Nc3ccnn3-c3cccc(Cl)c3)c2n1] | 5-Amino-pyrazolo[1,5-a]-pyrimidine-3-carboxylic acid [2-(3-chloro-phenyl)-2H-pyrazol-3-yl]-amide | 354.0 |

TABLE 2-continued

| Ex # | Structure | Name | LCMS (ESI) m/z |
|---|---|---|---|
| 272 | 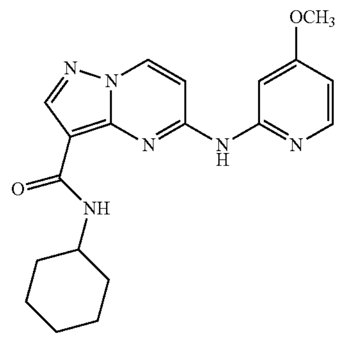 [SMILES: COc1ccnc(Nc2ccn3ncc(C(=O)NC4CCCCC4)c3n2)c1] | 5-(4-Methoxy-pyridin-2-ylamino)-pyrazolo[1,5-a]-pyrimidine-3-carboxylic acid cyclohexylamide | 367.2 |
| 273 | 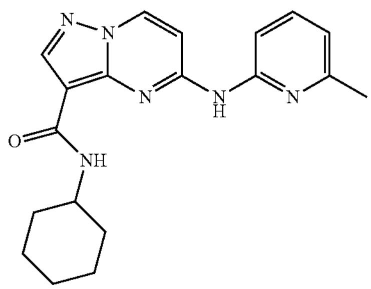 [SMILES: Cc1cccc(Nc2ccn3ncc(C(=O)NC4CCCCC4)c3n2)n1] | 5-(6-Methyl-pyridin-2-ylamino)-pyrazolo[1,5-a]-pyrimidine-3-carboxylic acid cyclohexylamide | 351.2 |
| 274 | 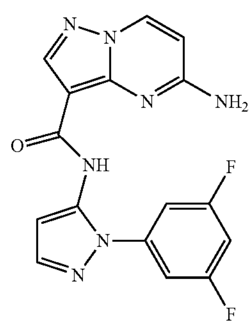 [SMILES: Nc1ccn2ncc(C(=O)Nc3ccnn3-c3cc(F)cc(F)c3)c2n1] | 5-Amino-pyrazolo[1,5-a]-pyrimidine-3-carboxylic acid [2-(3,5-difluoro-phenyl)-2H-pyrazol-3-yl]-amide | 356.6 |
| 275 | 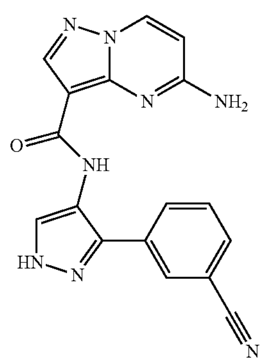 [SMILES: N#Cc1cccc(-c2n[nH]cc2NC(=O)c2cnn3ccc(N)nc23)c1] | 5-Amino-pyrazolo[1,5-a]-pyrimidine-3-carboxylic acid [3-(3-cyano-phenyl)-1H-pyrazol-4-yl]-amide | 345.1 |
| 276 | 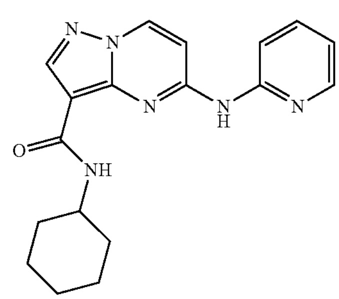 [SMILES: O=C(NC1CCCCC1)c1cnn2ccc(Nc3ccccn3)nc12] | 5-(Pyridin-2-ylamino)-pyrazolo[1,5-a]pyrimidine-3-carboxylic acid cyclohexylamide | 337.2 |

TABLE 2-continued

| Ex # | Structure | Name | LCMS (ESI) m/z |
|---|---|---|---|
| 277 | 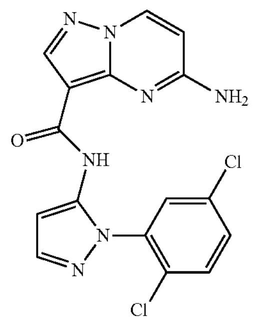 [SMILES: Nc1ccn2ncc(C(=O)Nc3ccnn3-c3cc(Cl)ccc3Cl)c2n1] | 5-Amino-pyrazolo[1,5-a]-pyrimidine-3-carboxylic acid [2-(2,5-dichloro-phenyl)-2H-pyrazol-3-yl]-amide | 388.0 |
| 278 | 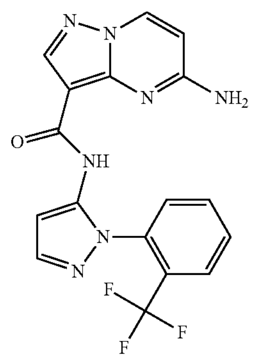 [SMILES: Nc1ccn2ncc(C(=O)Nc3ccnn3-c3ccccc3C(F)(F)F)c2n1] | 5-Amino-pyrazolo[1,5-a]-pyrimidine-3-carboxylic acid [2-(2-trifluoromethyl-phenyl)-2H-pyrazol-3-yl]-amide | 388.0 |
| 279 | 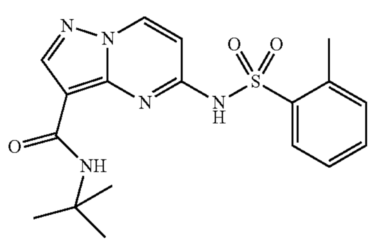 [SMILES: Cc1ccccc1S(=O)(=O)Nc1ccn2ncc(C(=O)NC(C)(C)C)c2n1] | 5-(Toluene-2-sulfonylamino)-pyrazolo[1,5-a]pyrimidine-3-carboxylic acid tert-butylamide | 388.2 |
| 280 | 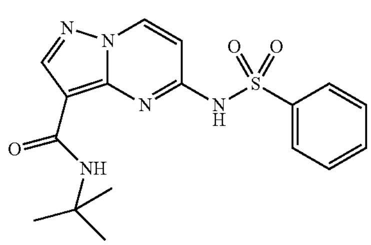 [SMILES: CC(C)(C)NC(=O)c1cnn2ccc(NS(=O)(=O)c3ccccc3)nc12] | 5-Benzenesulfonylamino-pyrazolo[1,5-a]pyrimidine-3-carboxylic acid tert-butylamide | 374.2 |
| 281 | 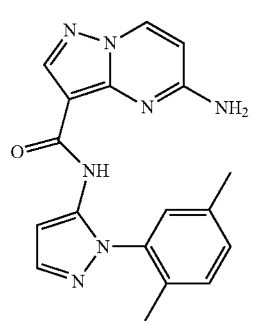 [SMILES: Cc1ccc(C)c(-n2nccc2NC(=O)c2cnn3ccc(N)nc23)c1] | 5-Amino-pyrazolo[1,5-a]-pyrimidine-3-carboxylic acid [2-(2,5-dimethyl-phenyl)-2H-pyrazol-3-yl]-amide | 348.0 |

TABLE 2-continued

| Ex # | Structure | Name | LCMS (ESI) m/z |
|---|---|---|---|
| 282 | 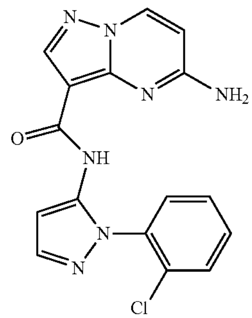 | 5-Amino-pyrazolo[1,5-a]-pyrimidine-3-carboxylic acid [2-(2-chloro-phenyl)-2H-pyrazol-3-yl]-amide | 353.9 |
| 283 | 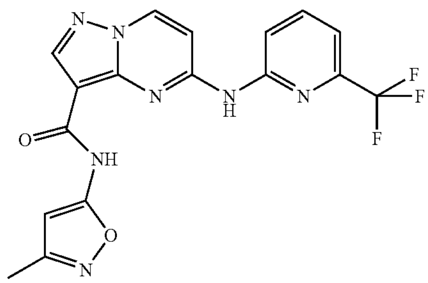 [SMILES: Cc1cc(NC(=O)c2cnn3ccc(Nc4cccc(C(F)(F)F)n4)nc23)on1] | 5-(6-Trifluoromethyl-pyridin-2-ylamino)-pyrazolo-[1,5-a]pyrimidine-3-carboxylic acid (3-methyl-isoxazol-5-yl)-amide | 404.2 |
| 284 | 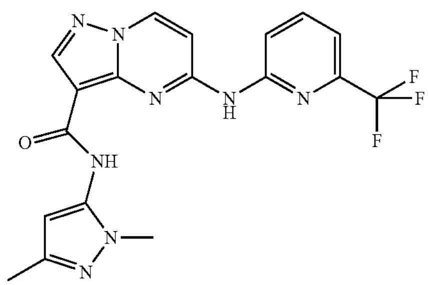 [SMILES: Cc1cc(NC(=O)c2cnn3ccc(Nc4cccc(C(F)(F)F)n4)nc23)n(C)n1] | 5-(6-Trifluoromethyl-pyridin-2-ylamino)-pyrazolo[1,5-a]pyrimidine-3-carboxylic acid (2,5-dimethyl-2H-pyrazol-3-yl)-amide | 417.2 |
| 285 | 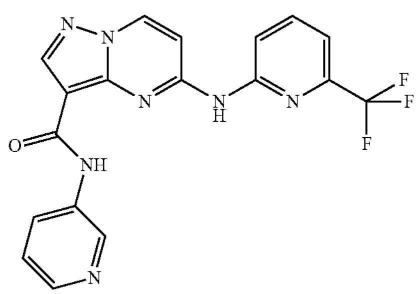 [SMILES: O=C(Nc1cccnc1)c1cnn2ccc(Nc3cccc(C(F)(F)F)n3)nc12] | 5-(6-Trifluoromethyl-pyridin-2-ylamino)-pyrazolo[1,5-a]pyrimidine-3-carboxylic acid pyridin-3-ylamide | 400.2 |
| 286 | 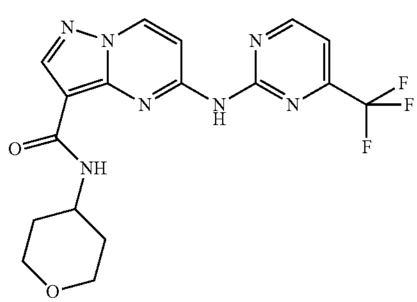 [SMILES: O=C(NC1CCOCC1)c1cnn2ccc(Nc3nccc(C(F)(F)F)n3)nc12] | 5-(4-Trifluoromethyl-pyrimidin-2-ylamino)-pyrazolo[1,5-a]pyrimidine-3-carboxylic acid (tetrahydro-pyran-4-yl)-amide | 408.2 |

TABLE 2-continued

| Ex # | Structure | Name | LCMS (ESI) m/z |
|---|---|---|---|
| 287 | 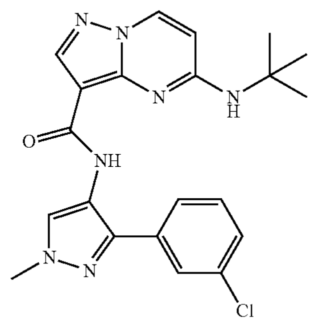 [SMILES: Cn1cc(NC(=O)c2cnn3ccc(NC(C)(C)C)nc23)c(-c2cccc(Cl)c2)n1] | 5-tert-Butylamino-pyrazolo[1,5-a]pyrimidine-3-carboxylic acid [3-(3-chloro-phenyl)-1-methyl-1H-pyrazol-4-yl]-amide | 424.1 |
| 288 | 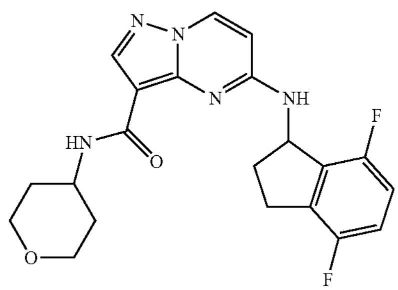 [SMILES: O=C(NC1CCOCC1)c1cnn2ccc(NC3CCc4c(F)ccc(F)c43)nc12] | 5-(4,7-Difluoro-indan-1-ylamino)-pyrazolo[1,5-a]-pyrimidine-3-carboxylic acid (tetrahydro-pyran-4-yl)-amide | 414.1 |
| 289 | 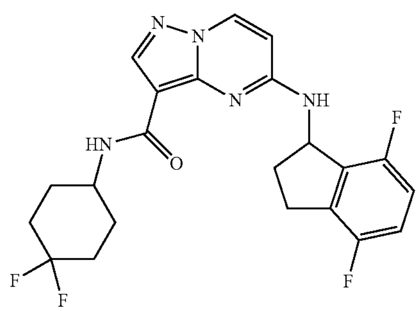 [SMILES: O=C(NC1CCC(F)(F)CC1)c1cnn2ccc(NC3CCc4c(F)ccc(F)c43)nc12] | 5-(4,7-Difluoro-indan-1-ylamino)-pyrazolo[1,5-a]-pyrimidine-3-carboxylic acid (4,4-difluoro-cyclohexyl)-amide | 448.1 |
| 290 | 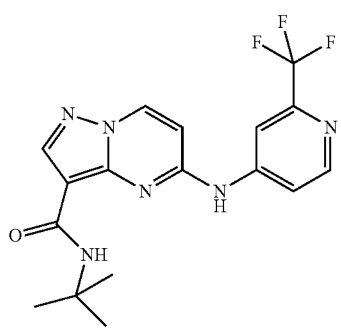 [SMILES: CC(C)(C)NC(=O)c1cnn2ccc(Nc3ccnc(C(F)(F)F)c3)nc12] | 5-(2-Trifluoromethyl-pyridin-4-ylamino)-pyrazolo[1,5-a]pyrimidine-3-carboxylic acid tert-butylamide | 379.2 |
| 291 | 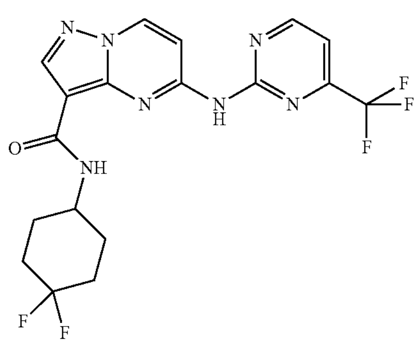 [SMILES: O=C(NC1CCC(F)(F)CC1)c1cnn2ccc(Nc3nccc(C(F)(F)F)n3)nc12] | 5-(4-Trifluoromethyl-pyrimidin-2-ylamino)-pyrazolo[1,5-a]pyrimidine-3-carboxylic acid (4,4-difluoro-cyclohexyl)-amide | 442.1 |

TABLE 2-continued

| Ex # | Structure | Name | LCMS (ESI) m/z |
|---|---|---|---|
| 292 | 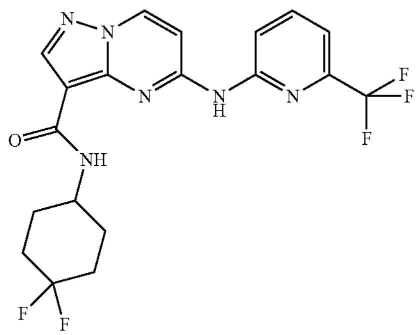 [SMILES: O=C(NC1CCC(F)(F)CC1)c1cnn2ccc(Nc3cccc(C(F)(F)F)n3)nc12] | 5-(6-Trifluoromethyl-pyridin-2-ylamino)-pyrazolo[1,5-a]pyrimidine-3-carboxylic acid (4,4-difluoro-cyclohexyl)-amide | 441.1 |
| 293 | 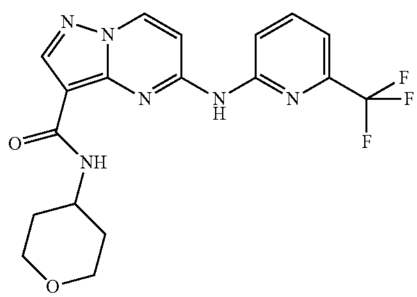 [SMILES: O=C(NC1CCOCC1)c1cnn2ccc(Nc3cccc(C(F)(F)F)n3)nc12] | 5-(6-Trifluoromethyl-pyridin-2-ylamino)-pyrazolo[1,5-a]pyrimidine-3-carboxylic acid (tetrahydro-pyran-4-yl)-amide | 407.2 |
| 294 | 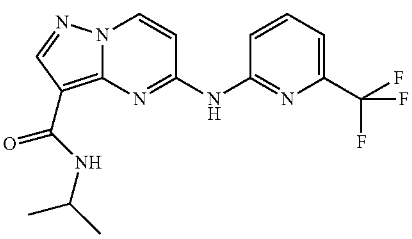 [SMILES: CC(C)NC(=O)c1cnn2ccc(Nc3cccc(C(F)(F)F)n3)nc12] | 5-(6-Trifluoromethyl-pyridin-2-ylamino)-pyrazolo[1,5-a]pyrimidine-3-carboxylic acid isopropylamide | 365.1 |
| 295 | 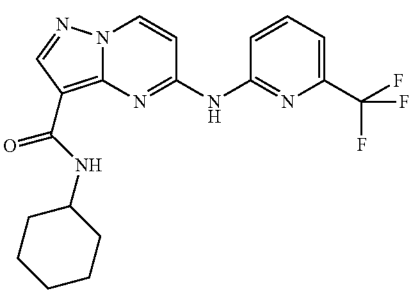 [SMILES: O=C(NC1CCCCC1)c1cnn2ccc(Nc3cccc(C(F)(F)F)n3)nc12] | 5-(6-Trifluoromethyl-pyridin-2-ylamino)-pyrazolo[1,5-a]pyrimidine-3-carboxylic acid cyclohexylamide | 405.2 |
| 296 | 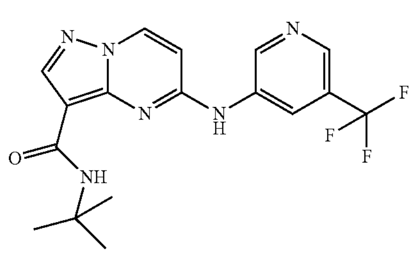 [SMILES: CC(C)(C)NC(=O)c1cnn2ccc(Nc3cncc(C(F)(F)F)c3)nc12] | 5-(5-Trifluoromethyl-pyridin-3-ylamino)-pyrazolo[1,5-a]pyrimidine-3-carboxylic acid tert-butylamide | 379.2 |

TABLE 2-continued

| Ex # | Structure | Name | LCMS (ESI) m/z |
|---|---|---|---|
| 297 | 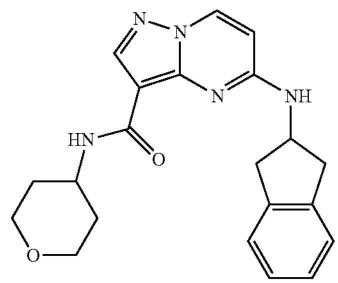 [SMILES: O=C(NC1CCOCC1)c1cnn2ccc(NC3Cc4ccccc4C3)nc12] | 5-(Indan-2-ylamino)-pyrazolo[1,5-a]pyrimidine-3-carboxylic acid (tetrahydro-pyran-4-yl)-amide | 378.2 |
| 298 | 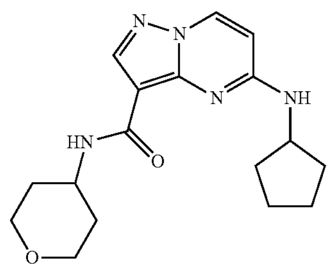 [SMILES: O=C(NC1CCOCC1)c1cnn2ccc(NC3CCCC3)nc12] | 5-Cyclopentylamino-pyrazolo[1,5-a]pyrimidine-3-carboxylic acid (tetrahydro-pyran-4-yl)-amide | 330.1 |
| 299 | 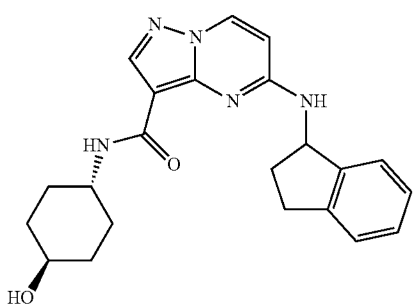 [SMILES: O=C(N[C@H]1CC[C@H](O)CC1)c1cnn2ccc(NC3CCc4ccccc43)nc12] | 5-(Indan-1-ylamino)-pyrazolo[1,5-a]pyrimidine-3-carboxylic acid (4-hydroxy-cyclohexyl)-amide | 392.2 |
| 300 | 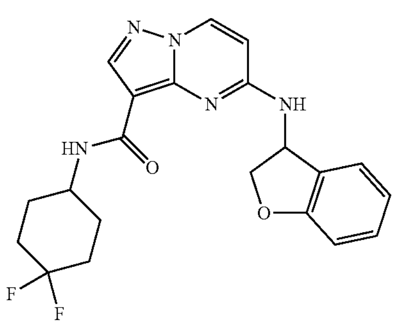 [SMILES: O=C(NC1CCC(F)(F)CC1)c1cnn2ccc(NC3COc4ccccc43)nc12] | 5-(2,3-Dihydro-benzofuran-3-ylamino)-pyrazolo[1,5-a]-pyrimidine-3-carboxylic acid (4,4-difluoro-cyclohexyl)-amide | 414.1 |
| 301 | 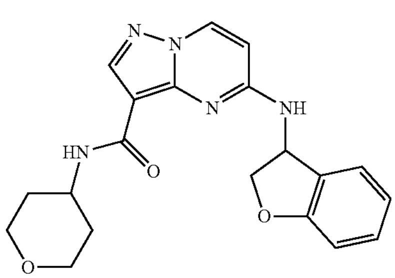 [SMILES: O=C(NC1CCOCC1)c1cnn2ccc(NC3COc4ccccc43)nc12] | 5-(2,3-Dihydro-benzofuran-3-ylamino)-pyrazolo[1,5-a]-pyrimidine-3-carboxylic acid (tetrahydro-pyran-4-yl)-amide | 380.1 |

TABLE 2-continued

| Ex # | Structure | Name | LCMS (ESI) m/z |
|---|---|---|---|
| 302 | 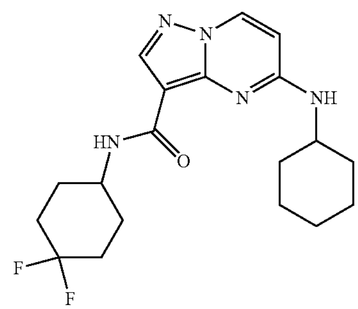 [SMILES: O=C(NC1CCC(F)(F)CC1)c1cnn2ccc(NC3CCCCC3)nc12] | 5-Cyclohexylamino-pyrazolo[1,5-a]pyrimidine-3-carboxylic acid (4,4-difluoro-cyclohexyl)-amide | 378.2 |
| 303 | 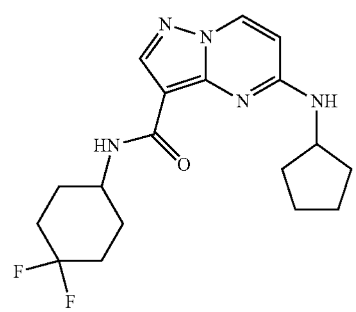 [SMILES: O=C(NC1CCC(F)(F)CC1)c1cnn2ccc(NC3CCCC3)nc12] | 5-Cyclopentylamino-pyrazolo[1,5-a]pyrimidine-3-carboxylic acid (4,4-difluoro-cyclohexyl)-amide | 364.1 |
| 304 | 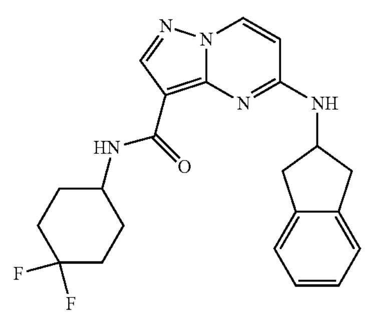 [SMILES: O=C(NC1CCC(F)(F)CC1)c1cnn2ccc(NC3Cc4ccccc4C3)nc12] | 5-(Indan-2-ylamino)-pyrazolo[1,5-a]pyrimidine-3-carboxylic acid (4,4-difluoro-cyclohexyl)-amide | 412.1 |
| 305 | 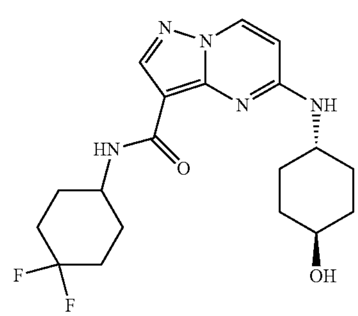 [SMILES: O=C(NC1CCC(F)(F)CC1)c1cnn2ccc(N[C@H]3CC[C@H](O)CC3)nc12] | 5-(4-Hydroxy-cyclohexyl-amino)-pyrazolo[1,5-a]-pyrimidine-3-carboxylic acid (4,4-difluoro-cyclohexyl)-amide | 394.2 |
| 306 | 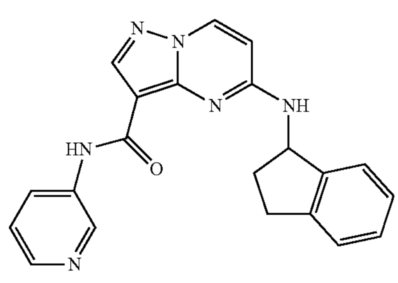 [SMILES: O=C(Nc1cccnc1)c1cnn2ccc(NC3CCc4ccccc43)nc12] | 5-(Indan-1-ylamino)-pyrazolo[1,5-a]pyrimidine-3-carboxylic acid pyridin-3-ylamide | 371.1 |

TABLE 2-continued

| Ex # | Structure | Name | LCMS (ESI) m/z |
| --- | --- | --- | --- |
| 307 | 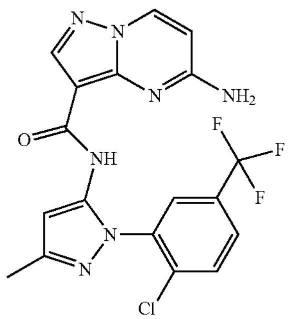 [SMILES: Cc1cc(NC(=O)c2cnn3ccc(N)nc23)n(-c2cc(C(F)(F)F)ccc2Cl)n1] | 5-Amino-pyrazolo[1,5-a]-pyrimidine-3-carboxylic acid [2-(2-chloro-5-trifluoromethyl-phenyl)-5-methyl-2H-pyrazol-3-yl]-amide | 436.0 |
| 308 | 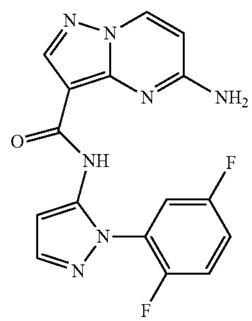 [SMILES: Nc1ccn2ncc(C(=O)Nc3ccnn3-c3cc(F)ccc3F)c2n1] | 5-Amino-pyrazolo[1,5-a]-pyrimidine-3-carboxylic acid [2-(2,5-difluoro-phenyl)-2H-pyrazol-3-yl]-amide | 356.0 |
| 309 | 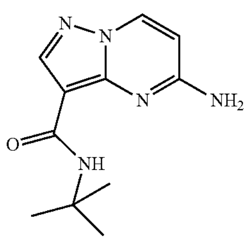 [SMILES: CC(C)(C)NC(=O)c1cnn2ccc(N)nc12] | 5-Amino-pyrazolo[1,5-a]-pyrimidine-3-carboxylic acid tert-butylamide | 234.3 |
| 310 | 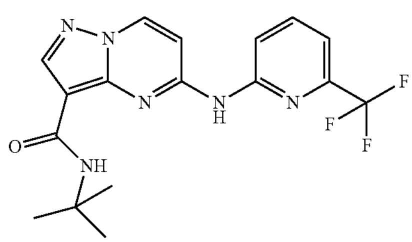 [SMILES: CC(C)(C)NC(=O)c1cnn2ccc(Nc3cccc(C(F)(F)F)n3)nc12] | 5-(6-Trifluoromethyl-pyridin-2-ylamino)-pyrazolo[1,5-a]pyrimidine-3-carboxylic acid tert-butylamide | 379.2 |
| 311 | 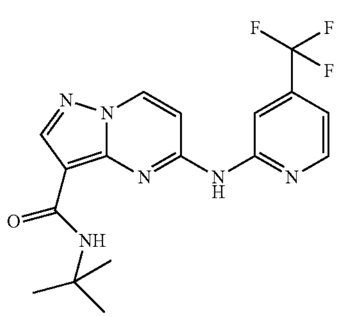 [SMILES: CC(C)(C)NC(=O)c1cnn2ccc(Nc3cc(C(F)(F)F)ccn3)nc12] | 5-(4-Trifluoromethyl-pyridin-2-ylamino)-pyrazolo[1,5-a]pyrimidine-3-carboxylic acid tert-butylamide | 379.2 |

| Ex # | Structure | Name | LCMS (ESI) m/z |
|---|---|---|---|
| 312 | 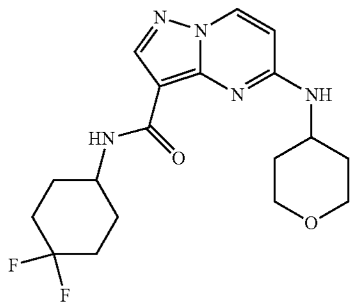 [SMILES: O=C(NC1CCC(F)(F)CC1)c1cnn2ccc(NC3CCOCC3)nc12] | 5-(Tetrahydro-pyran-4-ylamino)-pyrazolo[1,5-a]-pyrimidine-3-carboxylic acid (4,4-difluoro-cyclohexyl)-amide | 380.1 |
| 313 | 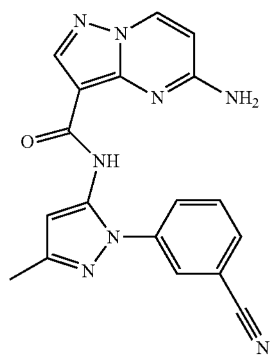 [SMILES: Cc1cc(NC(=O)c2cnn3ccc(N)nc23)n(-c2cccc(C#N)c2)n1] | 5-Amino-pyrazolo[1,5-a]-pyrimidine-3-carboxylic acid [2-(3-cyano-phenyl)-5-methyl-2H-pyrazol-3-yl]-amide | 359.1 |
| 314 | 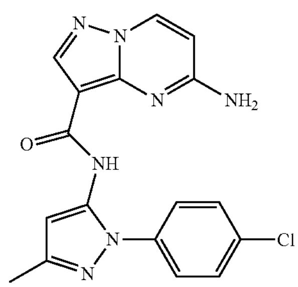 [SMILES: Cc1cc(NC(=O)c2cnn3ccc(N)nc23)n(-c2ccc(Cl)cc2)n1] | 5-Amino-pyrazolo[1,5-a]-pyrimidine-3-carboxylic acid [2-(4-chloro-phenyl)-5-methyl-2H-pyrazol-3-yl]-amide | 368.0 |
| 315 | 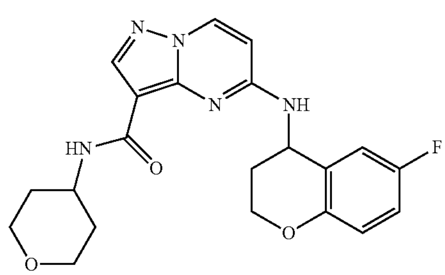 [SMILES: O=C(NC1CCOCC1)c1cnn2ccc(NC3CCOc4ccc(F)cc43)nc12] | 5-(6-Fluoro-chroman-4-ylamino)-pyrazolo[1,5-a]-pyrimidine-3-carboxylic acid (tetrahydro-pyran-4-yl)-amide | 412.1 |
| 316 | 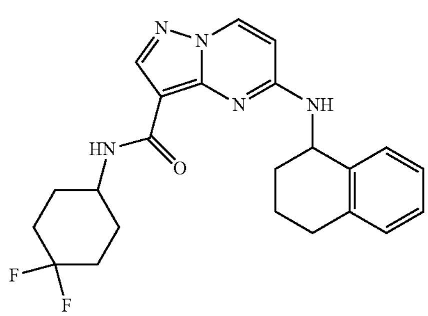 [SMILES: O=C(NC1CCC(F)(F)CC1)c1cnn2ccc(NC3CCCc4ccccc43)nc12] | 5-(1,2,3,4-Tetrahydro-naphthalen-1-ylamino)-pyrazolo[1,5-a]pyrimidine-3-carboxylic acid (4,4-difluoro-cyclohexyl)-amide | 426.2 |

TABLE 2-continued

| Ex # | Structure | Name | LCMS (ESI) m/z |
|---|---|---|---|
| 317 | 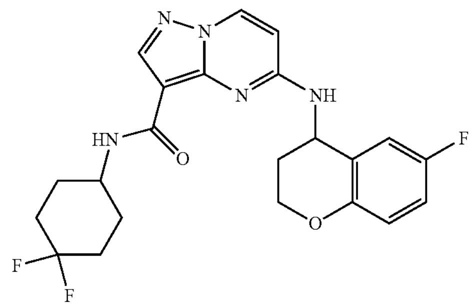 [SMILES: O=C(NC1CCC(F)(F)CC1)c1cnn2ccc(NC3CCOc4ccc(F)cc43)nc12] | 5-(6-Fluoro-chroman-4-ylamino)-pyrazolo[1,5-a]pyrimidine-3-carboxylic acid (4,4-difluoro-cyclohexyl)-amide | 446.1 |
| 318 | 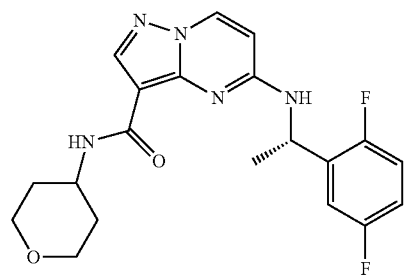 [SMILES: C[C@H](Nc1ccn2ncc(C(=O)NC3CCOCC3)c2n1)c1cc(F)ccc1F] | 5-[(S)-1-(2,5-Difluoro-phenyl)-ethylamino]-pyrazolo[1,5-a]pyrimidine-3-carboxylic acid (tetrahydro-pyran-4-yl)-amide | 402.1 |
| 319 | 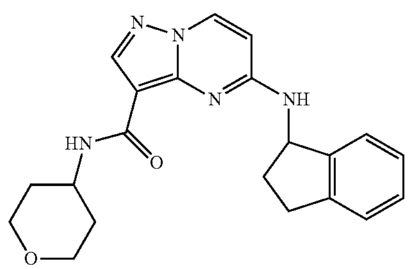 [SMILES: O=C(NC1CCOCC1)c1cnn2ccc(NC3CCc4ccccc43)nc12] | 5-(Indan-1-ylamino)-pyrazolo[1,5-a]pyrimidine-3-carboxylic acid (tetrahydro-pyran-4-yl)-amide | 378.1 |
| 320 | 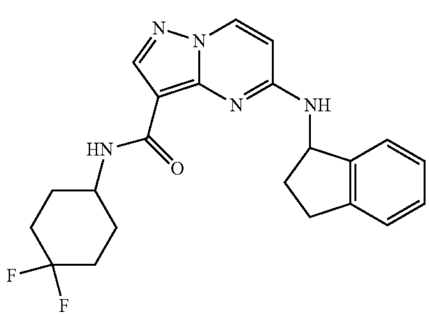 [SMILES: O=C(NC1CCC(F)(F)CC1)c1cnn2ccc(NC3CCc4ccccc43)nc12] | 5-(Indan-1-ylamino)-pyrazolo[1,5-a]pyrimidine-3-carboxylic acid (4,4-difluoro-cyclohexyl)-amide | 412.2 |
| 321 | 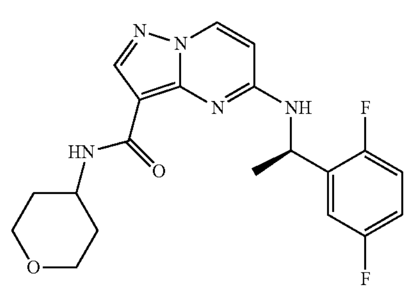 [SMILES: C[C@@H](Nc1ccn2ncc(C(=O)NC3CCOCC3)c2n1)c1cc(F)ccc1F] | 5-[(R)-1-(2,5-Difluoro-phenyl)-ethylamino]-pyrazolo[1,5-a]pyrimidine-3-carboxylic acid (tetrahydro-pyran-4-yl)-amide | 402.1 |

TABLE 2-continued

| Ex # | Structure | Name | LCMS (ESI) m/z |
|---|---|---|---|
| 322 | 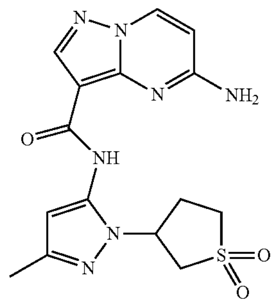 [SMILES: Cc1cc(NC(=O)c2cnn3ccc(N)nc23)n(C2CCS(=O)(=O)C2)n1] | 5-Amino-pyrazolo[1,5-a]-pyrimidine-3-carboxylic acid [2-(1,1-dioxo-tetrahydro-thiophen-3-yl)-5-methyl-2H-pyrazol-3-yl]-amide | 376.1 |
| 323 | 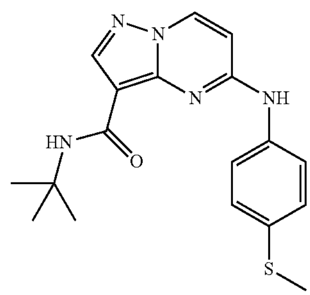 [SMILES: CSc1ccc(Nc2ccn3ncc(C(=O)NC(C)(C)C)c3n2)cc1] | 5-(4-Methylsulfanyl-phenylamino)-pyrazolo-[1,5-a]pyrimidine-3-carboxylic acid tert-butylamine | 356.1 |
| 324 | 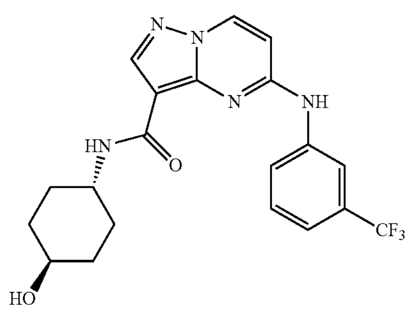 [SMILES: O=C(N[C@H]1CC[C@H](O)CC1)c1cnn2ccc(Nc3cccc(C(F)(F)F)c3)nc12] | 5-(3-Trifluoromethyl-phenylamino)-pyrazolo-[1,5-a]pyrimidine-3-carboxylic acid (4-hydroxy-cyclohexyl)-amide | 420.1 |
| 325 | 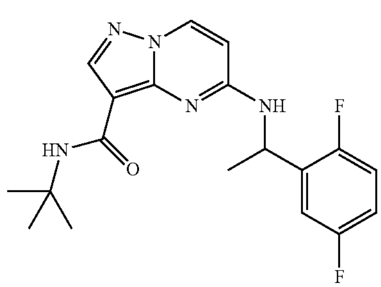 [SMILES: CC(Nc1ccn2ncc(C(=O)NC(C)(C)C)c2n1)c1cc(F)ccc1F] | 5-[1-(2,5-Difluoro-phenyl)-ethylamino]-pyrazolo[1,5-a]pyrimidine-3-carboxylic acid tert-butylamide | 374.1 |
| 326 | 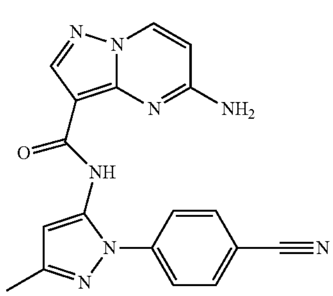 [SMILES: Cc1cc(NC(=O)c2cnn3ccc(N)nc23)n(-c2ccc(C#N)cc2)n1] | 5-Amino-pyrazolo[1,5-a]-pyrimidine-3-carboxylic acid [2-(4-cyano-phenyl)-5-methyl-2H-pyrazol-3-yl]-amide | 359.0 |

TABLE 2-continued

| Ex # | Structure | Name | LCMS (ESI) m/z |
|---|---|---|---|
| 327 | 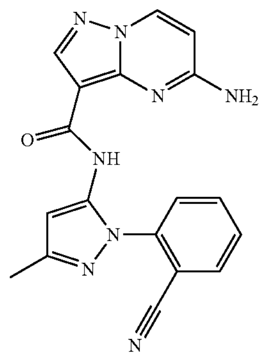 [SMILES: Cc1cc(NC(=O)c2cnn3ccc(N)nc23)n(-c2ccccc2C#N)n1] | 5-Amino-pyrazolo[1,5-a]-pyrimidine-3-carboxylic acid [2-(2-cyano-phenyl)-5-methyl-2H-pyrazol-3-yl]-amide | 359.0 |
| 328 | 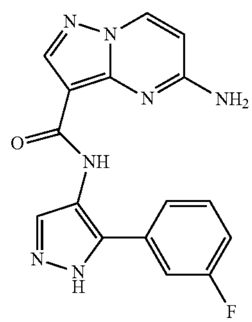 [SMILES: Nc1ccn2ncc(C(=O)Nc3cn[nH]c3-c3cccc(F)c3)c2n1] | 5-Amino-pyrazolo[1,5-a]-pyrimidine-3-carboxylic acid [5-(3-fluoro-phenyl)-1H-pyrazol-4-yl]-amide | 338.1 |
| 329 | 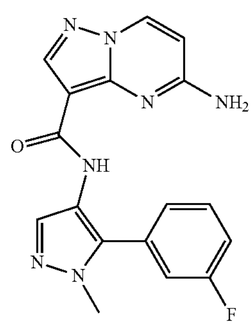 [SMILES: Cn1ncc(NC(=O)c2cnn3ccc(N)nc23)c1-c1cccc(F)c1] | 5-Amino-pyrazolo[1,5-a]-pyrimidine-3-carboxylic acid [5-(3-fluoro-phenyl)-1-methyl-1H-pyrazol-4-yl]-amide | 352.1 |
| 330 | 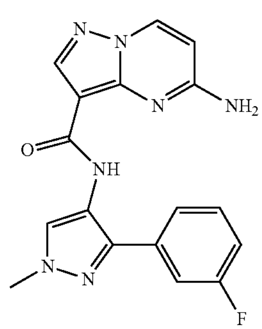 [SMILES: Cn1cc(NC(=O)c2cnn3ccc(N)nc23)c(-c2cccc(F)c2)n1] | 5-Amino-pyrazolo[1,5-a]-pyrimidine-3-carboxylic acid [3-(3-fluoro-phenyl)-1-methyl-1H-pyrazol-4-yl]-amide | 352.0 |

TABLE 2-continued

| Ex # | Structure | Name | LCMS (ESI) m/z |
|---|---|---|---|
| 331 | 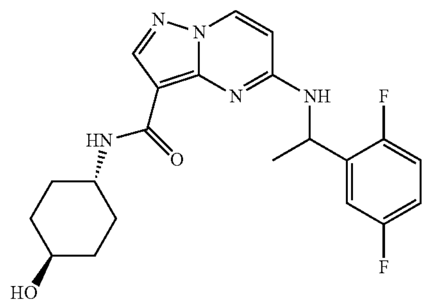 [SMILES: CC(Nc1ccn2ncc(C(=O)N[C@H]3CC[C@H](O)CC3)c2n1)c1cc(F)ccc1F] | 5-[1-(2,5-Difluoro-phenyl)-ethylamino]-pyrazolo[1,5-a]-pyrimidine-3-carboxylic acid (4-hydroxy-cyclohexyl)-amide | 416.2 |
| 332 | 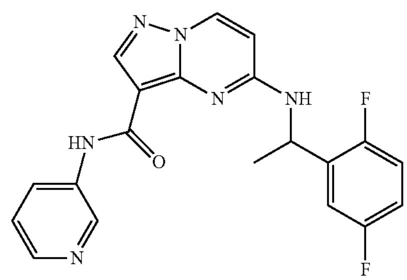 [SMILES: CC(Nc1ccn2ncc(C(=O)Nc3cccnc3)c2n1)c1cc(F)ccc1F] | 5-[1-(2,5-Difluoro-phenyl)-ethylamino]-pyrazolo[1,5-a]-pyrimidine-3-carboxylic acid pyridin-3-ylamide | 395.1 |
| 333 | 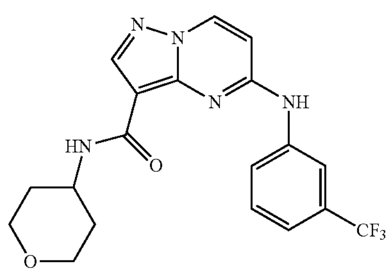 [SMILES: O=C(NC1CCOCC1)c1cnn2ccc(Nc3cccc(C(F)(F)F)c3)nc12] | 5-(3-Trifluoromethyl-phenylamino)-pyrazolo[1,5-a]-pyrimidine-3-carboxylic acid (tetrahydro-pyran-4-yl)-amide | 406.2 |
| 334 | 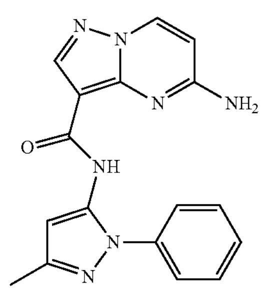 [SMILES: Cc1cc(NC(=O)c2cnn3ccc(N)nc23)n(-c2ccccc2)n1] | 5-Amino-pyrazolo[1,5-a]-pyrimidine-3-carboxylic acid (5-methyl-2-phenyl-2H-pyrazol-3-yl)-amide | 334.2 |
| 335 | 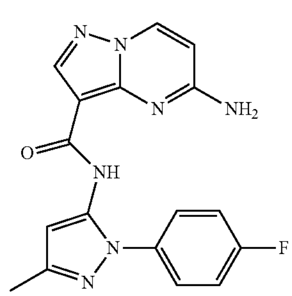 [SMILES: Cc1cc(NC(=O)c2cnn3ccc(N)nc23)n(-c2ccc(F)cc2)n1] | 5-Amino-pyrazolo[1,5-a]-pyrimidine-3-carboxylic acid [2-(4-fluoro-phenyl)-5-methyl-2H-pyrazol-3-yl]-amide | 352.2 |

TABLE 2-continued

| Ex # | Structure | Name | LCMS (ESI) m/z |
|---|---|---|---|
| 336 | 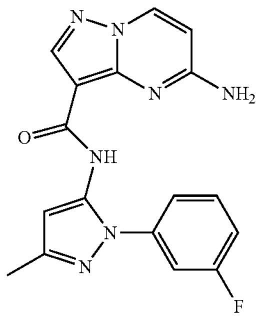 [SMILES: Cc1cc(NC(=O)c2cnn3ccc(N)nc23)n(-c2cccc(F)c2)n1] | 5-Amino-pyrazolo[1,5-a]-pyrimidine-3-carboxylic acid [2-(3-fluoro-phenyl)-5-methyl-2H-pyrazol-3-yl]-amide | 352.2 |
| 337 | 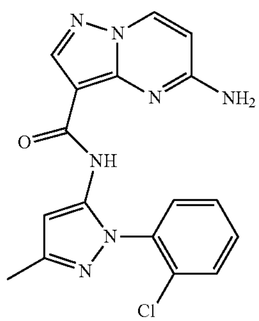 | 5-Amino-pyrazolo[1,5-a]-pyrimidine-3-carboxylic acid [2-(2-chloro-phenyl)-5-methyl-2H-pyrazol-3-yl]-amide | 368.2 |
| 338 | 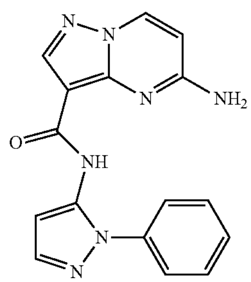 [SMILES: Nc1ccn2ncc(C(=O)Nc3ccnn3-c3ccccc3)c2n1] | 5-Amino-pyrazolo[1,5-a]-pyrimidine-3-carboxylic acid (2-phenyl-2H-pyrazol-3-yl)-amide | 320.1 |
| 339 | 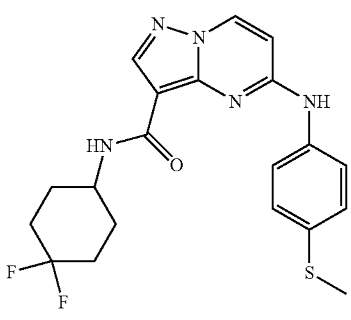 [SMILES: CSc1ccc(Nc2ccn3ncc(C(=O)NC4CCC(F)(F)CC4)c3n2)cc1] | 5-(4-Methylsulfanyl-phenylamino)-pyrazolo-[1,5-a]pyrimidine-3-carboxylic acid (4,4-difluoro-cyclohexyl)-amide | 418.1 |
| 340 | 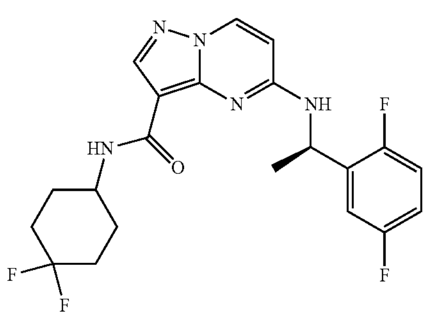 [SMILES: C[C@@H](Nc1ccn2ncc(C(=O)NC3CCC(F)(F)CC3)c2n1)c1cc(F)ccc1F] | 5-[(R)-1-(2,5-Difluoro-phenyl)-ethylamino]-pyrazolo[1,5-a]pyrimidine-3-carboxylic acid (4,4-difluoro-cyclohexyl)-amide | 436.1 |

TABLE 2-continued

| Ex # | Structure | Name | LCMS (ESI) m/z |
|---|---|---|---|
| 341 | 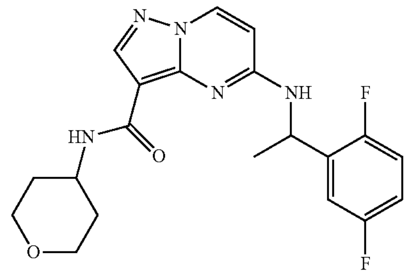 [SMILES: CC(Nc1ccn2ncc(C(=O)NC3CCOCC3)c2n1)c1cc(F)ccc1F] | 5-[1-(2,5-Difluoro-phenyl)-ethylamino]-pyrazolo-[1,5-a]pyrimidine-3-carboxylic acid (tetrahydro-pyran-4-yl)-amide | 402.1 |
| 342 | 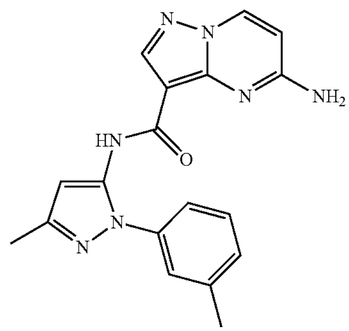 [SMILES: Cc1cccc(-n2nc(C)cc2NC(=O)c2cnn3ccc(N)nc23)c1] | 5-Amino-pyrazolo[1,5-a]-pyrimidine-3-carboxylic acid (5-methyl-2-m-tolyl-2H-pyrazol-3-yl)-amide | 348.1 |
| 343 | 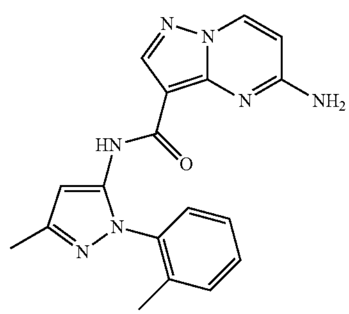 [SMILES: Cc1cc(NC(=O)c2cnn3ccc(N)nc23)n(-c2ccccc2C)n1] | 5-Amino-pyrazolo[1,5-a]-pyrimidine-3-carboxylic acid (5-methyl-2-o-tolyl-2H-pyrazol-3-yl)-amide | 348.1 |
| 344 | 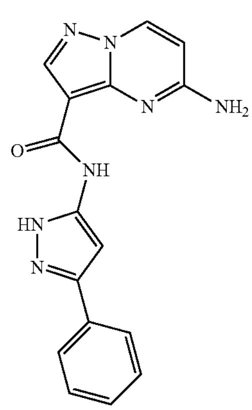 [SMILES: Nc1ccn2ncc(C(=O)Nc3cc(-c4ccccc4)n[nH]3)c2n1] | 5-Amino-pyrazolo[1,5-a]-pyrimidine-3-carboxylic acid (5-phenyl-2H-pyrazol-3-yl)-amide | 320.1 |

TABLE 2-continued

| Ex # | Structure | Name | LCMS (ESI) m/z |
|---|---|---|---|
| 345 | 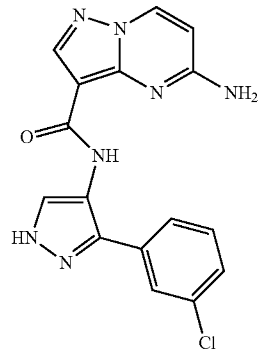 [SMILES: Nc1ccn2ncc(C(=O)Nc3c[nH]nc3-c3cccc(Cl)c3)c2n1] | 5-Amino-pyrazolo[1,5-a]-pyrimidine-3-carboxylic acid [3-(3-chloro-phenyl)-1H-pyrazol-4-yl]-amide | 354.0 |
| 346 | 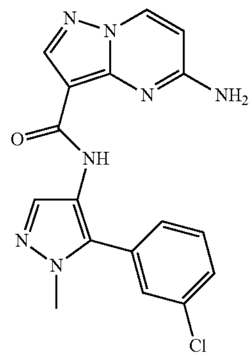 [SMILES: Cn1ncc(NC(=O)c2cnn3ccc(N)nc23)c1-c1cccc(Cl)c1] | 5-Amino-pyrazolo[1,5-a]-pyrimidine-3-carboxylic acid [5-(3-chloro-phenyl)-1-methyl-1H-pyrazol-4-yl]-amide | 348.1 |
| 347 | 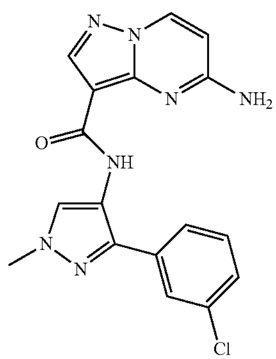 [SMILES: Cn1cc(NC(=O)c2cnn3ccc(N)nc23)c(-c2cccc(Cl)c2)n1] | 5-Amino-pyrazolo[1,5-a]-pyrimidine-3-carboxylic acid [3-(3-chloro-phenyl)-1-methyl-1H-pyrazol-4-yl]-amide | 368.1 |
| 348 | 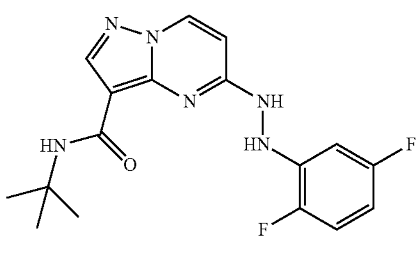 [SMILES: CC(C)(C)NC(=O)c1cnn2ccc(NNc3cc(F)ccc3F)nc12] | 5-[N'-(2,5-Difluoro-phenyl)-hydrazino]-pyrazolo[1,5-a]-pyrimidine-3-carboxylic acid tert-butylamide | 361.1 |
| 349 | 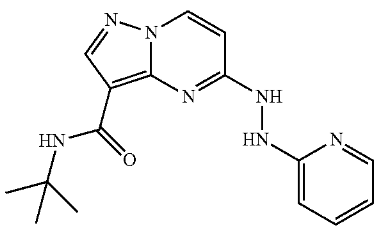 [SMILES: CC(C)(C)NC(=O)c1cnn2ccc(NNc3ccccn3)nc12] | 5-(N'-Pyridin-2-yl-hydrazino)-pyrazolo[1,5-a]-pyrimidine-3-carboxylic acid tert-butylamide | 326.1 |

TABLE 2-continued

| Ex # | Structure | Name | LCMS (ESI) m/z |
|---|---|---|---|
| 350 | 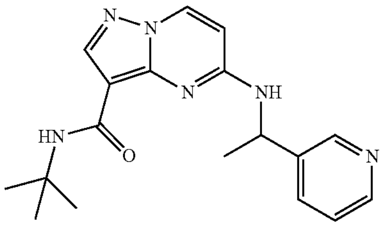 [SMILES: CC(Nc1ccn2ncc(C(=O)NC(C)(C)C)c2n1)c1cccnc1] | 5-(1-Pyridin-3-yl-ethylamino)-pyrazolo-[1,5-a]pyrimidine-3-carboxylic acid tert-butylamide | 339.2 |
| 351 | 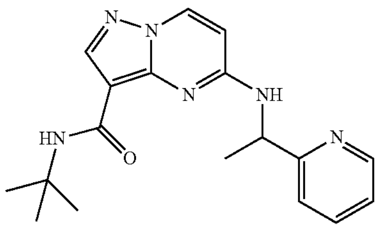 [SMILES: CC(Nc1ccn2ncc(C(=O)NC(C)(C)C)c2n1)c1ccccn1] | 5-(1-Pyridin-2-yl-ethylamino)-pyrazolo-[1,5-a]pyrimidine-3-carboxylic acid tert-butylamide | 339.1 |
| 352 | 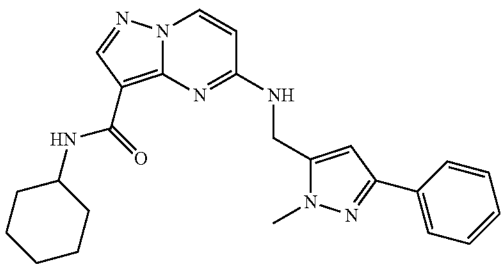 [SMILES: Cn1nc(-c2ccccc2)cc1CNc1ccn2ncc(C(=O)NC3CCCCC3)c2n1] | 5-[(2-Methyl-5-phenyl-2H-pyrazol-3-ylmethyl)-amino]-pyrazolo[1,5-a]-pyrimidine-3-carboxylic acid cyclohexylamide | 430.2 |
| 353 | 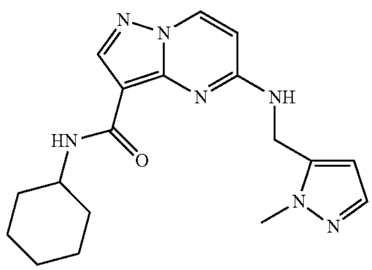 [SMILES: Cn1nccc1CNc1ccn2ncc(C(=O)NC3CCCCC3)c2n1] | 5-[(2-Methyl-2H-pyrazol-3-ylmethyl)-amino]-pyrazolo[1,5-a]pyrimidine-3-carboxylic acid cyclohexylamide | 354.2 |
| 354 | 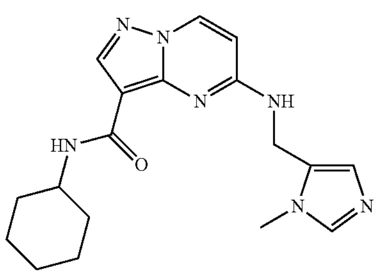 [SMILES: Cn1cncc1CNc1ccn2ncc(C(=O)NC3CCCCC3)c2n1] | 5-[(3-Methyl-3H-imidazol-4-ylmethyl)-amino]-pyrazolo[1,5-a]pyrimidine-3-carboxylic acid cyclohexylamide | 354.2 |
| 355 | 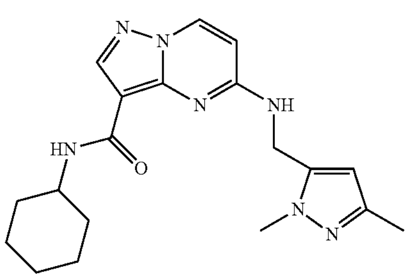 [SMILES: Cc1cc(CNc2ccn3ncc(C(=O)NC4CCCCC4)c3n2)n(C)n1] | 5-[(2,5-Dimethyl-2H-pyrazol-3-ylmethyl)-amino]-pyrazolo[1,5-a]-pyrimidine-3-carboxylic acid cyclohexylamide | 368.2 |

TABLE 2-continued

| Ex # | Structure | Name | LCMS (ESI) m/z |
|---|---|---|---|
| 356 | 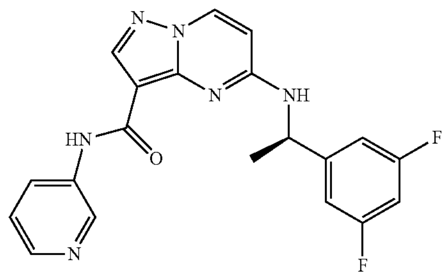 [SMILES: C[C@@H](Nc1ccn2ncc(C(=O)Nc3cccnc3)c2n1)c1cc(F)cc(F)c1] | 5-[(R)-1-(3,5-Difluoro-phenyl)-ethylamino]-pyrazolo[1,5-a]-pyrimidine-3-carboxylic acid pyridin-3-ylamide | 395.1 |
| 357 | 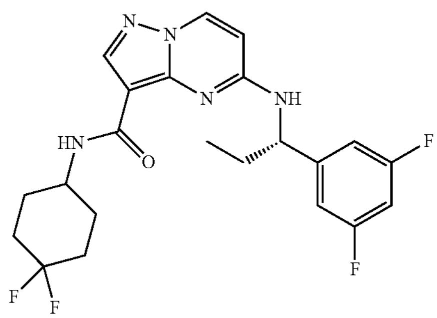 [SMILES: CC[C@H](Nc1ccn2ncc(C(=O)NC3CCC(F)(F)CC3)c2n1)c1cc(F)cc(F)c1] | 5-[(S)-1-(3,5-Difluoro-phenyl)-propylamino]-pyrazolo[1,5-a]pyrimidine-3-carboxylic acid (4,4-difluoro-cyclohexyl)-amide | 450.2 |
| 358 | 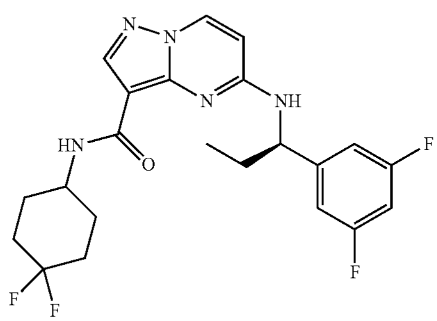 [SMILES: CC[C@@H](Nc1ccn2ncc(C(=O)NC3CCC(F)(F)CC3)c2n1)c1cc(F)cc(F)c1] | 5-[(R)-1-(3,5-Difluoro-phenyl)-propylamino]-pyrazolo[1,5-a]pyrimidine-3-carboxylic acid (4,4-difluoro-cyclohexyl)-amide | 450.2 |
| 359 | 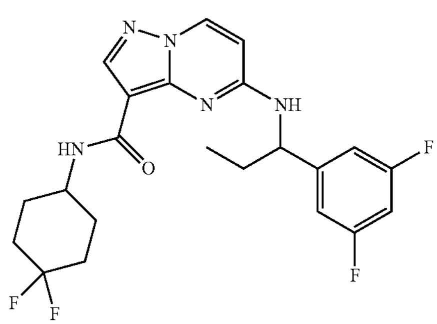 [SMILES: CCC(Nc1ccn2ncc(C(=O)NC3CCC(F)(F)CC3)c2n1)c1cc(F)cc(F)c1] | 5-[1-(3,5-Difluoro-phenyl)-propylamino]-pyrazolo-[1,5-a]pyrimidine-3-carboxylic acid (4,4-difluoro-cyclohexyl)-amide | 450.2 |
| 360 | 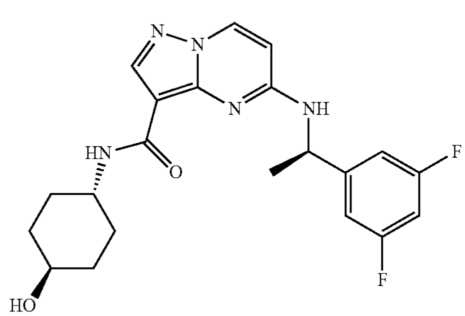 [SMILES: C[C@@H](Nc1ccn2ncc(C(=O)N[C@H]3CC[C@H](O)CC3)c2n1)c1cc(F)cc(F)c1] | 5-[(R)-1-(3,5-Difluoro-phenyl)-ethylamino]-pyrazolo[1,5-a]pyrimidine-3-carboxylic acid (4-hydroxy-cyclohexyl)-amide | 416.2 |

TABLE 2-continued

| Ex # | Structure | Name | LCMS (ESI) m/z |
|---|---|---|---|
| 361 | 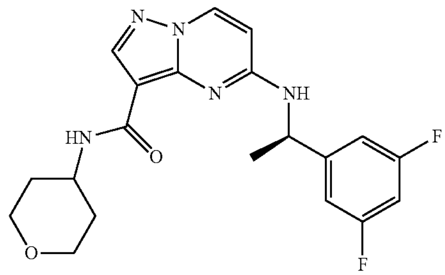 [SMILES: C[C@@H](Nc1ccn2ncc(C(=O)NC3CCOCC3)c2n1)c1cc(F)cc(F)c1] | 5-[(R)-1-(3,5-Difluoro-phenyl)-ethylamino]-pyrazolo[1,5-a]pyrimidine-3-carboxylic acid (tetrahydro-pyran-4-yl)-amide | 402.2 |
| 362 | 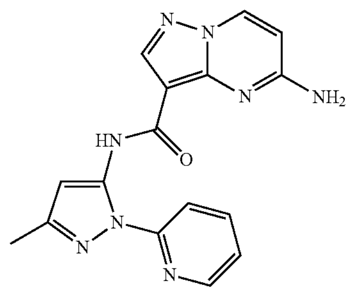 [SMILES: Cc1cc(NC(=O)c2cnn3ccc(N)nc23)n(-c2ccccn2)n1] | 5-Amino-pyrazolo[1,5-a]-pyrimidine-3-carboxylic acid (5-methyl-2-pyridin-2-yl-2H-pyrazol-3-yl)-amide | 335.1 |
| 363 | 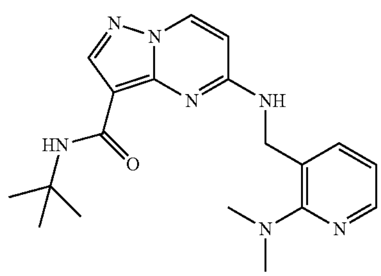 [SMILES: CN(C)c1ncccc1CNc1ccn2ncc(C(=O)NC(C)(C)C)c2n1] | 5-[(2-Dimethylamino-pyridin-3-ylmethyl)-amino]-pyrazolo[1,5-a]-pyrimidine-3-carboxylic acid tert-butylamide | 368.2 |
| 364 | 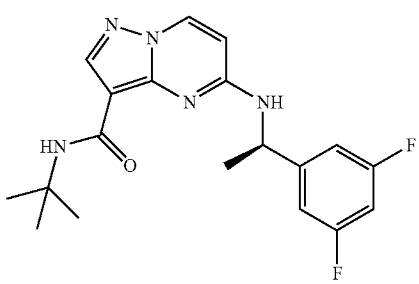 [SMILES: C[C@@H](Nc1ccn2ncc(C(=O)NC(C)(C)C)c2n1)c1cc(F)cc(F)c1] | 5-[(R)-1-(3,5-Difluoro-phenyl)-ethylamino]-pyrazolo[1,5-a]pyrimidine-3-carboxylic acid tert-butylamide | 374.2 |
| 365 | 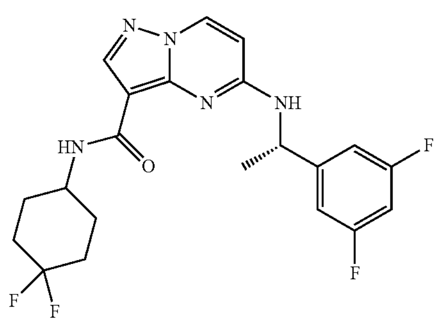 [SMILES: C[C@H](Nc1ccn2ncc(C(=O)NC3CCC(F)(F)CC3)c2n1)c1cc(F)cc(F)c1] | 5-[(S)-1-(3,5-Difluoro-phenyl)-ethylamino]-pyrazolo[1,5-a]pyrimidine-3-carboxylic acid (4,4-difluoro-cyclohexyl)-amide | 436.1 |

TABLE 2-continued

| Ex # | Structure | Name | LCMS (ESI) m/z |
|---|---|---|---|
| 366 | 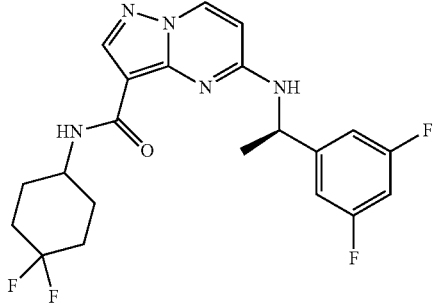 [SMILES: C[C@@H](Nc1ccn2ncc(C(=O)NC3CCC(F)(F)CC3)c2n1)c1cc(F)cc(F)c1] | 5-[(R)-1-(3,5-Difluoro-phenyl)-ethylamino]-pyrazolo[1,5-a]pyrimidine-3-carboxylic acid (4,4-difluoro-cyclohexyl)-amide | 436.1 |
| 367 | 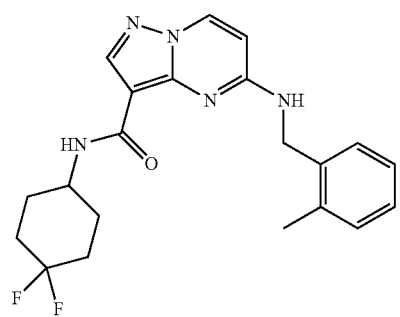 [SMILES: Cc1ccccc1CNc1ccn2ncc(C(=O)NC3CCC(F)(F)CC3)c2n1] | 5-(2-Methyl-benzylamino)-pyrazolo[1,5-a]pyrimidine-3-carboxylic acid (4,4-difluoro-cyclohexyl)-amide | 400.1 |
| 368 | 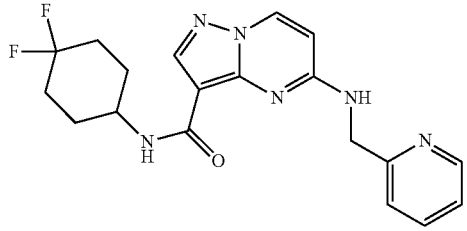 [SMILES: O=C(NC1CCC(F)(F)CC1)c1cnn2ccc(NCc3ccccn3)nc12] | 5-[(Pyridin-2-ylmethyl)-amino]-pyrazolo[1,5-a]-pyrimidine-3-carboxylic acid (4,4-difluoro-cyclohexyl)-amide | 386.9 |
| 369 | 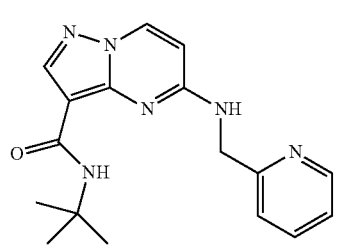 [SMILES: CC(C)(C)NC(=O)c1cnn2ccc(NCc3ccccn3)nc12] | 5-[(Pyridin-2-ylmethyl)-amino]-pyrazolo[1,5-a]-pyrimidine-3-carboxylic acid tert-butylamide | 224.9 |
| 370 | 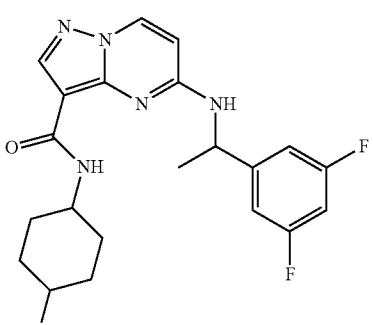 | 5-[1-(3,5-Difluoro-phenyl)-ethylamino]-pyrazolo[1,5-a]pyrimidine-3-carboxylic acid (4-hydroxy-cyclohexyl)-amide | 416.2 |

TABLE 2-continued

| Ex # | Structure | Name | LCMS (ESI) m/z |
|---|---|---|---|
| 371 | 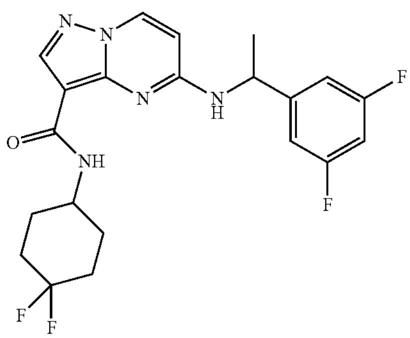 [SMILES: CC(Nc1ccn2ncc(C(=O)NC3CCC(F)(F)CC3)c2n1)c1cc(F)cc(F)c1] | 5-[1-(3,5-Difluoro-phenyl)-ethylamino]-pyrazolo[1,5-a]pyrimidine-3-carboxylic acid (4,4-difluoro-cyclohexyl)-amide | 436.0 |
| 372 | 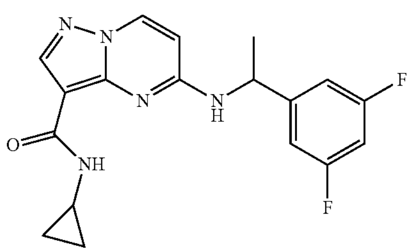 [SMILES: CC(Nc1ccn2ncc(C(=O)NC3CC3)c2n1)c1cc(F)cc(F)c1] | 5-[1-(3,5-Difluoro-phenyl)-ethylamino]-pyrazolo[1,5-a]pyrimidine-3-carboxylic acid cyclopropylamide | 358.0 |
| 373 | 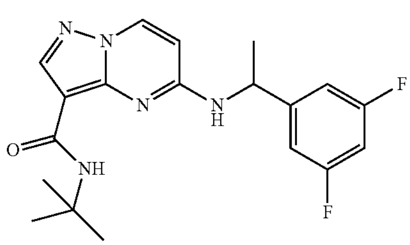 [SMILES: CC(Nc1ccn2ncc(C(=O)NC(C)(C)C)c2n1)c1cc(F)cc(F)c1] | 5-[1-(3,5-Difluoro-phenyl)-ethylamino]-pyrazolo[1,5-a]pyrimidine-3-carboxylic acid tert-butylamide | 373.9 |
| 374 | 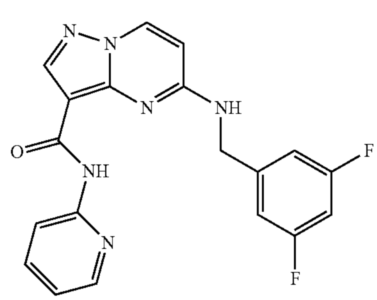 [SMILES: O=C(Nc1ccccn1)c1cnn2ccc(NCc3cc(F)cc(F)c3)nc12] | 5-(3,5-Difluoro-benzylamino)-pyrazolo[1,5-a]-pyrimidine-3-carboxylic acid pyridin-2-ylamide | 381.1 |
| 375 | 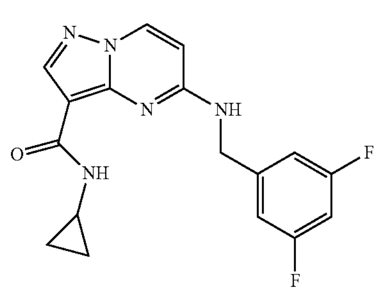 [SMILES: O=C(NC1CC1)c1cnn2ccc(NCc3cc(F)cc(F)c3)nc12] | 5-(3,5-Difluoro-benzylamino)-pyrazolo-[1,5-a]pyrimidine-3-carboxylic acid cyclo-propylamide | 343.9 |

TABLE 2-continued

| Ex # | Structure | Name | LCMS (ESI) m/z |
|---|---|---|---|
| 376 | 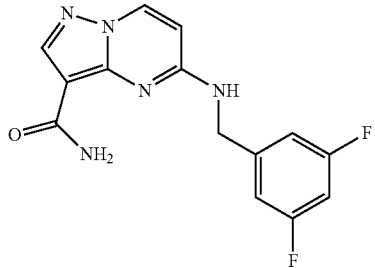 [SMILES: NC(=O)c1cnn2ccc(NCc3cc(F)cc(F)c3)nc12] | 5-(3,5-Difluoro-benzylamino)-pyrazolo-[1,5-a]pyrimidine-3-carboxylic acid amide | 303.9 |
| 377 | 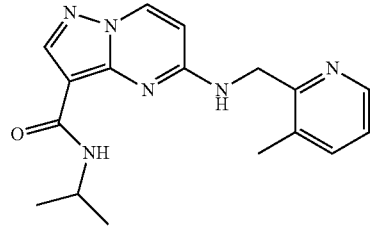 [SMILES: Cc1cccnc1CNc1ccn2ncc(C(=O)NC(C)C)c2n1] | 5-[(3-Methyl-pyridin-2-ylmethyl)-amino]-pyrazolo-[1,5-a]pyrimidine-3-carboxylic acid isopropylamide | 325.1 |
| 378 | 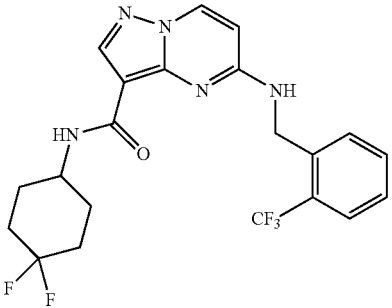 [SMILES: O=C(NC1CCC(F)(F)CC1)c1cnn2ccc(NCc3ccccc3C(F)(F)F)nc12] | 5-(2-Trifluoromethyl-benzylamino)-pyrazolo-[1,5-a]pyrimidine-3-carboxylic acid (4,4-difluoro-cyclohexyl)-amide | 454.1 |
| 379 | 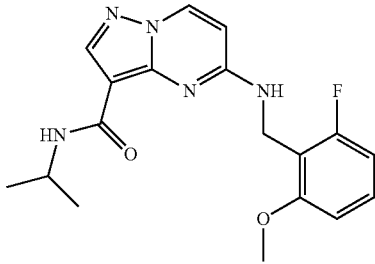 [SMILES: COc1cccc(F)c1CNc1ccn2ncc(C(=O)NC(C)C)c2n1] | 5-(2-Fluoro-6-methoxy-benzylamino)-pyrazolo[1,5-a]pyrimidine-3-carboxylic acid isopropylamide | 358.1 |
| 380 | 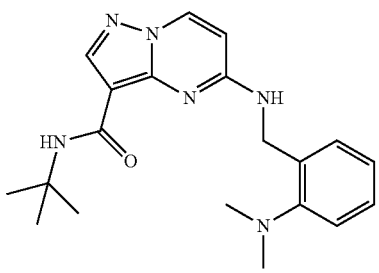 | 5-(2-Dimethylamino-benzylamino)-pyrazolo-[1,5-a]pyrimidine-3-carboxylic acid tert-butylamide | 367.2 |

TABLE 2-continued

| Ex # | Structure | Name | LCMS (ESI) m/z |
|---|---|---|---|
| 381 | 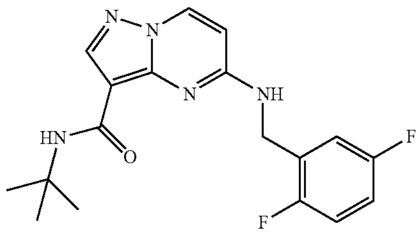 [SMILES: CC(C)(C)NC(=O)c1cnn2ccc(NCc3cc(F)ccc3F)nc12] | 5-(2,5-Difluoro-benzylamino)-pyrazolo-[1,5-a]pyrimidine-3-carboxylic acid tert-butylamide | 360.1 |
| 382 | 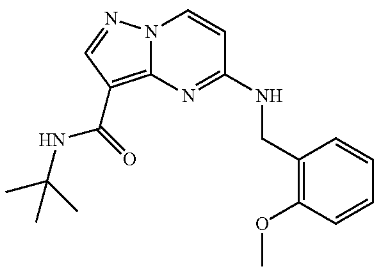 [SMILES: COc1ccccc1CNc1ccn2ncc(C(=O)NC(C)(C)C)c2n1] | 5-(2-Methoxy-benzylamino)-pyrazolo-[1,5-a]pyrimidine-3-carboxylic acid tert-butylamide | 354.2 |
| 383 | 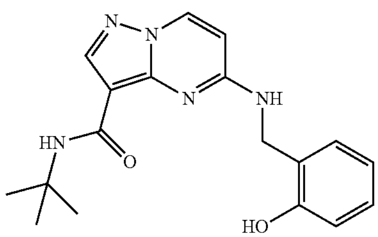 [SMILES: CC(C)(C)NC(=O)c1cnn2ccc(NCc3ccccc3O)nc12] | 5-(2-Hydroxy-benzylamino)-pyrazolo-[1,5-a]pyrimidine-3-carboxylic acid tert-butylamide | 340.1 |
| 384 | 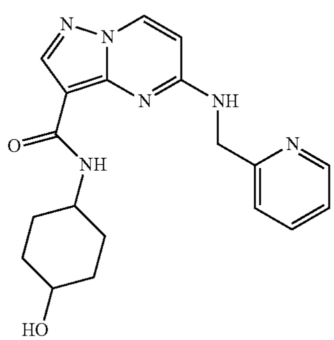 [SMILES: O=C(NC1CCC(O)CC1)c1cnn2ccc(NCc3ccccn3)nc12] | 5-[(Pyridin-2-ylmethyl)-amino]-pyrazolo[1,5-a]-pyrimidine-3-carboxylic acid (4-hydroxy-cyclohexyl)-amide | 367.1 |
| 385 | 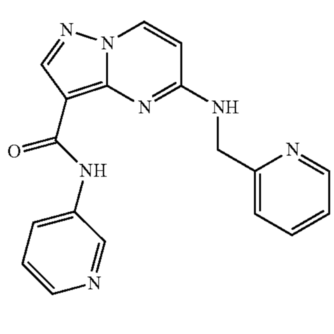 [SMILES: O=C(Nc1cccnc1)c1cnn2ccc(NCc3ccccn3)nc12] | 5-[(Pyridin-2-ylmethyl)-amino]-pyrazolo[1,5-a]-pyrimidine-3-carboxylic acid pyridin-3-ylamide | 346.0 |

TABLE 2-continued

| Ex # | Structure | Name | LCMS (ESI) m/z |
|---|---|---|---|
| 386 | 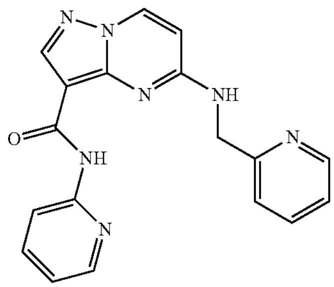 [SMILES: O=C(Nc1ccccn1)c1cnn2ccc(NCc3ccccn3)nc12] | 5-[(Pyridin-2-ylmethyl)-amino]-pyrazolo[1,5-a]-pyrimidine-3-carboxylic acid pyridin-2-ylamide | 346.0 |
| 387 | 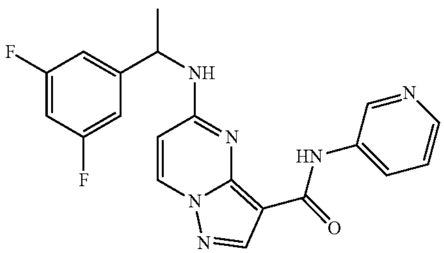 [SMILES: CC(Nc1ccn2ncc(C(=O)Nc3cccnc3)c2n1)c1cc(F)cc(F)c1] | 5-[1-(3,5-Difluoro-phenyl)-ethylamino]-pyrazolo-[1,5-a]pyrimidine-3-carboxylic acid pyridin-3-ylamide | 395.0 |
| 388 | 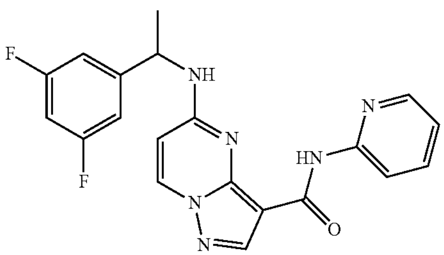 [SMILES: CC(Nc1ccn2ncc(C(=O)Nc3ccccn3)c2n1)c1cc(F)cc(F)c1] | 5-[1-(3,5-Difluoro-phenyl)-ethylamino]-pyrazolo-[1,5-a]pyrimidine-3-carboxylic acid pyridin-2-ylamide | 395.1 |
| 389 | 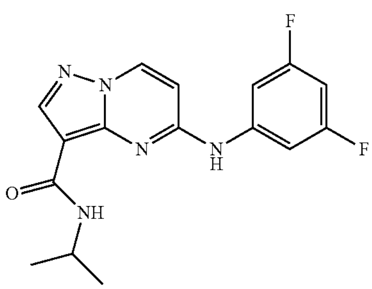 [SMILES: CC(C)NC(=O)c1cnn2ccc(Nc3cc(F)cc(F)c3)nc12] | 5-(3,5-Difluoro-phenylamino)-pyrazolo-[1,5-a]pyrimidine-3-carboxylic acid isopropylamide | 332.0 |
| 390 | 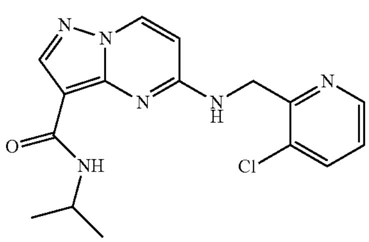 [SMILES: CC(C)NC(=O)c1cnn2ccc(NCc3ncccc3Cl)nc12] | 5-[(3-Chloro-pyridin-2-ylmethyl)-amino]-pyrazolo-[1,5-a]pyrimidine-3-carboxylic acid isopropylamide | 344.9 |
| 391 | 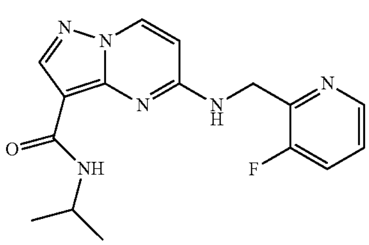 [SMILES: CC(C)NC(=O)c1cnn2ccc(NCc3ncccc3F)nc12] | 5-[(3-Fluoro-pyridin-2-ylmethyl)-amino]-pyrazolo-[1,5-a]pyrimidine-3-carboxylic acid isopropylamide | 329.4 |

TABLE 2-continued

| Ex # | Structure | Name | LCMS (ESI) m/z |
|---|---|---|---|
| 392 | 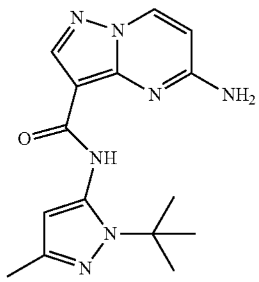 [SMILES: Cc1cc(NC(=O)c2cnn3ccc(N)nc23)n(C(C)(C)C)n1] | 5-Amino-pyrazolo[1,5-a]-pyrimidine-3-carboxylic acid (2-tert-butyl-5-methyl-2H-pyrazol-3-yl)-amide | 314.1 |
| 393 | 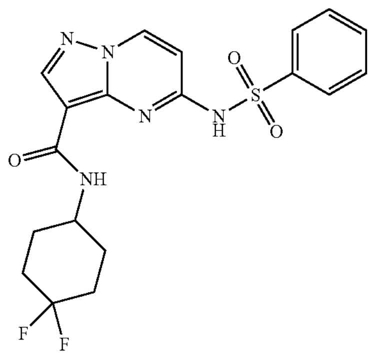 [SMILES: O=C(NC1CCC(F)(F)CC1)c1cnn2ccc(NS(=O)(=O)c3ccccc3)nc12] | 5-Benzenesulfonylamino-pyrazolo[1,5-a]pyrimidine-3-carboxylic acid (4,4-difluoro-cyclohexyl)-amide | 436.2 |
| 394 | 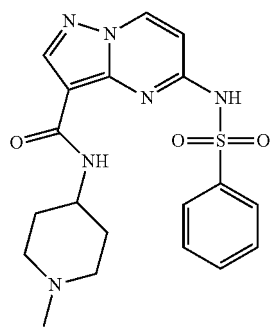 [SMILES: CN1CCC(NC(=O)c2cnn3ccc(NS(=O)(=O)c4ccccc4)nc23)CC1] | 5-Benzenesulfonylamino-pyrazolo[1,5-a]pyrimidine-3-carboxylic acid (1-methyl-piperidin-4-yl)-amide | 415.1 |
| 395 | 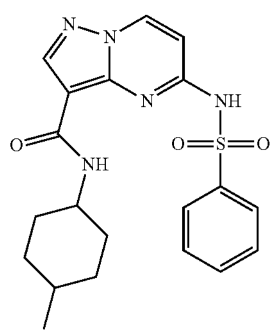 [SMILES: CC1CCC(NC(=O)c2cnn3ccc(NS(=O)(=O)c4ccccc4)nc23)CC1] | 5-Benzenesulfonylamino-pyrazolo[1,5-a]pyrimidine-3-carboxylic acid (4-methyl-cyclohexyl)-amide | 414.1 |
| 396 | 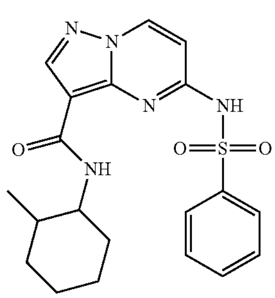 [SMILES: CC1CCCCC1NC(=O)c1cnn2ccc(NS(=O)(=O)c3ccccc3)nc12] | 5-Benzenesulfonylamino-pyrazolo[1,5-a]pyrimidine-3-carboxylic acid (2-methyl-cyclohexyl)-amide | 414.2 |

TABLE 2-continued

| Ex # | Structure | Name | LCMS (ESI) m/z |
|---|---|---|---|
| 397 | 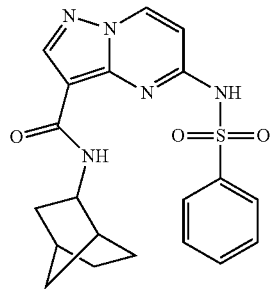 [SMILES: O=C(NC1CC2CCC1C2)c1cnn2ccc(NS(=O)(=O)c3ccccc3)nc12] | 5-Benzenesulfonylamino-pyrazolo[1,5-a]pyrimidine-3-carboxylic acid bicyclo-[2.2.1]hept-2-ylamide | 412.2 |
| 398 | 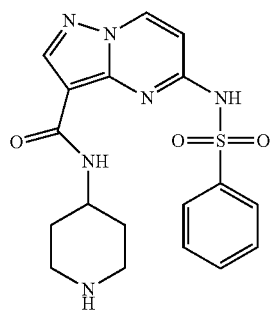 [SMILES: O=C(NC1CCNCC1)c1cnn2ccc(NS(=O)(=O)c3ccccc3)nc12] | 5-Benzenesulfonylamino-pyrazolo[1,5-a]pyrimidine-3-carboxylic acid piperidin-4-ylamide | 401.0 |
| 399 | 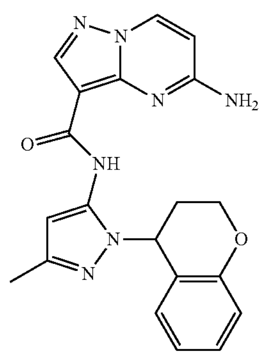 [SMILES: Cc1cc(NC(=O)c2cnn3ccc(N)nc23)n(C2CCOc3ccccc32)n1] | 5-Amino-pyrazolo[1,5-a]-pyrimidine-3-carboxylic acid (2-chroman-4-yl-5-methyl-2H-pyrazol-3-yl)-amide | 389.8 |
| 400 | 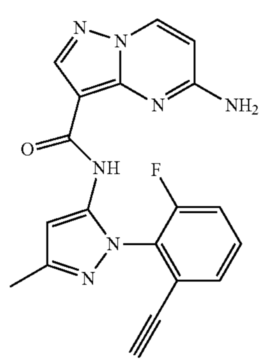 [SMILES: C#Cc1cccc(F)c1-n1nc(C)cc1NC(=O)c1cnn2ccc(N)nc12] | 5-Amino-pyrazolo[1,5-a]-pyrimidine-3-carboxylic acid [2-(2-ethynyl-6-fluoro-phenyl)-5-methyl-2H-pyrazol-3-yl]-amide | 376.1 |
| 401 | 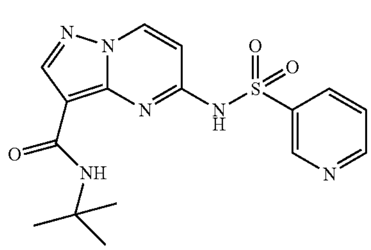 [SMILES: CC(C)(C)NC(=O)c1cnn2ccc(NS(=O)(=O)c3cccnc3)nc12] | 5-(Pyridine-3-sulfonylamino)-pyrazolo-[1,5-a]pyrimidine-3-carboxylic acid tert-butylamide | 375.1 |

TABLE 2-continued

| Ex # | Structure | Name | LCMS (ESI) m/z |
|---|---|---|---|
| 402 | 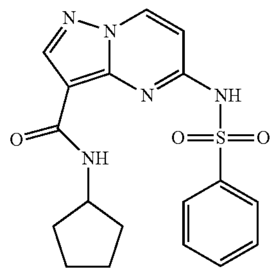 [SMILES: O=C(NC1CCCC1)c1cnn2ccc(NS(=O)(=O)c3ccccc3)nc12] | 5-Benzenesulfonylamino-pyrazolo[1,5-a]pyrimidine-3-carboxylic acid cyclopentylamide | 385.8 |
| 403 | 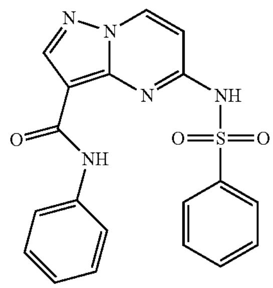 [SMILES: O=C(Nc1ccccc1)c1cnn2ccc(NS(=O)(=O)c3ccccc3)nc12] | 5-Benzenesulfonylamino-pyrazolo[1,5-a]pyrimidine-3-carboxylic acid phenylamide | 393.7 |
| 404 | 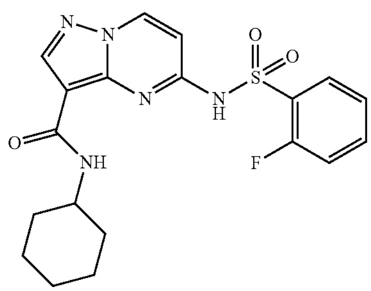 [SMILES: O=C(NC1CCCCC1)c1cnn2ccc(NS(=O)(=O)c3ccccc3F)nc12] | 5-(2-Fluoro-benzene-sulfonylamino)-pyrazolo-[1,5-a]pyrimidine-3-carboxylic acid cyclohexylamide | 418.1 |
| 405 | 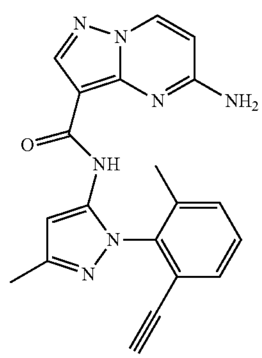 [SMILES: C#Cc1cccc(C)c1-n1nc(C)cc1NC(=O)c1cnn2ccc(N)nc12] | 5-Amino-pyrazolo[1,5-a]-pyrimidine-3-carboxylic acid [2-(2-ethynyl-6-methyl-phenyl)-5-methyl-2H-pyrazol-3-yl]-amide | 372.0 |
| 406 | 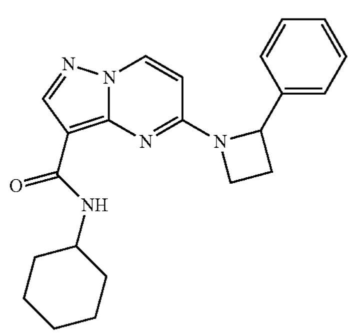 [SMILES: O=C(NC1CCCCC1)c1cnn2ccc(N3CCC3c3ccccc3)nc12] | 5-(2-Phenyl-azetidin-1-yl)-pyrazolo[1,5-a]-pyrimidine-3-carboxylic acid cyclohexylamide | 376.2 |

TABLE 2-continued

| Ex # | Structure | Name | LCMS (ESI) m/z |
|---|---|---|---|
| 407 | 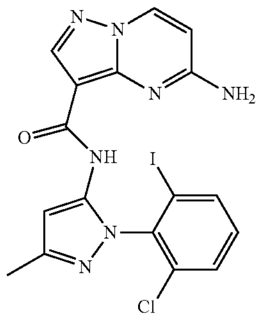 [SMILES: Cc1cc(NC(=O)c2cnn3ccc(N)nc23)n(-c2c(Cl)cccc2I)n1] | 5-Amino-pyrazolo[1,5-a]-pyrimidine-3-carboxylic acid [2-(2-chloro-6-iodo-phenyl)-5-methyl-2H-pyrazol-3-yl]-amide | 493.7 |
| 408 | 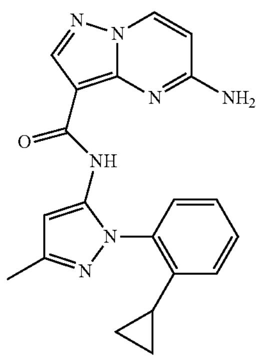 [SMILES: Cc1cc(NC(=O)c2cnn3ccc(N)nc23)n(-c2ccccc2C2CC2)n1] | 5-Amino-pyrazolo[1,5-a]-pyrimidine-3-carboxylic acid [2-(2-cyclopropyl-phenyl)-5-methyl-2H-pyrazol-3-yl]-amide | 373.8 |
| 409 | 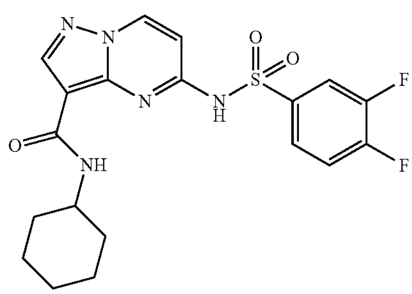 [SMILES: O=C(NC1CCCCC1)c1cnn2ccc(NS(=O)(=O)c3ccc(F)c(F)c3)nc12] | 5-(3,4-Difluoro-benzene-sulfonylamino)-pyrazolo-[1,5-a]pyrimidine-3-carboxylic acid cyclohexylamide | 436.1 |
| 410 | 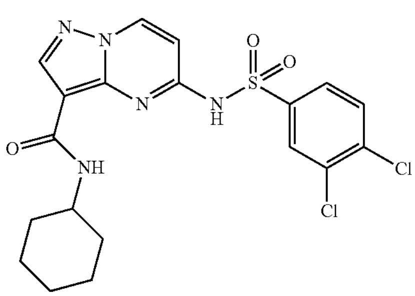 [SMILES: O=C(NC1CCCCC1)c1cnn2ccc(NS(=O)(=O)c3ccc(Cl)c(Cl)c3)nc12] | 5-(3,4-Dichloro-benzene-sulfonylamino)-pyrazolo-[1,5-a]pyrimidine-3-carboxylic acid cyclohexylamide | 468.0 |
| 411 | 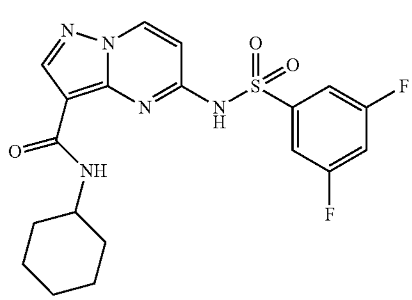 [SMILES: O=C(NC1CCCCC1)c1cnn2ccc(NS(=O)(=O)c3cc(F)cc(F)c3)nc12] | 5-(3,5-Difluoro-benzene-sulfonylamino)-pyrazolo-[1,5-a]pyrimidine-3-carboxylic acid cyclohexylamide | 436.1 |

TABLE 2-continued

| Ex # | Structure | Name | LCMS (ESI) m/z |
|---|---|---|---|
| 412 | 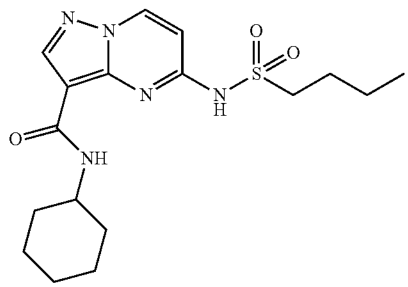 [SMILES: CCCCS(=O)(=O)Nc1ccn2ncc(C(=O)NC3CCCCC3)c2n1] | 5-(Butane-1-sulfonylamino)-pyrazolo[1,5-a]pyrimidine-3-carboxylic acid cyclohexylamide | 380.1 |
| 413 | 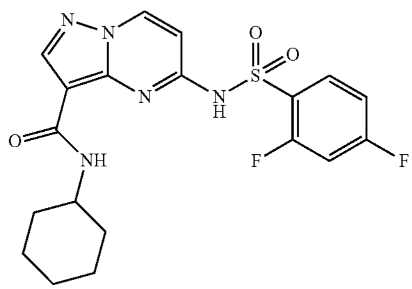 [SMILES: O=C(NC1CCCCC1)c1cnn2ccc(NS(=O)(=O)c3ccc(F)cc3F)nc12] | 5-(2,4-Difluoro-benzene-sulfonylamino)-pyrazolo-[1,5-a]pyrimidine-3-carboxylic acid cyclohexylamide | 436.1 |
| 414 | 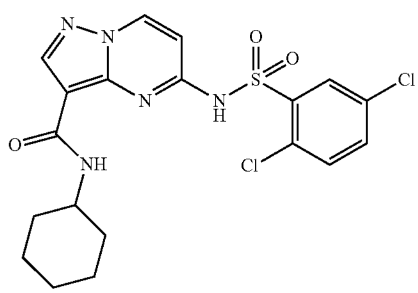 [SMILES: O=C(NC1CCCCC1)c1cnn2ccc(NS(=O)(=O)c3cc(Cl)ccc3Cl)nc12] | 5-(2,5-Dichloro-benzenesulfonylamino)-pyrazolo[1,5-a]pyrimidine-3-carboxylic acid cyclohexylamide | 468.0 |
| 415 | 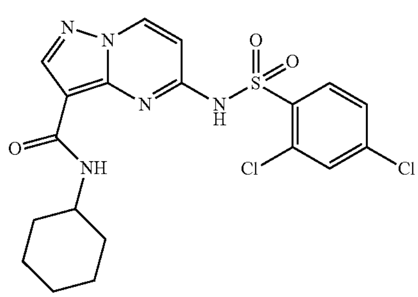 [SMILES: O=C(NC1CCCCC1)c1cnn2ccc(NS(=O)(=O)c3ccc(Cl)cc3Cl)nc12] | 5-(2,4-Dichloro-benzenesulfonylamino)-pyrazolo[1,5-a]pyrimidine-3-carboxylic acid cyclohexylamide | 468.0 |
| 416 | 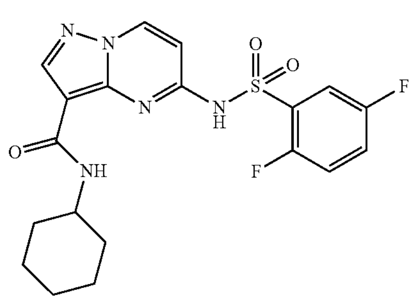 [SMILES: O=C(NC1CCCCC1)c1cnn2ccc(NS(=O)(=O)c3cc(F)ccc3F)nc12] | 5-(2,5-Difluoro-benzene-sulfonylamino)-pyrazolo-[1,5-a]pyrimidine-3-carboxylic acid cyclohexylamide | 436.1 |

TABLE 2-continued

| Ex # | Structure | Name | LCMS (ESI) m/z |
|---|---|---|---|
| 417 | 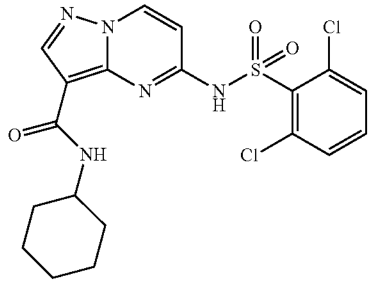 [SMILES: O=C(NC1CCCCC1)c1cnn2ccc(NS(=O)(=O)c3c(Cl)cccc3Cl)nc12] | 5-(2,6-Dichloro-benzene-sulfonylamino)-pyrazolo-[1,5-a]pyrimidine-3-carboxylic acid cyclohexylamide | 468.0 |
| 418 | 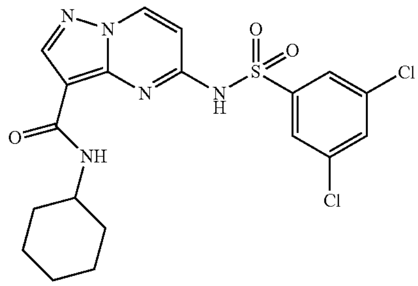 [SMILES: O=C(NC1CCCCC1)c1cnn2ccc(NS(=O)(=O)c3cc(Cl)cc(Cl)c3)nc12] | 5-(3,5-Dichloro-benzene-sulfonylamino)-pyrazolo-[1,5-a]pyrimidine-3-carboxylic acid cyclohexylamide | 468.0 |
| 419 | 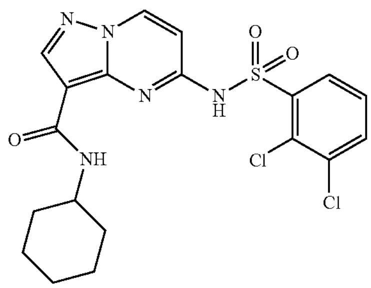 [SMILES: O=C(NC1CCCCC1)c1cnn2ccc(NS(=O)(=O)c3cccc(Cl)c3Cl)nc12] | 5-(2,3-Dichloro-benzene-sulfonylamino)-pyrazolo-[1,5-a]pyrimidine-3-carboxylic acid cyclohexylamide | 468.0 |
| 420 | 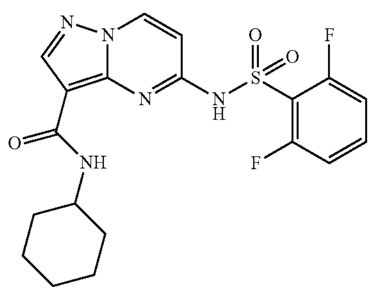 [SMILES: O=C(NC1CCCCC1)c1cnn2ccc(NS(=O)(=O)c3c(F)cccc3F)nc12] | 5-(2,6-Difluoro-benzene-sulfonylamino)-pyrazolo-[1,5-a]pyrimidine-3-carboxylic acid cyclohexylamide | 436.1 |
| 421 | 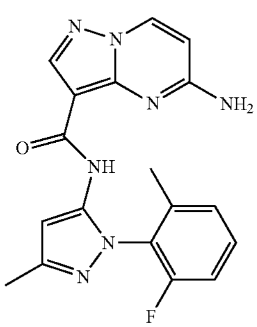 [SMILES: Cc1cc(NC(=O)c2cnn3ccc(N)nc23)n(-c2c(C)cccc2F)n1] | 5-Amino-pyrazolo[1,5-a]-pyrimidine-3-carboxylic acid [2-(2-fluoro-6-methyl-phenyl)-5-methyl-2H-pyrazol-3-yl]-amide | 366.1 |

TABLE 2-continued

| Ex # | Structure | Name | LCMS (ESI) m/z |
|---|---|---|---|
| 422 | 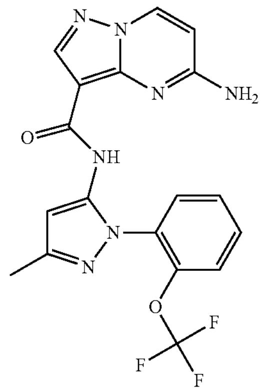 [SMILES: Cc1cc(NC(=O)c2cnn3ccc(N)nc23)n(-c2ccccc2OC(F)(F)F)n1] | 5-Amino-pyrazolo-[1,5-a]pyrimidine-3-carboxylic acid [5-methyl-2-(2-trifluoromethoxy-phenyl)-2H-pyrazol-3-yl]-amide | 418.1 |
| 423 | 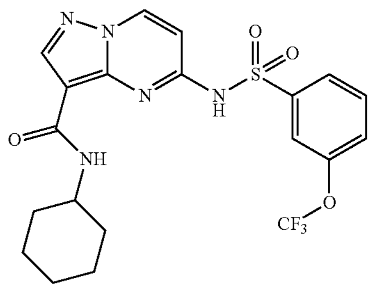 [SMILES: O=C(NC1CCCCC1)c1cnn2ccc(NS(=O)(=O)c3cccc(OC(F)(F)F)c3)nc12] | 5-(3-Trifluoromethoxy-benzenesulfonylamino)-pyrazolo[1,5-a]pyrimidine-3-carboxylic acid cyclohexylamide | 484.1 |
| 424 | 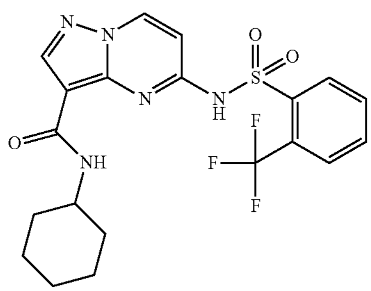 [SMILES: O=C(NC1CCCCC1)c1cnn2ccc(NS(=O)(=O)c3ccccc3C(F)(F)F)nc12] | 5-(2-Trifluoromethyl-benzenesulfonylamino)-pyrazolo[1,5-a]-pyrimidine-3-carboxylic acid cyclohexylamide | 468.1 |
| 425 | 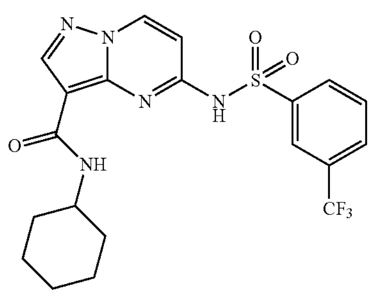 [SMILES: O=C(NC1CCCCC1)c1cnn2ccc(NS(=O)(=O)c3cccc(C(F)(F)F)c3)nc12] | 5-(3-Trifluoromethyl-benzenesulfonylamino)-pyrazolo[1,5-a]pyrimidine-3-carboxylic acid cyclohexylamide | 468.1 |
| 426 | 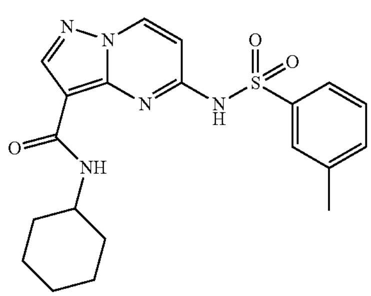 [SMILES: Cc1cccc(S(=O)(=O)Nc2ccn3ncc(C(=O)NC4CCCCC4)c3n2)c1] | 5-(Toluene-3-sulfonyl-amino)-pyrazolo-[1,5-a]pyrimidine-3-carboxylic acid cyclohexylamide | 414.1 |

TABLE 2-continued

| Ex # | Structure | Name | LCMS (ESI) m/z |
|---|---|---|---|
| 427 | 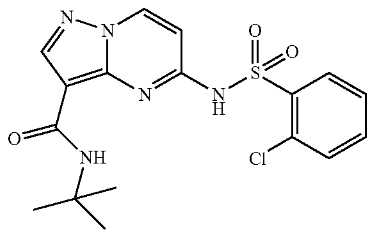 [SMILES: CC(C)(C)NC(=O)c1cnn2ccc(NS(=O)(=O)c3ccccc3Cl)nc12] | 5-(2-Chloro-benzene-sulfonylamino)-pyrazolo-[1,5-a]pyrimidine-3-carboxylic acid tert-butylamide | 408.0 |
| 428 | 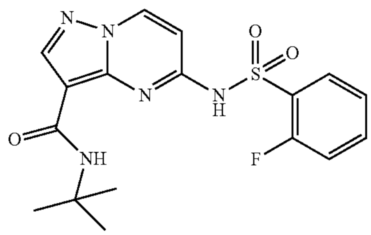 [SMILES: CC(C)(C)NC(=O)c1cnn2ccc(NS(=O)(=O)c3ccccc3F)nc12] | 5-(2-Fluoro-benzene-sulfonylamino)-pyrazolo-[1,5-a]pyrimidine-3-carboxylic acid tert-butylamide | 392.1 |
| 429 | 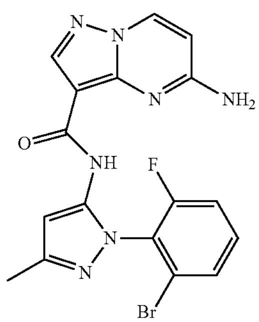 [SMILES: Cc1cc(NC(=O)c2cnn3ccc(N)nc23)n(-c2c(F)cccc2Br)n1] | 5-Amino-pyrazolo[1,5-a]-pyrimidine-3-carboxylic acid [2-(2-bromo-6-fluoro-phenyl)-5-methyl-2H-pyrazol-3-yl]-amide | 429.1 |
| 430 | 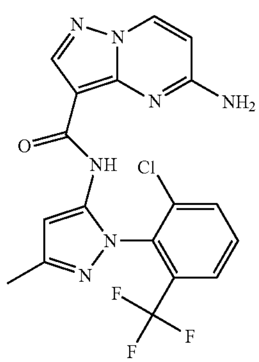 [SMILES: Cc1cc(NC(=O)c2cnn3ccc(N)nc23)n(-c2c(Cl)cccc2C(F)(F)F)n1] | 5-Amino-pyrazolo[1,5-a]-pyrimidine-3-carboxylic acid [2-(2-chloro-6-trifluoromethyl-phenyl)-5-methyl-2H-pyrazol-3-yl]-amide | 436.1 |
| 431 | 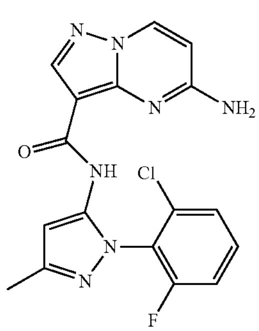 [SMILES: Cc1cc(NC(=O)c2cnn3ccc(N)nc23)n(-c2c(F)cccc2Cl)n1] | 5-Amino-pyrazolo[1,5-a]-pyrimidine-3-carboxylic acid [2-(2-chloro-6-fluoro-phenyl)-5-methyl-2H-pyrazol-3-yl]-amide | 386.1 |

TABLE 2-continued

| Ex # | Structure | Name | LCMS (ESI) m/z |
|---|---|---|---|
| 432 | 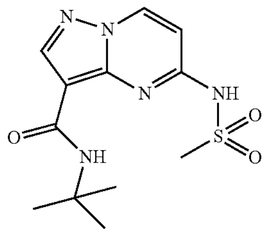 [SMILES: CC(C)(C)NC(=O)c1cnn2ccc(NS(C)(=O)=O)nc12] | 5-Methanesulfonylamino-pyrazolo[1,5-a]-pyrimidine-3-carboxylic acid tert-butylamide | 312.1 |
| 433 | 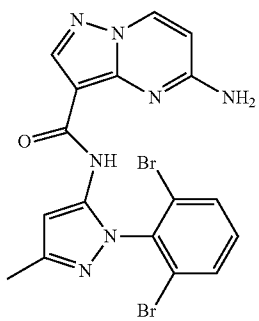 [SMILES: Cc1cc(NC(=O)c2cnn3ccc(N)nc23)n(-c2c(Br)cccc2Br)n1] | 5-Amino-pyrazolo[1,5-a]-pyrimidine-3-carboxylic acid [2-(2,6-dibromo-phenyl)-5-methyl-2H-pyrazol-3-yl]-amide | 491.7 |
| 434 | 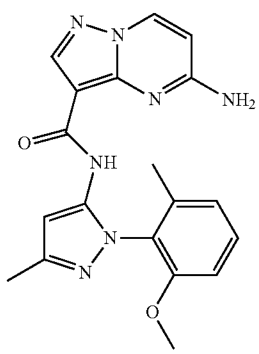 [SMILES: COc1cccc(C)c1-n1nc(C)cc1NC(=O)c1cnn2ccc(N)nc12] | 5-Amino-pyrazolo[1,5-a]-pyrimidine-3-carboxylic acid [2-(2-methoxy-6-methyl-phenyl)-5-methyl-2H-pyrazol-3-yl]-amide | 378.2 |
| 435 | 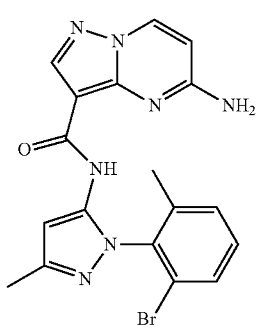 | 5-Amino-pyrazolo[1,5-a]-pyrimidine-3-carboxylic acid [2-(2-bromo-6-methyl-phenyl)-5-methyl-2H-pyrazol-3-yl]-amide | 425.8 |
| 436 | 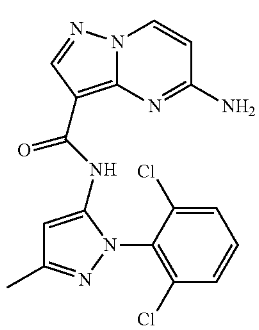 [SMILES: Cc1cc(NC(=O)c2cnn3ccc(N)nc23)n(-c2c(Cl)cccc2Cl)n1] | 5-Amino-pyrazolo[1,5-a]-pyrimidine-3-carboxylic acid [2-(2,6-dichloro-phenyl)-5-methyl-2H-pyrazol-3-yl]-amide | 402.1 |

| Ex # | Structure | Name | LCMS (ESI) m/z |
|---|---|---|---|
| 437 | 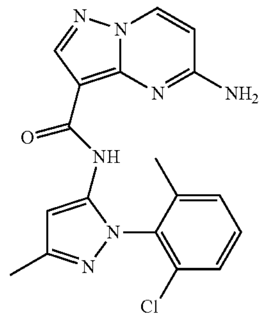 | 5-Amino-pyrazolo[1,5-a]-pyrimidine-3-carboxylic acid [2-(2-chloro-6-methyl-phenyl)-5-methyl-2H-pyrazol-3-yl]-amide | 382.1 |
| 438 | 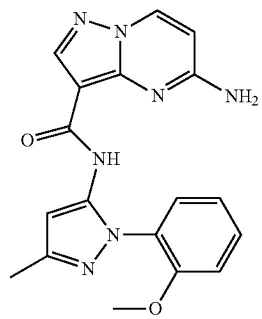 [SMILES: COc1ccccc1-n1nc(C)cc1NC(=O)c1cnn2ccc(N)nc12] | 5-Amino-pyrazolo[1,5-a]-pyrimidine-3-carboxylic acid [2-(2-methoxy-phenyl)-5-methyl-2H-pyrazol-3-yl]-amide | 364.0 |
| 439 | 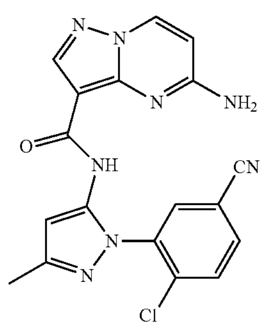 [SMILES: Cc1cc(NC(=O)c2cnn3ccc(N)nc23)n(-c2cc(C#N)ccc2Cl)n1] | 5-Amino-pyrazolo[1,5-a]-pyrimidine-3-carboxylic acid [2-(2-chloro-5-cyano-phenyl)-5-methyl-2H-pyrazol-3-yl]-amide | 393.2 |
| 440 | 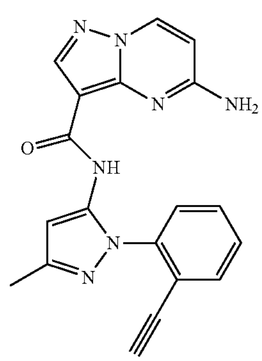 [SMILES: C#Cc1ccccc1-n1nc(C)cc1NC(=O)c1cnn2ccc(N)nc12] | 5-Amino-pyrazolo[1,5-a]-pyrimidine-3-carboxylic acid [2-(2-ethynyl-phenyl)-5-methyl-2H-pyrazol-3-yl]-amide | 358.0 |

TABLE 2-continued

| Ex # | Structure | Name | LCMS (ESI) m/z |
|---|---|---|---|
| 441 | 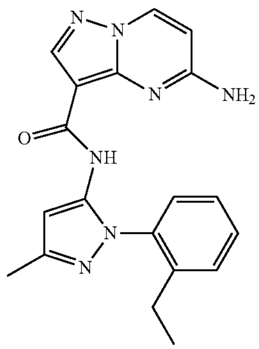 [SMILES: CCc1ccccc1-n1nc(C)cc1NC(=O)c1cnn2ccc(N)nc12] | 5-Amino-pyrazolo[1,5-a]-pyrimidine-3-carboxylic acid [2-(2-ethyl-phenyl)-5-methyl-2H-pyrazol-3-yl]-amide | 362.2 |
| 442 | 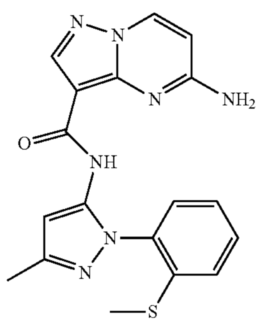 [SMILES: CSc1ccccc1-n1nc(C)cc1NC(=O)c1cnn2ccc(N)nc12] | 5-Amino-pyrazolo[1,5-a]-pyrimidine-3-carboxylic acid [5-methyl-2-(2-methylsulfanyl-phenyl)-2H-pyrazol-3-yl]-amide | 380.1 |
| 443 | 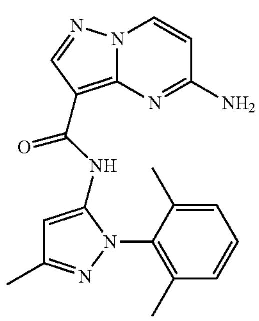 [SMILES: Cc1cc(NC(=O)c2cnn3ccc(N)nc23)n(-c2c(C)cccc2C)n1] | 5-Amino-pyrazolo[1,5-a]-pyrimidine-3-carboxylic acid [2-(2,6-dimethyl-phenyl)-5-methyl-2H-pyrazol-3-yl]-amide | 362.2 |
| 444 | 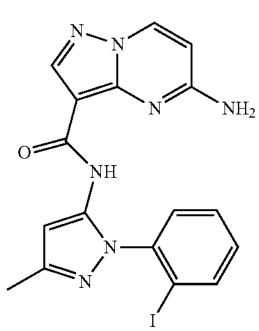 [SMILES: Cc1cc(NC(=O)c2cnn3ccc(N)nc23)n(-c2ccccc2I)n1] | 5-Amino-pyrazolo[1,5-a]-pyrimidine-3-carboxylic acid [2-(2-iodo-phenyl)-5-methyl-2H-pyrazol-3-yl]-amide | 460.1 |

TABLE 2-continued

| Ex # | Structure | Name | LCMS (ESI) m/z |
|---|---|---|---|
| 445 | 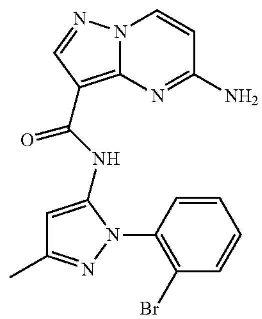 [SMILES: Cc1cc(NC(=O)c2cnn3ccc(N)nc23)n(-c2ccccc2Br)n1] | 5-Amino-pyrazolo[1,5-a]-pyrimidine-3-carboxylic acid [2-(2-bromo-phenyl)-5-methyl-2H-pyrazol-3-yl]-amide | 412.1 |
| 446 | 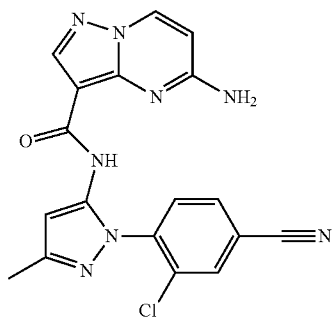 [SMILES: Cc1cc(NC(=O)c2cnn3ccc(N)nc23)n(-c2ccc(C#N)cc2Cl)n1] | 5-Amino-pyrazolo[1,5-a]-pyrimidine-3-carboxylic acid [2-(2-chloro-4-cyano-phenyl)-5-methyl-2H-pyrazol-3-yl]-amide | 393.0 |
| 447 | 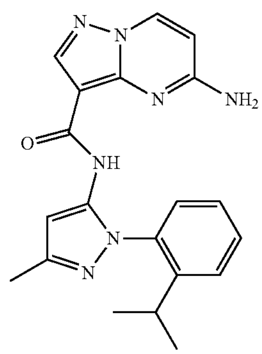 [SMILES: Cc1cc(NC(=O)c2cnn3ccc(N)nc23)n(-c2ccccc2C(C)C)n1] | 5-Amino-pyrazolo[1,5-a]-pyrimidine-3-carboxylic acid [2-(2-isopropyl-phenyl)-5-methyl-2H-pyrazol-3-yl]-amide | 376.3 |
| 448 | 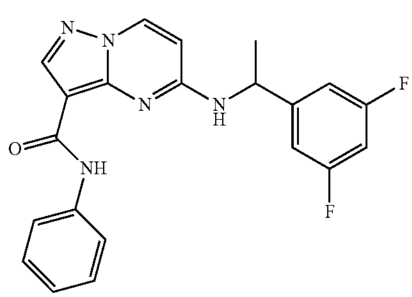 [SMILES: CC(Nc1ccn2ncc(C(=O)Nc3ccccc3)c2n1)c1cc(F)cc(F)c1] | 5-(1-(3,5-difluorophenyl)-ethylamino)-N-phenyl-pyrazolo[1,5-a]pyrimidine-3-carboxamide | 394.1 |
| 449 | 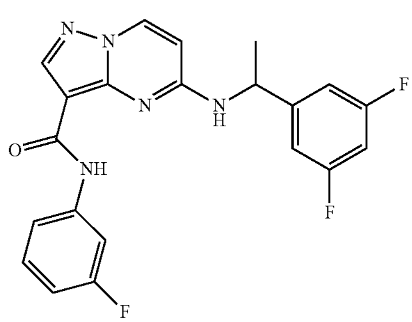 [SMILES: CC(Nc1ccn2ncc(C(=O)Nc3cccc(F)c3)c2n1)c1cc(F)cc(F)c1] | 5-(1-(3,5-difluorophenyl)-ethylamino)-N-(3-fluorophenyl)pyrazolo-[1,5-a]pyrimidine-3-carboxamide | 412.1 |

TABLE 2-continued

| Ex # | Structure | Name | LCMS (ESI) m/z |
|---|---|---|---|
| 450 | 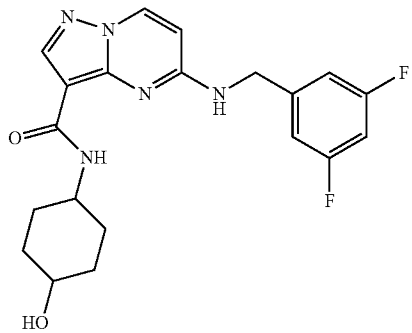 [SMILES: O=C(NC1CCC(O)CC1)c1cnn2ccc(NCc3cc(F)cc(F)c3)nc12] | 5-(3,5-difluorobenzyl-amino)-N-(4-hydroxy-cyclohexyl)pyrazolo-[1,5-a]pyrimidine-3-carboxamide | 402.2 |
| 451 | 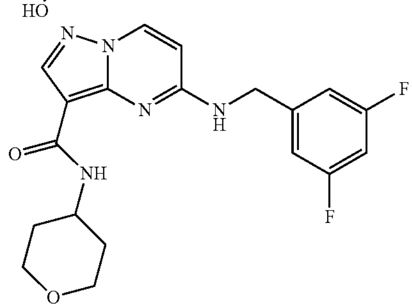 | 5-(3,5-difluorobenzyl-amino)-N-(tetrahydro-2H-pyran-4-yl)pyrazolo-[1,5-a]pyrimidine-3-carboxamide | 387.9 |
| 452 | 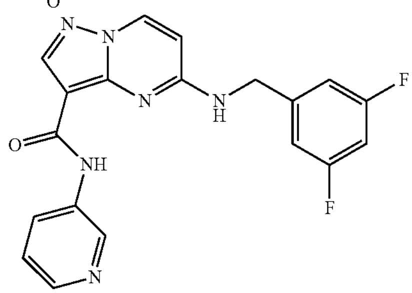 | 5-(3,5-difluorobenzyl-amino)-N-(pyridin-3-yl)pyrazolo[1,5-a]-pyrimidine-3-carboxamide | 380.9 |

The compounds of Examples 1-452 were tested for their capacity to inhibit a JAK kinase activity. The compounds of Examples 1-452 were found to have a $K_i$ of less than about 1 μM in JAK kinase activity assays (e.g. see Examples A-C). The compounds of the present invention are therefore useful as JAK kinase inhibitors.

Table 3 below shows enzymatic activity data ($K_i$) for certain compounds of the present invention run in the above assays (Examples A-C).

TABLE 3

| Example | JAK1 | JAK2$_i$ | JAK3 | TYK2$_i$ |
|---|---|---|---|---|
| 240 | 0.036 uM | 0.0032 uM | 0.0951 uM | 0.0624 uM |
| 231 | 0.0152 uM | 0.0018 uM | 0.0124 uM | 0.0438 uM |
| 225 | 0.0029 uM | 0.0003 uM | 0.0029 uM | 0.0073 uM |
| 226 | 0.0074 uM | 0.0005 uM | 0.0157 uM | 0.0328 uM |
| 248 | 0.0028 uM | 0.0001 uM | 0.0017 uM | 0.0041 uM |
| 250 | 0.0284 uM | 0.0020 uM | 0.0556 uM | 0.0361 uM |
| 277 | 0.0176 uM | 0.0009 uM | 0.0254 uM | 0.0435 uM |
| 343 | 0.0299 uM | 0.0042 uM | 0.0286 uM | 0.0976 uM |
| 297 | 0.0466 uM | 0.0016 uM | 0.0397 uM | 0.152 uM |
| 299 | 0.0287 uM | 0.0008 uM | 0.0145 uM | 0.0509 uM |

Table 4 below shows certain cellular pharmacological activity data ($EC_{50}$) for compounds of the present invention run in the above cellular assays (Example D).

TABLE 4

| Example | pSTAT5 SET2 | EPO pSTAT5 TF1 | IL6-pSTAT3 TF1 | IL12-pSTAT4 NK92 |
|---|---|---|---|---|
| 240 | 0.365 uM | 0.735 uM | 1.6 uM | 0.579 uM |
| 231 | 0.0802 uM | 0.23 uM | 0.371 uM | 3.3 uM |
| 225 | 0.0128 uM | 0.0404 uM | 0.13 uM | 0.119 uM |
| 226 | 0.017 uM | 0.103 uM | 0.17 uM | 0.336 uM |
| 248 | 0.018 uM | 0.0553 uM | 0.165 uM | 0.158 uM |
| 250 | 0.158 uM | 0.34 uM | 0.839 uM | 0.105 uM |
| 277 | 0.0434 uM | 0.148 uM | 0.514 uM | 0.603 uM |
| 343 | 0.301 uM | 0.368 uM | 0.380 uM | 5.3 uM |
| 297 | 0.170 uM | 0.207 uM | 1.4 uM | 1.1 uM |
| 299 | 0.256 uM | 0.228 uM | 1.88 uM | 1.77 uM |

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

Reference is made to International Application Serial No. PCT/US2009/063014 filed Nov. 2, 2009 and U.S. Provisional Application Serial No. 61/110,497, filed Oct. 31, 2008, which are incorporated herein by reference in its entirety for all purposes.

What is claimed is:

1. A compound of Formula Ia:

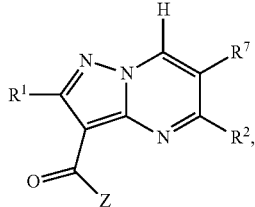

or an enantiomer, a diastereomer or a pharmaceutically acceptable salt thereof, wherein:

$R^1$ is H;

$R^2$ is $-OR^4$, $-NR^3R^4$, $-NR^3NR^{12}R^4$, $-NR^3S(O)R^4$ or $-NR^3S(O)_2R^4$;

$R^3$ is H or $C_1-C_6$ alkyl, $C_2-C_6$ alkenyl, $C_2-C_6$ alkynyl, wherein said alkyl, alkenyl and alkynyl are optionally substituted by oxo, F, $OR^a$ or $NR^aR^b$;

$R^4$ is H, $C_1-C_6$ alkyl, $C_2-C_6$ alkenyl, $C_2-C_6$ alkynyl, $-(C_0-C_5$ alkyl)$(C_1-C_9$ heterocyclyl), $-(C_0-C_5$ alkyl)$(C_3-C_6$ cycloalkyl), $-(C_0-C_5$ alkyl)$(C_1-C_9$ heteroaryl), $-(C_0-C_5$ alkyl)$(C_6-C_{10}$ aryl), wherein said alkyl, alkenyl and alkynyl are optionally substituted by $R^8$, and said aryl, cycloalkyl, heteroaryl and heterocyclyl are optionally substituted by $R^9$; or $R^3$ and $R^4$ are taken together with the nitrogen to which they are attached to form a $C_1-C_9$ heterocyclyl optionally substituted by $R^{13}$;

Z is $-NR^5R^6$;

$R^5$ is H or $C_1-C_3$ alkyl;

$R^6$ is H, $C_1-C_{10}$ alkyl, $C_2-C_{10}$ alkenyl, $C_2-C_{10}$ alkynyl, $-(C_0-C_5$ alkyl)$(C_1-C_9$ heterocyclyl), $-(C_0-C_5$ alkyl)$(C_3-C_8$ cycloalkyl), $-(C_0-C_5$ alkyl)$(C_1-C_9$ heteroaryl), $-(C_0-C_5$ alkyl)$(C_6-C_9$ aryl), wherein said alkyl, alkenyl and alkynyl are optionally substituted by $R^{10}$, and said aryl, cycloalkyl, heteroaryl and heterocyclyl are optionally substituted by $R^{11}$;

$R^7$ is H, halo, $C_1-C_3$ alkyl, $C_2-C_3$ alkenyl, $C_2-C_3$ alkynyl or $-O(C_1-C_3$ alkyl);

$R^8$ is independently oxo, halo, $OR^a$ or $NR^aR^b$;

$R^9$ is independently oxo, $-CN$, $-CF_3$, halo, $-C(O)C_1-C_6$ alkyl, $-C(O)OR^a$, $-C(O)NR^aR^b$, $-(C_0-C_5$ alkyl)$NR^aR^b$, $-(C_0-C_5$ alkyl)$OR^a$, $-(C_0-C_5$ alkyl)$SR^a$, $-O[C(R^a)_2]_{1-3}O-$, $C_1-C_3$ alkyl optionally substituted by oxo or F, $-(C_0-C_5$ alkyl)$(C_3-C_6$ cycloalkyl) optionally substituted by oxo or F, $-(C_0-C_5$ alkyl)$C_1-C_9$ heterocyclyl optionally substituted by halo, oxo, $C_1-C_3$ alkyl or $C(O)C_1-C_3$ alkyl, $-(C_0-C_5$ alkyl)$C_6$ aryl optionally substituted by halo or $C_1-C_3$ alkyl $-O(C_1-C_3$ alkyl), or $-(C_0-C_5$ alkyl)$C_1-C_9$ heteroaryl optionally substituted by halo or $C_1-C_3$ alkyl;

$R^{10}$ is independently oxo, halo, $OR^a$ or $NR^aR^b$;

$R^{11}$ is independently oxo, $-CN$, $-CF_3$, halo, $-O[C(R^a)_2]_{1-3}O-$, $-C(O)C_1-C_6$ alkyl, $-C(O)OR^a$, $-C(O)NR^aR^b$, $-(C_0-C_5$ alkyl)$NR^aR^b$, $-(C_0-C_5$ alkyl)$OR^a$, $C_1-C_6$ alkyl optionally substituted by oxo or F, $-(C_0-C_5$ alkyl)$C_1-C_9$ heterocyclyl optionally substituted by halo, oxo, $C_1-C_3$ alkyl or $C(O)C_1-C_3$ alkyl, $-(C_0-C_5$ alkyl)$C_1-C_9$ heteroaryl optionally substituted by halo or $C_1-C_3$ alkyl, $-(C_0-C_5$ alkyl)phenyl optionally substituted by $C_1-C_4$ alkyl, $C_1-C_4$ alkenyl, $C_1-C_4$ alkynyl, $C_3-C_6$ cycloalkyl, $-CF_3$, halo, $-CN$, $-OR^a$ or $-NR^aR^b$, or $-(C_0-C_5$ alkyl)$C_3-C_6$ cycloalkyl optionally substituted by oxo, $-NR^cR^d$, $C_1-C_3$ alkyl or F;

$R^{12}$ is H or $C_1-C_3$ alkyl;

$R^{13}$ is oxo, halo, $C_1-C_3$ alkyl, $-C(O)C_1-C_6$ alkyl, $-C(O)OR^a$, $C_6$ aryl, $C_3-C_6$ cycloalkyl, $C_1-C_5$ heteroaryl or $C_4-C_5$ heterocyclyl; wherein said aryl, cycloalkyl, heteroaryl and heterocyclyl are optionally substituted by $C_1-C_4$ alkyl, $-(C_0-C_3$ alkyl)$OR^c$, oxo, halo or $NR^cR^d$;

$R^a$ and $R^b$ are independently H, $-CF_3$, $-CHF_2$, $-CH_2F$, $C_1-C_6$ alkyl, $C_6$ aryl, $C_3-C_6$ cycloalkyl or $C_4-C_5$ heterocyclyl; wherein said alkyl, aryl and cycloalkyl are optionally substituted by $C_1-C_4$ alkyl, $-(C_0-C_3$ alkyl)$OR^c$, oxo, halo, $NR^cR^d$ or $C_4-C_5$ heterocyclyl; or $R^a$ and $R^b$ together with the atom to which they are attached form a $C_1-C_5$ heterocyclyl optionally substituted by oxo, F, $C_1-C_3$ alkyl, $-C(O)C_1-C_6$ alkyl or $-C(O)OR^a$; and $R^c$ and $R^d$ are independently H, $C_1-C_3$ alkyl, $C_3-C_6$ cycloalkyl or phenyl, wherein said alkyl, cycloalkyl and phenyl are optionally substituted by halo, $CH_3$, OH, $NH_2$, $C(O)O(C_1-C_6$ alkyl) or $C(O)NH(C_1-C_6$ alkyl).

2. A compound of claim 1, selected from Formula I:

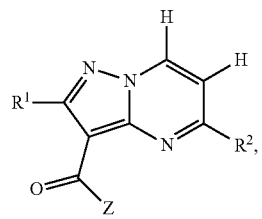

or an enantiomer, a diastereomer or a pharmaceutically acceptable salt thereof, wherein:

$R^1$ is H;

$R^2$ is $-OR^4$ or $-NR^3R^4$;

$R^3$ is H or $C_1-C_6$ alkyl, $C_2-C_6$ alkenyl, $C_2-C_6$ alkynyl, wherein said alkyl, alkenyl and alkynyl are optionally substituted by oxo, F, $OR^a$ or $NR^aR^b$;

$R^4$ is H, $C_1-C_6$ alkyl, $C_2-C_6$ alkenyl, $C_2-C_6$ alkynyl, $-(C_0-C_5$ alkyl)$(C_1-C_9$ heterocyclyl), $-(C_0-C_5$ alkyl)$(C_3-C_6$ cycloalkyl), $-(C_0-C_5$ alkyl)$(C_1-C_9$ heteroaryl), $-(C_0-C_5$ alkyl)$(C_6-C_9$ aryl), wherein said alkyl, alkenyl and alkynyl are optionally substituted by oxo, F, $OR^a$ or $NR^aR^b$, and said aryl, cycloalkyl, heteroaryl and heterocyclyl are optionally substituted by oxo, $-CN$, $-CF_3$, halo, $-C(O)C_1-C_6$ alkyl, $-C(O)OR^a$, $-C(O)NR^aR^b$, $-(C_0-C_5$ alkyl)$NR^aR^b$, $-(C_0-C_5$ alkyl)$OR^a$, $-O[C(R^a)_2]_{1-3}O-$ $C_1-C_3$ alkyl optionally substituted by oxo or F, $-(C_0-C_5$ alkyl)$C_1-C_9$ heterocyclyl optionally substituted by halo, oxo, $C_1-C_3$ alkyl or $C(O)C_1-C_3$ alkyl, or $-(C_0-C_5$ alkyl)$C_1-C_9$ heteroaryl optionally substituted by halo or $C_1-C_3$ alkyl; or $R^3$ and $R^4$ are taken together with the nitrogen to which they are attached to form a $C_1-C_5$ heterocyclyl optionally substituted by oxo, F, $C_1-C_3$ alkyl, $-C(O)C_1-C_6$ alkyl or $-C(O)OR^a$;

Z is $-NR^5R^6$;

$R^5$ is H or $C_1-C_3$ alkyl;

$R^6$ is H, $C_1-C_{10}$ alkyl, $C_2-C_{10}$ alkenyl, $C_2-C_{10}$ alkynyl, $-(C_0-C_5$ alkyl)$(C_1-C_9$ heterocyclyl), $-(C_0-C_5$ alkyl)$(C_3-C_8$ cycloalkyl), $-(C_0-C_5$ alkyl)$(C_1-C_9$ heteroaryl), $-(C_0-C_5$ alkyl)$(C_6-C_9$ aryl), wherein said alkyl, alkenyl and alkynyl are optionally substituted by oxo, F, $OR^a$ or NR$^a$R$^b$, and said aryl, cycloalkyl, heteroaryl and heterocyclyl are optionally substituted by
oxo, —CN, —CF$_3$, halo, —O[C(R$^a$)$_2$]$_{1-3}$O—, —C(O)C$_1$-C$_6$ alkyl, —C(O)OR$^a$, —C(O)NR$^a$R$^b$, —(C$_0$-C$_5$ alkyl)NR$^a$R$^b$, —(C$_0$-C$_5$ alkyl)OR$^a$,
C$_1$-C$_6$ alkyl optionally substituted by oxo or F,
—(C$_0$-C$_5$ alkyl)C$_1$-C$_9$ heterocyclyl optionally substituted by halo, oxo, C$_1$-C$_3$ alkyl or C(O)C$_1$-C$_3$ alkyl,
—(C$_0$-C$_5$ alkyl)C$_1$-C$_9$ heteroaryl optionally substituted by halo or C$_1$-C$_3$ alkyl,
—(C$_0$-C$_5$ alkyl)phenyl optionally substituted by C$_1$-C$_3$ alkyl, —CF$_3$, halo, —CN, —OR$^a$ or —NR$^a$R$^b$, or
—(C$_0$-C$_5$ alkyl)C$_3$-C$_6$ cycloalkyl optionally substituted by oxo, —NR$^c$R$^d$, C$_1$-C$_3$ alkyl or F;
R$^a$ and R$^b$ are independently H, —CF$_3$, —CHF$_2$, —CH$_2$F, C$_1$-C$_6$ alkyl, C$_6$ aryl, C$_3$-C$_6$ cycloalkyl or C$_4$-C$_5$ heterocyclyl; wherein said alkyl, aryl and cycloalkyl are optionally substituted by C$_1$-C$_4$ alkyl, —(C$_0$-C$_3$ alkyl)OR$^c$, oxo, halo, NR$^c$R$^d$ or C$_4$-C$_5$ heterocyclyl; or
R$^a$ and R$^b$ together with the atom to which they are attached form a C$_1$-C$_5$ heterocyclyl optionally substituted by oxo, F, C$_1$-C$_3$ alkyl, —C(O)C$_1$-C$_6$ alkyl or —C(O)OR$^a$; and
R$^c$ and R$^d$ are independently H, C$_1$-C$_3$ alkyl, C$_3$-C$_6$ cycloalkyl or phenyl, wherein said alkyl, cycloalkyl and phenyl are optionally substituted by halo, CH$_3$, OH, NH$_2$, C(O)O(C$_1$-C$_6$ alkyl) or C(O)NH(C$_1$-C$_6$ alkyl).

3. The compound of claim 1, wherein R$^2$ is —NHR$^4$.
4. The compound of claim 3, wherein R$^2$ is —NH$_2$.
5. The compound of claim 3, wherein R$^4$ is C$_1$-C$_6$ alkyl, —(C$_0$-C$_5$ alkyl)(C$_1$-C$_9$ heterocyclyl), —(C$_0$-C$_5$ alkyl)(C$_3$-C$_6$ cycloalkyl), —(C$_0$-C$_5$ alkyl)(C$_1$-C$_9$ heteroaryl), —(C$_0$-C$_5$ alkyl)(C$_6$-C$_{10}$ aryl), wherein said alkyl is optionally substituted by R$^8$, and said aryl, cycloalkyl, heteroaryl and heterocyclyl are optionally substituted by R$^9$.
6. The compound of claim 1, wherein R$^3$ and R$^4$ are taken together with the nitrogen to which they are attached to form a C$_1$-C$_9$ heterocyclyl optionally substituted by R$^{13}$.
7. The compound of claim 1, wherein R$^2$ is —NHS(O)$_2$R$^4$.
8. The compound of claim 7, wherein R$^4$ is —(C$_6$-C$_{10}$ aryl) optionally substituted by R$^9$.
9. The compound of claim 1, wherein R$^6$ is C$_1$-C$_{10}$ alkyl, —(C$_0$-C$_5$ alkyl)(C$_1$-C$_9$ heterocyclyl), —(C$_0$-C$_5$ alkyl)(C$_3$-C$_8$ cycloalkyl), —(C$_0$-C$_5$ alkyl)(C$_1$-C$_9$ heteroaryl), —(C$_0$-C$_5$ alkyl)(C$_6$-C$_9$ aryl), wherein said alkyl is optionally substituted by R$^{10}$, and said aryl, cycloalkyl, heteroaryl and heterocyclyl are optionally substituted by R$^{11}$.
10. The compound of claim 1, wherein R$^7$ is H; R$^2$ is —NR$^3$S(O)$_2$R$^4$; R$^3$ is H; and R$^4$ is phenyl optionally substituted by 1-3 substituents selected from C$_1$-C$_3$ alkyl, —CF$_3$ and halo; Z is —NR$^5$R$^6$; R$^5$ is H; and R$^6$ is cyclopropyl, cyclobutyl, cyclopentyl, cyclohexyl, cycloheptyl or cyclooctyl, and wherein R$^6$ is optionally substituted by 1 to 3 substituents selected from oxo, halo and C$_1$-C$_6$ alkyl.
11. The compound of claim 1, wherein R$^7$ is H; R$^2$ is —NR$^3$R$^4$; R$^3$ is H; R$^5$ is H; R$^6$ is pyrazolyl substituted by phenyl and further optionally substituted by methyl, and wherein said phenyl is optionally substituted by one or two substituents selected from methyl, halo, methoxy, cyano, trifluoromethyl, hydroxy and trifluoromethoxy.
12. The compound of claim 1, wherein R$^4$ is phenyl, —(CH$_2$)phenyl, —(CH$_2$CH$_2$)phenyl, —CH(CH$_3$)phenyl, —CH(CH$_2$CH$_3$)phenyl, —(R)—CH(CH$_3$)phenyl, —(S)—CH(CH$_3$)phenyl, —(R)—CH(CH$_2$CH$_3$)phenyl, —(S)—CH(CH$_2$CH$_3$)phenyl or —C(CH$_3$)$_2$-phenyl, wherein said phenyl is optionally substituted by R$^9$.
13. The compound of claim 1, wherein R$^9$ is independently selected from methyl, ethyl, i-propyl, cyclopropyl, F, Cl, —OCH$_2$O—, —OCH$_2$CH$_2$O—, —OCH$_2$CH$_2$CH$_2$O—, —OCH$_2$CH$_2$NH$_2$, —OCH$_2$CH$_2$NMe$_2$, —O(CH$_2$)$_{1-3}$(C$_4$-C$_5$ heterocyclyl), C$_3$-C$_5$ heteroaryl, —(CH$_2$)$_{0-3}$C$_3$-C$_5$ heterocyclyl optionally substituted by C$_1$-C$_3$ alkyl or halo, —OH, —OCH$_3$, —OCH$_2$CH$_3$, —SH, —SCH$_3$, —SCH$_2$CH$_3$, —N(CH$_3$)$_2$ —N(CH$_2$CH$_3$)$_2$, —CN, —CF$_3$, —OCF$_3$, —OCHF$_2$ and C(O)O(C$_1$-C$_3$ alkyl).

14. The compound of claim 1, wherein R$^4$ is selected from: H, methyl, ethyl, i-propyl, —CH$_2$CH$_2$OH,

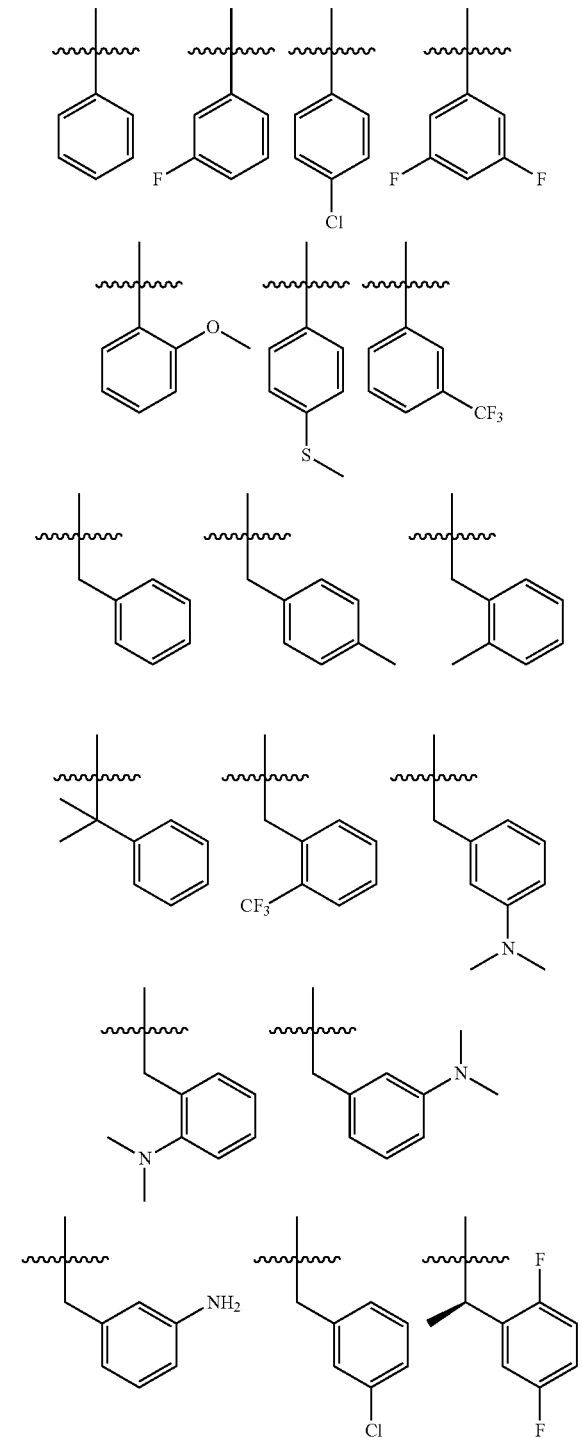

279
-continued
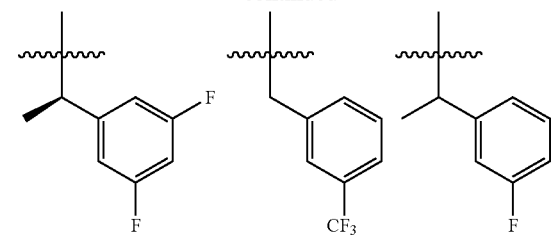
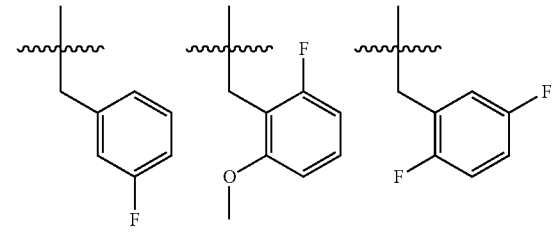
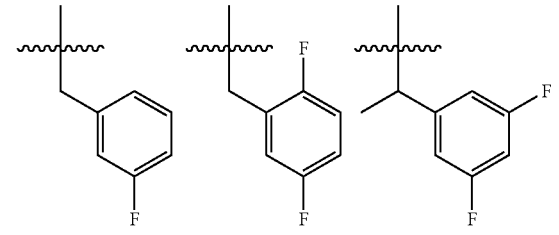
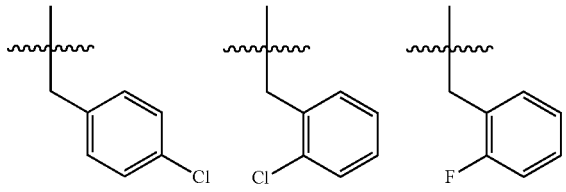
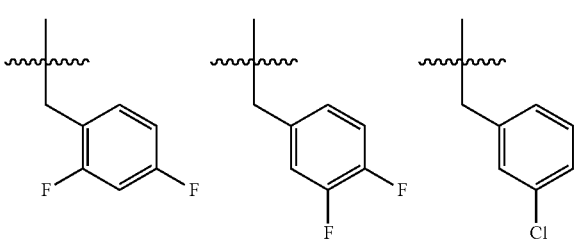
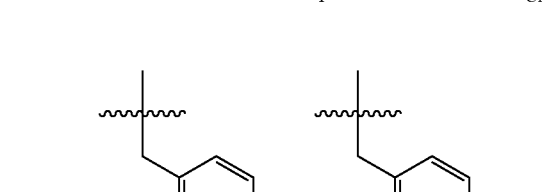
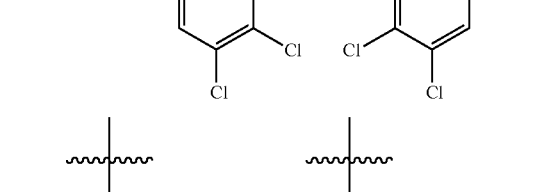
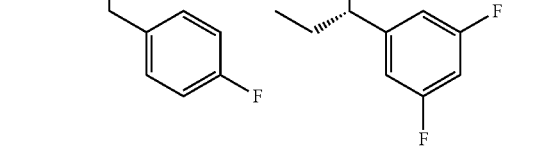
280
-continued
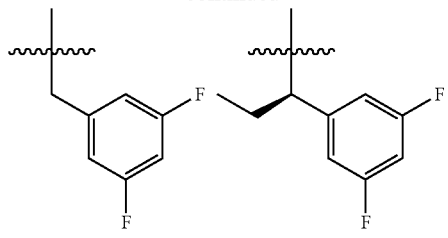
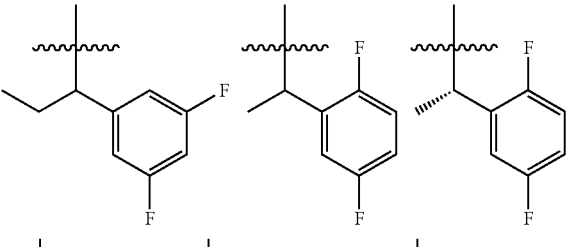
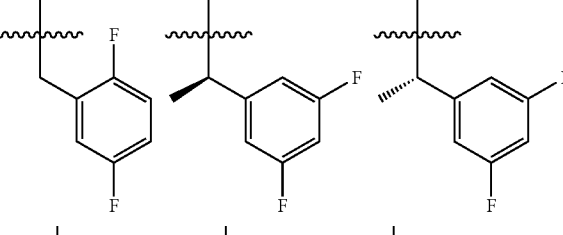
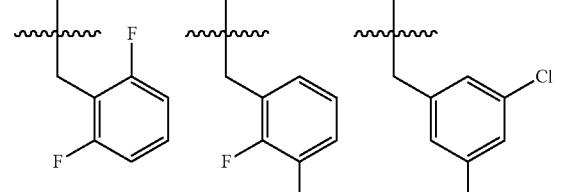
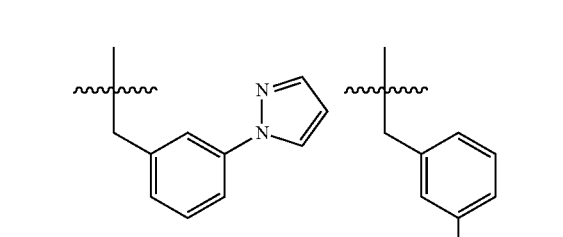
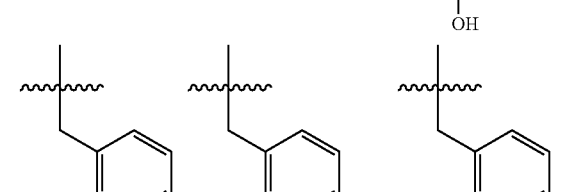
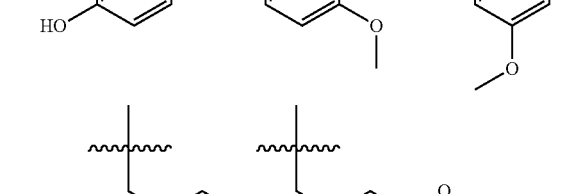
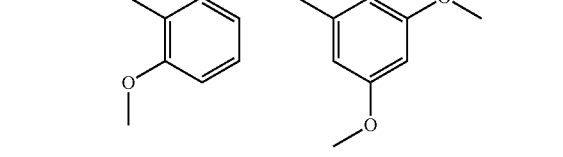

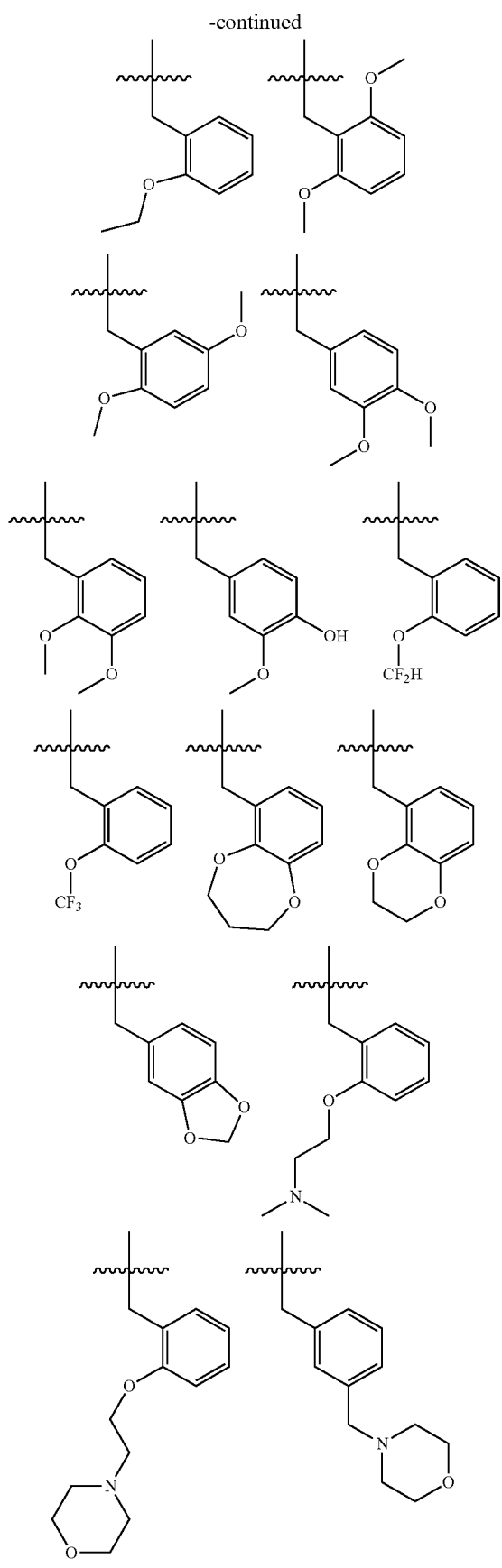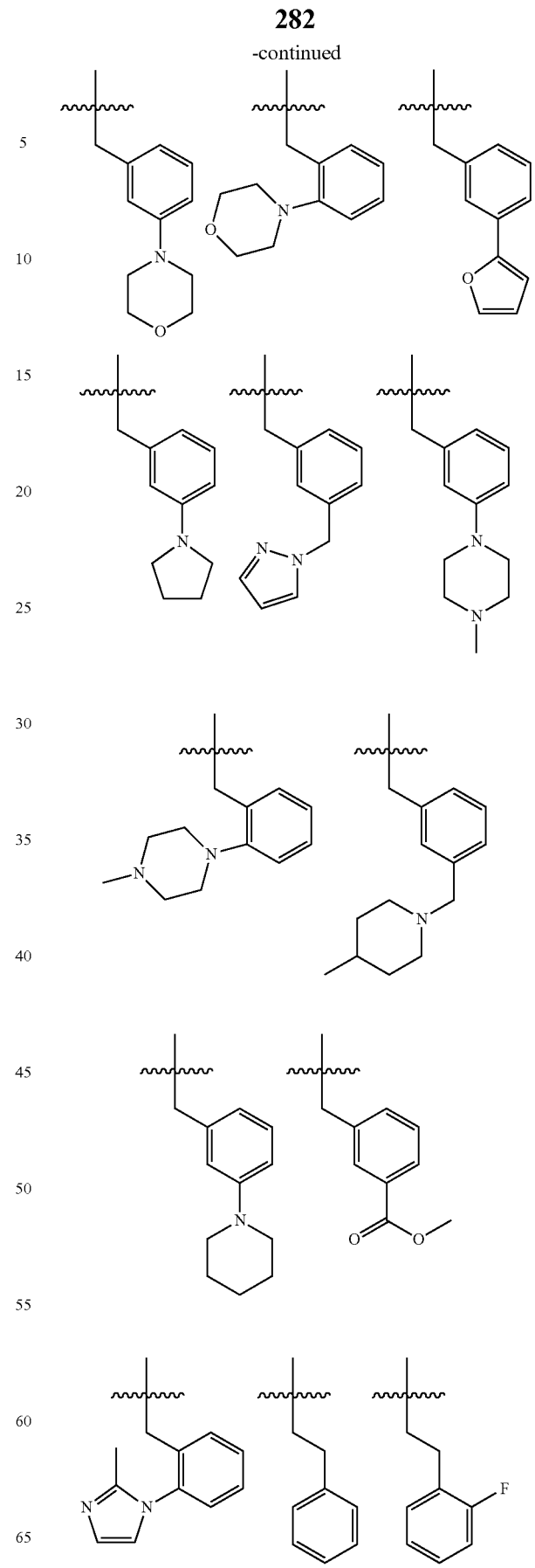

283
-continued
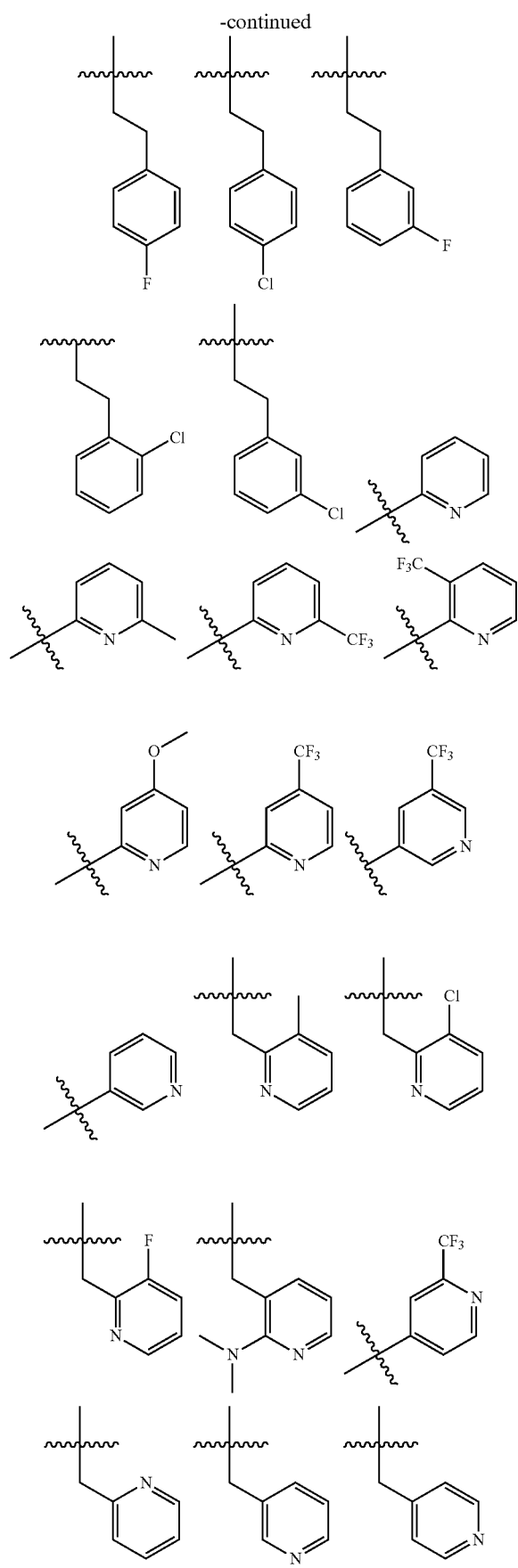
284
-continued
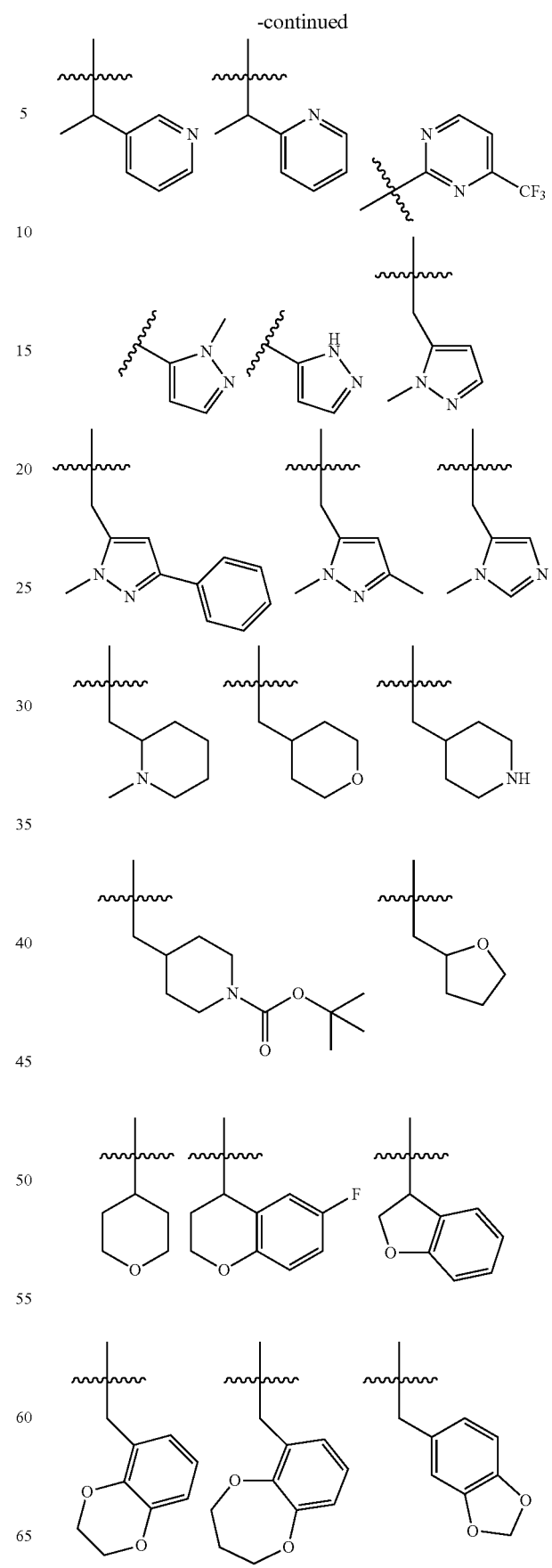

-continued

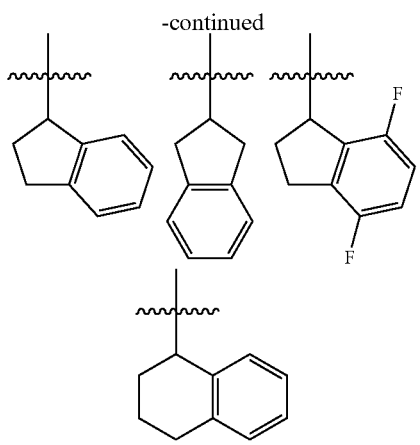

wherein the wavy lines represent the point of attachment of R⁴.

15. The compound of claim 1, wherein $R^6$ is
—($C_0$-$C_1$ alkyl)($C_6$-$C_8$ cycloalkyl) optionally substituted by oxo, —CN, —$CF_3$, halo, —C(O)$C_1$-$C_6$ alkyl, —C(O)$OR^a$, —C(O)$NR^aR^b$, —($C_0$-$C_5$ alkyl)$NR^aR^b$, —($C_0$-$C_5$ alkyl)$OR^a$ or $C_1$-$C_6$ alkyl optionally substituted by oxo or F,
—($C_0$-$C_2$ alkyl)$C_4$-$C_5$ heterocyclyl optionally substituted by halo, oxo, $C_1$-$C_3$ alkyl or C(O)$C_1$-$C_3$ alkyl,
—($C_0$-$C_2$ alkyl)$C_3$-$C_5$ heteroaryl optionally substituted by halo, $C_1$-$C_3$ alkyl or phenyl, wherein said phenyl is optionally substituted by $C_1$-$C_3$ alkyl, —$CF_3$, halo, —CN, —$OR^a$ or —$NR^aR^b$,
—($C_0$-$C_2$ alkyl)phenyl optionally substituted by halo, —CN, —$OR^a$ or —$NR^aR^b$, or
—($C_0$-$C_2$ alkyl)$C_6$-$C_7$ cycloalkyl optionally substituted by oxo, $C_1$-$C_3$ alkyl or F.

16. A pharmaceutical composition comprising a compound of claim 1 and a pharmaceutically acceptable carrier, adjuvant or vehicle.

17. A method of manufacturing a compound of claim 1, comprising contacting a compound of formula i:

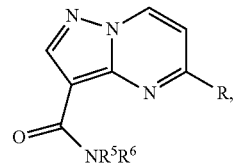

(i)

wherein R is independently halogen, with a compound of formula $NHR^3R^4$, under conditions sufficient to form the compound of claim 1.

18. The method of claim 17, wherein R is Cl.

* * * * *